US008008287B2

(12) United States Patent
Cai et al.

(10) Patent No.: US 8,008,287 B2
(45) Date of Patent: *Aug. 30, 2011

(54) INTEGRASE INHIBITORS

(75) Inventors: Zhenhong R. Cai, Foster City, CA (US); Salman Y. Jabri, San Francisco, CA (US); Haolun Jin, Foster City, CA (US); Rachael A. Lansdown, San Francisco, CA (US); Samuel E. Metobo, Newark, CA (US); Michael R. Mish, La Honda, CA (US); Richard M. Pastor, San Francisco, CA (US)

(73) Assignee: Gilead Sciences, Inc., Foster City, CA (US)

( * ) Notice: Subject to any disclaimer, the term of this patent is extended or adjusted under 35 U.S.C. 154(b) by 917 days.

This patent is subject to a terminal disclaimer.

(21) Appl. No.: 11/804,041

(22) Filed: May 16, 2007

(65) Prior Publication Data

US 2008/0058315 A1    Mar. 6, 2008

Related U.S. Application Data

(60) Provisional application No. 60/801,020, filed on May 16, 2006.

(51) Int. Cl.
*A61K 31/54* (2006.01)
*A01N 43/58* (2006.01)
*A01N 43/60* (2006.01)
*C07D 471/00* (2006.01)
*C07D 487/00* (2006.01)
*C07D 401/00* (2006.01)

(52) U.S. Cl. ............... 514/196; 514/222.8; 514/250; 544/346; 544/361

(58) Field of Classification Search .................. 514/169, 514/222.8, 250; 544/346, 361
See application file for complete search history.

(56) References Cited

U.S. PATENT DOCUMENTS

| 4,816,570 | A | | 3/1989 | Farquhar |
| 4,968,788 | A | | 11/1990 | Farquhar |
| 5,663,159 | A | | 9/1997 | Starrett, Jr. et al. |
| 5,683,999 | A | * | 11/1997 | Jadhav et al. ............... 514/218 |
| 5,792,756 | A | | 8/1998 | Starrett, Jr. et al. |
| 6,245,806 | B1 | | 6/2001 | Dombrowski et al. |
| 6,271,402 | B1 | | 8/2001 | Singh et al. |
| 6,312,662 | B1 | | 11/2001 | Erion et al. |
| 6,395,743 | B1 | | 5/2002 | Heimbuch et al. |
| 2003/0055071 | A1 | | 3/2003 | Anthony et al. |

FOREIGN PATENT DOCUMENTS

| WO | WO-91/19721 | | 12/1991 |
| WO | WO-96/15111 | | 5/1996 |
| WO | WO-99/62513 | | 12/1999 |
| WO | WO-99/62520 | | 12/1999 |
| WO | WO-00/39086 | | 7/2000 |
| WO | WO-00/75122 | | 12/2000 |
| WO | WO-01/00578 | | 1/2001 |
| WO | WO-02/30426 | | 4/2002 |
| WO | WO-02/30930 | | 4/2002 |
| WO | WO-02/30931 | | 4/2002 |
| WO | WO-02/36734 | | 5/2002 |
| WO | WO-02/055079 | | 7/2002 |
| WO | WO-2004/035576 | | 4/2004 |
| WO | WO 2004/035577 | * | 4/2004 |
| WO | WO-2004/035577 | | 4/2004 |
| WO | WO-2004/096807 | | 11/2004 |
| WO | WO-2005/016927 | | 2/2005 |
| WO | WO-2005/075475 | | 8/2005 |
| WO | WO-2005/117904 | | 12/2005 |
| WO | WO-2006/125048 | | 11/2006 |
| WO | WO-2007/076005 | | 7/2007 |

OTHER PUBLICATIONS

Verschueren, W. et al. (2005) "Design and Optimization of Tricyclic Phtalimide Analogues as Novel Inhibitors of HIV-1 Integrase" J. Med. Chem 48:1930-1940.
Daelemans, D. et al. (2007) "Characterization of a Replication-Competent, Integrase-Defective Human Immunodeficiency Virus (HIV)/Simian Virus 40 Chimera as a Powerful Tool for the Discovery and Validation of HIV Integrase Inhibitors" J. of Vir. 81 (8): 4381-4385.
Anan'eva et al. (1983) "(2-Iodoethyl) Phosphonic Derivatives," *Zhurnal Obshchei Khimii* 53(3):554-559.
Artico et al. (1998) "Geometrically and Conformationally Restrained Cinnamoyl Compounds as Inhibitors of HIV-1 Integrase: Synthesis, Biological Evaluation, and Molecular Modeling," *J. Med. Chem.* 41:3948-3960.
Asante-Appiah et al. (1999) "HIV-1 Integrase: Structural Organization, Conformational Changes, and Catalysis," *Advances in Virus Research* 52:351-363.
Benzaria et al. (1996) "Synthesis, in Vitro Antiviral Evaluation, and Stability Studies of Bis(S-acyl-2-thioethyl) Ester Derivatives of 9-2-(Phosphonomethoxy)ethyl]adenine (PMEA) as Potential PMEA Prodrugs with Improved Oral Bioavailability," *J. Med. Chem.* 39:4958-4965.
Bhuta et al. (1980) "Analogues of Chloramphenicol: Circular Dichroism Spectra, Inhibition of Ribosomal Peptidyltransferase, and Possible Mechanism of Action," *J. Med. Chem.* 23:1299-1305.
Buolamwini et al. (2002) "CoMFA and CoMSIA 3D QSAR and Docking Studies on Conformationally-Restrained Cinnamoyl HIV-1 Integrase Inhibitors: Exploration of a Binding Mode at the Active Site," *J. Med. Chem.* 45:841-852. Campagne et al. (1995) "1H-Benzotriazol-1-yloxy)tris(dimethylamino)phorphonium Hexafluorophosphate- and (1H-Benzotriazol-1-yloxy)tripyrroludinophosphonium Hexafluorophosphate-Mediated Activation of Monophosphonate Esters: Synthesis of Mixed Phosphonate Diesters, the Reactivity of the Benzotriazolyl Phosphonic Esters vs the Reactivity of the Benzotriazolyl Carboxylic Esters," *J. Org. Chem.* 60:5214-5223.
Chen et al. (1997) "Design, Synthesis, and Biochemical Evaluation of Phosphonate and Phosphonamidate Analogs of Glutathionylspermidine as Inhibitors of Glutathionylspermidine Synthetase/Amidase from *Escherichia coli*," *J. Med. Chem.* 40:3842-3850.
Darby, G. (1995) "In Search of the Perfect Antiviral," *Antiviral Chemistry & Chemotherapy* 6(Suppl. 1):54-63.
Davies et al. (1988) "Dinucleotide Analogues as Inhibitors of Thymidine Kinase, Thymidylate Kinase, and Ribonucleotide Reductase," *J. Med. Chem.* 31:1305-1308.
De Lombaert et al. (1994) "N-Phosphonomethyl Dipeptides and Their Phosphonate Prodrugs, a New Generation of Neutral Endopeptidase (NEP, EC 3.4.24.11) Inhibitors," *J. Med. Chem.* 37:498-511.

(Continued)

*Primary Examiner* — Marcos Sznaidman
(74) *Attorney, Agent, or Firm* — Eric K. Voelk

(57) ABSTRACT

Tricyclic compounds, protected intermediates thereof, and methods for inhibition of HIV-integrase are disclosed.

52 Claims, No Drawings

OTHER PUBLICATIONS

Espeseth et al. (2000) "HIV-1 Integrase Inhibitors that Compete with the Target DNA Substrate Define a Unique Strand Transfer Conformation for Integrase," *PNAS* 97(21):11244-11249.

Farnet et al. (1996) "Differential Inhibtion of HIV-1 Preintegration Complexes and Purified Integrase Protein by Small Molecules," *Proc. Natl. Acad. Sci. USA* 93:9742-9747.

Farquhar et al. (1983) "Biologically Reversible Phosphate-Protective Groups," *Journal of Pharmaceutical Sciences* 72(3):324-325.

Galeotti et al. (1996) "A Straightforward Synthesis of α-Amino Phosphonate Monoesters Using BroP or TPyClU," *Tetrahedron Letters* 37(23):3997-3998.

Goldgur et al. (1999) "Structure of the HIV-1 Integrase Catalytic Domain Complexed with an Inhibitor: A Platform for Antiviral Drug Design," *PNAS* 96(23):13040-13043.

Hazuda et al. (1994) "A Novel Assay for the DNA Strand-Transfer Reaction of HIV-1 Integrase," *Nucleic Acids Research* 22(6):1121-1122.

Hazuda et al. (1997) "Differential Divalent Cation Requirements Uncouple the Assembly and Catalytic Reactions of Human Immunodeficiency Virus Type I Intergrase," *Journal of Virology* 71(9):7005-7011.

Hazuda et al. (1997) "Discovery and Analysis of Inhibitors of the Human Immunodeficiency Integrase," *Drug Design and Discovery* 15:17-24.

Hazuda et al. (2000) "Inhibitors of Strand Transfer that Prevent Integration and Inhibit HIV-1 Replication in Cells," *Science* 287:646-650.

Jacob, P. III (1982) "Resolution of -5-Bromonornicotine. Synthesis of (R)- and (S)- Nornicotine of High Enantiomeric Purity," *J. Org. Chem.* 47:4165-4167.

Jing et al. (2002) "Potassium-Dependent Folding: A Key to Intracellular Delivery of G-Quartet Oligonucleotides as HIV Inhibitors," *Biochemistry* 41:5397-5403.

Katzman et al. (1999) "Substrate Recognition by Retroviral Integrases," *Advances in Virus Research* 52:371-395.

Khamnei et al. (1996) "Neighboring Group Catalysis in the Design of Nucleotide Prodrugs," *J. Med. Chem.* 39:4109-4115.

Lafemina et al. (1992) "Requirement of Active Human Immunodeficiency Virus-Type 1 Integrase Enzyme for Productive Infection of Human T-Lymphoid Cells," *Journal of Virology* 66(12):7414-7419.

Le Bas et al. (2001) "Oxidation of 2-and 3-Halogenated Quinolines: An Easy Access to 5- and 6-Halogenopyridine-2,3-dicarboxylic Acids," *Synthesis* 16:2495-2499.

Lochmuller, C. (1975) "Chromatographic Resolution of Enantiomers Selective Review," *Journal of Chromatography* 113:283-302.

Mikhailopulo et al. (2000) "Pyrophosphoryl, Derivatives of 1-(2-Deoxy-3-O Phosphonomethyl -β-and -α-D-erythro-Pentofuranosyl)Thymine: Synthesis and Substrate Properties Towards Some DNA Polymerases," *Nucleosides, Nucleotides & Nucleic Acids* 19(10-12):1885-1909.

Mitchell et al. (1992) "Bioreversible Protection for the Phospho Group: Bioactivation of the Di-(4-acyloxybenzyl) and Mono(4-acyloxybenzyl) Phosphoesters of Methylphosphonate and Phosphonoacetate," *J. Chem. Soc. Perkin Trans. I* 2345-2353.

Morgan et al. (1994) "Structure-Based Design of an Inhibitor of the Zinc Peptidase Thermolysin," *J. Am. Chem. Soc.* 116:3251-3260.

Musiol et al. (1994) "On the Synthesis of Phosphonamidate Peptides," *J. Org. Chem.* 59:6144-6146.

Nair, V. (2002) "HIV Integrase as a Target for Antiviral Chemotherapy," *Rev. Med. Virol.* 12:179-193.

Okamoto et al. (1990) "Optical Resolution of Dihydropyridine Enantiomers by High-Perfomance Liquid Chromatography Using Phenylcarbamates of Polysaccharides as a Chiral Stationary Phase," *Journal of Chromatography* 513:375-378.

Pais et al. (2002) "Structure Activity of 3-Aryl-1-1,3-diketo-Containing Compounds as HIV-1 Integrase Inhibitors," *J. Med. Chem* 45:3184-3194.

Palella et al. (1998) "Declining Morbidity and Mortality Among Patients with Advanced Human Immunodeficiency Virus Infection," *The New England Journal of Medicine* 338(13):853-860.

Pommier et al. (1999) Inhibitors of Human Immunodeficiency Virus Integrase, *Advances in Virus Research* 52:427-459.

Pommier et al. (2000) "Retroviral Integrase Inhibitors Year 2000: Update and Perspectives," *Antiviral Research* 47:139-148.

Puech et al. (1993) "Intracellular Delivery of Nucleoside Monophosphates Through a Reductase-Mediated Activation Process," *Antiviral Research* 22:155-174.

Richman, D. (2001) "HIV Chemotherapy," *Nature* 410:95/1001.

Roach et al. (1987) "Fluorescence Detection of Alkylphosphonic Acids Using p-(9-Anthroyloxy)phenacyl Bromide," *Anal. Chem.* 59:1056-1059.

Rosenberg et al. (1987) "Synthesis of Potential Prodrugs and Metabolites of 9-(S)-(3-Hydroxy-2-Phosphonylmethoxypropyl)Adenine," *Coll Czech Chem Comm* 52:2792-2800.

Serafinowska et al. (1995) "Synthesis and in Vivo Evaluation of Prodrugs of 9-[2-(Phosphonomethoxy)ethoxy]adenine," *J. Med. Chem.* 38:1372-1379.

Skulnick et al. (1995) "Structure-Based Design of Sulfonamide-Substituted Non-Peptidic HIV Protease Inhibitors," *J. Med. Chem.* 38:4968-4971.

Smith et al. (2003) "A Novel MyD-1 (SIRP-1α) Signaling Pathway that Inhibits LPS-Induced TNFα Production by Monocytes," *Blood* 102(7):2532-2540.

Sun et al. (2002) "A General Synthesis of Dioxolenone Prodrug Moieties," *Tetrahedron Letters* 43:1161-1164.

Szabo et al. (1995) "Solid Phase Synthesis of 5'-Methylenephosphonate DNA," *Nucleosides & Nucleotides* 14(3-5):871-874.

Thomson et al. (1993) "Synthesis and Bioactivation of Bis(aroyloxymethyl) and Mono(aroyloxymethyl) Esters of Benzylphosphonate and Phosphonoacetate," *J. Chem. Soc. Perkin Trans I* 2303-2308.

Van Der Laan et al. (1996) "An Approach Towards the Synthesis of Oligomers Containing A N-2-Hydroxyethyl-aminomethylphosphonate Backbone: A Novel PNA Analogue," *Tetrahederon Letters* 37(43):7857-7860.

Wang et al. (2001) "Synthesis of 1-(2-Deoxy-β-D-Ribofuranosyl)-2,4-Difluoro-5-Substituted-Benzene Thymidine Mimics, Some Related α-Anomers, and Their Evaluation as Antiviral and Anticancer Agents," *Nucleosides, Nucleotides & Nucleic Acids* 20(1&2):11-40.

Wolfe et al. (1996) "The Role of Manganese in Promoting Multimerization and Assembly of Human Immunodeficiency Virus Type I Integrase as a Catalytically Active Complex on Immobilized Long Terminal Repeat Substrates," *Journal of Virology* 70(3):1424-1432.

Zhang et al. (2001) "Novel Synthesis of [33P]-(2-Chloroethyl)phosphonic Acid," *J. Org. Chem.* 66:327-329.

\* cited by examiner

INTEGRASE INHIBITORS

FIELD OF THE INVENTION

The invention relates generally to compounds having antiviral activity, and more specifically, compounds having HIV-integrase inhibitory properties.

BACKGROUND OF THE INVENTION

Human immunodeficiency virus (HIV) infection and related diseases are a major public health problem worldwide. A virally encoded integrase protein mediates specific incorporation and integration of viral DNA into the host genome. Integration is necessary for viral replication. Accordingly, inhibition of HIV integrase is an important therapeutic pursuit for treatment of HIV infection of the related diseases.

Human immunodeficiency virus type 1 (HIV-1) encodes three enzymes which are required for viral replication: reverse transcriptase, protease, and integrase. Although drugs targeting reverse transcriptase and protease are in wide use and have shown effectiveness, particularly when employed in combination, toxicity and development of resistant strains have limited their usefulness (Palella, et al *N. Engl. J. Med.* (1998) 338:853-860; Richman, D. D. *Nature* (2001) 410:995-1001). There is a need for new agents directed against alternate sites in the viral life cycle. Integrase has emerged as an attractive target, because it is necessary for stable infection and homologous enzymes are lacking in the human host (LaFemina, et al *J. Virol.* (1992) 66:7414-7419). The function of integrase is to catalyze integration of proviral DNA, resulting from the reverse transcription of viral RNA, into the host genome, by a stepwise fashion of endonucleolytic processing of proviral DNA within a cytoplasmic preintegration complex (termed 3'-processing or "3'-P") with specific DNA sequences at the end of the HIV-1 long terminal repeat (LTR) regions, followed by translocation of the complex into the nuclear compartment where integration of 3'-processed proviral DNA into host DNA occurs in a "strand transfer" (ST) reaction (Hazuda, et al *Science* (2000) 287:646-650; Katzman, et al *Adv. Virus Res.* (1999) 52:371-395; Asante-Applah, et al *Adv. Virus Res.* (1999) 52:351-369). Although numerous agents potently inhibit 3'-P and ST in extracellular assays that employ recombinant integrase and viral long-terminal-repeat oligonucleotide sequences, often such inhibitors lack inhibitory potency when assayed using fully assembled preintegration complexes or fail to show antiviral effects against HIV-infected cells (Pommier, et al *Adv. Virus Res.* (1999) 52:427-458; Farnet, et al *Proc. Natl. Acad. Sci. U.S.A.* (1996) 93:9742-9747; Pommier, et al *Antiviral Res.* (2000) 47:139-148).

HIV integrase inhibitory compounds with improved antiviral and pharmacokinetic properties are desirable, including enhanced activity against development of HIV resistance, improved oral bioavailability, greater potency and extended effective half-life in vivo (Nair, V. "HIV integrase as a target for antiviral chemotherapy" *Reviews in Medical Virology* (2002) 12(3):179-193). Three-dimensional quantitative structure-activity relationship studies and docking simulations (Buolamwini, et al *Jour. Med. Chem.* (2002) 45:841-852) of conformationally-restrained cinnamoyl-type integrase inhibitors (Artico, et al *Jour. Med. Chem.* (1998) 41:3948-3960) have correlated hydrogen-bonding interactions to the inhibitory activity differences among the compounds.

Certain HIV integrase inhibitors have been disclosed which seek to block integration in extracellular assays and exhibit antiviral effects against HIV-infected cells (Anthony, et al WO 02/30426; Anthony, et al WO 02/30930; Anthony, et al WO 02/30931; WO 02/055079; Zhuang, et al WO 02/36734; U.S. Pat. No. 6,395,743; U.S. Pat. No. 6,245,806; U.S. Pat. No. 6,271,402; Fujishita, et al WO 00/039086; Uenaka et al WO 00/075122; Selnick, et al WO 99/62513; Young, et al WO 99/62520; Payne, et al WO 01/00578; Jing, et al *Biochemistry* (2002) 41:5397-5403; Pais, et al *J. Med. Chem.* (2002) 45:3184-94; Goldgur, et al *Proc. Natl. Acad. Sci. U.S.A.* (1999) 96:13040-13043; Espeseth, et al *Proc. Natl. Acad. Sci. U.S.A.* (2000) 97:11244-11249). Recent HIV integrase inhibitors are shown in WO 2005/016927, WO 2004/096807, WO 2004/035577, WO 2004/035576 and US 2003/0055071.

There exists a need to find additional compounds for the treatment of HIV, particularly, improved integrase inhibitors having beneficial properties and good efficacy.

SUMMARY OF THE INVENTION

One aspect the invention provides a compound of formula (I):

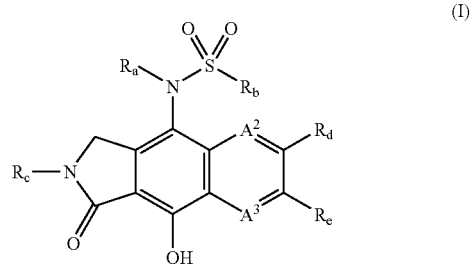

wherein:
$A^2$ and $A^3$ are each independently N or $CR_a$;
each $R_a$ is independently H or $C_1$-$C_4$ alkyl;
$R_b$ is H or $C_1$-$C_4$ alkyl;
$R_c$ is H, $R_k$, -M-$R_m$, or -Q-$R_n$;
$R_d$ is H, halo, or $C_1$-$C_4$ alkyl that is optionally substituted with Rj;
$R_e$ is H, halo, or $C_1$-$C_4$ alkyl that is optionally substituted with Rj;
$R_f$ is H or $C_1$-$C_4$ alkyl;
M is branched $C_2$-$C_4$ alkylene;
Q is $C_1$-$C_4$ alkylene;
each $R_j$ is phenyl, optionally substituted with one or more F, Cl, Br, I, hydroxy, cyano, trifluoromethyl, trifluoromethoxy, or $C_1$-$C_4$ alkyl;
$R_k$ is —$SO_2R_r$, $C_1$-$C_6$ alkyl, $C_2$-$C_6$ alkenyl, or $C_2$-$C_6$ alkynyl, each of which is optionally substituted with one or more halo, hydroxy, carboxy, $C_1$-$C_6$ alkoxy, dimethylamino, diethylamino, N-ethyl-N-methylamino, morpholino, thiomorpholino, piperidino, —C(=O)$NR_{aa}R_{ab}$, —N($R_{aa}$)$SO_2R_{ab}$, —$SO_2R_{ab}$, $C_1$-$C_6$ alkanoyl, $C_3$-$C_6$ carbocycle, pyrrolidino, 2-oxopyrrolidino, or piperazino;
$R_m$ is phenyl optionally substituted with one or more F, Cl, Br, I, hydroxy, cyano, trifluoromethyl, trifluoromethoxy, or $C_1$-$C_4$ alkyl; and
$R_n$ is a 5- or 6-membered heteroaryl ring optionally substituted with one or more F, Cl, Br, I, hydroxy, cyano, trifluoromethyl, trifluoromethoxy, or $C_1$-$C_4$ alkyl; or $R_n$ is a phenyl ring substituted with at least one group selected from hydroxy, trifluoromethyl, $R_rSO_2NH$—, or $R_rC(=O)NH$—, and optionally substituted with one or more F, Cl, Br, I, hydroxy, cyano, trifluoromethyl, trifluoromethoxy, or $C_1$-$C_4$ alkyl; or $R_n$ is a $C_3$-$C_6$ carbocycle;

each $R_{aa}$ and $R_{ab}$ is independently H or $C_1$-$C_6$ alkyl;

or a pharmaceutically acceptable salt or prodrug thereof.

In another aspect the invention provides a compound of the invention which is a compound of formula (II):

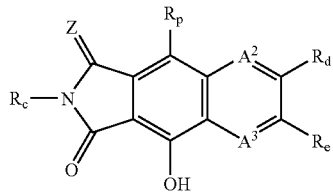

(II)

wherein:

$A^2$ and $A^3$ are each independently N or $CR_a$;

each $R_a$ is independently H or $C_1$-$C_4$ alkyl;

$R_c$ is H, $R_k$, or -Q-$R_n$;

$R_d$ is H, halo, or $C_1$-$C_4$ alkyl that is optionally substituted with Rj;

$R_e$ is H, halo, or $C_1$-$C_4$ alkyl that is optionally substituted with Rj;

Q is $C_1$-$C_4$ alkylene;

Z is O or two hydrogens;

each $R_j$ is phenyl, optionally substituted with one or more F, Cl, Br, I, hydroxy, cyano, trifluoromethyl, trifluoromethoxy, or $C_1$-$C_4$ alkyl;

$R_k$ is $C_1$-$C_6$ alkyl, $C_2$-$C_6$ alkenyl, or $C_2$-$C_6$ alkynyl, each of which is optionally substituted with one or more halo, hydroxy, $C_1$-$C_6$ alkoxy, dimethylamino, diethylamino, N-ethyl-N-methylamino, morpholino, thiomorpholino, piperidino, or piperazino;

$R_n$ is a $C_3$-$C_6$ carbocycle, a phenyl ring, or a 5- or 6-membered heteroaryl ring, which phenyl ring or 5- or 6-membered heteroaryl ring is optionally substituted with one or more F, Cl, Br, I, hydroxy, cyano, trifluoromethyl, trifluoromethoxy, or $C_1$-$C_4$ alkyl;

$R_p$ is OH, $C_1$-$C_4$ alkyl, $C_1$-$C_4$ alkanoyl, $C_1$-$C_4$ alkoxy, $C_2$-$C_6$ alkenyl, $C_2$-$C_6$ alkynyl, —C(=O)$NR_xR_x$, —C(=$NR_{ak}$)$R_{am}$, $NH_2$, —N($R_a$)—C(=O)$NR_xR_x$, 4,5-dihydro-4,4-dimethyloxazole, or —N($R_s$)—S(O)$_2$—$R_t$, wherein each $C_1$-$C_4$ alkyl of $R_p$ is substituted with —C(=O)$NR_xR_x$, —N($R_{ag}$)—C(=O)—$R_{ah}$, or —N($R_{ag}$)—S(O)$_2$—$R_{ah}$; and wherein each $C_1$-$C_4$ alkoxy, $C_2$-$C_6$ alkenyl and $C_2$-$C_6$ alkynyl of $R_p$ is optionally substituted with phenyl, hydroxy, $C_3$-$C_6$ carbocycle or —C(=O)$NR_xR_x$;

$R_s$ is —S(O)$_2$—$R_w$, and $R_t$ is $C_1$-$C_4$ alkyl optionally substituted with $R_v$; or $R_s$ is $C_1$-$C_4$ alkyl substituted with $R_u$, and $R_t$ is $C_1$-$C_4$ alkyl optionally substituted with $R_v$; or $R_s$ is $C_1$-$C_4$ alkyl optionally substituted with $R_u$, and $R_t$ is $R_z$, $NR_xR_x$, or $C_1$-$C_4$ alkyl substituted with $R_v$;

each $R_v$ is fluoro, chloro, phenyl, pyridyl, 1,4 diazepanyl, or piperazino, wherein each phenyl, pyridyl, 1,4-diazepanyl, and piperazino is optionally substituted with one or more fluoro, chloro, bromo, iodo, $C_1$-$C_4$ alkyl, $C_1$-$C_4$ alkyl-C(=O)—, $C_1$-$C_4$ alkyl-S(O)$_2$—, —C(=O)$NR_aR_a$, or —C(=O)$OR_a$;

each $R_u$ is independently dimethylamino, diethylamino, N-ethyl-N-methylamino, or a ring selected from $C_3$-$C_6$ carbocycle, pyrrolidino, morpholino, thiomorpholino, piperidino, and piperazino, which ring is optionally substituted with one or more $C_1$-$C_4$ alkyl; and $R_w$ is $C_1$-$C_4$ alkyl;

each $R_x$ is independently H, $C_1$-$C_4$ alkyl, $C_3$-$C_6$ carbocycle, or $C_1$-$C_4$ alkyl-$R_y$; or $NR_xR_x$ taken together form a piperidino, morpholino, azetidino, pyrrolidino, or piperazino ring, which ring is optionally substituted with one or more $C_1$-$C_4$ alkyl or halo;

each $R_y$ is independently cyano, phenyl or pyridyl, wherein each phenyl or pyridyl is optionally substituted with one or more fluoro, chloro, bromo, iodo, $C_1$-$C_4$ alkyl, $C_1$-$C_4$ alkyl-C(=O)—, $C_1$-$C_4$ alkyl-S(O)$_2$—, —C(=O)$NR_aR_a$, or —C(=O)$OR_a$;

$R_z$ is phenyl which is optionally substituted with one or more fluoro, chloro, bromo, iodo, $C_1$-$C_4$ alkyl, $C_1$-$C_4$ alkyl-C(=O)—, $C_1$-$C_4$ alkyl-S(O)$_2$—, —C(=O)$NR_aR_a$, or —C(=O)$OR_a$;

each $R_{ag}$ and $R_{ah}$ is independently H or $C_1$-$C_4$ alkyl;

each $R_{ak}$ is hydroxy, $C_1$-$C_4$ alkoxy, or $NR_{am}R_{an}$;

each $R_{ah}$ is independently H or $C_1$-$C_4$ alkyl;

each $R_{am}$ and $R_{an}$ is independently H or $C_1$-$C_4$ alkyl;

or a pharmaceutically acceptable salt or prodrug thereof.

In another aspect the invention provides a compound of the invention which is a compound of formula (III):

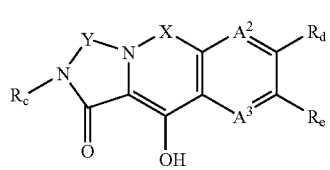

(III)

wherein:

$A^2$ and $A^3$ are each independently N or $CR_g$; wherein each $R_g$ is independently H or alkyl;

$R_c$ is H, $R_k$, or -L-Ar $R_d$ is H, halo, or $C_1$-$C_4$ alkyl that is optionally substituted with Rj;

$R_e$ is H, halo, or $C_1$-$C_4$ alkyl that is optionally substituted with Rj;

L is $C_1$-$C_4$ alkylene;

$R_k$ is $C_1$-$C_6$ alkyl, $C_2$-$C_6$ alkenyl, or $C_2$-$C_6$ alkynyl, each of which is optionally substituted with one or more halo, hydroxy, $C_1$-$C_6$ alkoxy, dimethylamino, diethylamino, N-ethyl-N-methylamino, morpholino, thiomorpholino, piperidino, or piperazino;

X is —C(=O)— or —S(O)$_2$—;

Y is —CH$_2$—, or —CH$_2$—CH$_2$—;

Ar is a $C_3$-$C_{12}$ carbocycle, a substituted $C_3$-$C_{12}$ carbocycle, $C_6$-$C_{20}$ aryl, substituted $C_6$-$C_{20}$ aryl, $C_6$-$C_{20}$ heteroaryl, substituted $C_6$-$C_{20}$ heteroaryl;

each $R_j$ is phenyl, optionally substituted with one or more F, Cl, Br, I, hydroxy, cyano, trifluoromethyl, trifluoromethoxy, or $C_1$-$C_4$ alkyl;

or a pharmaceutically acceptable salt or prodrug thereof.

In another aspect the invention provides a compound of the invention which is a compound of formula (II):

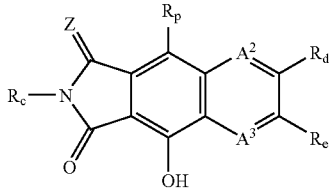

wherein:
A² and A³ are each independently N or $CR_a$;
each $R_a$ is independently H or $C_1$-$C_4$ alkyl;
$R_c$ is H, $R_k$, or -Q-$R_n$;
$R_d$ is $C_1$-$C_4$ alkyl that is substituted with Rj;
$R_e$ is H, halo, or $C_1$-$C_4$ alkyl that is optionally substituted with Rj;
Q is $C_1$-$C_4$ alkylene;
Z is O or two hydrogens;
each $R_j$ is phenyl, optionally substituted with one or more F, Cl, Br, I, hydroxy, cyano, trifluoromethyl, trifluoromethoxy, or $C_1$-$C_4$ alkyl;
$R_k$ is $C_1$-$C_6$ alkyl, $C_2$-$C_6$ alkenyl, or $C_2$-$C_6$ alkynyl, each of which is optionally substituted with one or more halo, hydroxy, $C_1$-$C_6$ alkoxy, dimethylamino, diethylamino, N-ethyl-N-methylamino, morpholino, thiormorpholino, piperidino, or piperazino;
$R_n$ is a $C_3$-$C_6$ carbocycle, a phenyl ring, or a 5- or 6-membered heteroaryl ring, which phenyl ring or 5- or 6-membered heteroaryl ring is optionally substituted with one or more F, Cl, Br, I, hydroxy, cyano, trifluoromethyl, trifluoromethoxy, —C(=O)$NR_{ac}R_{ad}$, or $C_1$-$C_4$ alkyl;
$R_p$ is —N($R_{ae}$)—S(O)$_2$—$R_{af}$;
$R_w$ is $C_1$-$C_4$ alkyl;
each $R_x$ is independently H, $C_1$-$C_4$ alkyl, or $C_1$-$C_4$ alkyl-$R_y$; or $NR_xR_x$ taken together form a piperidino or piperazino ring, which ring is optionally substituted with one or more $C_1$-$C_4$ alkyl;
each $R_y$ is independently phenyl or pyridyl, wherein each phenyl or pyridyl is optionally substituted with one or more fluoro, chloro, bromo, iodo, $C_1$-$C_4$ alkyl, $C_1$-$C_4$ alkyl-C(=O)—, $C_1$-$C_4$ alkyl-S(O)$_2$—, —C(=O)$NR_aR_a$, or —C(=O)$OR_a$;
$R_z$ is phenyl which is optionally substituted with one or more fluoro, chloro, bromo, iodo, $C_1$-$C_4$ alkyl, $C_1$-$C_4$ alkyl-C(=O)—, $C_1$-$C_4$ alkyl-S(O)$_2$—, —C(=O)$NR_aR_a$, or —C(=O)$OR_a$;
each $R_{ac}$ and $R_{ad}$ is independently H or $C_1$-$C_6$ alkyl;
each $R_{ae}$ and $R_{af}$ is independently H or $C_1$-$C_6$ alkyl;
or a pharmaceutically acceptable salt or prodrug thereof.

In another aspect the invention provides a compound of the invention which is a compound of formula (II):

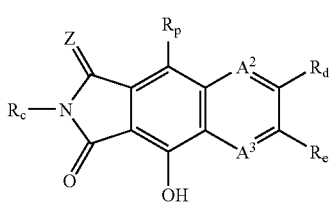

wherein:
A² and A³ are each independently N or $CR_a$;
each $R_a$ is independently H or $C_1$-$C_4$ alkyl;
$R_c$ is H, $R_k$, or -Q-$R_n$;
$R_d$ is $C_1$-$C_4$ alkyl that is substituted with Rj;
$R_e$ is H, halo, or $C_1$-$C_4$ alkyl that is optionally substituted with Rj;
Q is $C_1$-$C_4$ alkylene;
Z is O or two hydrogens;
each $R_j$ is phenyl, optionally substituted with one or more F, Cl, Br, I, hydroxy, cyano, trifluoromethyl, trifluoromethoxy, or $C_1$-$C_4$ alkyl;
$R_k$ is $C_1$-$C_6$ alkyl, $C_2$-$C_6$ alkenyl, or $C_2$-$C_6$ alkynyl, each of which is optionally substituted with one or more halo, hydroxy, $C_1$-$C_6$ alkoxy, dimethylamino, diethylamino, N-ethyl-N-methylamino, morpholino, thiomorpholino, piperidino, or piperazino;
$R_n$ is a $C_3$-$C_6$ carbocycle, a phenyl ring, or a 5- or 6-membered heteroaryl ring, which phenyl ring or 5- or 6-membered heteroaryl ring is optionally substituted with one or more F, Cl, Br, I, hydroxy, cyano, trifluoromethyl, trifluoromethoxy, $C_1$-$C_4$ alkoxy, —C(=O)$NR_{ac}R_{ad}$, or $C_1$-$C_4$ alkyl;
$R_p$ is H, $NH_2$, —C(=O)$NR_xR_x$, $C_1$-$C_4$ alkyl, pyridyl, 1,3,4-oxadiazole, 5-methyl-1,3,4-oxadiazole, or phenyl that is optionally substituted with one or more F, Cl, CN, hydroxy, or trifluoromethyl, wherein any $C_1$-$C_4$ alkyl of $R_p$ is optionally substituted with one or more hydroxy, cyano, —C(=O)$NR_xR_x$, or —$NR_{ar}R_{as}$;
$R_w$ is $C_1$-$C_4$ alkyl;
each $R_x$ is independently H, $C_1$-$C_4$ alkyl, $C_3$-$C_6$ carbocycle, or $C_1$-$C_4$ alkyl-$R_y$; or $NR_xR_x$ taken together form a piperidino, morpholino, azetidino, pyrrolidino, or piperazino ring, which ring is optionally substituted with one or more $C_1$-$C_4$ alkyl or halo;
each $R_y$ is independently cyano, trifluoromethyl, hydroxy, $C_1$-$C_4$ alkoxy, phenyl or pyridyl, wherein each phenyl or pyridyl is optionally substituted with one or more fluoro, chloro, bromo, iodo, $C_1$-$C_4$ alkyl, $C_1$-$C_4$ alkyl-C(=O)—, $C_1$-$C_4$ alkyl-S(O)$_2$—, —C(=O)$NR_aR_a$, or —C(=O)$OR_a$;
$R_z$ is phenyl which is optionally substituted with one or more fluoro, chloro, bromo, iodo, $C_1$-$C_4$ alkyl, $C_1$-$C_4$ alkyl-C(=O)—, $C_1$-$C_4$ alkyl-S(O)$_2$—, —C(=O)$NR_aR_a$, or —C(=O)$OR_a$;
each $R_{ac}$ and $R_{ad}$ is independently H or $C_1$-$C_6$ alkyl;
each $R_{ae}$ and $R_{af}$ is independently H or $C_1$-$C_6$ alkyl;
each $R_{ar}$ and $R_{as}$ is independently H, $C_1$-$C_6$ alkyl, or $C_1$-$C_6$ alkanoyl;
or a pharmaceutically acceptable salt or prodrug thereof.

The invention also includes a pharmaceutical composition comprising a therapeutically effective amount of a compound of the invention, or a pharmaceutically acceptable salt thereof, in combination with a pharmaceutically acceptable diluent, excipient or carrier.

The invention also includes a pharmaceutical composition comprising a therapeutically effective amount of a compound of the invention, or a pharmaceutically acceptable salt thereof, in combination with a booster agent and/or a therapeutically effective amount of one or more of the following agents: another compound of the invention, an AIDS treatment agent, such as an HIV inhibitor agent, an anti-infective agent or an immunomodulator agent. The HIV inhibitor agent may include an HIV-protease inhibitor, a nucleoside reverse transcriptase inhibitor, a non-nucleoside reverse transcriptase inhibitor or a mixture thereof.

The invention also includes methods of treating (for example, preventing, mediating, inhibiting, etc.) the proliferation of HIV virus, treating AIDS, delaying the onset of AIDS or ARC symptoms and generally inhibiting HIV integrase. The methods comprise administering to a mammal in need of such treatment an effective amount of a compound of the invention (e.g. an amount effective to inhibit the growth of HIV infected cells of the mammal).

In another aspect of the invention, the activity of HIV integrase is inhibited by a method comprising the step of treating a mammal or sample suspected of containing HIV virus with a compound or composition of the invention.

The invention also includes processes and novel intermediates which are useful for preparing compounds of the invention. Some of the compounds of the invention are useful to prepare other compounds of the invention.

This invention also includes a method of increasing cellular accumulation, bioavailability or retention of drug compounds, thus improving their therapeutic and diagnostic value, by administering a phosphonate prodrug form of a compound of the invention.

In other aspects, methods for the synthesis, analysis, separation, isolation, crystallization, purification, characterization, resolution of isomers (including enantiomers and diastereomers) and testing of the compounds of the invention are provided.

The invention, in part, provides compounds possessing improved anti-HIV and/or pharmaceutical properties.

DEFINITIONS

Unless stated otherwise, the following terms and phrases as used herein are intended to have the following meanings:

The terms "phosphonate" and "phosphonate group" mean a functional group or moiety within a molecule that comprises at least one phosphorus-carbon bond, and at least one phosphorus-oxygen double bond. The phosphorus atom is further substituted with oxygen, sulfur, and nitrogen substituents. These substituents may be part of a prodrug moiety. As defined herein, "phosphonate" and "phosphonate group" include molecules with phosphonic acid, phosphonic monoester, phosphonic diester, phosphonamidate, phosphondiamidate, and phosphonthioate functional groups.

The term "prodrug" as used herein refers to any compound that when administered to a biological system generates the drug substance, i.e. active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically-active compound.

"Pharmaceutically acceptable prodrug" refers to a compound that is metabolized in the host, for example hydrolyzed or oxidized, by either enzymatic action or by general acid or base solvolysis, to form an active ingredient. Typical examples of prodrugs of the compounds of the invention have biologically labile protecting groups on a functional moiety of the compound. Prodrugs include compounds that can be oxidized, reduced, aminated, deaminated, esterified, deesterified, alkylated, dealkylated, acylated, deacylated, phosphorylated, dephosphorylated, photolyzed, hydrolyzed, or other functional group change or conversion involving forming or breaking chemical bonds on the prodrug.

"Prodrug moiety" means a labile functional group which separates from the active inhibitory compound during metabolism, systemically, inside a cell, by hydrolysis, enzymatic cleavage, or by some other process (Bundgaard, H., "Design and Application of Prodrugs" in Textbook of Drug Design and Development (1991), P. Krogsgaard-Larsen and H. Bundgaard, Eds. Harwood Academic Publishers, pp. 113-191). Enzymes which are capable of an enzymatic activation mechanism with the prodrug compounds of the invention include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy. A "prodrug" is thus a covalently modified analog of a therapeutically-active compound.

Exemplary prodrug moieties include the hydrolytically sensitive or labile acyloxymethyl esters —$CH_2C(=O)R^{20}$ and acyloxymethyl carbonates —$CH_2C(=O)OR^{20}$ where $R^{20}$ is $C_1$-$C_6$ alkyl, $C_1$-$C_6$ substituted alkyl, $C_6$-$C_{20}$ aryl or $C_6$-$C_{20}$ substituted aryl. The acyloxyalkyl ester was first used as a prodrug strategy for carboxylic acids and then applied to phosphates and phosphonates by Farquhar et al., (1983) J. Pharm. Sci. 72: 324; also U.S. Pat. Nos. 4,816,570, 4,968,788, 5,663,159 and 5,792,756, which are all incorporated by reference. In certain compounds of the invention, a prodrug moiety is part of a phosphonate group. Subsequently, the acyloxyalkyl ester was used to deliver phosphonic acids across cell membranes and to enhance oral bioavailability. A close variant of the acyloxyalkyl ester, the alkoxycarbonyloxyalkyl ester (carbonate), may also enhance oral bioavailability as a prodrug moiety in the compounds of the invention. An exemplary acyloxymethyl ester is pivaloyloxymethoxy, (POM)-$CH_2C(=O)C(CH_3)_3$. An exemplary acyloxymethyl carbonate prodrug moiety is pivaloyloxymethylcarbonate (POC) —$CH_2C(=O)OC(CH_3)_3$.

The phosphonate group may be a phosphonate prodrug moiety. The prodrug moiety may be sensitive to hydrolysis, such as, but not limited to a pivaloyloxymethyl carbonate (POC) or POM group. Alternatively, the prodrug moiety may be sensitive to enzymatic potentiated cleavage, such as a lactate ester or a phosphonamidate-ester group. Exemplary phosphonate prodrug moieties include by way of example and not limitation groups of the structure $A^5$ as described herein.

Aryl esters of phosphorus groups, especially phenyl esters, are reported to enhance oral bioavailability (DeLambert et al (1994) J. Med. Chem. 37: 498). Phenyl esters containing a carboxylic ester ortho to the phosphate have also been described (Khamnei and Torrence, (1996) J. Med. Chem. 39:4109-4115). Benzyl esters are reported to generate the parent phosphonic acid. In some cases, substituents at the ortho- or para-position may accelerate the hydrolysis. Benzyl analogs with an acylated phenol or an alkylated phenol may generate the phenolic compound through the action of enzymes, e.g. esterases, oxidases, etc., which in turn undergoes cleavage at the benzylic C—O bond to generate the phosphoric acid and the quinone methide intermediate. Examples of this class of prodrugs are described by Mitchell et al., (1992) J. Chem. Soc. Perkin Trans. I 2345; Brook et al., WO 91/19721. Still other benzylic prodrugs have been described containing a carboxylic ester-containing group attached to the benzylic methylene (Glazier et al., WO 91/19721). Thio-containing prodrugs are reported to be useful for the intracellular delivery of phosphonate drugs. These proesters contain an ethylthio group in which the thiol group is either esterified with an acyl group or combined with another thiol group to form a disulfide. Deesterification or reduction of the disulfide generates the free thio intermediate which subsequently breaks down to the phosphoric acid and episulfide (Puech et al., (1993) Antiviral Res., 22: 155-174; Benzaria et al., (1996) J. Med. Chem. 39: 4958). Cyclic phosphonate esters have also been described as prodrugs of phosphorus-containing compounds (Erion et al., U.S. Pat. No. 6,312,662).

"Protecting group" refers to a moiety of a compound that masks or alters the properties of a functional group or the properties of the compound as a whole. The chemical substructure of a protecting group varies widely. One function of a protecting group is to serve as intermediates in the synthesis of the parental drug substance. Chemical protecting groups and strategies for protection/deprotection are well known in the art. See: "Protective Groups in Organic Chemistry", Theodora W. Greene (John Wiley & Sons, Inc., New York, 1991, which is incorporated herein by reference. Protecting groups are often utilized to mask the reactivity of certain functional groups, to assist in the efficiency of desired chemical reactions, e.g. making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

The term "hydroxyl protecting group," as used herein, refers to an easily removable group which is known in the art to protect a hydroxyl group against undesirable reaction during synthetic procedures and/or during biodelivery and which group can be selectively removed. The use of hydroxy-protecting groups is well known in the art for protecting groups and many such protecting groups are known, for example, T. H. Greene and P. G. M. Wuts, Protective Groups in Organic Synthesis, 2nd edition, John Wiley & Sons, New York (1991). Examples of hydroxy-protecting groups include, but are not limited to, Ethers (methyl);

Substituted methyl ethers (methoxymethyl, methylthiomethyl, t-butylthiomethyl, (phenyldimethylsilyl)methoxymethyl, benzyloxymethyl, p-methoxybenzyloxymethyl, (4-methoxyphenoxy)methyl, guaiacolmethyl, t-butoxymethyl, 4-pentenyloxymethyl, siloxymethyl, 2-methoxyethoxymethyl, 2,2,2-trichloroethoxymethyl, bis(2-chloroethoxy)methyl, 2-(trimethylsilyl)ethoxymethyl, tetrahydropyranyl, 3-bromotetrahydropyranyl, tetrahydrothiopyranyl, 1-methoxycyclohexyl, 4-methoxytetrahydropyranyl, 4-methoxytetrahydro-thiopyranyl, 4-methoxytetrahydropthiopyranyl S,S-dioxido, 1->(2-chloro-4-methyl)phenyl-4-methoxypiperidin-4-yl, 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl));

Substituted ethyl ethers (1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl);

Substituted benzyl ethers (p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxy)phenyldiphenylmethyl, 4,4',4"-tris(4,5-dichlorophthalimidophenyl)methyl, 4,4',4"-tris(levulinoyloxyphenyl)-methyl, 4,4',4"-tris(benzoyloxyphenyl)methyl, 3-(imidazol-1-ylmethyl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-Dioxido);

Silyl ethers (trimethylsilyl, triethylsilyl, triisopropylsilyl, dimethylisopropylsilyl, diethylisopropylsily, dimethylthexylsilyl, t-butyldimethyl-silyl, t-butyldiphenylsilyl, tribenzylsilyl, tri-p-xylylsilyl, triphenylsilyl, diphenylmethylsilyl, t-butylmethoxyphenylsilyl);

Esters (formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, p-poly-phenylacetate, 3-phenyl-propionate, 4-oxopentanoate (Levulinate), 4,4-(ethylenedithio) pentanoate, pivaloate, adamantoate, crotonate, 4-methoxycrotonate, benzoate, p-phenyl-benzoate, 2,4,6-trimethylbenzoate (Mesitoate));

Carbonates (methyl, 9-fluorenylmethyl, ethyl, 2,2,2-trichloroethyl, 2-(trimethylsilyl)ethyl, 2-(phenylsulfonyl) ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, methyl dithiocarbonate);

Groups with assisted cleavage (2-iodobenzoate, 4-azidobutyrate, 4-nitro-4-methylpentanoate, o-(dibromomethyl) benzoate, 2-formylbenzenesulfonate, 2-(methylthiomethoxy)ethyl carbonate, 4-(methylthiomethoxy)butyrate, 2-(methylthiomethoxymethyl)benzoate);

Miscellaneous Esters (2,6-dichloro-4-methylphenoxyacetate, 2,6-dichloro-4-(1,1,3,3-tetramethylbutyl)phenoxyacetate, 2,4-bis(1,1-dimethylpropyl)-phenoxyacetate, chlorodiphenylacetate, isobutyrate, monosuccinoate, (E)-2-methyl-2-butenoate (Tigloate), o-(methoxycarbonyl) benzoate, p-poly-benzoate, α-naphthoate, nitrate, alkyl N,N,N',N'-tetramethylphosphorodiamidate, N-phenylcarbamate, borate, dimethylphosphinothioyl, 2,4-dinitrophenylsulfenate); and Sulfonates (sulfate, methanesulfonate (Mesylate), benzylsulfonate, Tosylate).

More typically, hydroxy protecting groups include substituted methyl ethers, substituted benzyl ethers, silyl ethers, and esters including sulfonic acid esters, still more typically, trialkylsilyl ethers, tosylates and acetates.

The term "amino protecting group," as used herein, refers to an easily removable group which is known in the art to protect an amino group against undesired reaction during synthetic procedures and/or during biodelivery and which group can be selectively removed. Such protecting groups are described by Greene at pages 315-385. They include:

Carbamates (methyl and ethyl, 9-fluorenylmethyl, 9(2-sulfo)fluoroenyl-methyl, 9-(2,7-dibromo)fluorenylmethyl, 2,7-di-t-buthyl-[9-(10,10-dioxo-10,10,10,10-tetrahydrothioxanthyl)]methyl, 4-methoxyphenacyl);

Substituted ethyl (2,2,2-trichoroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl) ethyl, 1-(3,5-di-t-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chorobenzyl, 2,4-dichlorobenzyl, 4-methylsulfinylbenzyl, 9-anthrylmethyl, diphenylmethyl);

Groups With Assisted Cleavage (2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2-cyanoethyl, m-choro-p-acyloxybenzyl, p-(dihydroxyboryl)benzyl, 5-benzisoxazolylmethyl, 2-(trifluoromethyl)-6-chromonylmethyl);

Groups Capable of Photolytic Cleavage (m-nitrophenyl, 3,5-dimethoxybenzyl, o-nitrobenzyl, 3,4-dimethoxy-6-nitrobenzyl, phenyl(o-nitrophenyl)methyl);

Urea-Type Derivatives (phenothiazinyl-(10)-carbonyl, N'-p-toluenesulfonylaminocarbonyl, N'-phenylaminothiocarbonyl);

Miscellaneous Carbamates (t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethyl-carboxamido)benzyl, 1,1-dimethyl-3-(N,N-dimethylcarboxamido) propyl, 1,1-dimethylpropynyl, di(2-pyridyl)methyl, 2-furanylmethyl, 2-Iodoethyl, Isobornyl, Isobutyl, Isonicotinyl, p-(p'-Methoxyphenylazo)benzyl, 1-methylcyclobutyl, 1-methylcyclohexyl, 1-methyl-1-cyclopropylmethyl, 1-methyl-1-(3,5-dimethoxyphenyl)ethyl, 1-methyl-1-(p-phenylazophenyl)ethyl, 1-methyl-1-phenylethyl, 1-methyl-1-(4-pyridyl) ethyl, phenyl, p-(phenylazo)benzyl, 2,4,6-tri-t-butylphenyl, 4-(trimethylammonium)benzyl, 2,4,6-trimethylbenzyl);

Amides (N-formyl, N-acetyl, N-choroacetyl, N-trichoroacetyl, N-trifluoroacetyl, N-phenylacetyl, N-3-phenylpropionyl, N-picolinoyl, N-3-pyridylcarboxamide, N-benzoylphenylalanyl, N-benzoyl, N-p-phenylbenzoyl); Amides With Assisted Cleavage (N-o-nitrophenylacetyl, N-o-nitrophenoxyacetyl, N-acetoacetyl, (N'-dithiobenzyloxycarbonylamino)acetyl, N-3-(p-hydroxyphenyl)propionyl, N-3-(o-nitrophenyl)propionyl, N-2-methyl-2-(o-nitrophenoxy) propionyl, N-2-methyl-2-(o-phenylazophenoxy)propionyl, N-4-chlorobutyryl, N-3-methyl-3-nitrobutyryl, N-o-nitrocinnamoyl, N-acetylmethionine, N-o-nitrobenzoyl, N-o-(benzoyloxymethyl)benzoyl, 4,5-diphenyl-3-oxazolin-2-one);

Cyclic Imide Derivatives (N-phthalimide, N-dithiasuccinoyl, N-2,3-diphenylmaleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl-1,3-5-triazacyclohexan-2-one, 1-substituted 3,5-dinitro-4-pyridonyl);

N-Alkyl and N-Aryl Amines (N-methyl, N-allyl, N-[2-(trimethylsilyl)ethoxy]methyl, N-3-acetoxypropyl, N-(1-isopropyl-4-nitro-2-oxo-3-pyrrolin-3-yl), Quaternary Ammonium Salts, N-benzyl, N-di(4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, N-2-picolylamine N'-oxide), Imine Derivatives (N-1,1-dimethylthiomethylene, N-benzylidene, N-p-methoxybenzylidene, N-diphenylmethylene, N-[(2-pyridyl)mesityl]methylene, N,(N',N'-dimethylaminomethylene, N,N'-isopropylidene, N-p-nitrobenzylidene, N-salicylidene, N-5-chlorosalicylidene, N-(5-chloro-2-hydroxyphenyl)phenyl-methylene, N-cyclohexylidene); Enamine Derivatives (N-(5,5-dimethyl-3-oxo-1-cyclohexenyl));

N-Metal Derivatives (N-borane derivatives, N-diphenylborinic acid derivatives, N-[phenyl(pentacarbonylchromium- or -tungsten)]carbenzyl, N-copper or N-zinc chelate);

N—N Derivatives (N-nitro, N-nitroso, N-oxide); N—P Derivatives (N-diphenylphosphinyl, N-dimethylthiophosphinyl, N-diphenylthiophosphinyl, N-dialkyl phosphoryl, N-dibenzyl phosphoryl, N-diphenyl phosphoryl);

N—Si Derivatives; N—S Derivatives; N-Sulfenyl Derivatives (N-benzenesulfenyl, N-o-nitrobenzenesulfenyl, N-2,4-dinitrobenzenesulfenyl, N-pentachlorobenzenesulfenyl, N-2-nitro-4-methoxybenzenesulfenyl, N-triphenylmethylsulfenyl, N-3-nitropyridinesulfenyl); and N-sulfonyl Derivatives (N-p-toluenesulfonyl, N-benzenesulfonyl, N-2,3,6-trimethyl-4-methoxybenzenesulfonyl, N-2,4,6-trimethoxybenzenesulfonyl, N-2,6-dimethyl-4-methoxybenzenesulfonyl, N-pentamethylbenzenesulfonyl, N-2,3,5,6-tetramethyl-4-methoxybenzenesulfonyl, N-4-methoxybenzenesulfonyl, N-2,4,6-trimethylbenzenesulfonyl, N-2,6-dimethoxy-4-methylbenzenesulfonyl, N-2,2,5,7,8-pentamethylchroman-6-sulfonyl, N-methanesulfonyl, N-.beta.-trimethylsilyl-ethanesulfonyl, N-9-anthracenesulfonyl, N-4-(4',8'-dimethoxynaphthyl-methyl)benzenesulfonyl, N-benzylsulfonyl, N-trifluoromethylsulfonyl, N-phenacylsulfonyl).

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g. alcohols, be physiologically acceptable, although in general it is more desirable if the products are pharmacologically innocuous. Exemplary protecting groups include by way of example and not limitation groups of the structure $R^X$ other than hydrogen.

Examples of physiologically acceptable salts of the compounds of the invention include salts derived from an appropriate base, such as an alkali metal (for example, sodium), an alkaline earth (for example, magnesium), ammonium and $NX_4^+$ (wherein X is $C_1$-$C_4$ alkyl). Physiologically acceptable salts of a hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound having a hydroxy group include the anion of said compound in combination with a suitable cation such as $Na^+$ and $NX_4^+$ (wherein X is independently selected from the group consisting of H and a $C_1$-$C_4$ alkyl group).

For therapeutic use, salts of active ingredients of the compounds of the invention will be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived form a physiologically acceptable acid or base, are within the scope of the present invention.

"Alkyl" is $C_1$-$C_{18}$ hydrocarbon containing normal, secondary, tertiary or cyclic carbon atoms. Examples are methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —CH₂CH₂CH₂CH₂CH₃), 2-pentyl (—CH(CH₃)CH₂CH₂CH₃), 3-pentyl (—CH(CH₂CH₃)₂), 2-methyl-2-butyl (—C(CH₃)₂CH₂CH₃), 3-methyl-2-butyl (—CH(CH₃)CH(CH₃)₂), 3-methyl-1-butyl (—CH₂CH₂CH(CH₃)₂), 2-methyl-1-butyl (—CH₂CH(CH₃)CH₂CH₃), 1-hexyl (—CH₂CH₂CH₂CH₂CH₂CH₃), 2-hexyl (—CH(CH₃)CH₂CH₂CH₂CH₃), 3-hexyl (—CH(CH₂CH₃)(CH₂CH₂CH₃)), 2-methyl-2-pentyl (—C(CH₃)₂CH₂CH₂CH₃), 3-methyl-2-pentyl (—CH(CH₃)CH(CH₃)CH₂CH₃), 4-methyl-2-pentyl (—CH(CH₃)CH₂CH(CH₃)₂), 3-methyl-3-pentyl (—C(CH₃)(CH₂CH₃)₂), 2-methyl-3-pentyl (—CH(CH₂CH₃)CH(CH₃)₂), 2,3-dimethyl-2-butyl (—C(CH₃)₂CH(CH₃)₂), 3,3-dimethyl-2-butyl (—CH(CH₃)C(CH₃)₃.

"Alkenyl" is $C_2$-$C_{18}$ hydrocarbon containing normal, secondary, tertiary or cyclic carbon atoms with at least one site of unsaturation, i.e. a carbon-carbon, $sp^2$ double bond. Examples include, but are not limited to: ethylene or vinyl (—CH═CH₂), allyl (—CH₂CH═CH₂), cyclopentenyl (—C₅H₇), and 5-hexenyl (—CH₂CH₂CH₂CH₂CH═CH₂).

"Alkynyl" is $C_2$-$C_{18}$ hydrocarbon containing normal, secondary, tertiary or cyclic carbon atoms with at least one site of unsaturation, i.e. a carbon-carbon, sp triple bond. Examples include, but are not limited to: acetylenic (—C≡CH) and propargyl (—CH₂C≡CH), The terms "alkylene" and "alkyldiyl" each refer to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to: methylene (—CH₂—), methylmethylene (—C(CH₃)H—) 1,2-ethyl (—CH₂CH₂—), 1,3-propyl (—CH₂CH₂CH₂—), 1,4-butyl (—CH₂CH₂CH₂CH₂—), and the like.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene, i.e. double carbon-carbon bond moiety. Typical alkenylene radicals include, but are not limited to: 1,2-ethylene (—CH═CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne, i.e. triple carbon-carbon bond moiety. Typical alkynylene radicals include, but are not limited to: acetylene (—C≡C—), propargyl (—CH₂C≡C—), and 4-pentynyl (—CH₂CH₂CH₂C≡CH—).

"Aryl" means a monovalent aromatic hydrocarbon radical of 6-20 carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like.

"Heteroaryl" means a monovalent aromatic radical of one or more carbon atoms and one or more atoms selected from the group consisting of N, O, S and P, derived by the removal of one hydrogen atom from a single atom of a parent aromatic ring system. Heteroaryl groups may be a monocycle having 3 to 7 ring members (2 to 6 carbon atoms and 1 to 3 heteroatoms selected from the group consisting of N, O, P and S) or a bicycle having 7 to 10 ring members (4 to 9 carbon atoms and 1 to 3 heteroatoms selected from the group consisting of N, O, P and S). Heteroaryl bicycles have 7 to 10 ring atoms (6 to 9 carbon atoms and 1 to 2 heteroatoms selected from the group consisting of N, O and S) arranged as a bicyclo[4,5], [5,5], [5,6], or [6,6] system; or 9 to 10 ring atoms (8 to 9 carbon atoms and 1 to 2 hetero atoms selected from the group consisting of N and S) arranged as a bicyclo[5,6] or [6,6] system. The heteroaryl group may be bonded to the drug scaffold through a carbon, nitrogen, sulfur, phosphorus or other atom by a stable covalent bond.

Heteroaryl groups include, for example: pyridyl, dihydropyridyl isomers, pyridazinyl, pyrimidinyl, pyrazinyl, s-triazinyl, oxazolyl, imidazolyl, thiazolyl, isoxazolyl, pyrazolyl, isothiazolyl, furanyl, thiofuranyl, thienyl, and pyrrolyl.

"Arylalkyl" refers to an acyclic alkyl radical in which one of the hydrogen atoms bonded to a carbon atom, typically a terminal or $sp^3$ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g. the alkyl moiety, including alkanyl, alkenyl or alkynyl groups, of the arylalkyl group is 1 to 6 carbon atoms and the aryl moiety is 5 to 14 carbon atoms.

Substituted substituents such as "substituted alkyl", "substituted aryl", "substituted heteroaryl", "substituted heterocyclic" and "substituted arylalkyl" mean alkyl, aryl, heteroaryl, heterocyclic and arylalkyl respectively, in which one or more hydrogen atoms are each independently replaced with a substituent. Typical substituents include, but are not limited to, —X, —R, ═O, —O⁻, —OR, —S⁻, —SR, —NR₂, —NR₃, ═NR, —CX₃, —CN, —OCN, —SCN, —N═C═O, —NCS, —NO, —NO₂, ═N₂, —N₃, NC(═O)R, —C(═O)R, —C(═O)NRR—S(═O)₂O⁻, —S(═O)₂OH, —S(═O)₂R, —OS(═O)₂OR, —S(═O)₂NR, —S(═O)R, —OP(═O)O₂RR, —P(═O)O₂RR—P(═O)(O⁻)₂, —P(═O)(OH)₂, —C(═O)R, —C(═O)X, —C(S)R, —C(O)OR, —C(O)O⁻, —C(S)OR, —C(O)SR, —C(S)SR, —C(O)NRR, —C(S)NRR, —C(NR)NRR, where each X is independently a halogen: F, Cl, Br, or I; and each R is independently H, alkyl, aryl, heterocycle, protecting group or prodrug moiety. Alkylene, alkenylene, and alkynylene groups may also be similarly substituted.

"Heterocycle" means a saturated, unsaturated or aromatic ring system including at least one N, O, S, or P. Heterocycle thus include heteroaryl groups. Heterocycle as used herein includes by way of example and not limitation these heterocycles described in Paquette, Leo A. "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; Katritzky, Alan R., Rees, C. W. and Scriven, E. "Comprehensive Heterocyclic Chemistry" (Pergamon Press, 1996); and *J. Am. Chem. Soc.* (1960) 82:5566.

Examples of heterocycles include by way of example and not limitation pyridyl, dihydropyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4H-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

One embodiment of the bis-tetrahydrofuranyl group is:

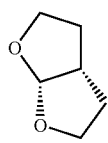

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Carbocycle" means a saturated or partially unsaturated ring system having 3 to 7 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g. arranged as a bicyclo [4,5], [5,5], [5,6] or [6,6] system, or 9 or 10 ring atoms arranged as a bicyclo[5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and spiryl.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

DETAILED DESCRIPTION OF EXEMPLARY EMBODIMENTS

The invention also provides compounds of formula I, II, and III that are attached to one or more phosphonate groups or phosphonate prodrug groups. Such compounds can be prepared by removing one or more hydrogen atoms from a compound of formula I, II, or III and by replacing that hydrogen atom with a group $A^5$, wherein each $A^5$ is independently:

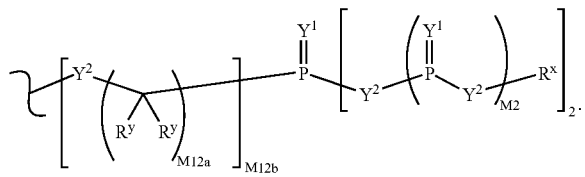

$Y^1$ is independently O, S, $N(R^x)$, $N(O)(R^x)$, $N(OR^x)$, $N(O)(OR^x)$, or $N(N(R^x)_2$.

$Y^2$ is independently a bond, O, $N(R^x)$, $N(O)(R^x)$, $N(OR^x)$, $N(O)(OR^x)$, $N(N(R^x)_2)$, —S(=O)— (sulfoxide), —S(=O)$_2$— (sulfone), —S-(sulfide), or —S—S-(disulfide).

M2 is 0, 1 or 2.

M12a is 1, 2, 3, 4, 5, 6, 7, 8, 9, 10, 11, or 12.

M12b is 0, 1, 2, 3, 4, 5, 6, 7, 8, 9, 10, 11, or 12.

$R^y$ is independently H, $C_1$-$C_6$ alkyl, $C_1$-$C_6$ substituted alkyl, aryl, substituted aryl, or a protecting group. Alternatively, taken together at a carbon atom, two vicinal $R^y$ groups form a ring, i.e. a spiro carbon. The ring may be all carbon atoms, for example, cyclopropyl, cyclobutyl, cyclopentyl, or cyclohexyl, or alternatively, the ring may contain one or more heteroatoms, for example, piperazinyl, piperidinyl, pyranyl, or tetrahydrofuryl.

$R^x$ is independently H, $C_1$-$C_6$ alkyl, $C_1$-$C_6$ substituted alkyl, $C_6$-$C_{20}$ aryl, $C_6$-$C_{20}$ substituted aryl, or a protecting group, or the formula:

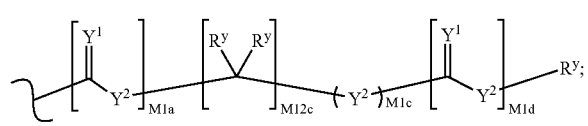

M1a, M1c, and M1d are independently 0 or 1.
M12c is 0, 1, 2, 3, 4, 5, 6, 7, 8, 9, 10, 11 or 12.

A linker may be interposed between the compound of formula I, II, or III, and each substituent $A^5$. The linker may be O, S, NR, N—OR, $C_1$-$C_{12}$ alkylene, $C_1$-$C_{12}$ substituted alkylene, $C_2$-$C_{12}$ alkenylene, $C_2$-$C_{12}$ substituted alkenylene, $C_2$-$C_{12}$ alkynylene, $C_2$-$C_{12}$ substituted alkynylene, C(=O)NH, C(=O), S(=O)$_2$, C(=O)NH(CH$_2$)$_n$, and (CH$_2$CH$_2$O)$_n$, where n may be 1, 2, 3, 4, 5, or 6. Linkers may also be repeating units of alkyloxy (e.g. polyethylenoxy, PEG, polymethyleneoxy) and alkylamino (e.g. polyethyleneamino, Jeffamine™); and diacid ester and amides including succinate, succinamide, diglycolate, malonate, and caproamide.

Specific embodiments of $A^5$ include where M2 is 0, such as:

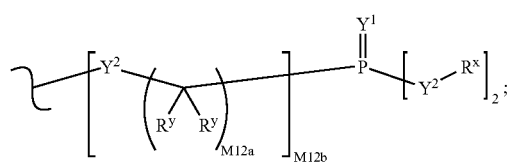

and where M12b is 1, $Y^1$ is oxygen, and $Y^{2b}$ is independently oxygen (O) or nitrogen (N($R^x$)) such as:

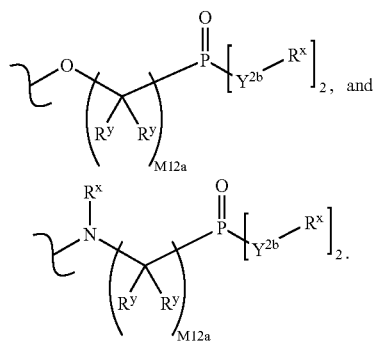

An embodiment of $A^5$ includes:

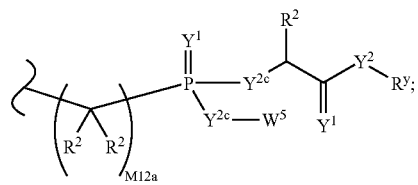

where $W^5$ is a carbocycle such as phenyl or substituted phenyl, and $Y^{2c}$ is independently O, N($R^y$) or S. For example, $R^1$ may be H and n may be 1.

$W^5$ also includes, but is not limited to, aryl and heteroaryl groups such as:

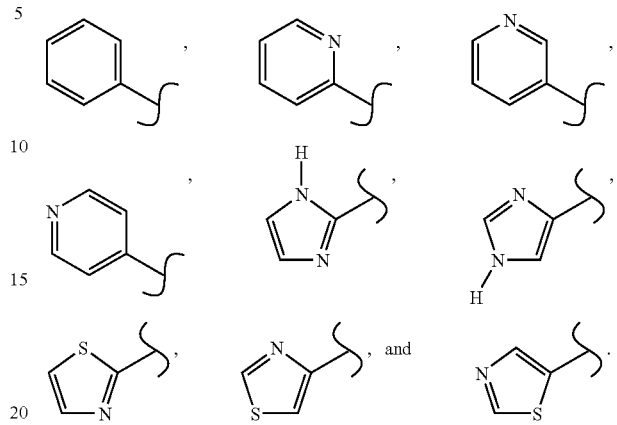

Another embodiment of $A^5$ includes:

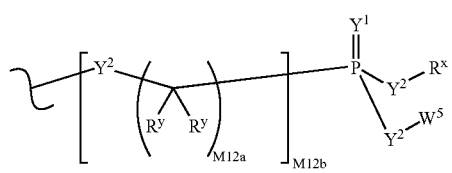

Such embodiments include:

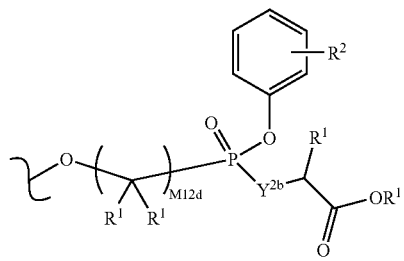

where $Y^{2b}$ is O or N($R^x$); M12d is 1, 2, 3, 4, 5, 6, 7 or 8; $R^1$ is H or $C_1$-$C_6$ alkyl; and the phenyl carbocycle is substituted with 0 to 3 $R^2$ groups where $R^2$ is $C_1$-$C_6$ alkyl or substituted alkyl. Such embodiments of $A^5$ include phenyl phosphonamidate amino acid, e.g. alanate esters and phenyl phosphonate-lactate esters:

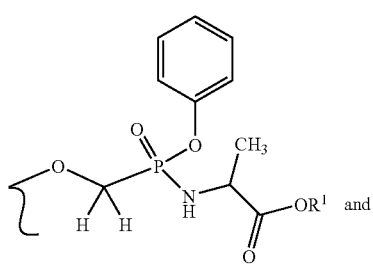

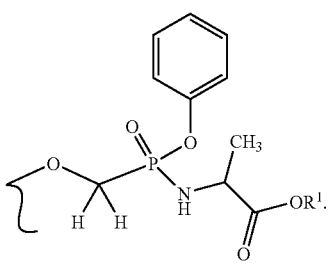

Embodiments of R<sup>x</sup> include esters, carbamates, carbonates, thioesters, amides, thioamides, and urea groups:

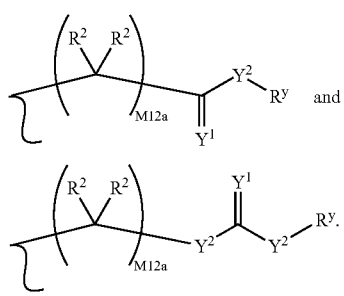

In one embodiment, the prodrug entity, PRD, is selected from the group consisting of $C_1$-$C_6$ alkoxycarbonyl, $C_1$-$C_6$ alkoxycarbonyloxymethylene, and $C_3$-$C_7$ cycloalkoxycarbonyloxymethylene.

In one embodiment, the prodrug entity, PRD is selected from the group consisting of isopropoxycarbonyl, cyclobutoxycarbonyloxymethylene, pent-3-oxycarbonyloxymethylene, cyclopentyloxycarbonyloxymethylene and isopropoxycarbonyloxymethylene.

In one embodiment, the prodrug entity, PRD, is selected from the group consisting of $C_1$-$C_6$ alkoxycarbonyl, $C_1$-$C_6$ alkoxycarbonyloxymethylene, and $C_3$-$C_7$ cycloalkoxycarbonyloxymethylene.

In one embodiment, the prodrug entity, PRD, is selected from the group consisting of isopropoxycarbonyl, cyclobutoxycarbonyloxymethylene, pent-3-oxycarbonyloxymethylene, cyclopentyloxycarbonyloxymethylene and isopropoxycarbonyloxymethylene.

Compounds of the invention bearing one or more prodrug moieties may increase or optimize the bioavailability of the compounds as therapeutic agents. For example, bioavailability after oral administration may be beneficial and may depend on resistance to metabolic degradation in the gastrointestinal tract or circulatory system, and eventual uptake inside cells. Prodrug moieties are considered to confer said resistance by slowing certain hydrolytic or enzymatic metabolic processes. Lipophilic prodrug moieties may also increase active or passive transport of the compounds of the invention across cellular membranes (Darby, G. *Antiviral Chem. & Chemotherapy* (1995) Supp. 1, 6:54-63).

Exemplary embodiments of the invention includes phosphonamidate and phosphoramidate (collectively "amidate") prodrug compounds. General formulas for phosphonamidate and phosphoramidate prodrug moieties include:

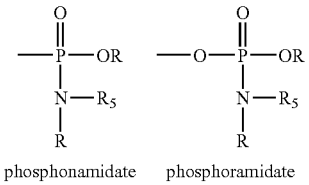

phosphonamidate     phosphoramidate

The phosphorus atom of the phosphonamidate group is bonded to a carbon atom of a compound of formula I, II, or III. The nitrogen substituent $R_5$ may include an ester, an amide, or a carbamate functional group. For example, $R_5$ may be —$CR_2C$(=O)OR' where R' is H, $C_1$-$C_6$ alkyl, $C_1$-$C_6$ substituted alkyl, $C_6$-$C_{20}$ aryl, $C_6$-$C_{20}$ substituted aryl, $C_2$-$C_{20}$ heteroaryl, or $C_2$-$C_{20}$ substituted heteroaryl.

Exemplary embodiments of phosphonamidate and phosphoramidate prodrugs include:

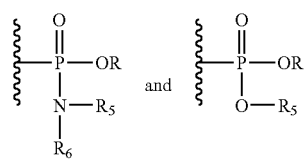

wherein $R_5$ is —$CR_2CO_2R_7$ where $R_6$ and $R_7$ are independently H or $C_1$-$C_8$ alkyl.

The nitrogen atom may comprise an amino acid residue within the prodrug moiety, such as a glycine, alanine, or valine ester (e.g. valacyclovir, see: Beauchamp, et al *Antiviral Chem. Chemotherapy* (1992) 3:157-164), such as the general structure:

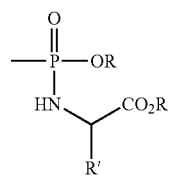

where R' is the amino acid side-chain, e.g. H, $CH_3$, CH($CH_3)_2$, etc.

An exemplary embodiment of a phosphonamidate prodrug moiety is:

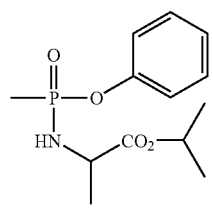

Specific values listed herein for radicals, substituents, and ranges, are for illustration only; they do not exclude other defined values or other values within defined ranges for the radicals and substituents A specific value for $R_k$ is $C_1$-$C_6$ alkyl, $C_2$-$C_6$ alkenyl, or $C_2$-$C_6$ alkynyl, each of which is optionally substituted with one or more halo, hydroxy, $C_1$-$C_6$ alkoxy, dimethylamino, diethylamino, N-ethyl-N-methylamino, morpholino, thiomorpholino, piperidino, or piperazino.

A specific value for $R_a$ is methyl.
A specific value for $R_b$ is methyl.
A specific value for $R_c$ is H.
A specific value for $R_c$ is $R_k$.
A specific value for $R_d$ is H
A specific value for $R_d$ is or $C_1$-$C_4$ alkyl that is substituted with Rj;
A specific value for $R_e$ is H
A specific value for $R_e$ is or $C_1$-$C_4$ alkyl that is substituted with Rj;
A specific value for M is a branched $C_2$ alkylene.
A specific value for Q is —$CH_2$—.
A specific value for $R_j$ is 4-fluorophenyl.
A specific value for $R_k$ is propyl, 2-propynyl, 2-butynyl, methyl, 2-methoxyethyl, 2-hydroxyethyl, ethyl, 2-morpholinoethyl, 3-hydroxy-3-methylbutyl, 2-fluoroethyl, or 2-(N,N-dimethylamino)ethyl.
A specific value for $R_k$ is N-methylamino-carbonylmethyl, N,N-dimethylaminocarbonylmethyl, 2-[N-(methylsulfonyl)-N-methylamino]ethyl, cyclopropylmethyl, 2-(2-oxopyrrolidono)ethyl, 2-(methylsulfonyl)ethyl, methylsulfonyl, or acetylmethyl.
A specific value for $R_m$ is 4-fluorophenyl.
A specific value for $R_n$ is 4-fluoro-2-hydroxyphenyl, 4-fluoro-2-methylsulfonylaminophenyl, 4-fluoro-2-acylaminophenyl, 2-furyl, 2-thienyl, 5-chloro-[1,2,4]thiadiazol-2-yl, 5-chloro-2-hydroxyphenyl, 3-methylisooxazol-5-yl, 4-fluoro-3-trifluoromethylphenyl, 5-trifluoromethylfur-2-yl, 4-hydroxyphenyl, 4-pyridyl(N-oxide), or 3-chloro-2-hydroxyphenyl.
A specific value for $R_p$ is OH, $C_1$-$C_4$ alkoxy, $NH_2$, $N(R_a)$—C(=O)$NR_xR_x$, or —$N(R_s)$—$S(O)_2$—$R_t$; for each $R_x$ is independently H, $C_1$-$C_4$ alkyl, or $C_1$-$C_4$ alkyl-$R_y$; or $NR_xR_x$ taken together form a piperidino or piperazino ring, which ring is optionally substituted with one or more $C_1$-$C_4$ alkyl; and for each $R_y$ is independently phenyl or pyridyl, wherein each phenyl or pyridyl is optionally substituted with one or more fluoro, chloro, bromo, iodo, $C_1$-$C_4$ alkyl, $C_1$-$C_4$ alkyl-C(=O)—, $C_1$-$C_4$ alkyl-$S(O)_2$—, —C(=O)$NR_aR_a$, or —C(=O)$OR_a$.
A specific value for $A^2$ is CH and $A^3$ is N.
A specific value for $A^2$ is N and $A^3$ is CH.
A specific value for $R_c$ is -Q-$R_n$.
A specific value for $R_k$ is ethyl, 2-morpholinoethyl, 2-methoxyethyl, methyl, 2-hydroxyethyl, or 3-hydroxy-3-methylbutyl.
A specific value for Q is —$CH_2$—, and $R_n$ is 4-fluorophenyl.
A specific value for $R_p$ is OH.
A specific value for $R_p$ is $C_1$-$C_4$ alkoxy.
A specific value for $R_p$ is $N(R_a)$—C(=O)$NR_xR_x$,
A specific value for $R_p$ is —$N(R_s)$—$S(O)_2$—$R_t$.
A specific value for $R_s$ is —$S(O)_2$—$R_w$, and $R_t$ is $C_1$-$C_4$ alkyl optionally substituted with $R_v$. A specific value for $R_s$ is $C_1$-$C_4$ alkyl substituted with $R_u$, and $R_t$ is $C_1$-$C_4$ alkyl optionally substituted with $R_v$.
A specific value for $R_s$ is $C_1$-$C_4$ alkyl optionally substituted with $R_u$, and $R_t$ is $NR_xR_x$ or $C_1$-$C_4$ alkyl substituted with $R_v$.
A specific value for $R_s$ is —$S(O)_2$—$CH_3$ or —$S(O)_2$—$CH_2CH_3$, and $R_t$ is methyl or ethyl.
A specific value for $R_s$ is cyclopropylmethyl, 2-(2,5-dimethylpyrrolidino)ethyl, or 2-morpholinoethyl.
A specific value for $R_t$ is 2-chloroethyl, benzyl, pyrid-4-ylmethyl, 4-methylphenyl, 4-chlorophenyl, 2-(4-ethylpiperazin-1-yl)ethyl, 2-(4-ethylsulfonylpiperazin-1-yl)ethyl, 2-(4-acylpiperazin-1-yl)ethyl, 2-(4-isopropylpiperazin-1-yl)ethyl, N-(4-fluoro-2-methylaminocarbonylbenzyl)-N-methylamino, N-(4-fluoro-2-methoxycarbonylbenzyl)amino, N-(4-fluoro-2-carboxybenzyl)-N-methylamino, and N,N-diethylamino.

A specific value for $R_p$ is N-methyl-N-(4-methylpiperazin-1-ylcarbonyl)amino.
A specific value for $R_p$ is methoxy.
A specific value for $R_p$ is $C_1$-$C_4$ alkyl, $C_1$-$C_4$ alkanoyl, $C_1$-$C_4$ alkoxy, $C_2$-$C_6$ alkenyl, $C_2$-$C_6$ alkynyl, —C(=O)$NR_xR_x$, —C(=$NR_{ak}$)$R_{am}$, or 4,5-dihydro-4,4-dimethyloxazole, wherein each $C_1$-$C_4$ alkyl of $R_p$ is substituted with —C(=O)$NR_xR_x$, —$N(R_{ag})$—C(=O)—$R_{ah}$, or —$N(R_{ag})$—$S(O)_2$—$R_{ah}$; and wherein each $C_1$-$C_4$ alkoxy, $C_2$-$C_6$ alkenyl and $C_2$-$C_6$ alkynyl of $R_p$ is optionally substituted with phenyl, hydroxy, $C_3$-$C_6$ carbocycle or —C(=O)$NR_xR_x$;

A specific value for $R_p$ is 2-(N,N-dimethylaminocarbonyl)-2-methylethoxy, allyl, piperidinocarbonyl, 4,4-difluoropiperidinocarbonyl, N-cyclopropyl-N-(2-cyanoethyl)aminocarbonyl, 2-[N-methyl-N-(methylsulfonyl)amino]ethyl, N,N-dimethylaminocarbonylmethyl, N-methylaminocarbonyl, N-(2,2,2-trifluoroethyl)aminocarbonyl, acetyl, piperidinocarbonylmethyl, morpholinocarbonylmethyl, 2-cyclopropylethynyl, azetidinocarbonyl, 4-fluoropiperidinocarbonyl, pyrrolidinocarbonyl, 3,3-difluoropyrrolidinocarbonyl, ethynyl, 1-hydroximinoethyl, 2-phenylethynyl, 4,5-dihydro-4,4-dimethyloxazole, 4-methylpiperazin-1-ylcarbonyl, N-acetyl-N-methylamino, 3,3-dimethylbutyn-1-yl, 1-[N—(N',N'-dimethylamino)imino]ethyl, 2-[N—(N'-methylamino)imino]ethyl, 3-hydroxy-3-methylbutyn-1-yl, 1-methylvinyl, or 1-(N-methoxyimino)ethyl.

A specific value for W is 4-fluorobenzyl, or methyl.
A specific value for X is —C(=O)—.
A specific value for X is —$S(O)_2$—.
A specific value for Y is —$CH_2$—.
A specific value for Y is —$CH_2$—$CH_2$—.
A specific value for $R_c$ is 3-chloro-4,6-difluorobenzyl, 4-fluorobenzyl, 3-chloro-4-fluoeobenzyl, 4-fluoro-2-(N,N-dimethylaminocarbonyl)benzyl, or 4-fluoro-2-(N-methylaminocarbonyl)benzyl.
A specific value for $R_d$ is 4-fluorobenzyl.

In one specific embodiment the invention provides a compound of formula (I):

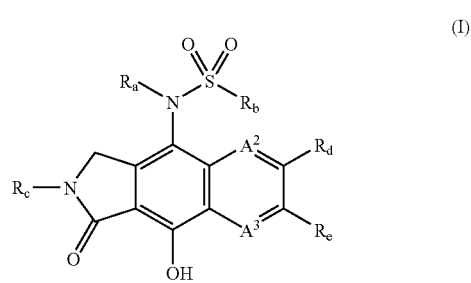

(I)

wherein:
$A^2$ and $A^3$ are each independently N or $CR_a$;
each $R_a$ is independently H or $C_1$-$C_4$ alkyl;
$R_b$ is H or $C_1$-$C_4$ alkyl;
$R_c$ is H, $R_k$, -M-$R_m$, or -Q-$R_n$;
$R_d$ is H, halo, or $C_1$-$C_4$ alkyl that is optionally substituted with Rj;
$R_e$ is H, halo, or $C_1$-$C_4$ alkyl that is optionally substituted with Rj;
$R_f$ is H or $C_1$-$C_4$ alkyl;

M is branched $C_2$-$C_4$ alkylene;

Q is $C_1$-$C_4$ alkylene;

each $R_j$ is phenyl, optionally substituted with one or more F, Cl, Br, I, hydroxy, cyano, trifluoromethyl, trifluoromethoxy, or $C_1$-$C_4$ alkyl;

$R_k$ is $C_1$-$C_6$ alkyl, $C_2$-$C_6$ alkenyl, or $C_2$-$C_6$ alkynyl, each of which is optionally substituted with one or more halo, hydroxy, $C_1$-$C_6$ alkoxy, dimethylamino, diethylamino, N-ethyl-N-methylamino, morpholino, thiomorpholino, piperidino, or piperazino;

$R_m$ is phenyl optionally substituted with one or more F, Cl, Br, I, hydroxy, cyano, trifluoromethyl, trifluoromethoxy, or $C_1$-$C_4$ alkyl; and $R_n$ is a 5- or 6-membered heteroaryl ring optionally substituted with one or more F, Cl, Br, I, hydroxy, cyano, trifluoromethyl, trifluoromethoxy, or $C_1$-$C_4$ alkyl; or $R_n$ is a phenyl ring substituted with at least one group selected from hydroxy, trifluoromethyl, $R_jSO_2NH$—, or $R_jC(=O)NH$—, and optionally substituted with one or more F, Cl, Br, I, hydroxy, cyano, trifluoromethyl, trifluoromethoxy, or $C_1$-$C_4$ alkyl; or $R_n$ is a $C_3$-$C_6$ carbocycle or a pharmaceutically acceptable salt or prodrug thereof.

In another specific embodiment the invention provides a compound of formula (II):

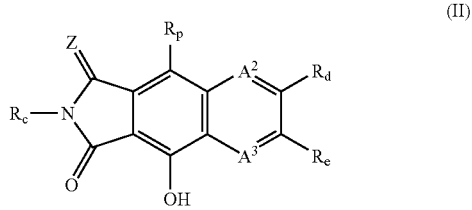

(II)

wherein:

$A^2$ and $A^3$ are each independently N or $CR_a$;

each $R_a$ is independently H or $C_1$-$C_4$ alkyl;

$R_c$ is H, $R_k$, or -Q-$R_n$;

$R_d$ is H, halo, or $C_1$-$C_4$ alkyl that is optionally substituted with Rj;

$R_e$ is H, halo, or $C_1$-$C_4$ alkyl that is optionally substituted with Rj;

Q is $C_1$-$C_4$ alkylene;

Z is O or two hydrogens;

each $R_j$ is phenyl, optionally substituted with one or more F, Cl, Br, I, hydroxy, cyano, trifluoromethyl, trifluoromethoxy, or $C_1$-$C_4$ alkyl;

$R_k$ is $C_1$-$C_6$ alkyl, $C_2$-$C_6$ alkenyl, or $C_2$-$C_6$ alkynyl, each of which is optionally substituted with one or more halo, hydroxy, $C_1$-$C_6$ alkoxy, dimethylamino, diethylamino, N-ethyl-N-methylamino, morpholino, thiomorpholino, piperidino, or piperazino;

$R_n$ is a $C_3$-$C_6$ carbocycle, a phenyl ring, or a 5- or 6-membered heteroaryl ring, which phenyl ring or 5- or 6-membered heteroaryl ring is optionally substituted with one or more F, Cl, Br, I, hydroxy, cyano, trifluoromethyl, trifluoromethoxy, or $C_1$-$C_4$ alkyl;

$R_p$ is OH, $C_1$-$C_4$ alkoxy, $NH_2$, $N(R_a)$—$C(=O)NR_xR_x$, or —$N(R_s)$—$S(O)_2$—$R_t$;

$R_s$ is —$S(O)_2$—$R_w$, and $R_t$ is $C_1$-$C_4$ alkyl optionally substituted with $R_v$; or $R_s$ is $C_1$-$C_4$ alkyl substituted with $R_u$, and $R_t$ is $C_1$-$C_4$ alkyl optionally substituted with $R_v$; or $R_s$ is $C_1$-$C_4$ alkyl optionally substituted with $R_u$, and $R_t$ is $R_z$, $NR_xR_x$, or $C_1$-$C_4$ alkyl substituted with $R_v$;

each $R_v$ is fluoro, chloro, phenyl, pyridyl, 1,4 diazepanyl, or piperazino, wherein each phenyl, pyridyl, 1,4-diazepanyl, and piperazino is optionally substituted with one or more fluoro, chloro, bromo, iodo, $C_1$-$C_4$ alkyl, $C_1$-$C_4$ alkyl-C(=O)—, $C_1$-$C_4$ alkyl-$S(O)_2$—, —$C(=O)NR_aR_a$, or —$C(=O)OR_a$;

each $R_u$ is independently dimethylamino, diethylamino, N-ethyl-N-methylamino, or a ring selected from $C_3$-$C_6$ carbocycle, pyrrolidino, morpholino, thiomorpholino, piperidino, and piperazino, which ring is optionally substituted with one or more $C_1$-$C_4$ alkyl; and $R_w$ is $C_1$-$C_4$ alkyl;

each $R_x$ is independently H, $C_1$-$C_4$ alkyl, or $C_1$-$C_4$ alkyl-$R_y$; or $NR_xR_x$ taken together form a piperidino or piperazino ring, which ring is optionally substituted with one or more $C_1$-$C_4$ alkyl;

each $R_y$ is independently phenyl or pyridyl, wherein each phenyl or pyridyl is optionally substituted with one or more fluoro, chloro, bromo, iodo, $C_1$-$C_4$ alkyl, $C_1$-$C_4$ alkyl-C(=O)—, $C_1$-$C_4$ alkyl-$S(O)_2$—, —$C(=O)NR_aR_a$, or —$C(=O)OR_a$;

$R_z$ is phenyl which is optionally substituted with one or more fluoro, chloro, bromo, iodo, $C_1$-$C_4$ alkyl, $C_1$-$C_4$ alkyl-C(=O)—, $C_1$-$C_4$ alkyl-$S(O)_2$—, —$C(=O)NR_aR_a$, or —$C(=O)OR_a$;

or a pharmaceutically acceptable salt or prodrug thereof.

Another embodiment of the invention is directed toward an HIV integrase inhibitor tricyclic compound of the invention which is capable of accumulating in human PBMC (peripheral blood mononuclear cells). PBMC refer to blood cells having round lymphocytes and monocytes. Physiologically, PBMC are critical components of the mechanism against infection. PBMC may be isolated from heparinized whole blood of normal healthy donors or buffy coats, by standard density gradient centrifugation and harvested from the interface, washed (e.g. phosphate-buffered saline) and stored in freezing medium. PBMC may be cultured in multi-well plates. At various times of culture, supernatant may be either removed for assessment, or cells may be harvested and analyzed (Smith R. et al (2003) *Blood* 102(7):2532-2540). The compounds of this embodiment may further comprise a phosphonate or phosphonate prodrug. Typically, the phosphonate or phosphonate prodrug has the structure $A^5$ as described herein.

Optionally, the compounds of this embodiment demonstrate improved intracellular half-life of the compounds or intracellular metabolites of the compounds in human PBMC when compared to analogs of the compounds not having the phosphonate or phosphonate prodrug. Typically, the half-life is improved by at least about 50%, more typically at least in the range 50-100%, still more typically at least about 100%, more typically yet greater than about 100%.

In another embodiment, the intracellular half-life of a metabolite of the compound in human PBMCs is improved when compared to an analog of the compound not having the phosphonate or phosphonate prodrug. In such embodiments, the metabolite may be generated intracellularly, or it is generated within human PBMC. The metabolite may be a product of the cleavage of a phosphonate prodrug within human PBMCs. The phosphonate prodrug may be cleaved to form a metabolite having at least one negative charge at physiological pH. The phosphonate prodrug may be enzymatically cleaved within human PBMC to form a phosphonate having at least one active hydrogen atom of the form P—OH.

Those of skill in the art will also recognize that the compounds of the invention may exist in many different protonation states, depending on, among other things, the pH of their environment. While the structural formulae provided herein depict the compounds in only one of several possible protonation states, it will be understood that these structures are illustrative only, and that the invention is not limited to any particular protonation state—any and all protonated forms of the compounds are intended to fall within the scope of the invention.

The compounds of this invention optionally comprise salts of the compounds herein, especially pharmaceutically acceptable non-toxic salts containing, for example, $Na^+$, $Li^+$, $K^+$, $Ca^{+2}$ and $Mg^{+2}$. Such salts may include those derived by combination of appropriate cations such as alkali and alkaline earth metal ions or ammonium and quaternary amino ions with an acid anion moiety, typically a carboxylic acid. The compounds of the invention may bear multiple positive or negative charges. The net charge of the compounds of the invention may be either positive or negative. Any associated counter ions are typically dictated by the synthesis and/or isolation methods by which the compounds are obtained. Typical counter ions include, but are not limited to ammonium, sodium, potassium, lithium, halides, acetate, trifluoroacetate, etc., and mixtures thereof. It will be understood that the identity of any associated counter ion is not a critical feature of the invention, and that the invention encompasses the compounds in association with any type of counter ion. Moreover, as the compounds can exists in a variety of different forms, the invention is intended to encompass not only forms of the compounds that are in association with counter ions (e.g., dry salts), but also forms that are not in association with counter ions (e.g., aqueous or organic solutions).

Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound. In addition, salts may be formed from acid addition of certain organic and inorganic acids, e.g., HCl, HBr, $H_2SO_4$, $H_3PO_4$ or organic sulfonic acids, to basic centers, typically amines, or to acidic groups. Finally, it is to be understood that the compositions herein comprise compounds of the invention in their unionized, as well as zwitterionic form, and combinations with stoichiometric amounts of water as in hydrates.

Also included within the scope of this invention are the salts of the parental compounds with one or more amino acids, especially the naturally-occurring amino acids found as protein components. The amino acid typically is one bearing a side chain with a basic or acidic group, e.g., lysine, arginine or glutamic acid, or a neutral group such as glycine, serine, threonine, alanine, isoleucine, or leucine.

The compounds of the invention can also exist as tautomeric, resonance isomers in certain cases. Typically, the structures shown herein exemplify only one tautomeric or resonance form of the compounds. For example, hydrazine, oxime, hydrazone groups may be shown in either the syn or anti configurations. The corresponding alternative configuration is contemplated as well. All possible tautomeric and resonance forms are within the scope of the invention.

One enantiomer of a compound of the invention can be separated substantially free of its opposing enantiomer by a method such as formation of diastereomers using optically active resolving agents (*Stereochemistry of Carbon Compounds* (1962) by E. L. Eliel, McGraw Hill; Lochmuller, C. H., (1975) *J. Chromatogr.*, 113:(3) 283-302). Separation of diastereomers formed from the racemic mixture can be accomplished by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure enantiomers. Alternatively, enantiomers can be separated directly under chiral conditions, method (3).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved may be reacted with one enantiomer of a chiral compound to form a diastereomeric pair (Eliel, E. and Wilen, S. (1994) *Stereochemistry of Organic Compounds*, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched xanthene. A method of determining optical purity involves making chiral esters, such as a menthyl ester or Mosher ester, α-methoxy-α-(trifluoromethyl)phenyl acetate (Jacob III. (1982) *J. Org. Chem.* 47:4165), of the racemic mixture, and analyzing the NMR spectrum for the presence of the two atropisomeric diastereomers. Stable diastereomers can be separated and isolated by normal- and reverse-phase chromatography following methods for separation of atropisomeric naphthyl-isoquinolines (Hoye, T., WO 96/15111).

By method (3), a racemic mixture of two asymmetric enantiomers can be separated by chromatography using a chiral stationary phase (*Chiral Liquid Chromatography* (1989) W. J. Lough, Ed. Chapman and Hall, New York; Okamoto, (1990) "Optical resolution of dihydropyridine enantiomers by High-performance liquid chromatography using phenylcarbamates of polysaccharides as a chiral stationary phase", *J. of Chromatogr.* 513:375-378).

Enantiomers can be distinguished by methods used to distinguish other chiral molecules with asymmetric carbon atoms, such as optical rotation and circular dichroism.

Improving the delivery of drugs and other agents to target cells and tissues has been the focus of considerable research for many years. Though many attempts have been made to develop effective methods for importing biologically active molecules into cells, both in vivo and in vitro, none has proved to be entirely satisfactory. Optimizing the association of the inhibitory drug with its intracellular target, while minimizing intercellular redistribution of the drug, e.g. to neighboring cells, is often difficult or inefficient.

Most agents currently administered parenterally to a patient are not targeted, resulting in systemic delivery of the agent to cells and tissues of the body where it is unnecessary, and often undesirable. This may result in adverse drug side effects, and often limits the dose of a drug (e.g., cytotoxic agents and other anti-cancer or anti-viral drugs) that can be administered. By comparison, although oral administration of drugs is generally recognized as a convenient and economical method of administration, oral administration can result in either (a) uptake of the drug through the cellular and tissue barriers, e.g. blood/brain, epithelial, cell membrane, resulting in undesirable systemic distribution, or (b) temporary residence of the drug within the gastrointestinal tract.

Accordingly, a major goal has been to develop methods for specifically targeting agents to cells and tissues. Benefits of such treatment include avoiding the general physiological effects of inappropriate delivery of such agents to other cells and tissues, such as uninfected cells. Intracellular targeting may be achieved by methods and compositions which allow accumulation or retention of biologically active agents inside cells.

Preparation of Compounds of the Invention

The compounds of the invention may be prepared by a variety of synthetic routes and methods known to those skilled in the art. The invention also relates to methods of making the compounds of the invention. The compounds may be prepared by any of the applicable techniques of organic synthesis. For example, known techniques are elaborated in: "Compendium of Organic Synthetic Methods", John Wiley & Sons, New York, Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, jr., 1980; Vol. 5, Leroy G. Wade, Jr., 1984; and Vol. 6, Michael B. Smith; as well as March, J., "Advanced Organic Chemistry", Third Edition, John Wiley & Sons, New York, 1985; "Comprehensive Organic Synthesis. Selectivity, Strategy & Efficiency in Modern Organic Chemistry" (9 Volume set) Barry M. Trost, Editor-in-Chief, Pergamon Press, New York, 1993.

A number of exemplary methods for the preparation of the compounds of the invention are provided herein. These methods are intended to illustrate the nature of such preparations and are not intended to limit the scope of applicable methods.

Deliberate use may be made of protecting groups to mask reactive functionality and direct reactions regioselectively (Greene, et al (1991) "Protective Groups in Organic Synthesis", 2nd Ed., John Wiley & Sons). For example, useful protecting groups for the 8-hydroxyl group and other hydroxyl substituents include methyl, MOM (methoxymethyl), trialkylsilyl, benzyl, benzoyl, trityl, and tetrahydropyranyl. Certain aryl positions may be blocked from substitution, such as the 2-position as fluorine.

Protection of Reactive Substituents.

Depending on the reaction conditions employed, it may be necessary to protect certain reactive substituents from unwanted reactions by protection before the sequence described, and to deprotect the substituents afterwards, according to the knowledge of one skilled in the art. Protection and deprotection of functional groups are described, for example, in Protective Groups in Organic Synthesis, by T. W. Greene and P. G. M Wuts, Wiley, Second Edition 1990. Reactive substituents which may be protected are shown in the accompanying schemes as, for example, [OH], [SH], etc.

Preparation of Carboalkoxy-Substituted Phosphonate Bisamidates, Monoamidates, Diesters and Monoesters.

A number of methods are available for the conversion of phosphonic acids into amidates and esters. In one group of methods, the phosphonic acid is either converted into an isolated activated intermediate such as a phosphoryl chloride, or the phosphonic acid is activated in situ for reaction with an amine or a hydroxy compound.

The conversion of phosphonic acids into phosphoryl chlorides is accomplished by reaction with thionyl chloride, for example as described in $J.$ $Gen.$ $Chem.$ $USSR,$ 1983, 53, 480, Zh. Obschei Khim., 1958, 28, 1063, or $J.$ $Org.$ $Chem.,$ 1994, 59, 6144, or by reaction with oxalyl chloride, as described in $J.$ $Am.$ $Chem.$ $Soc.,$ 1994, 116, 3251, or $J.$ $Org.$ $Chem.,$ 1994, 59, 6144, or by reaction with phosphorus pentachloride, as described in $J.$ $Org.$ $Chem.,$ 2001, 66, 329, or in $J.$ $Med.$ $Chem.,$ 1995, 38, 1372. The resultant phosphoryl chlorides are then reacted with amines or hydroxy compounds in the presence of a base to afford the amidate or ester products.

Phosphonic acids are converted into activated imidazolyl derivatives by reaction with carbonyl diimidazole, as described in $J.$ $Chem.$ $Soc.,$ $Chem.$ $Comm.,$ 1991, 312, or Nucleosides Nucleotides 2000, 19, 1885. Activated sulfonyloxy derivatives are obtained by the reaction of phosphonic acids with trichloromethylsulfonyl chloride, as described in $J.$ $Med.$ $Chem.$ 1995, 38, 4958, or with triisopropylbenzenesulfonyl chloride, as described in $Tet.$ $Lett.,$ 1996, 7857, or $Bioorg.$ $Med.$ $Chem.$ $Lett.,$ 1998, 8, 663. The activated sulfonyloxy derivatives are then reacted with amines or hydroxy compounds to afford amidates or esters.

Alternatively, the phosphonic acid and the amine or hydroxy reactant are combined in the presence of a diimide coupling agent. The preparation of phosphonic amidates and esters by means of coupling reactions in the presence of dicyclohexyl carbodiimide is described, for example, in $J.$ $Chem.$ $Soc.,$ $Chem.$ $Comm.,$ 1991, 312, or $J.$ $Med.$ $Chem.,$ 1980, 23, 1299 or Coll. Czech. Chem. Comm., 1987, 52, 2792. The use of ethyl dimethylaminopropyl carbodiimide for activation and coupling of phosphonic acids is described in $Tet.$ $Lett.,$ 2001, 42, 8841, or Nucleosides Nucleotides, 2000, 19, 1885.

A number of additional coupling reagents have been described for the preparation of amidates and esters from phosphonic acids. The agents include Aldrithiol-2, and PYBOP and BOP, as described in $J.$ $Org.$ $Chem.,$ 1995, 60, 5214, and $J.$ $Med.$ $Chem.,$ 1997, 40, 3842, mesitylene-2-sulfonyl-3-nitro-1,2,4-triazole (MSNT), as described in $J.$ $Med.$ $Chem.,$ 1996, 39, 4958, diphenylphosphoryl azide, as described in $J.$ $Org.$ $Chem.,$ 1984, 49, 1158, 1-(2,4,6-triisopropylbenzenesulfonyl-3-nitro-1,2,4-triazole (TPSNT) as described in $Bioorg.$ $Med.$ $Chem.$ $Lett.,$ 1998, 8, 1013, bromotris(dimethylamino)phosphonium hexafluorophosphate (BroP), as described in $Tet.$ $Lett.,$ 1996, 37, 3997, 2-chloro-5,5-dimethyl-2-oxo-1,3,2-dioxaphosphinane, as described in Nucleosides Nucleotides 1995, 14, 871, and diphenyl chlorophosphate, as described in $J.$ $Med.$ $Chem.,$ 1988, 31, 1305.

Phosphonic acids can be converted into amidates and esters by means of the Mitsonobu reaction, in which the phosphonic acid and the amine or hydroxy reactant are combined in the presence of a triaryl phosphine and a dialkyl azodicarboxylate. The procedure is described in $Org.$ $Lett.,$ 2001, 3, 643, or $J.$ $Med.$ $Chem.,$ 1997, 40, 3842.

Phosphonic esters can also be obtained by the reaction between phosphonic acids and halo compounds, in the presence of a suitable base. The method is described, for example, in $Anal.$ $Chem.,$ 1987, 59, 1056, or $J.$ $Chem.$ $Soc.$ $Perkin$ $Trans.,$ $I,$ 1993, 19, 2303, or $J.$ $Med.$ $Chem.,$ 1995, 38, 1372, or $Tet.$ $Lett.,$ 2002, 43, 1161.

Biological Activity of HIV-Integrase Inhibitor Compounds

Representative compounds of the invention were tested for biological activity by methods including anti-HIV assay, measuring inhibition of HIV-integrase strand transfer catalysis, and cytotoxicity. See: Wolfe, et al $J.$ $Virol.$ (1996) 70:1424-1432; Hazuda, et al Nucleic Acids Res. (1994) 22:1121-22; Hazuda, et al $J.$ $Virol.$ (1997) 71:7005-7011; Hazuda, et al Drug Design and Discovery (1997) 15:17-24; and Hazuda, et al Science (2000) 287:646-650. The antiviral activity of a compound of the invention can be determined using pharmacological models which are well known in the art. While many of the compounds of the present invention demonstrate inhibition of integration of HIV reverse-transcribed DNA, there may be other mechanisms of action whereby HIV replication or proliferation is affected. The compounds of the invention may be active via inhibition of HIV-integrase or other enzymes associated with HIV infection, AIDS, or ARC. Furthermore, the compounds of the invention may have significant activity against other viral diseases. Thus, the specific assays embodied herein are not intended to limit the present invention to a specific mechanism of action.

HIV Integrase Assay ($IC_{50}$ Determination)

The HIV Integrase assay is carried out in Reacti-Bind High Binding Capacity Streptavidin coated plates (Pierce #15502) in 100 μl reactions. The wells of the plate are rinsed once with PBS. Each well is then coated at room temperature for 1 h with 100 μl of 0.14 μM Donor DNA with the following sequence:

```
                                           (SEQ ID NO: 1)
5'Biotin-ACC CTT TTA GTC AGT GTG GAA AAT CTC TAG
CAG T-3'

(SEQ ID NO: 2)
3'-GAA AAT CAG TCA CAC CTT TTA GAG ATC GTC A-5'
```

After coating, the plate was washed twice with PBS. 3' processing of the Donor DNA is started by adding 80 μl of Integrase/buffer mixture (25 mM HEPES, pH 7.3, 12.5 mM DTT, 93.75 mM NaCl, 12.5 mM $MgCl_2$, 1.25% Glycerol, 0.3125 uM integrase) to each well. 3' processing is allowed to proceed for 30 min at 37° C., after which, 10 μl of test compound and 10 μl of 2.5 uM DIG-labeled Target DNA with the following sequence:

```
5'-TGA CCA AGG GCT AAT TCA CT-3'DIG   (SEQ ID NO: 3)

3'DIG-ACT GGT TCC CGA TTA AGT GA-5'   (SEQ ID NO: 4)
``` are added to each well to allow strand transfer to proceed for 30 min at 37° C. The plate is then washed three times with 2×SSC for 5 min and rinsed once with PBS. For detection of integrated product, 100 μl of a 1/2000 dilution of HRP-conjugated anti-DIG antibody (Pierce #31468) are added to each well and incubated for 1 hour. The plate was then washed three times for 5 min each, with 0.05% Tween-20 in PBS. For signal development and amplification, 100 μl of SuperSignal ELISA Femto Substrate (Pierce #37075) are added to each well. Chemiluminescence (in relative light units) is read immediately at 425 nm in the SPECTRAmax GEMINI Microplate Spectrophotometer using the end point mode at 5 sec per well.

For $IC_{50}$ determinations, eight concentrations of test compounds in a 1/2.2 dilution series are used.

Antiviral Assays in MT2 and MT4 Cells

For the antiviral assay utilizing MT-2 cells, 50 μl of 2× test concentration of 5-fold serially diluted compound in culture medium with 10% FBS was added to each well of a 96-well plate (9 concentrations) in triplicate. MT-2 cells were infected with HIV-IIIb at a multiplicity of infection (m.o.i) of 0.01 for 3 hours. Fifty microliters of infected cell suspension in culture medium with 10% FBS (~1.5×10⁴ cells) was then added to each well containing 50 μl of diluted compound. The plates were then incubated at 37° C. for 5 days. For the antiviral assay utilizing MT-4 cells, 20 μl of 2× test concentration of 5-fold serially diluted compound in culture medium with 10% FBS was added to each well of a 384-well plate (7 concentrations) in triplicate. MT-4 cells were next mixed with HIV-IIIb at an m.o.i. of 0.1 and 20 μl of virus/cell mixture (~2000 cells) was immediately added to each well containing 20 μl of diluted compound. The plates were then incubated at 37° C. for 5 days. After 5 days of incubation, 100 μl of CellTiter-Glo™ Reagent (catalog #G7571, Promega Biosciences, Inc., Madison, Wis.) was added to each well containing MT-2 cells and 40 μl to each well containing MT-4 cells. Cell lysis was carried out by incubating at room temperature for 10 min and then chemiluminescence was read.

Cytotoxicity Assays in MT-2 and MT-4 Cells

For compound cytotoxicity assessment in MT-2 cells, the protocol was similar to that of the antiviral assay in MT-2 cells, except that uninfected cells and a 3-fold serial dilution of compounds were used. For cytotoxicity assessment in MT-4 cells, the protocol is similar to that of the antiviral assay in MT-4 cells, except that no virus was added.

Typically the compounds of the invention have an $IC_{50}$ of less than or equal to about 1 μM. Certain specific compounds of the invention have an $IC_{50}$ of less than or equal to about 60 nM, while other compounds have an $IC_{50}$ of less than or equal to about 25 nM. The compounds of the invention typically have an $EC_{50}$ of less than or equal to about 1 μM. Certain specific compounds of the invention have an $EC_{50}$ of less than or equal to about 60 nM, while other compounds of the invention have an $IC_{50}$ of less than or equal to about 25 nM. Certain compounds of the invention have an $IC_{50}$ of between >0 μM and about 1 μM, and an $EC_{50}$ of between >0 μM and about 1 μM. Other compounds of the invention have an $IC_{50}$ of between >0 μM and about 60 nM and an $EC_{50}$ of between >0 μM and about 60 nM. While other compounds of the invention have an $IC_{50}$ of between >0 μM and about 25 nM and an $EC_{50}$ of between >0 μM and about 25 nM.

Pharmaceutical Formulations and Routes of Administration

Examples of pharmaceutically acceptable carriers and methods of manufacture for various compositions may be found in *Remington's Pharmaceutical Sciences*, 18$^{th}$ Ed., Mack Publishing Co. (1990), which is incorporated in its entirety by reference herein.

The compounds of the invention may be formulated with conventional carriers, diluents and excipients, which will be selected in accord with ordinary practice. Tablets will contain excipients, glidants, fillers, binders, diluents and the like. Aqueous formulations are prepared in sterile form, and when intended for delivery by other than oral administration generally will be isotonic. Formulations optionally contain excipients such as those set forth in the "Handbook of Pharmaceutical Excipients" (1986) and include ascorbic acid and other antioxidants, chelating agents such as EDTA, carbohydrates such as dextrin, hydroxyalkylcellulose, hydroxyalkylmethylcellulose, stearic acid and the like.

Compounds of the invention and their physiologically acceptable salts (hereafter collectively referred to as the active ingredients) may be administered by any route appropriate to the condition to be treated, suitable routes including oral, rectal, nasal, topical (including ocular, buccal and sublingual), vaginal and parenteral (including subcutaneous, intramuscular, intravenous, intradermal, intrathecal and epidural). The preferred route of administration may vary with for example the condition of the recipient.

While it is possible for the active ingredients to be administered alone it is preferably to present them as pharmaceutical formulations. The formulations, both for veterinary and for human use, of the present invention comprise at least one active ingredient, as above defined, together with one or more pharmaceutically acceptable carriers (excipients, diluents, etc.) thereof and optionally other therapeutic ingredients. The carrier(s) must be "acceptable" in the sense of being compatible with the other ingredients of the formulation and not deleterious to the recipient thereof.

The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

For infections of the eye or other external tissues e.g. mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG400) and mixtures thereof. The topical formulations may desirably include a compound which enhances absorption or penetration of the active ingredient through the skin or other affected areas. Examples of such dermal penetration enhancers include dimethylsulfoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the present invention include Tween™ 60, Span™ 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties, since the solubility of the active compound in most oils likely to be used in pharmaceutical emulsion formulations is very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for nasal administration wherein the carrier is a solid include a coarse powder having a particle size for example in the range 20 to 500 microns (including particle sizes in a range between 20 and 500 microns in increments of 5 microns such as 30 microns, 35 microns, etc), which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents such as pentamidine for treatment of pneumocystis pneumonia.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described. Preferred unit dosage formulations are those containing a daily dose or unit daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavoring agents.

The present invention further provides veterinary compositions comprising at least one active ingredient as above defined together with a veterinary carrier. Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can be used to provide controlled release pharmaceutical formulations containing as active ingredient one or more compounds of the invention ("controlled release formulations") in which the release of the active ingredient can be controlled and regulated to allow less frequency dosing or to improve the pharmacokinetic or toxicity profile of a given invention compound. Controlled release formulations adapted for oral administration in which discrete units comprising one or more compounds of the invention can be prepared according to conventional methods. Controlled release formulations may be employed for the treatment or prophylaxis of various microbial infections particularly human bacterial, human parasitic protozoan or human viral infections caused by microbial species including Plasmodium, Pneumocystis, herpes viruses (CMV, HSV 1, HSV 2, VZV, and the like), retroviruses, adenoviruses and the like. The controlled release formulations can be used to treat HIV infections and related conditions such as tuberculosis, malaria, pneumocystis pneumonia, CMV retinitis, AIDS, AIDS-related complex (ARC) and progressive generalized lymphadeopathy (PGL), and AIDS-related neurological conditions such as multiple sclerosis, and tropical spastic paraparesis. Other human retroviral infections that may be treated with the controlled release formulations according to the invention include Human T-cell Lymphotropic virus (HTLV)-I and IV and HIV-2 infections. The invention accordingly provides pharmaceutical formulations for use in the treatment or prophylaxis of the above-mentioned human or veterinary conditions and microbial infections.

Combination Therapy

The compounds of the invention may be employed in combination with other therapeutic agents for the treatment or prophylaxis of the infections or conditions indicated above. Examples of such further therapeutic agents include agents that are effective for the treatment or prophylaxis of viral, parasitic or bacterial infections or associated conditions or for treatment of tumors or related conditions include 3'-azido-3'-deoxythymidine (zidovudine, AZT), 2'-deoxy-3'-thiacytidine (3TC), 2',3'-dideoxy-2',3'-didehydroadenosine (D4A), 2',3'-dideoxy-2',3'-didehydrothymidine (D4T), carbovir (carbocyclic 2',3'-dideoxy-2',3'-didehydroguanosine), 3'-azido-2',3'-dideoxyuridine, 5-fluorothymidine, (E)-5-(2-bromovinyl)-2'-deoxyuridine (BVDU), 2-chlorodeoxyadenosine, 2-deoxycoformycin, 5-fluorouracil, 5-fluorouridine, 5-fluoro-2'-deoxyuridine, 5-trifluoromethyl-2'-deoxyuridine, 6-azauridine, 5-fluoroorotic acid, methotrexate, triacetyluridine, 1-(2'-deoxy-2'-fluoro-1-β-arabinosyl)-5-iodocytidine (FIAC), tetrahydro-imidazo(4,5,1-jk)-(1,4)-benzodiazepin-2 (1H)-thione (TIBO), 2'-nor-cyclicGMP, 6-methoxypurine arabinoside (ara-M), 6-methoxypurine arabinoside 2'-O-valerate, cytosine arabinoside (ara-C), 2',3'-dideoxynucleosides such as 2',3'-dideoxycytidine (ddC), 2',3'-dideoxyadenosine (ddA) and 2',3'-dideoxyinosine (ddI), acyclic nucleosides such as acyclovir, penciclovir, famciclovir, ganciclovir, HPMPC, PMEA, PMEG, PMPA, PMPDAP, FPMPA, HPMPA, HPMPDAP, (2R,5R)-9->tetrahydro-5-(phosphonomethoxy)-2-furanyladenine, (2R,5R)-1->tetrahydro-5-(phosphonomethoxy)-2-furanylthymine, other antivirals including ribavirin (adenine arabinoside), 2-thio-6-azauridine, tubercidin, aurintricarboxylic acid, 3-deazaneoplanocin, neoplanocin, rimantidine, adamantine, and foscarnet (trisodium phosphonoformate), antibacterial agents including bactericidal fluoroquinolones (ciprofloxacin, pefloxacin and the like), aminoglycoside bactericidal antibiotics (streptomycin, gentamicin, amicacin and the like) β-lactamase inhibitors (cephalosporins, penicillins and the like), other antibacterials including tetracycline, isoniazid, rifampin, cefoperazone, claithromycin and azithromycin, antiparasite or antifungal agents including pentamidine (1,5-bis(4'-aminophenoxy) pentane), 9-deaza-inosine, sulfamethoxazole, sulfadiazine, quinapyramine, quinine, fluconazole, ketoconazole, itraconazole, Amphotericin B, 5-fluorocytosine, clotrimazole, hexadecylphosphocholine and nystatin, renal excretion inhibitors such as probenicid, nucleoside transport inhibitors such as dipyridamole, dilazep and nitrobenzylthioinosine, immunomodulators such as FK506, ☐yclosporine A, thymosin α-1, cytokines including TNF and TGF-β, interferons including IFN-α, IFN-β, and IFN-γ, interleukins including various interleukins, macrophage/granulocyte colony stimulating factors including GM-CSF, G-CSF, M-CSF, cytokine antagonists including anti-TNF antibodies, anti-interleukin antibodies, soluble interleukin receptors, protein kinase C inhibitors and the like.

The compounds of the invention may be employed in combination with booster agents. One aspect of the invention provides the use of an effective amount of a booster agent to boost the pharmacokinetics of a compound of the invention. An effective amount of a booster agent, for example, the amount required to boost an HIV integrase inhibitor of the invention, is the amount necessary to improve the pharmacokinetic profile of the compound when compared to its profile when used alone. The inventive compound possesses a better efficacious pharmacokinetic profile than it would without the addition of the boosting agent. The amount of booster agent used to boost the integrase inhibitor potency of the inventive compound is, preferably, subtherapeutic (e.g., dosages below the amount of booster agent conventionally used for therapeutically treating HIV infection in a patient). A boosting dose for the compounds of the invention is subtherapeutic for treating HIV infection, yet high enough to effect modulation of the metabolism of the compounds of the invention, such that their exposure in a patient is boosted by increased bioavailability, increased blood levels, increased half life, increased time to peak plasma concentration, increased/faster inhibition of HIV integrase and/or reduced systematic clearance. An example of a boosting agent is Ritonavir® (ABBOTT Laboratories).

The compounds of the invention are preferably administered in an oral dosage form. The inventive compounds (or pharmaceutically acceptable salts thereof) are useful for the treatment of AIDS. The compounds (or pharmaceutically acceptable salts thereof) are useful for therapy. They are useful as a medicament. The compounds or pharmaceutically acceptable salts of the invention are useful in the manufacture of a medicament for the treatment of a viral infection (e.g. HIV). The pharmaceutical compositions of the invention may be used in the treatment of AIDS.

Still another aspect of this invention is to provide a kit for the treatment of disorders, symptoms and diseases where integrase inhibition plays a role, comprising two or more separate containers in a single package, wherein a compound, salt or composition of the invention is placed in combination with one or more of the following: a pharmaceutically acceptable carrier (excipient, diluent, etc.), a booster agent, and a therapeutically effective amount of another inventive compound, salt or composition thereof, an AIDS treatment agent, such as an HIV inhibitor agent, an anti-infective agent or an immunomodulator agent.

The compounds can be made though a variety of synthetic routes. Generic procedures known in the art, such as those disclosed in WO/2004035577, which is hereby incorporated herein in its entirety, may be applied to synthesize a number of compounds of the invention. The following two compounds can also be prepared using the procedures described in WO/2004035577.

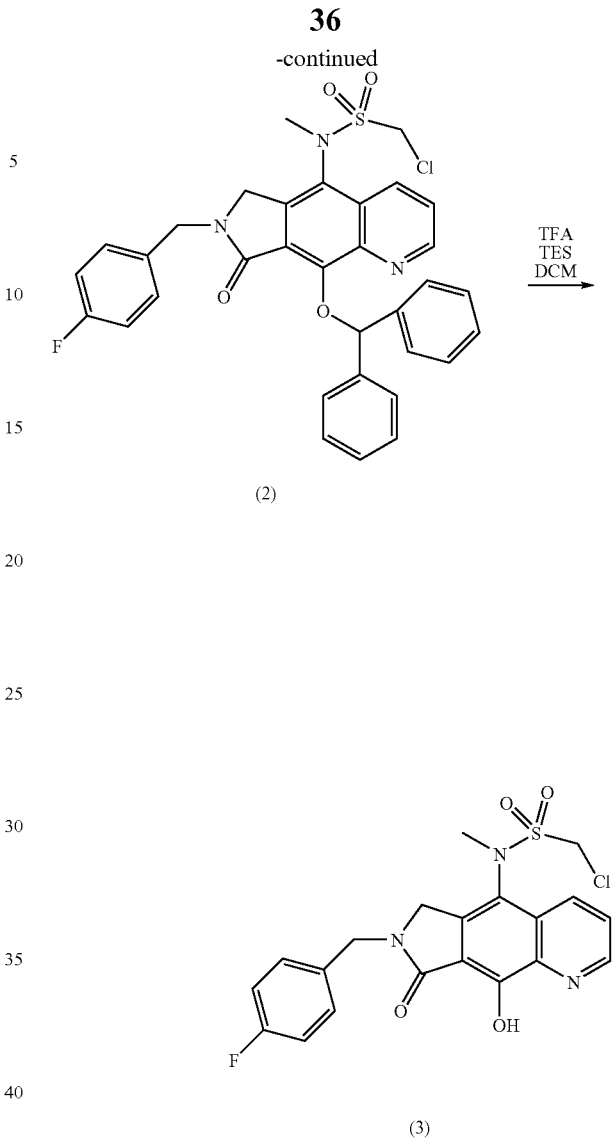

The invention will now be illustrated by the following non-limiting Examples.

EXAMPLES

Example 1

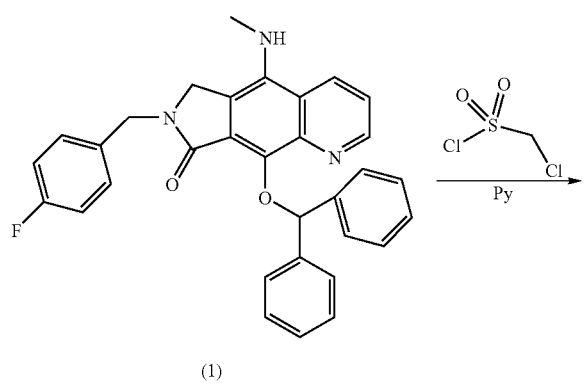

Compound (1) (107 mg, 213 μmol) was dissolved in 5 mL of pyridine and flashed with nitrogen, It was cold to 0° C. and added sulfonyl chloride (200 μl) and stirred for 2 h under nitrogen. It became dark. The reaction was diluted with 20 mL of EtOAc, washed with 0.1N HCl, brine, sat'd NaHCO$_3$ and brine again. It was dried over Na$_2$SO$_4$ and filtered through a pile of Celite, then concentrated in vacuum to give crude product (2). The crude product was purified by flash chromatography with 30% EtOAc/Hexane to yield 81 mg of desired product in 62%.

General Procedure for the Deprotection of DPM Group at C8-OH:

The compound (2) (20 mg) was dissolved in 1 mL of DCM and treated with TFA (100 μl) and triethylsilane (200 μl). After stirring for 30 minutes at room temperature, the reaction mixture was azeotroped with toluene once. The resulting residue was then purified by reverse-phase prep HPLC to provide 11.5 mg of (3), as the TFA salt.

General HPLC conditions: mobile phase A was 0.1% TFA in water, mobile phase b was 0.1% TFA in CH$_3$CN; gradient from 5% to 60% B in 20 min; flow rate was 20 mL/min; column was Phenomenex, luna 5μ, C18 (2), 150 mm×21.1 mm.

300 MHz $^1$H NMR (CDCl$_3$) (ppm): 9.1 (d, 1H); 8.6 (d, 1H); 7.7 (m, 11H); 7.3-7.2 (m, 2H); 7.1 (t, 2H); 5.0-4.7 (dd, 2H); 4.6-4.3 (m, 4H); 3.4 (s, 3H). $^{19}$F NMR (ppm): −76.2; −114.5. m/z 450, 452.

Example 2

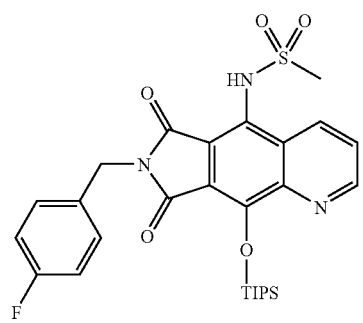

9


10


11

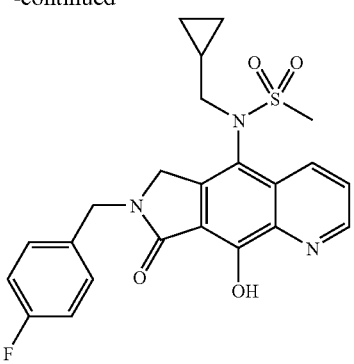

12

9 (100 mg, 0.18 mmol) was dissolved in 1.0 ml of THF. Cyclopropylmethanol (21.3 ul, 0.27 mmol), Triphenylphosphine (71 mg, 0.27 mmol), and DIAD (53 uL, 0.27 mmol) were then added to this solution successively and the reaction was allowed to stir at room temperature for 45 minutes. The reaction was then diluted with Ethyl Acetate and the organic was washed once with sat. NaHCO3, twice with water, and once with Brine. The organic was then dried over Magnesium Sulfate and concentrated in vacuo to afford a crude residue which was then purified by silica gel chromatography (3:1— Hexane:EthylAcetate) to afford 10 (90 mg, 81%).

Example 3

9

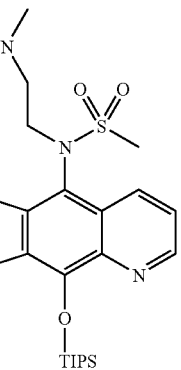

13

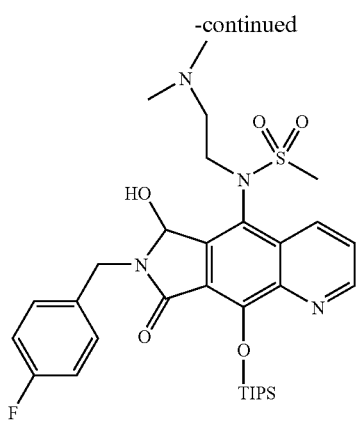

4

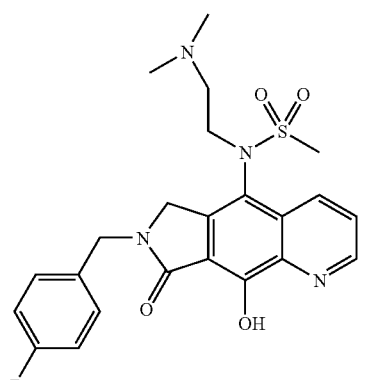

15

9 (100 mg, 0.18 mmol) was dissolved in 1.0 ml of THF. N,N-Dimethylaminoethanol (81 ul, 0.8 mmol), Triphenylphosphine (210 mg, 0.8 mmol), and DIAD (155 ul, 0.8 mmol) were then added to this solution successively and the reaction was allowed to stir at room temperature for 45 minutes. The reaction was then diluted with Ethyl Acetate and the organic was washed once with sat. NaHCO3, twice with water, and once with Brine. The organic was then dried over Magnesium Sulfate and concentrated in vacuo to afford a crude residue which was then purified by silica gel chromatography (1% Triethylamine in EthylAcetate) to afford 13 (84 mg, 72%).

13 (84 mg, 0.13 mmol) was dissolved in 1 ml of THF and 100 ul of water. LiBH4 (22 mg, 1.05 mmol) was then added and the reaction then stirred at room temperature for 1 hour. The reaction was then diluted with Ethyl Acetate and the organic was washed once with water and once with Brine. The organic was then dried over Mg2SO4 and concentrated in vacuo to afford crude 14 which was taken forward with no further purification (crude yield=60 mg, 71%).

14 (60 mg, 90 umol) was then dissolved in 1 ml of DCM and treated with 187 ul (2.3 mmol) of TFA and 480 ul (3 mmol) of Triethylsilane. After stirring at room temperature for 30 minutes, the mixture was azeotroped two times with toluene. The residue was then triturated with 3:1—Hexane:Ether to afford a crude solid which was then purified by reverse phase prep HPLC to afford 15 (40 mg, 46% over 2 steps). 300 MHz $^1$H NMR (CDCl$_3$) δppm): 9.01 (bs, 1H); 8.28 (d, 1H); 7.65 (m, 1H); 7.30 (t, 2H); 7.02 (t, 2H); 4.73 (m, 3H); 4.21 (d, 1H); 3.46-3.05 (b, 4H); 2.95 (s, 3H), 2.54 (d, 6H). MS=473 (M+1).

Example 4

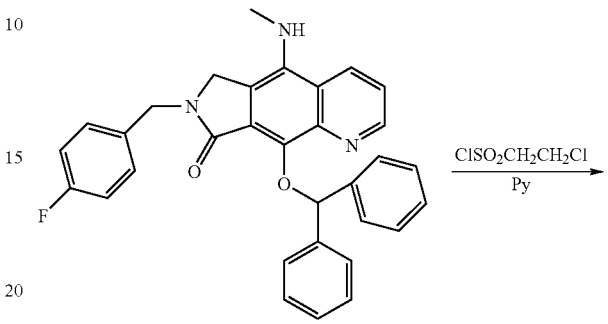

(1)

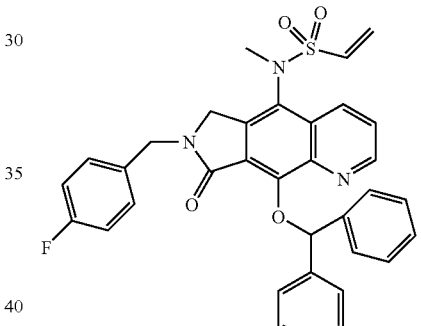

(8)

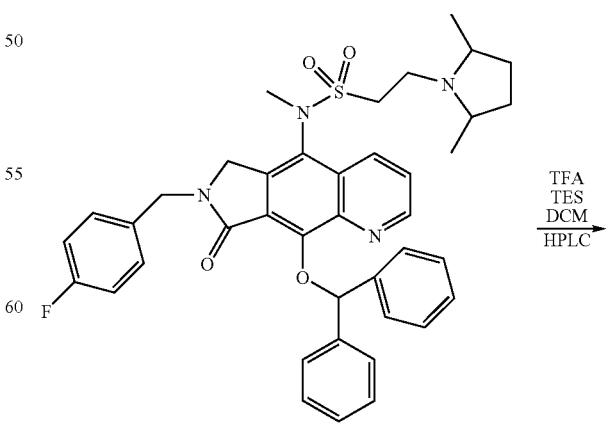

(9)

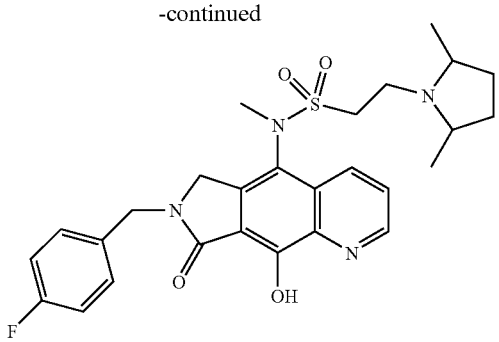

(10)

Compound (8) (300 mg, 596 μmol) was dissolved in 6 mL of pyridine and flashed with nitrogen, It was cold to 0° C. and added chloroethyl-sulfonyl chloride (188 μl, 1.8 mmol). The mixture was stirred for 10 min under nitrogen. The reaction was diluted with cold water and extracted with EtOAc, The organic phase was washed with 0.1N HCl and brine, dried over $Na_2SO_4$ and concentrated in vacuum to give crude product (8). It was precipitated out from ether/DCM. After drying, it gave clean product (8) as pale colored solid (443 mg). m/z=594.

The solid (8) (36 mg, 0.06 mmol) was dissolved in 1 mL of THF. Amine (0.1 mL) was added. The reaction mixture was stirred at room temperature for 2 hours under nitrogen. The reagent and solvent were removed under reduced pressure evaporation. The residue was solidified with hexane to give desired product (9).

The deprotection of DPM group at C8-OH to compound (10) was carried out as in Example 2. The resulting residue was then purified by reverse-phase prep HPLC. It gave 26 mg (57% yield) of (10) as bis-TFA salt. 300 MHz $^1$H NMR $(CD_3OD)$ δ (ppm): 8.9 (d, 1H); 8.5, 8.4 (d & d, 1H); 7.7 (m, 1H); 7.4 (m, 2H); 7.1 (m, 2H); 5.0-4.0 (m, 6H); 4.0 (m, 2H); 3.6-1.2 (m, complicated peaks). $^{19}$F NMR (ppm): −76. m/z=527 (M+1).

Examples 5, 6, 7

Representative Procedure for the Synthesis of Compounds 5002a-d

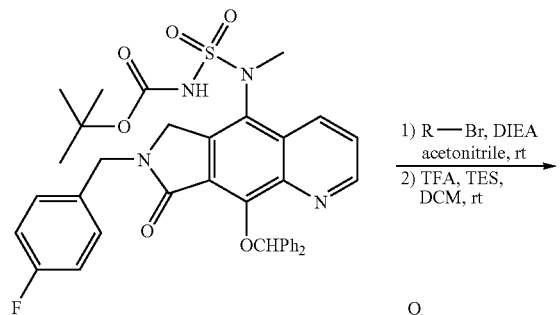

5001

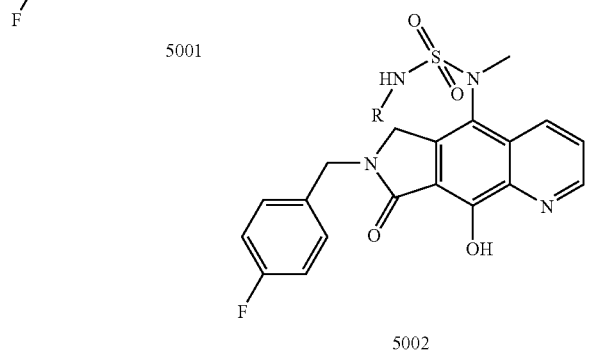

5002

| | R group | Example |
|---|---|---|
| 5002a) | $CH_2(C_6H_5)$ | 5 |
| 5002b) | $CH_2(p-C_5H_5N)$ | 6 |
| 5002c) | 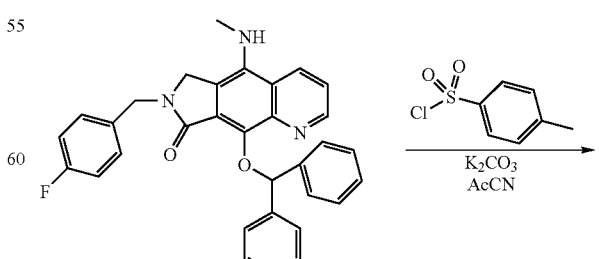 | 7 |

To 60 mg of sulfonyl urea 5001 in 2 ml acetonitrile at rt was added 47 uL DIEA, followed by 32 uL of benzyl bromide (0.3 mmol, 3 equiv). After 3 h the reaction was shown to be complete by LC/MS, and the reaction was diluted with 50 mL ethyl acetate. The organics were washed with 25 mL water and then 25 mL aq. brine solution. After drying over $Na_2SO_4$, solvent was removed by rotary evaporation to give 37 mg of the alkylated sulfonyl urea intermediate as an orange oil. Treatment of this product material with excess TFA and TES in a 1.0M solution of DCM resulted in global deprotection of the BOC and DPM protecting groups. 14 mg (31% yield over 2 steps) of the mono-alkylated sulfonyl urea product 5002a as the TFA salt was recovered after purification by reverse phase HPLC.

5002a—: 300 MHz $^1$H NMR $(CDCl_3)$ δ (ppm): 9.1 (d, 1H), 8.5 (d, 1H), 7.7 (m, 1H), 7.3 (m, 2H), 7.2 (t, 1H), 7.1 (m, 2H), 7.0 (t, 2H), 6.1 (s, 1H), 5.0 (s, 1H), 4.9-4.5 (dd, 2H), 4.7-4.3 (dd, 2H), 4.2 (s, 2H). 2.78 (s, 3H). m/z=507 (M+H).

5002b—(GS-331475): 300 MHz $^1$H NMR $(CD_3OD)$ δ (ppm): 8.9 (d, 1H), 8.8 (d, 1H), 7.8 (m, 1H), 7.4 (m, 2H), 7.1 (t, 2H), 4.9 (d, 2H), 4.5 (d, 2H), 3.2 (s, 3H). m/z=508 (M+H).

5002c—(GS-331572): 300 MHz $^1$H NMR $(CD_3OD)$ δ (ppm): 9.0 (s, 1 h), 8.9 (d, 1H), 7.9 (d, 1H), 7.6 (m, 1H), 7.5 (m, 3H), 7.2 (t, 1H), 7.1 (t, 2H), 4.8 (d, 2H), 4.5 (d, 2H), 3.3 (s, 3H), 3.2 (s, 3H). m/z 583 (m+H).

Example 9

(1)

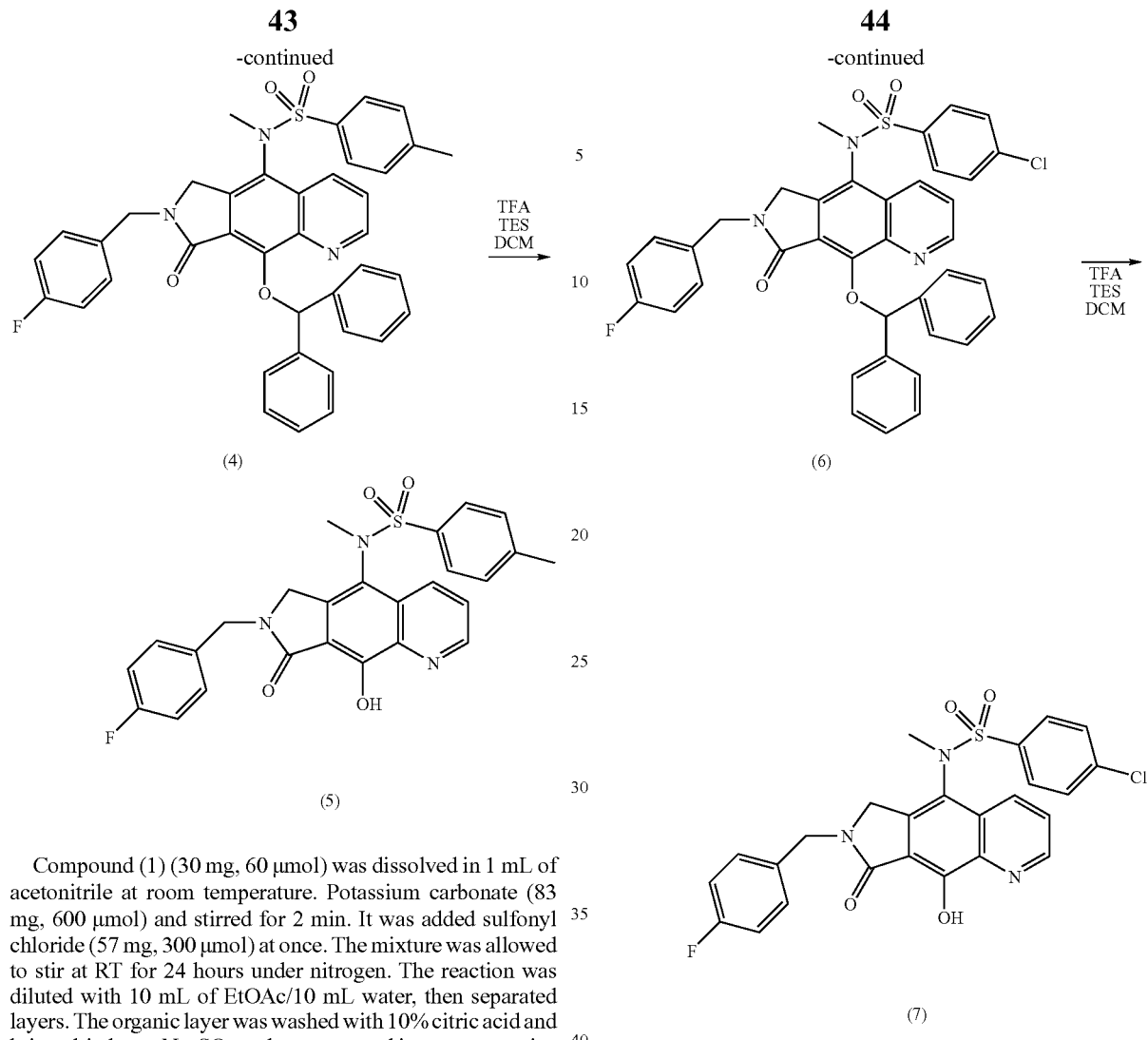

Compound (1) (30 mg, 60 μmol) was dissolved in 1 mL of acetonitrile at room temperature. Potassium carbonate (83 mg, 600 μmol) and stirred for 2 min. It was added sulfonyl chloride (57 mg, 300 μmol) at once. The mixture was allowed to stir at RT for 24 hours under nitrogen. The reaction was diluted with 10 mL of EtOAc/10 mL water, then separated layers. The organic layer was washed with 10% citric acid and brine, dried over $Na_2SO_4$ and concentrated in vacuum to give crude product (4). The crude product was purified by combiflash with EtOAc/Hexane.

The deprotection of DPM group at C8-OH was carried out as in Example 2. The resulting residue was triturated with ether/hexane to generate yellow solid of (5), as free base (15.0 mg, 51% in yield. 300 MHz $^1$H NMR (CDCl$_3$) δ (ppm): 9.0 (d, 1H); 8.0 (d, 1H); 7.6 (m, 2H); 7.5 (m, 1H); 7.3 (m, 4H); 7.1 (t, 2H); 4.8-4.5 (q, 2H); 4.2-4.0 (q, 2H); 3.2 (s, 3H); 2.4 (s, 3H). $^{19}$F NMR (ppm): −76.2; −114.3. m/z=492 (M+1).

Example 10

The experiment was carried out as described previously. The resulting residue was triturated with ether/hexane to generate yellow solid of (7) as free base (15.0 mg, 49% in yield. 300 MHz $^1$H NMR (CDCl$_3$) δ (ppm): 9.0 (d, 1H); 8.0 (d, 1H); 7.6 (m, 2H); 7.6 (m, 1H); 7.4 (m, 2H); 7.4 (m, 2H); 7.1 (t, 2H); 4.8-4.6 (q, 2H); 4.2-4.0 (q, 2H); 3.3 (s, 3H). $^{19}$F NMR (ppm): −76. m/z=512, 514, 515.

Example 11

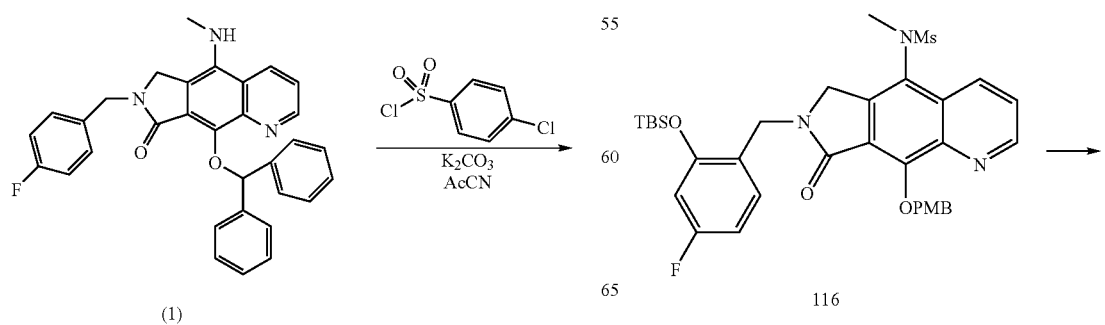

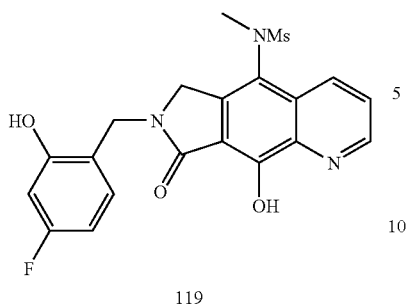

119

Phenol 119 was made in a similar fashion as described elsewhere.

300 MHz $^1$H NMR (CDCl$_3$) δ (ppm) 9.07 (d, J=5.3 Hz, 1H), 8.38 (d, J=8.1 Hz, 1H), 7.73 (dd, J$_1$=12.4 Hz, J$_2$=6.8 Hz, 1H), 7.23-7.18 (m, 1H), 6.72 (d, J=10.8 Hz, 1H), 6.64-6.60 (m, 1H), 4.96 (d, J=17.7 Hz, 1H), 4.86 (d, J=15.6 Hz, 1H), 4.71 (d, J=17.4 Hz, 1H), 4.48 (d, J=15.0 Hz, 1H), 3.36 (s, 3H), 3.13 (s, 3H).

300 MHz $^{19}$F NMR (CDCl$_3$) δ (ppm) −111.40, −76.14 (TFA salt).

MS: 432.06 (M+1).

Example 12

2-Bromo-7-(4-fluoro-benzyl)-5,9-dihydroxy-pyrrolo[3,4-g]quinoline-6,8-dione 1008

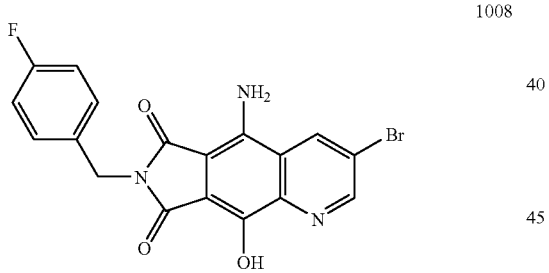

1008

Following the literature procedure of M.-D. Le Bas et al. (*Synthesis* 2001, 16, p. 2495), 100 ml CCl$_4$ was mixed with 250 ml of an aqueous NaOCl solution. To this mixture was added 40 mg of RuO$_2$, followed by 3 g 3-bromoquinoline dissolved in 50 ml CCl$_4$. Additional 30 ml portions of bleach were added at 2, 4, and 6 h. After 24 h, the aqueous layer was collected and acidified to pH 1 with 3N HCl. The aqueous layer was then extracted with ethyl acetate, dried over Na$_2$SO$_4$ and volatiles removed by evaporation to give the 1.7 g product as a yellow resin, (48% yield). $^1$H NMR and MS data matched that reported in the literature.

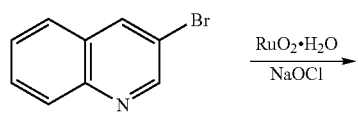

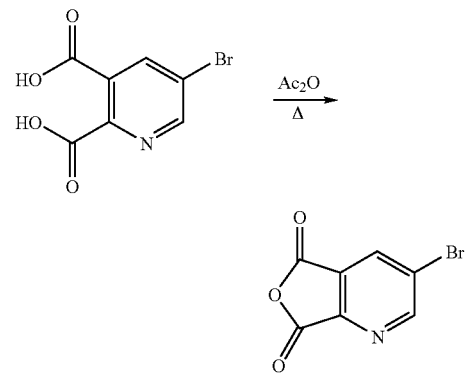

The resulting anhydride, 1 g, was then carried through the previously reported multistep sequence to afford the corresponding cyano-ester.

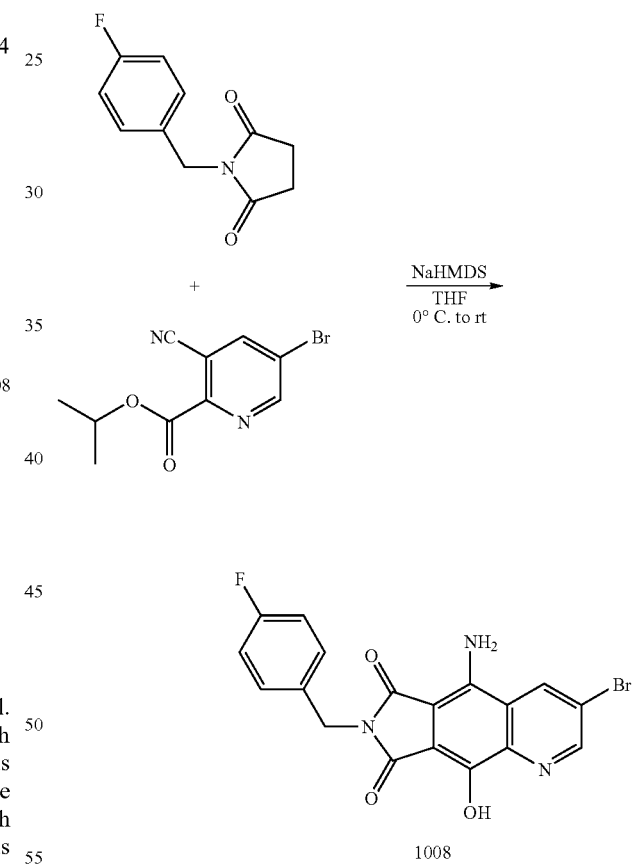

1008

Dieckmann condensation between 80 mg (0.3 mmol) of the ester and 80 mg (3.6 mmol) of the imide utilizing 900 uL LiHMDS in 2 ml dry THF gave the crude product.

After the typical work-up, approximately 60 mg (30%) of unpurified product was obtained as a yellow solid which was further refined by trituration with diethyl ether to provide 2 mg highly pure product 1008.

¹H NMR (300 MHz, d₆-DMSO) δ 9.20 (d, 1H), 9.05 (d, 1H) and 4.85 (s, 2H) ppm, MS=416.1 (M+H).

Example 13, 14, 15, 16

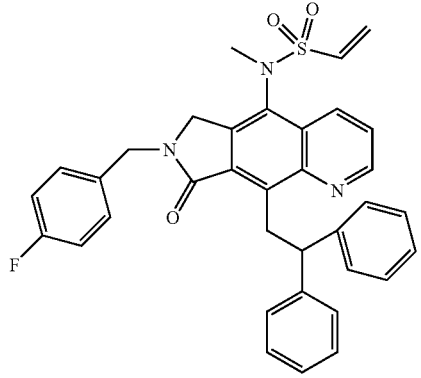
(8)

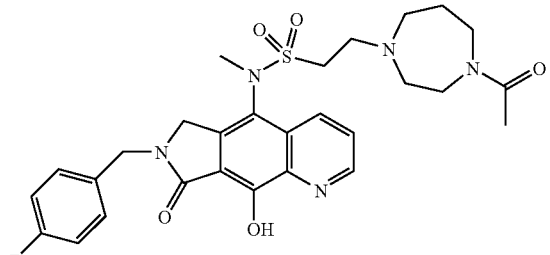

Product List:

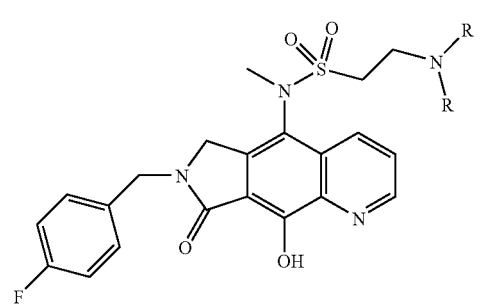
11

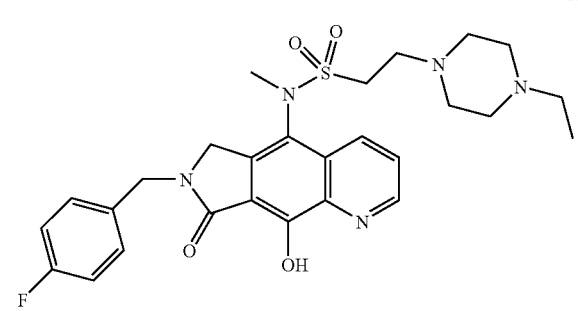
12

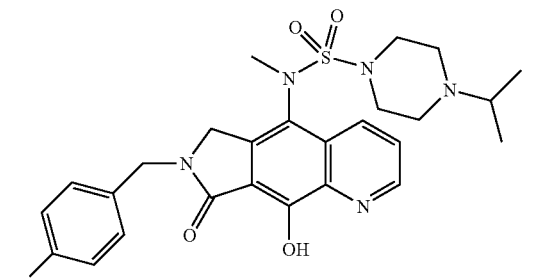
13

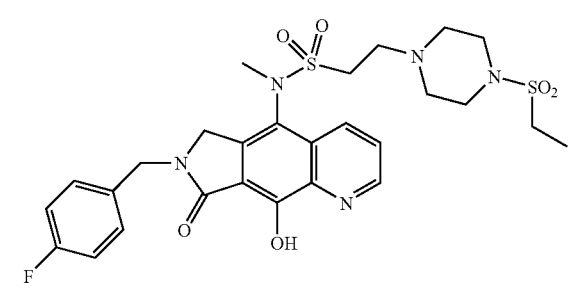
14

General procedure for the alkylation on terminal amine:

The solid (8) (30 mg, 0.05 mmol) was dissolved in 1 mL of THF. Amine (5 eq.) was added. The reaction mixture was stirred at room temperature for 2 hours under nitrogen. The reagent and solvent were removed under reduced pressure evaporation. The residue was solidified with hexane to give desired intermediates. The deprotection of DPM group at C8-OH to desired compounds was carried out as in Example 2. The resulting residue was then purified by reverse-phase prep HPLC.

From N-ethyl-piperazine, it gave 34.1 mg (89% yield) of 11 as tris-TFA salt. 300 MHz ¹H NMR (CD₃OD) δ (ppm): 8.9 (d, 1H); 8.6 (d, 1H); 7.8 (m, 1H); 7.4 (m, 2H); 7.1 (t, 2H); 4.8-4.5 (m, 4H); 3.6-3.4 (m, 4H); 3.3 (m, 6H); 3.2-2.9 (m, 8H); 1.3 (t, 3H). ¹⁹F NMR (ppm): −78.0; −117.2. m/z=542 (M+1).

From N-ethylsulfonyl-piperazine, it gave 34.3 mg (82% yield) of 12 as tris-TFA salt. 300 MHz ¹H NMR (CD₃OD) δ (ppm): 8.9 (d, 1H); 8.5 (d, 1H); 7.8 (m, 1H); 7.4 (m, 2H); 7.1 (t, 2H); 4.8 (d, 2H); 4.7-4.5 (q, 2H); 4.0-3.2 (m, 15H); 3.1 (q, 2H); 1.3 (t, 3H). ¹⁹F NMR (ppm): −77.7; −117.2. m/z=606 (M+1).

From N-acetyl-homo-piperazine, it gave 33.3 mg (83% yield) of 13 as tris-TFA salt. 300 MHz ¹H NMR (CD₃OD) δ (ppm): 8.9 (d, 1H); 8.6 (d, 1H); 7.8 (m, 1H); 7.4 (m, 2H); 7.1 (t, 2H); 4.8-4.5 (m, 4H); 4.0-3.5 (m, 8H); 3.4 (s, 3H); 2.2 (m, 2H); 2.1 (s, 3H). ¹⁹F NMR (ppm): −77.6; −117.2. m/z=570 (M+1).

From N-isopropyl-piperazine, it gave 35.3 mg (90% yield) of 14 as tris-TFA salt. 300 MHz ¹H NMR (CD₃OD) δ (ppm): 8.9 (d, 1H); 8.6 (d, 1H); 7.4 (m, 2H); 7.1 (t, 2H); 4.8-4.5 (m, 4H); 3.6-3.4 (m, 4H); 3.3 (s,s, 3H); 3.1 (m, 4H);

2.9 (t, 2H); 2.7-2.4 (m, 2H); 1.3 (s,s, 6H). $^{19}$F NMR (ppm): −77.8; −117.2. m/z=556 (M+1).

Example 17

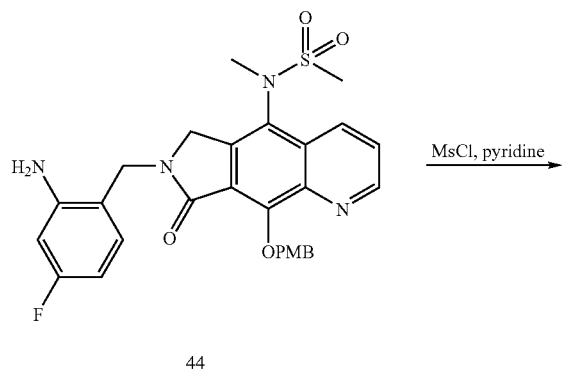

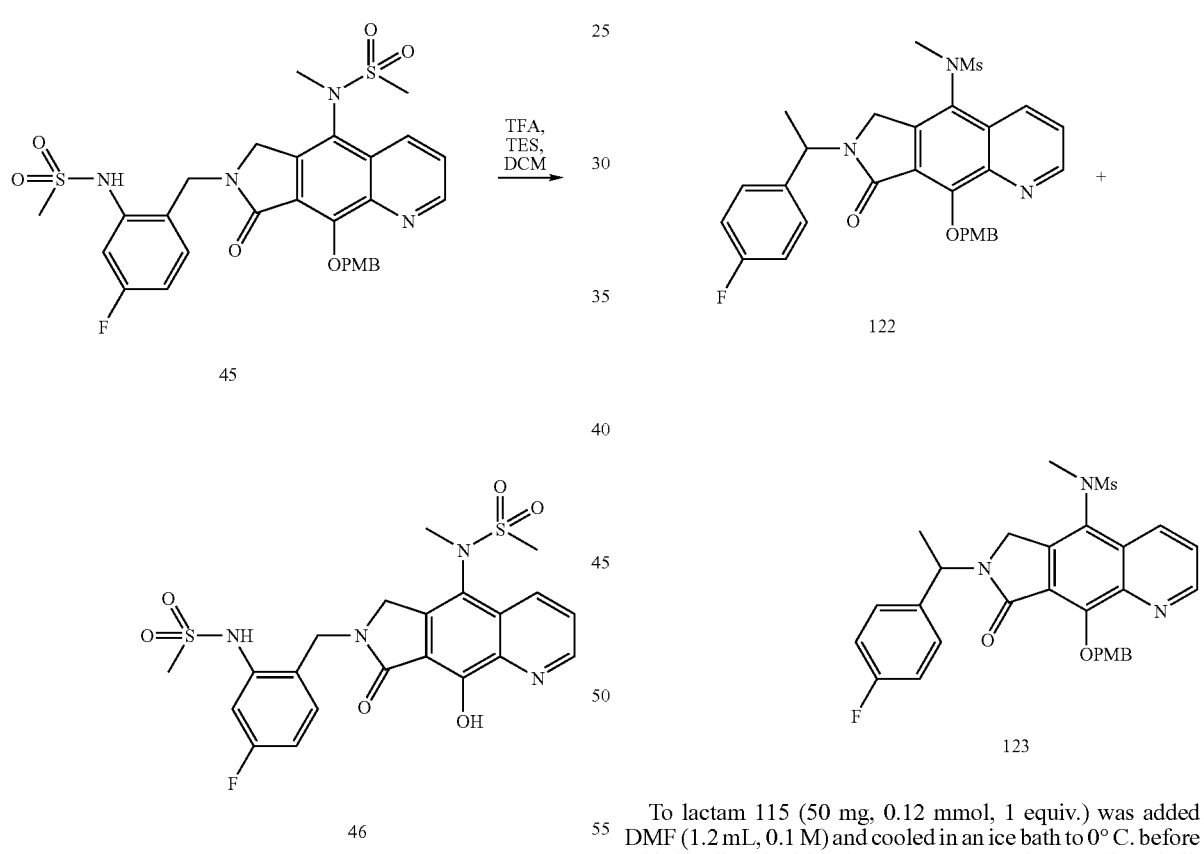

45: To a solution of the intermediate 44 (20 mg, 0.036 mmol) dissolved in pyridine (0.360 mL) was added methanesulfonyl chloride (5.6 µL, 0.073 mmol). The reaction was stirred at room temperature under an inert atmosphere for 2 hours, upon which it was diluted with ethyl acetate and quenched with H$_2$O. The organic layer was washed with 10% Citric acid solution, H$_2$O, then brine, and dried (over Na$_2$SO$_4$), filtered and concentrated in vacuo to afford the desired crude product 45 (20 mg) with no purification nor further characterization; MS: 629 (M+1).

46: The compound was made in a similar fashion as compound 3 to afford the desired product 46 (12 mg, 53%) as the TFA salt: 300 MHz $^1$H NMR (CDCl$_3$) δ (ppm) 9.52 (dd, 1H), 9.06 (dd, 1H), 8.32 (m, 1H), 7.73 (m, 1H), 7.4-7.3 (m, 2H), 6.85 (m, 1H), 4.95-4.45 (m, 4H), 3.36 (s, 3H), 3.16 (s, 3H), 3.12 (s, 3H); 300 MHz $^{19}$F NMR (CDCl$_3$) δ (ppm) −76.21, −109.75; MS: 509 (M+1).

Example 18, 19

To lactam 115 (50 mg, 0.12 mmol, 1 equiv.) was added DMF (1.2 mL, 0.1 M) and cooled in an ice bath to 0° C. before added sodium hydride (5.5 mg, 0.14 mmol, 60% mineral oil, 1.2 equiv.) and stirred for 5 minutes under nitrogen atmosphere. Bromide 121 (50 mg, 0.17 mmol, 1.5 equiv) was added and the reaction was allowed to stir for 30 minutes at 0° C. The reaction was quenched with water and diluted with Ethyl Acetate. The organic layer was washed with water and brine before being dried over sodium sulfate, filtered and concentrated in vacuo. The crude residue was purified by silica gel chromatography eluting with 4/1 EtOAc/Hexanes to afford the desired products 122 diastereomer A (first to elute off column) and 123 diastereomer B (second to elute of column) 121.

See below after PMB deprotection for compound characterization.

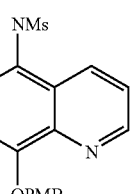
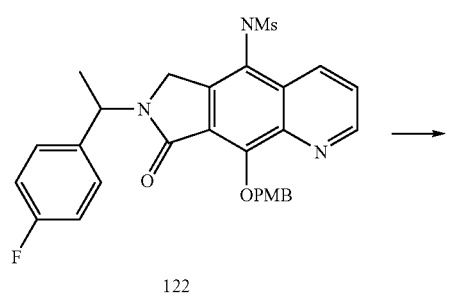

122

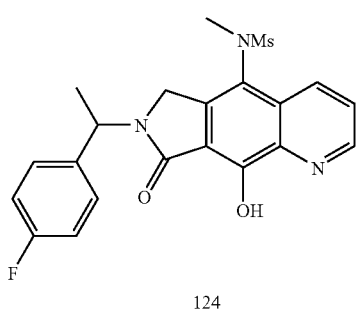

124

Phenol 124 was made in a similar fashion as described elsewhere.

300 MHz $^1$H NMR (CDCl$_3$) δ (ppm) 9.07 (d, J=3.9 Hz, 1H), 8.32 (d, J=8.4 Hz, 1H), 7.71 (dd, J$_1$=4.2 Hz, J$_2$=3.6 Hz, 1H), 7.40-7.35 (m, 2H), 7.11-7.05 (m, 2H), 5.79 (q, J=6.6 Hz, 1H), 4.81 (d, J=17.1 Hz, 1H), 4.12 (d, J=16.8 Hz, 1H), 3.37 (d, J=12.4 Hz, 1H), 3.08 (d, J=25.9 Hz, 1H), 1.76 (d, J=6.9 Hz, 1H).

300 MHz $^{19}$F NMR (CDCl$_3$) δ (ppm) −111.59, −76.24 (TFA salt).

MS: 432.10 (M+1).

123

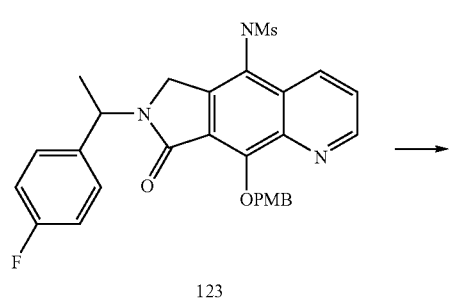

125

Phenol 125 was made in a similar fashion as described elsewhere

300 MHz $^1$H NMR (CDCl$_3$) δ (ppm) 9.07 (d, J=3.9 Hz, 1H), 8.37-8.31 (d, J=8.4 Hz, 1H), 7.71 (dd, J$_1$=5.1 Hz, J$_2$=4.5 Hz, 1H), 7.47-7.27 (m, 2H), 7.10-7.07 (m, 2H), 5.79 (q, J=6.3 Hz, 1H), 4.81 (d, J=18.0 Hz, 1H), 4.47 (s, 2H), 4.12 (d, J=16.8 Hz, 1H), 3.37 (d, J=24.6 Hz, 1H), 3.08 (d, J=25.2 Hz, 1H), 1.76 (dd, J$_1$=3.0 Hz, J$_2$=2.7 Hz, 1H).

300 MHz $^{19}$F NMR (CDCl$_3$) δ (ppm) −111.59, −76.24 (TFA salt).

MS: 432.10 (M+1).

Example 20, 21, 22

Representative procedure for the synthesis of compounds 5008a-c.

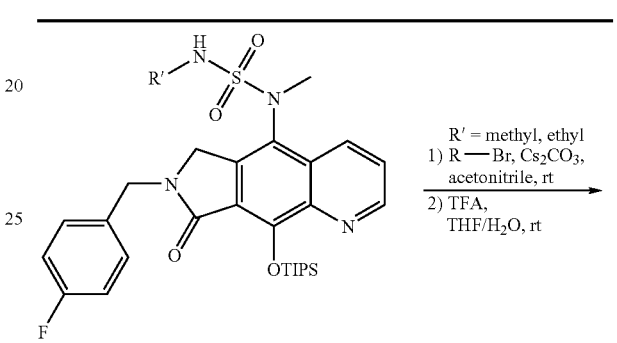

5005

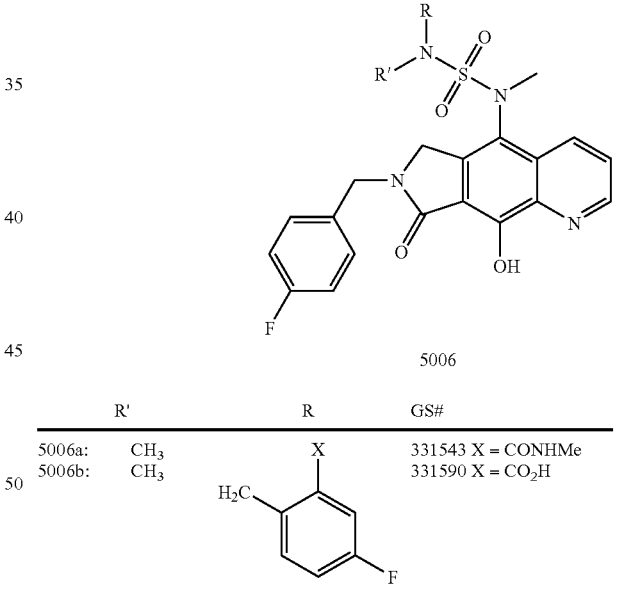

5006

| | R' | R | GS# |
|---|---|---|---|
| 5006a: | CH$_3$ | X | 331543 X = CONHMe |
| 5006b: | CH$_3$ | | 331590 X = CO$_2$H |
| 5006c: | Et | Et | 331697 |

To 100 mg of sulfonyl urea 5005 in 4 mL acetonitrile at rt was added 261 mg Cs$_2$CO$_3$ (0.8 mmol, 5 equiv.), followed by 38 uL of iodoethane (0.5 mmol, 3 equiv). After 18 h the reaction was shown to be complete by LC/MS, and the reaction was diluted with 50 mL ethyl acetate. The organics were washed with 25 mL 0.1 M HCl, 25 mL water, and then 25 mL aq. brine solution. After drying over Na$_2$SO$_4$, solvent was removed by rotary evaporation to give 112 mg of the alkylated sulfonyl urea intermediate. Treatment of this product material with excess TFA in a 1.0M solution of THF resulted in deprotection of TIPS protecting group. 34 mg (43% yield over 2 steps) of the bis-alkylated sulfonyl urea product 5006c as the TFA salt was recovered after purification by reverse phase HPLC.

5006a—: 300 MHz $^1$H NMR (CD$_3$OD) δ (ppm): 8.9 (d, 1H), 8.8 (d, 1H), 8.4 (s, 1H), 7.8 (m, 1H), 7.4 (m, 4H), 7.2 (d, 2H), 7.1 (t, 2H), 4.9 (d, 2H), 4.5 (d, 2H), 3.4 (s, 3H), 3.3 (s, 3H), 3.2 (s, 3H). m/z=596 (M+H).

5006b—: 300 MHz $^1$H NMR (CDCl$_3$) δ (ppm): 9.2 (s, 1H), 8.9 (d, 1H), 7.9 (m, 1H), 7.7 (d, 1H), 7.5 (m, 1H), 7.3 (m, 4H), 7.0 (t, 2H), 4.9-4.5 (dd, 2H), 4.7-4.3 (dd, 2H), 4.2 (s, 2H), 3.3 (s, 3H), 2.9 (s, 3H). m/z=583 (m+H).

5006c—: 300 MHz $^1$H NMR (CDCl$_3$) δ (ppm): 9.2 (s, 1H), 8.8 (d, 1H), 7.8 (m, 1H), 7.4 (t, 2H), 7.1 (t, 2H), 4.9-4.5 (dd, 2H), 4.7-4.3 (dd, 2H), 3.4 (m, 4H), 3.1 (s, 3H), 1.2 (m, 6H). m/z=473 (M+H).

Example 23

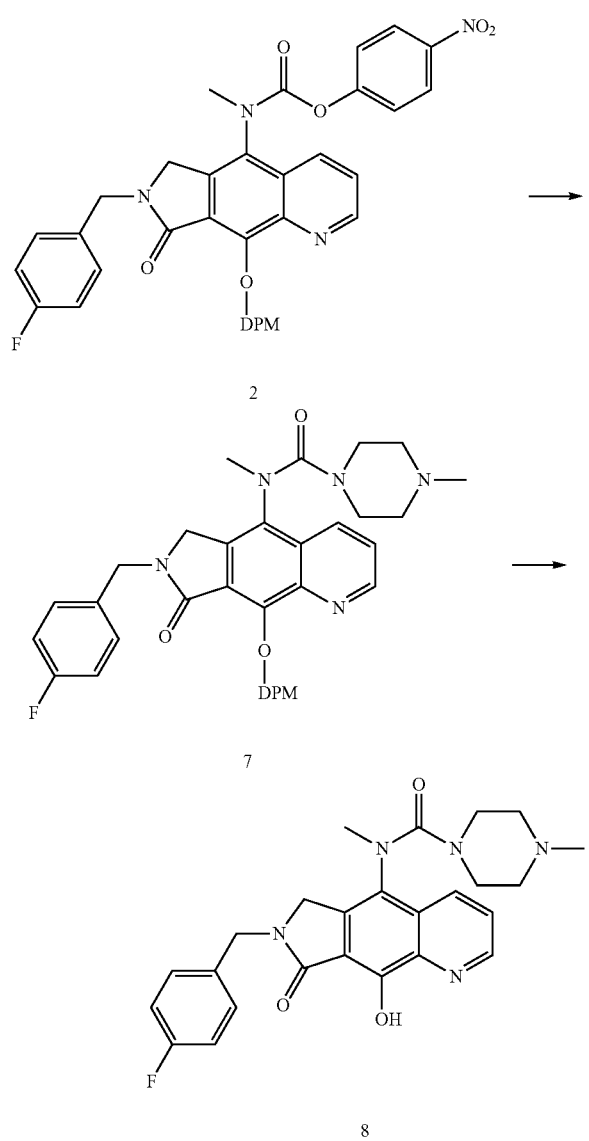

Intermediate 2 (50 mg, 75 umol) was dissolved in 500 uL of neat N-Methylpiperazine, after which the reaction was heated to 150° C. using microwave heating. After stirring at 150° C. for 2 hours, the reaction was diluted with Ethyl Acetate. The organic was then washed once with water and once with Brine. The organic was dried over Mg$_2$SO$_4$ and concentrated in vacuo. The crude residue was then purified by silica gel chromatography (6:2:1:1—Ethyl Acetate:Methanol:Acetic Acid:Water) to afford 7 (20 mg, 42%).

7 (20 mg, 32 umol) was then dissolved in 400 umol of DCM and treated with 30 ul (400 umol) of TFA and 31 ul (160 umol) of Triethylsilane. After stirring at room temperature for 30 minutes, the mixture was azeotroped two times with toluene. The residue was then triturated with 3:1—Hexane:Ether to afford 8 (8 mg, 43%). 300 MHz $^1$H NMR (CDCl$_3$) δ (ppm): 9.05 (bs, 1H); 8.20 (d, 1H); 7.69 (m, 1H); 7.48 (t, 2H); 7.37 (b, 2H), 7.08 (t, 2H); 4.76 (s, 2H); 4.20 (m, 4H); 3.50 (s, 3H); 3.20-3.0 (b (8H); 3.16 (s, 3H). MS=464 (M+1)

Example 24

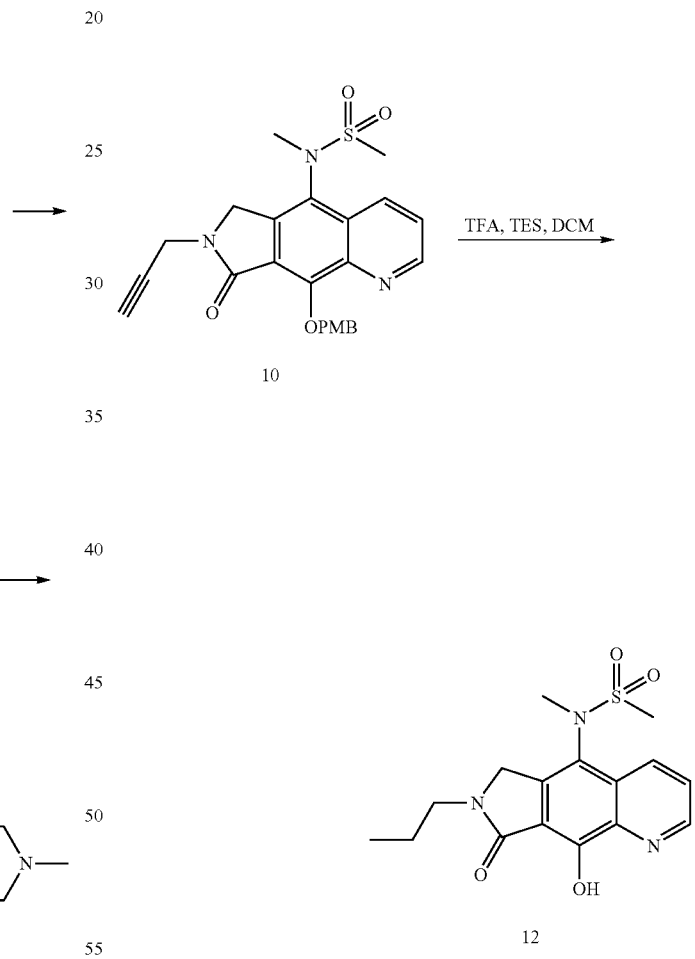

3: A solution of intermediate 2 (29 mg, 0.056 mmol) in dichloromethane (0.5 mL) was treated with trifluoroacetic acid (0.1 mL) and triethylsilane (0.05 mL). The reaction mixture was stirred at room temperature under an inert atmosphere for 30 minutes upon which the mixture was azeotroped with toluene/THF repeatedly. The reaction resulted in a mixture of products of which 12 was an isolatable species. The solid was purified by reversed phase HPLC to afford 12 (2.5 mg) as the TFA salt: 300 MHz $^1$H NMR (CD$_3$OD) δ (ppm) 8.97 (dd, 1H), 8.66 (dd, 1H), 7.83 (m, 1H), 4.74 (dd, 2H), 3.61

(t, 2H), 3.40 (s, 3H), 3.23 (s, 3H), 1.76 (m, 2H), 1.01 (t, 3H); 300 MHz $^{19}$F NMR (CD$_3$OD) δ (ppm) −78.01; MS: 350 (M+1).

Example 25

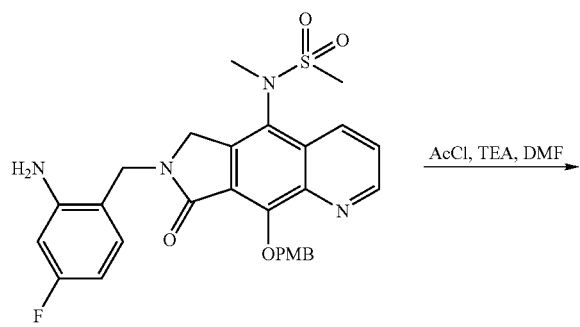

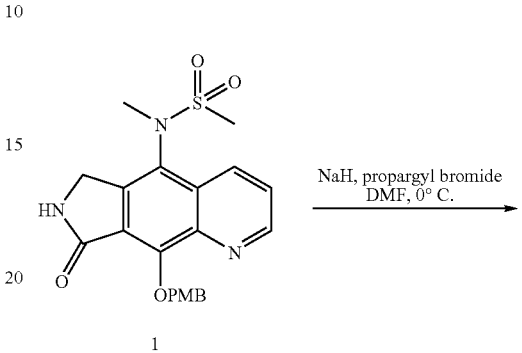

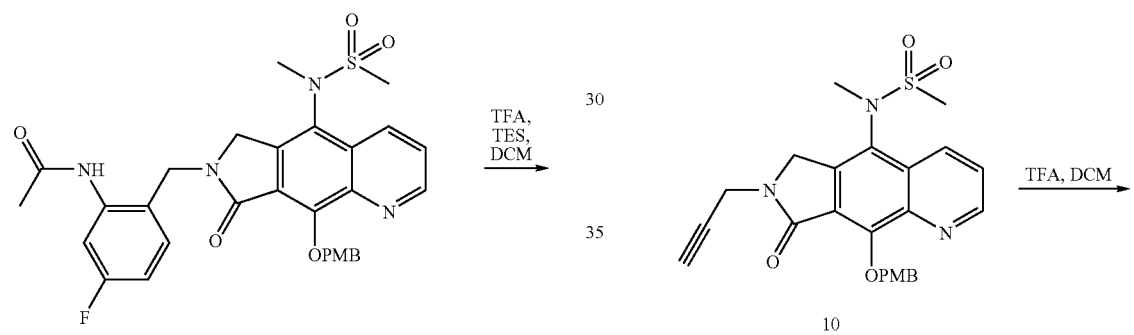

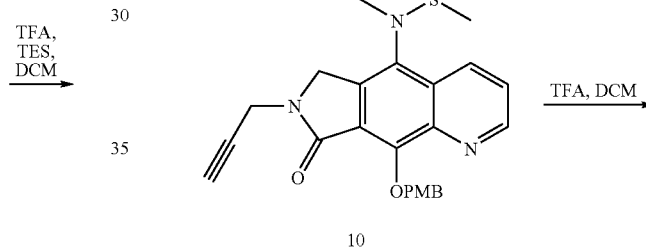

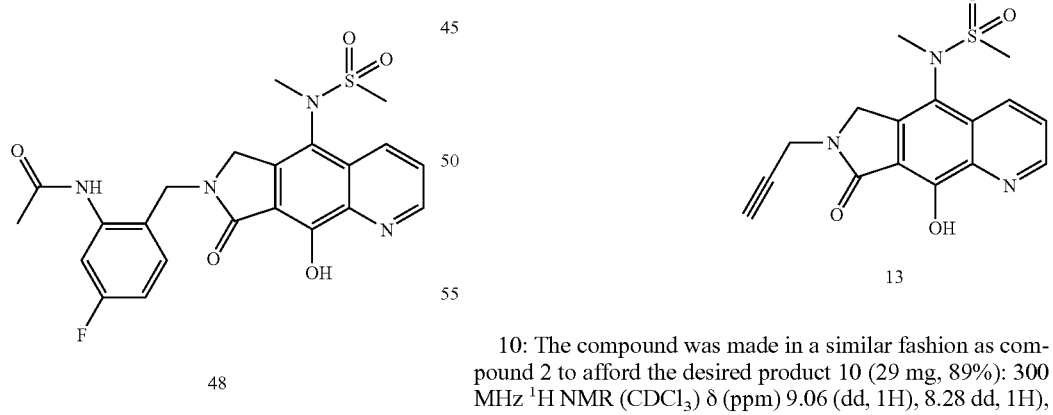

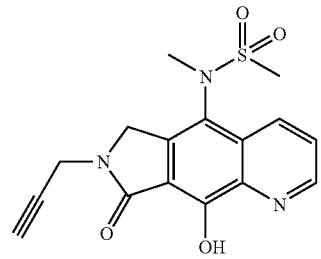

47: To a solution of the intermediate 44 (23 mg, 0.042 mmol) dissolved in DMF (0.418 mL) was added triethylamine (23 μL, 0.167 mmol) and acetyl chloride (6 μL, 0.084 mmol). The reaction was sluggish at room temperature so xs reagents were added and the mixture was heated to 50° C. while stirring for 48 hours upon which it was diluted with ethyl acetate and quenched with H$_2$O. The organic layer was washed with H$_2$O, aqueous LiCl, then brine, and dried (over Na$_2$SO$_4$), filtered and concentrated in vacuo. The crude residue was purified by chromatography on silica gel (3/1—ethyl acetate/hexane) to afford the desired product 47 (25 mg, >100% contaminated with starting material) with no further characterization: MS: 593 (M+1).

Example 26

10: The compound was made in a similar fashion as compound 2 to afford the desired product 10 (29 mg, 89%): 300 MHz $^1$H NMR (CDCl$_3$) δ (ppm) 9.06 (dd, 1H), 8.28 dd, 1H), 7.62 (m, 3H), 6.87 (d, 2H), 5.76 (m, 2H), 5.57 (d, 2H), 4.75 (d, 1H), 4.50 (d, 1H), 3.80 (s, 3H), 3.40 (s, 3H), 3.14 (s, 3H); MS: 466 (M+1).

11: The compound was made in a similar fashion as compound 3 except no triethylsilane was added to the reaction to afford the desired product 11 (11 mg, 38%) as the TFA salt: 300 MHz $^1$H NMR (CD$_3$OD) δ (ppm) 8.99 (dd, 1H), 8.67 (dd, 1H), 7.86 (m, 1H), 4.8 (dd, 2H), 4.47 (d, 2H), 3.41 (s, 3H), 3.24 (s, 3H), 2.82 (m, 1H); 300 MHz $^{19}$F NMR (CD$_3$OD) δ (ppm) −78.11; MS: 346 (M+1).

Example 27

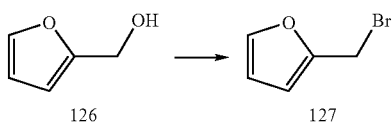

To benzyl alcohol 126 (1000 mg, 10.12 mmol, 1 equiv.) was added diethyl ether (40 mL, 0.25 M) and to it added phosphorus tribromide (960 μL, 10.12 mmol, 1 equiv.). The mixture was stirred under an inert atmosphere for several hours and then quenched with water and extracted with ether. The organic layer was washed with water, saturated sodium bicarbonate solution and brine before being dried over sodium sulfate. The material was concentrated in vacuo with a bath at 0° C. to obtain volatile bromide 127.

Material was not characterized but used in next reaction immediately.

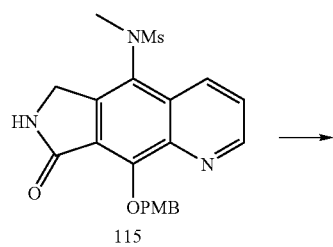

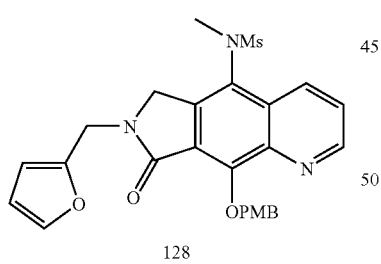

To lactam 115 (25 mg, 0.058 mmol, 1 equiv.) was added DMF (3 mL) and cooled in an ice bath to 0° C. before added sodium hydride (2.5 mg, 0.058 mmol, 60% mineral oil, 1 equiv.) and stirred for 5 minutes under nitrogen atmosphere. Bromide 127 (107 mg, 0.34 mmol, 1.2 equiv.) was added and the reaction was allowed to stir for 30 minutes at 0° C. The reaction was quenched with water and diluted with Ethyl Acetate. The organic layer was washed with water and brine before being dried over sodium sulfate, filtered and concentrated in vacuo. The crude residue was purified by silica gel chromatography eluting with 4/1 EtOAc/Hexanes to afford the desired product 128.

MS: 508.14 (M+1).

Example 28

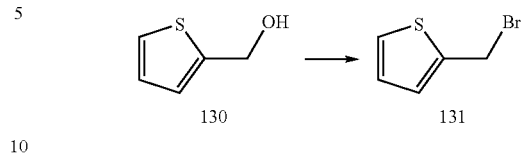

To alcohol 130 (500 mg, 4.38 mmol, 1 equiv.) was added diethyl ether (40 mL, 0.1 M) and to it added phosphorus tribromide (413 μL, 4.38 mmol, 1 equiv.). The mixture was stirred under an inert atmosphere for several hours and then quenched with water and extracted with ether. The organic layer was washed with water, saturated sodium bicarbonate solution and brine before being dried over sodium sulfate and concentrated in vacuo to obtain volatile bromide 131.

Because of instability of bromide 131, it was used immediately.

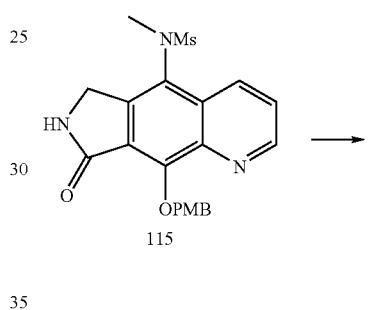

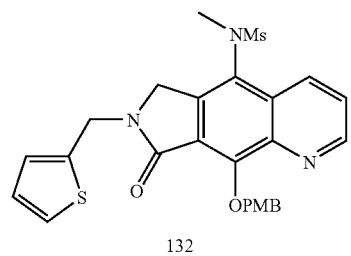

To lactam 115 (30 mg, 0.07 mmol, 1 equiv.) was added DMF (0.7 mL, 0.1 M) and cooled in an ice bath to 0° C. before added sodium hydride (3.7 mg, 0.091 mmol, 60% mineral oil, 1.3 equiv.) and stirred for 5 minutes under nitrogen atmosphere. Bromide 131 (1.40 ml, 0.14 mmol, 2 equiv., stock solution) was added and the reaction was allowed to stir for 30 minutes at 0° C. The reaction was quenched with water and diluted with Ethyl Acetate. The organic layer was washed with water and brine before being dried over sodium sulfate, filtered and concentrated in vacuo. The crude residue was purified by silica gel chromatography eluting with 4/1 EtOAc/Hexanes to afford the desired product 132.

See below for characterization after PMB deprotection.

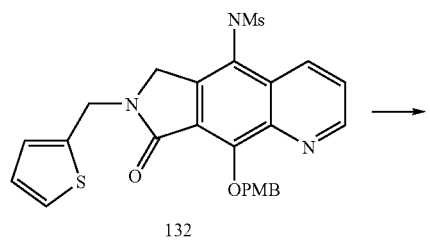

132

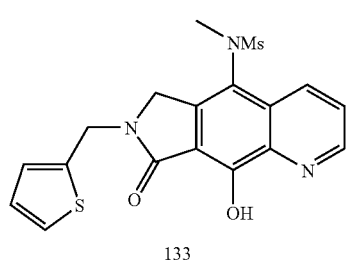

133

Phenol 133 was made in a similar fashion as described elsewhere

300 MHz $^1$H NMR (CDCl$_3$) δ (ppm) 9.07 (d, J=4.6 Hz, 1H), 8.37 (d, J=8.4 Hz, 1H), 7.71 (dd, J$_1$=4.2 Hz, J$_2$=18.2 Hz, 1H), 7.28-7.26 (s, 1H), 7.12-7.14 (s, 1H), 7.03-7.00 (m, 1H), 5.18 (d, J=15.3 Hz, 1H), 4.85 (d, J=15.0 Hz, 1H), 4.81 (d, J=15.0 Hz, 1H), 4.54 (d, 15.3 Hz, 1H), 3.34 (s, 1H), 3.09 (s, 1H).

300 MHz $^{19}$F NMR (CDCl$_3$) δ (ppm) −76.22.

MS: 404.06 (M+1).

Example 29

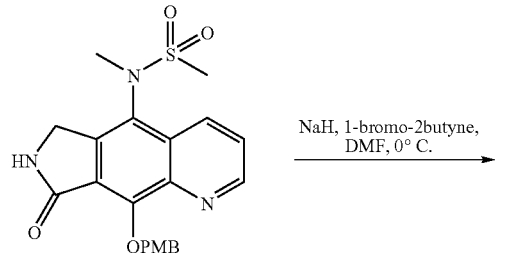

1 -

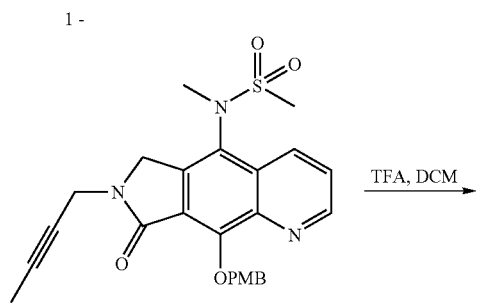

13

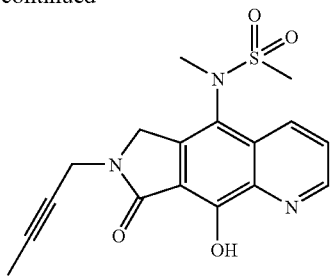

14

13: The compound was made in a similar fashion as compound 2, however the desired product was not purified by silica gel chromatography, instead isolated as the crude product 13 (35 mg): MS: 480 (M+1).

14: The compound was made in a similar fashion as compound 3 except no triethylsilane was added to the reaction to afford the desired product 14 (11 mg, 38%) as the TFA salt: 300 MHz $^1$H NMR (CDCl$_3$) δ (ppm) 9.11 (dd, 1H), 8.42 (dd, 1H), 7.73 (m, 1H), 4.85 (d, 1H), 4.65 (d, 1H), 4.50 (d. 1H), 4.30 (d, 1H), 3.41 (s, 3H), 3.14 (s, 3H), 1.86 (s, 3H); 300 MHz $^{19}$F NMR (CDCl$_3$) δ (ppm) −76.26; MS: 360 (M+1).

Example 30

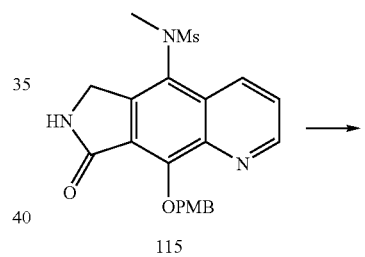

115

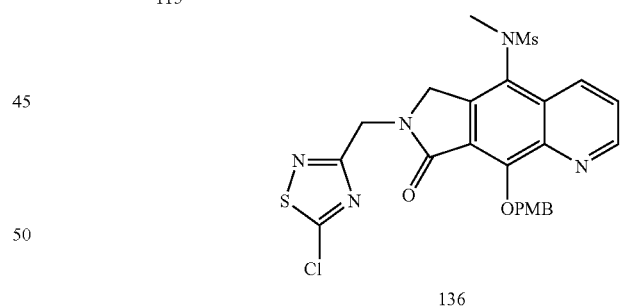

136

To lactam 115 (30 mg, 0.07 mmol, 1 equiv.) was added DMF (1 ml, 0.07 M) and cooled in an ice bath to 0° C. before sodium hydride (3.3 mg, 0.084 mmol, 60% mineral oil, 1.2 equiv.) was added and stirred for 5 minutes under a nitrogen atmosphere. 5-Chloro-3-chloromethyl-[1,2,4]thiadiazole (18 mg, 0.11 mmol, 1.5 equiv.) was added and the reaction was allowed to stir for 60 minutes at 0° C. The reaction was quenched with water and diluted with Ethyl Acetate. The organic layer was washed with water and brine before being dried over sodium sulfate, filtered and concentrated in vacuo. The crude residue was purified by silica gel chromatography eluting with 4/1 EtOAc/Hexanes to afford the desired product 136.

See below for characterization after PMB deprotection.

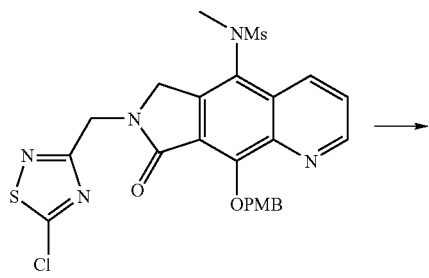

136

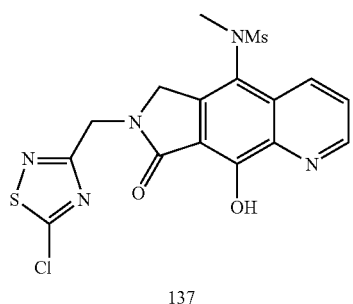

137

Phenol 137 was made in a similar fashion as described elsewhere

300 MHz $^1$H NMR (CDCl$_3$) δ (ppm) 9.05 (d, J=2.7 Hz, 1H), 8.33 (d, J=7.5 Hz, 1H), 7.70 (dd, J$_1$=4.4 Hz, J$_2$=4.5 Hz, 1H), 5.20 (d, J=16.9 Hz, 1H), 4.99 (d, J=6.5 Hz, 1H), 4.93 (d, J=6.5 Hz, 1H), 4.77 (d, J=16.9 Hz, 1H), 3.39 (s, 3H), 3.12 (s, 3H).

300 MHz $^{19}$F NMR (CDCl$_3$) δ (ppm) −76.23 (TFA salt).

MS: 440.05 (M+1).

Example 31

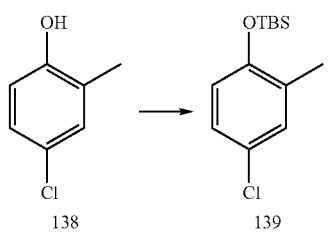

138    139

To phenol 138 (5 g, 35.06 mmol, 1 equiv.) was added CH$_2$Cl$_2$ (110 mL) and treated with triethylamine (7.33 mL, 52.59 mmol, 1.2 equiv.) and DMAP (856 mg, 7.02 mmol, 0.2 equiv.). TBSCl (6.34 g, 61.08 mmol, 1.2 equiv.) was slowly added and the reaction mixture was stirred at room temperature for 2 h under a nitrogen atmosphere. The reaction mixture was diluted with CH$_2$Cl$_2$ (400 mL) and quenched with water (200 mL). The layers were separated and the aqueous layer was extracted with ethyl acetate (200 mL). The combined organic layer was washed with water and brine then dried (over Na$_2$SO$_4$), filtered and concentrated in vacuo to obtain a clear oil of 139.

See below for characterization after bromination.

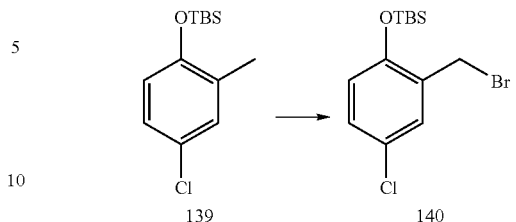

139    140

To 139 (10.14 g, 39.51 mmol, 1 equiv.) was added CCl$_4$ (160 mL, 0.25 M) and to it added N-Bromosuccinimide (7.0 g, 39.51 mmol, 1 equiv.) and benzoyl peroxide (955 mg, 3.95 mmol, 0.1 equiv.). The mixture was stirred under an inert atmosphere, refluxed and a ultra violet lamp shined to the reaction flask. The reaction was cooled and the solid filtered over a sintered funnel and the filtrate concentrated in vacuo. Purification was carried out by ISCO flash column chromatography was carried out with Hexanes to yield 140.

300 MHz $^1$H NMR (CDCl$_3$) δ (ppm) 7.31 (d, J=2.1 Hz, 1H), 7.13 (d, J=2.7 Hz, 1H), 6.73 (d, J=9 Hz, 1H), 4.45 (s, 2H), 1.05 (s, 9H), 0.29 (s, 6H).

R$_f$(100% Hexanes): 0.35

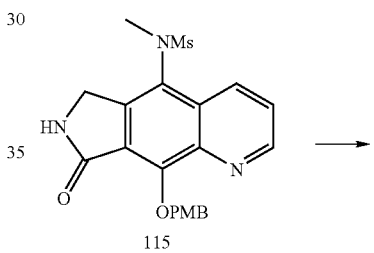

115

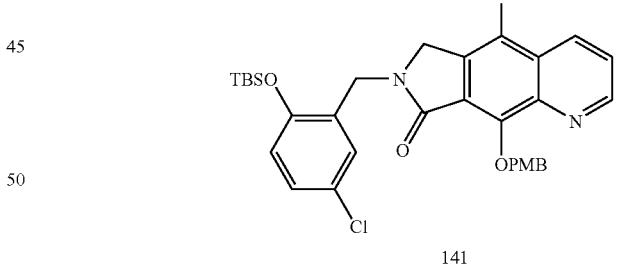

141

To lactam 115 (30 mg, 0.07 mmol, 1 equiv.) was added DMF (1 mL) and cooled in an ice bath to 0° C. before added sodium hydride (3.4 mg, 0.08 mmol, 60% mineral oil, 1.2 equiv.) and stirred for 5 minutes under a nitrogen atmosphere. Bromide 140 (70 mg, 0.21 mmol, 3 equiv.) was added and the reaction was allowed to stir for 30 minutes at 0° C. The reaction was quenched with water and diluted with Ethyl Acetate. The organic layer was washed with water and brine before being dried over sodium sulfate, filtered and concentrated in vacuo. The crude residue was purified by silica gel chromatography eluting with 4/1 EtOAc/Hexanes to afford the desired product 141.

See below for characterization after PMB deprotection.

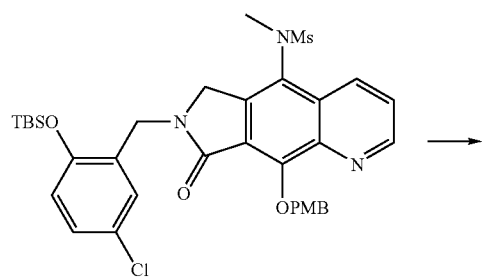

141

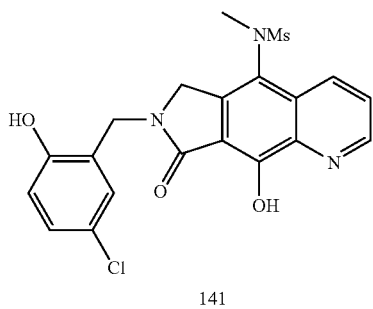

141

Bisphenol 141 was made in a similar fashion as described elsewhere.

300 MHz $^1$H NMR (CDCl$_3$) δ (ppm) 9.05 (d, J=4.2 Hz, 1H), 8.35 (d, J=8.7 Hz, 1H), 7.74 (dd, J$_1$=4.5 Hz, J$_2$=4.2 Hz, 1H), 7.23-7.20 (m, 2H), 6.94-6.92 (d, J=8.1 Hz, 1H), 4.95 (d, J=17.4 Hz, 1H), 4.92 (d, J=15.0 Hz, 1H), 4.67 (d, J=17.4 Hz, 1H), 4.47 (d, J=15.0 Hz, 1H), 3.37 (s, 3H), 3.14 (s, 3H).

300 MHz $^{19}$F NMR (CDCl$_3$) δ (ppm) −76.23 (TFA salt).

MS: 448.20 (M+1).

Example 32

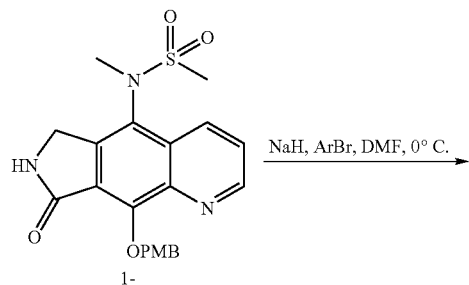
1-

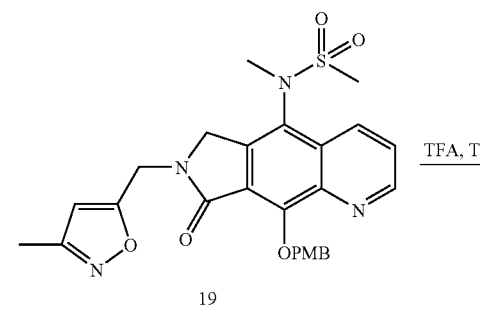
19

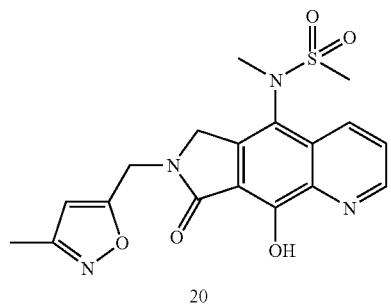
20

19: The compound was made in a similar fashion as compound 2 to afford the desired product 19 (30 mg, 82%): 300 MHz $^1$H NMR (CDCl$_3$) δ (ppm) 9.05 (dd, 1H), 8.45 (dd, 1H), 7.65 (m, 3H), 6.9 (m, 2H), 6.1 (s, 1H), 5.78 (m, 2H), 4.85 (m, 2H), 4.65 (m, 2H), 3.8 (s, 3H), 3.38 (s, 3H), 3.15 (s, 3H), 2.45 (s, 3H); MS: 523 (M+1).

20: The compound was made in a similar fashion as compound 18 to afford the desired product 20 (12 mg, 52%) as the free parent: 300 MHz $^1$H NMR (CDCl$_3$) δ (ppm) 8.98 (dd, 1H), 8.34 (dd, 1H), 7.66 (m, 1H), 6.08 (s, 1H), 4.95 (d, 1H), 4.76 (m, 2H), 4.55 (d, 1H), 3.35 (s, 3H), 3.11 (s, 3H), 2.42 (s, 3H); MS: 403 (M+1).

Example 33

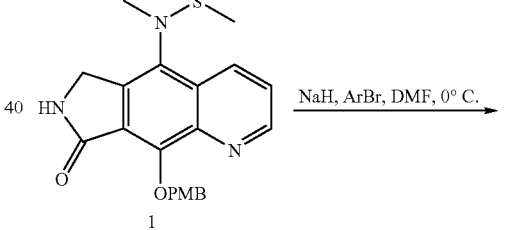
1

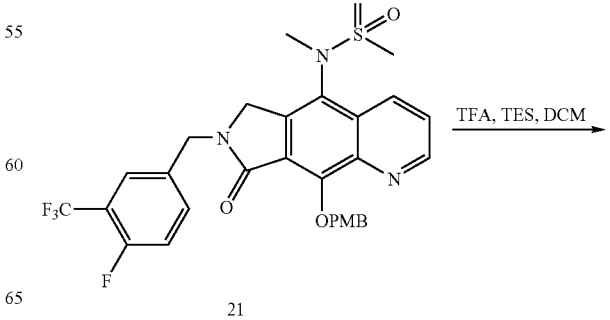
21

-continued

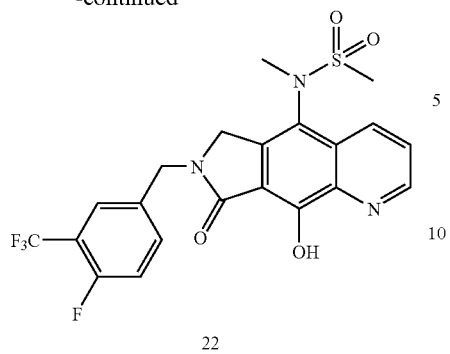

22

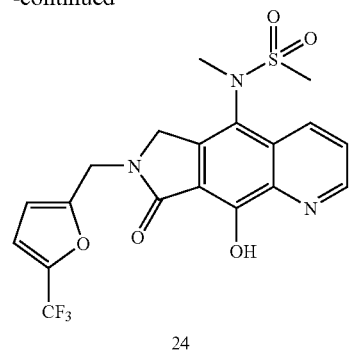

24

21: The compound was made in a similar fashion as compound 2 to afford the desired product 21 (33 mg, 80%): 300 MHz $^1$H NMR (CDCl$_3$) δ (ppm) 9.1 (dd, 1H), 8.25 (dd, 1H), 7.6 (m, 5H), 7.22 (t, 1H), 6.9 (m, 2H), 5.8 (m, 2H), 4.85 (m, 2H), 4.55 (m, 2H), 3.8 (s, 3H), 3.35 (s, 3H), 3.1 (s, 3H); 300 MHz $^{19}$F NMR (CDCl$_3$) δ (ppm) −61.88, −116.0; MS: 604 (M+1).

22: The compound was made in a similar fashion as compound 3 to afford the desired product 22 (13 mg, 40%) as the TFA salt: 300 MHz $^1$H NMR (CDCl$_3$) δ (ppm) 9.07 (dd, 1H), 8.35 (dd, 1H), 7.72 (m, 1H), 7.6 (m, 2H), 7.23 (t, 1H), 5.0 (d, 1H), 4.75 (m, 1H), 4.63 (d, 1H), 4.40 (d, 1H), 3.34 (s, 3H), 3.09 (s, 3H); 300 MHz $^{19}$F NMR (CDCl$_3$) δ (ppm) −61.90, −76.28, −115.5; MS: 484 (M+1).

23: The compound was made in a similar fashion as compound 2 to afford the desired product 23 (29 mg, 72%): 300 MHz $^1$H NMR (CDCl$_3$) δ (ppm) 9.06 (dd, 1H), 8.30 (dd, 1H), 7.62 (m, 3H), 6.88 (m, 2H), 6.77 (d, 1H), 6.45 (d, 1H), 5.77 (m, 2H), 4.85 (m, 2H), 4.66 (m, 2H), 3.8 (s, 3H), 3.37 (s, 3H), 3.13 (s, 3H); 300 MHz $^{19}$F NMR (CDCl$_3$) δ (ppm) −64.6; MS: 576 (M+1).

24: The compound was made in a similar fashion as compound 3 to afford the desired product 24 (17 mg, 59%) as the TFA salt: 300 MHz $^1$H NMR (CDCl$_3$) δ (ppm) 9.08 (dd, 1H), 8.4 (dd, 1H), 7.23 (m, 1H), 6.78 (d, 1H), 6.48 (d, 1H), 4.98 (d, 1H), 4.85 (m, 1H), 4.75 (d, 1H), 4.60 (d, 1H), 3.38 (s, 3H), 3.12 (s, 3H); 300 MHz $^{19}$F NMR (CDCl$_3$) δ (ppm) −64.66, −76.27; MS: 456 (M+1).

Example 34

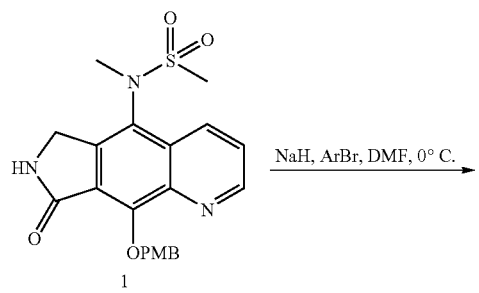

Example 35

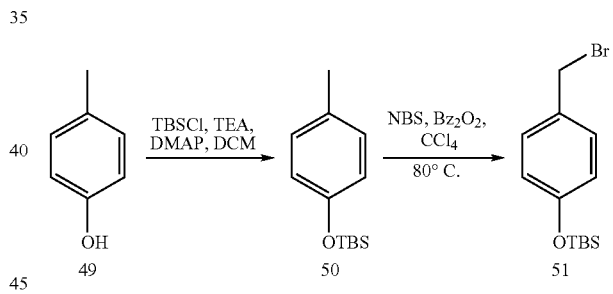

50: To a solution of p-Cresol (5 g, 46.3 mmol) dissolved in Dichloromethane (154 mL) was added Triethylamine (9.63 mL, 69.4 mmol) and DMAP (1.13 g, 9.3 mmol). The reaction mixture was treated with tert-Butyldimethylsilyl chloride (8.37 g, 55.5 mmol) and stirred overnight at room temperature under an inert atmosphere. The reaction mixture was diluted with ethyl acetate and quenched with H$_2$O. The organic layer was washed with H$_2$O (twice) then brine, and dried (over Na$_2$SO$_4$), filtered and concentrated in vacuo to afford the crude desired product 50 (12.76 g): 300 MHz $^1$H NMR (CDCl$_3$) δ (ppm) 7.05 (d, 2H), 6.75 (d, 2H), 2.28 (s, 3H), 1.02 (s, 9H), 0.2 (s, 6H).

51: To a solution of intermediate 50 (1 g, 4.5 mmol) in carbon tetrachloride (18 mL) was added recrystallized NBS (780 mg, 4.5 mmol) and benzoyl peroxide (110 mg, 0.45 mmol). The reaction was stirred at 80° C. under an inert atmosphere while shining a UV lamp on the reaction mixture for 2 hours. After cooling back to room temperature, the solids were filtered off and the mother liquor was concentrated down and the residue was purified by chromatography on silica gel (hexane) to afford the desired product 51 (200

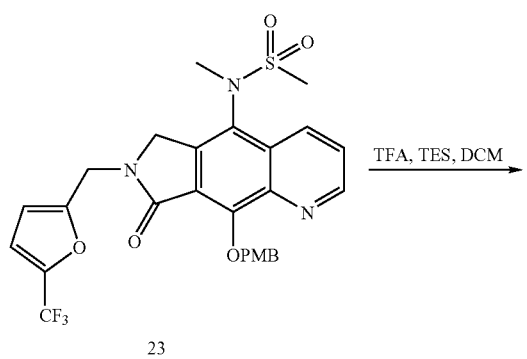

mg): 300 MHz $^1$H NMR (CDCl$_3$) δ (ppm) 7.27 (d, 2H), 6.8 (d, 2H), 4.50 (s, 2H), 0.99 (s, 9H), 0.2 (s, 6H).

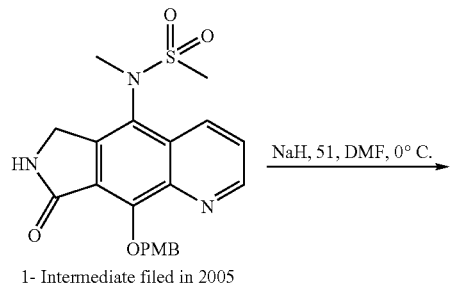

1- Intermediate filed in 2005

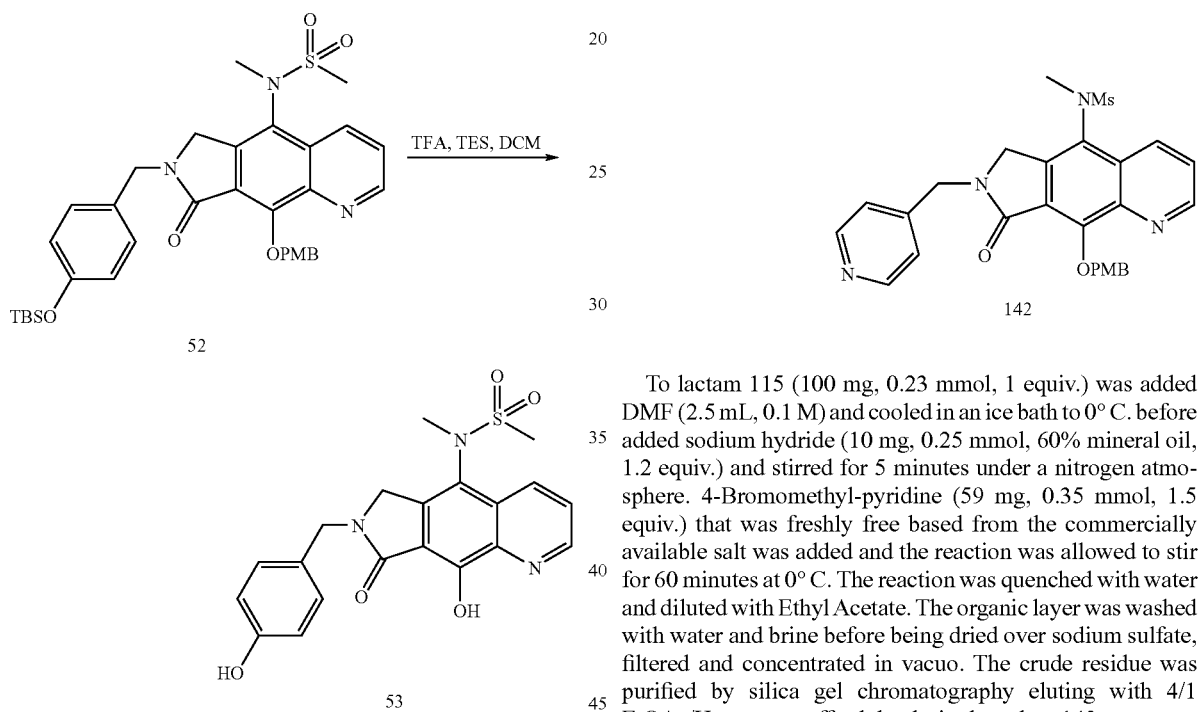

52: The compound was made in a similar fashion as compound 2 to afford the desired product 52 (42 mg, 92%): 300 MHz $^1$H NMR (CDCl$_3$) δ (ppm) 9.06 (dd, 1H), 8.26 (dd, 1H), 7.65 (d, 2H), 7.6 (m, 1H), 7.22 (d, 2H), 6.88 (d, 2H), 6.82 (d, 2H), 5.77 (m, 2H), 4.8 (m, 2H), 4.45 (m, 2H), 3.8 (s, 3H), 3.32 (s, 3H), 3.08 (s, 3H), 0.98 (s, 9H), 0.195 (s, 6H); MS: 648 (M+1).

53: A solution of intermediate 52 (42 mg, 0.065 mmol) in dichloromethane (0.65 mL) was treated with trifluoroacetic acid (15 μL) and triethylsilane (21 μL). The reaction mixture was stirred at room temperature under an inert atmosphere for 30 minutes upon which the silyl protecting group had not been cleaved. Therefore trifluoroacetic acid (0.200 mL), trethylsilane (20 μL) and a drop of water were added and the reaction was heated to 50° C. while stirring for a few hours to completion. The volatiles were removed in vacuo with toluene/THF. The solid was triturated in diethyl ether/hexane to afford the desired product 25 (24 mg, 90%) as the parent solid: 300 MHz $^1$H NMR (DMSO) δ (ppm) 9.37 (bs, 1H), 8.96 (dd, 1H), 8.42 (dd, 1H), 7.65 (m, 1H), 7.13 (d, 2H), 6.72 (d, 2H), 4.58 (dd, 2H), 4.48 (dd, 2H), 3.24 (s, 3H), 3.21 (s, 3H); MS: 414 (M+1).

Example 36

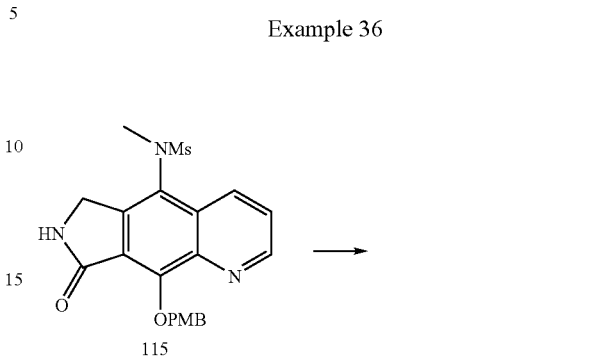

115

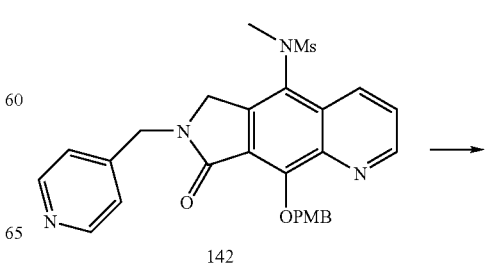

142

To lactam 115 (100 mg, 0.23 mmol, 1 equiv.) was added DMF (2.5 mL, 0.1 M) and cooled in an ice bath to 0° C. before added sodium hydride (10 mg, 0.25 mmol, 60% mineral oil, 1.2 equiv.) and stirred for 5 minutes under a nitrogen atmosphere. 4-Bromomethyl-pyridine (59 mg, 0.35 mmol, 1.5 equiv.) that was freshly free based from the commercially available salt was added and the reaction was allowed to stir for 60 minutes at 0° C. The reaction was quenched with water and diluted with Ethyl Acetate. The organic layer was washed with water and brine before being dried over sodium sulfate, filtered and concentrated in vacuo. The crude residue was purified by silica gel chromatography eluting with 4/1 EtOAc/Hexanes to afford the desired product 142.

300 MHz $^1$H NMR (CDCl$_3$) δ (ppm) 9.07 (dd, J$_1$=1.8 Hz, J$_2$=4.2 Hz, 1H), 8.61 (d, J=5.7 Hz, 1H), 8.27 (dd, J$_1$=2.1 Hz, J$_2$=8.4 Hz, 1H), 7.65-7.60 (m, 3H), 7.23-7.20 (m, 2H), 6.90 (dd, J$_1$=8.1 Hz, J$_2$=1.8 Hz, 2H), 5.80 (d, J=11.0 Hz, 1H), 5.79 (d, J=11.0 Hz, 1H), 5.07 (d, J=15.6 Hz, 1H), 4.76 (d, J=16.9 Hz, 1H), 4.60 (d, J=15.6 Hz, 1H), 4.34 (d, J=16.9 Hz, 1H), 3.80 (s, 3H), 3.34 (s, 3H), 3.10 (s, 3H).

MS: 519.15 (M+1).

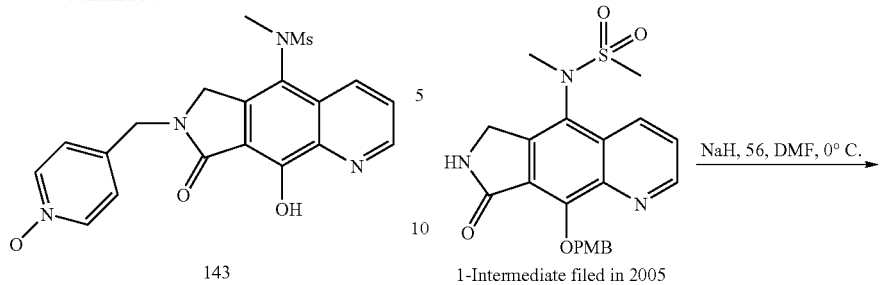

143

1-Intermediate filed in 2005

Compound 142 (56 mg, 0.11 mmol, 1 equiv.) was stirred in CHCl$_3$ (3 mL) and mCBPA (73 mg, 0.32 mmol, 3 equiv., 77%) was stirred under an inert atmosphere overnight. The crude material was then redissolved in CH$_2$Cl$_2$ and added TFA (150 μL, excess) and allowed to stir at room temperature under an inert atmosphere. The resulting material was purified by HPLC to obtain the desired phenol 143.

300 MHz $^1$H NMR (DMSO-d$_6$) δ (ppm) 8.97 (d, J=4.4 Hz, 1H), 8.44 (d, J=8.4 Hz, 1H), 8.23 (d, J=6.4 Hz, 2H), 7.78 (dd, J$_1$=8.1 Hz, J$_2$=4.3 Hz, 1H), 7.39-7.36 (m, 2H), 4.81 (d, J=16.5 Hz, 1H), 4.62 (d, J=16.5 Hz, 1H), 4.61 (s, 2H), 3.26 (s, 3H), 3.19 (s, 3H).

MS: 415.40 (M+1).

Example 37

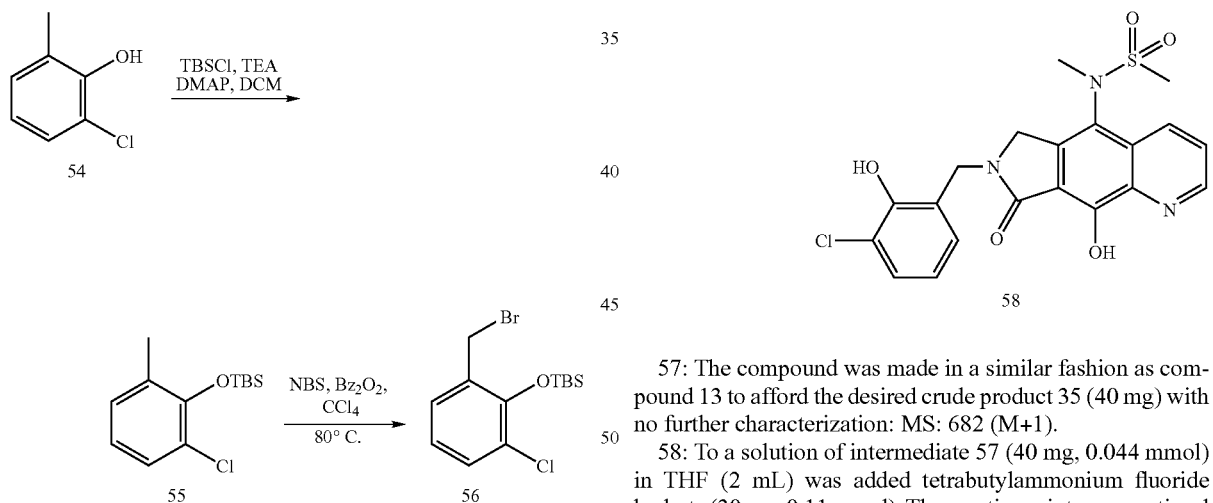

55: The compound was made in a similar fashion as compound 50 to afford the desired product 55 (5.12 g, from 2.36 g of starting alcohol 54): 300 MHz $^1$H NMR (CDCl$_3$) δ (ppm) 7.19 (d, 1H), 7.04 (d, 1H), 6.8 (m, 1H), 2.26 (s, 3H), 1.06 (s, 9H), 0.27 (s, 6H).

56: The compound was made in a similar fashion as compound 51 to afford the desired product 56 (1.06 g, 72%): 300 MHz $^1$H NMR (CDCl$_3$) δ (ppm) 7.27 (m, 2H), 6.93 (m, 1H), 4.53 (s, 2H), 1.095 (s, 9H), 0.31 (s, 6H).

57: The compound was made in a similar fashion as compound 13 to afford the desired crude product 35 (40 mg) with no further characterization: MS: 682 (M+1).

58: To a solution of intermediate 57 (40 mg, 0.044 mmol) in THF (2 mL) was added tetrabutylammonium fluoride hydrate (30 mg, 0.11 mmol). The reaction mixture was stirred under nitrogen atmosphere while warming to room temperature for 2.5 hours upon which it was diluted with ethyl acetate, and quenched with H$_2$O. The organic layer was washed with 5% Citric Acid solution, H$_2$O and brine, then dried (over Na$_2$SO$_4$), filtered and concentrated in vacuo to afford the phenol intermediate: MS: 568 (M+1). The crude residue was immediately redissolved in dichloromethane (1 mL) and THF (1 mL) and treated with triethylsilane (0.2 mL) and trifluoroacetic acid (0.4 mL). The reaction was stirred overnight then the volatiles were removed in vacuo with toluene/THF. The solid was purified by reversed phase HPLC to afford the desired product 58 (8 mg) as the TFA salt: 300 MHz $^1$H NMR (DMSO) δ (ppm) 9.83 (bs, 1H), 8.96 (dd, 1H), 8.43 (dd, 1H), 7.78 (m, 1H), 7.31 (d, 1H), 7.15 (d, 1H), 6.84 (m, 1H), 4.72

(dd, 2H), 4.64 (dd, 2H), 3.26 (s, 3H), 3.23 (s, 3H); 300 MHz $^{19}$F NMR (DMSO) δ (ppm) −74.92; MS: 448 (M+1).

Example 38

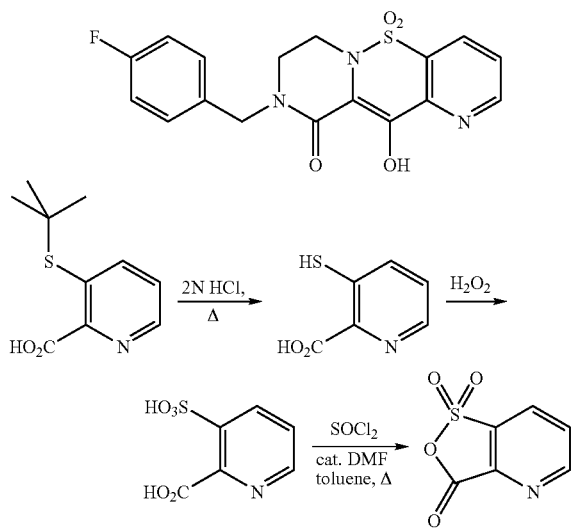

500 mg of the known t-butyl mercaptan was deprotected via treatment with 2N hydrochloric acid, oxidized with $H_2O_2$ treatment and subjected to subsequent anhydride formation via $SOCl_2$ to give the intermediate sulfonyl anhydride. 200 mg of the resulting anhydride was submitted to solvolysis via refluxing methanol to give 100 mg of the intermediate sulfonic acid.

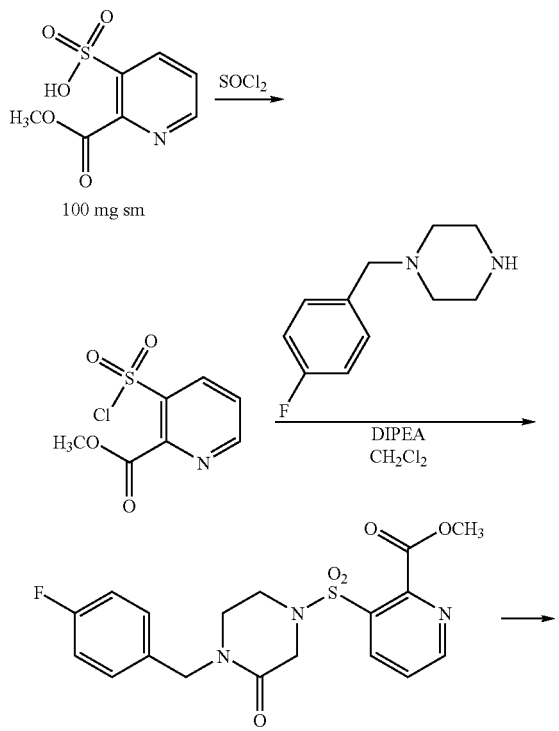

-continued

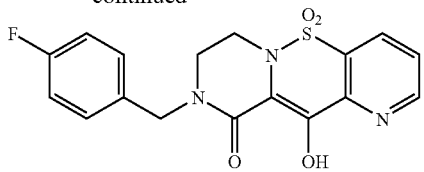

Standard coupling chemistry with 4-fluorobenzyl-derived piperazinone using conditions reported in previous patent filings gave 40 mg of the cyclization precursor.

To 40 mg of the cyclization precursor in 1 mL dry methanol is added 100 uL NaOMe solution. The reaction is stirred for 1 h, at which time and additional 100 uL NaOMe solution is added. After 20 h, s.m. appears complete. The reaction is concentrated, diluted with dichloromethane (25 mL) and washed with saturated ammonium chloride solution (10 mL). The organic layer is concentrated to give 25 mg of unpurified product. HPLC purification gave 2.5 mg pure 1012, characterized by $^1$H and MS analysis.

$^1$H NMR (300 MHz, $CD_3CN$) shows diagnostic peaks at δ 13.2 (s, 1H) 9.05 (d, 1H), 8.25 (d, 1H) 4.75 (d, 2H), 3.95 (dd, 2H) and 3.84 (dd, 2H). MS 376.1 (M+H).

Example 39

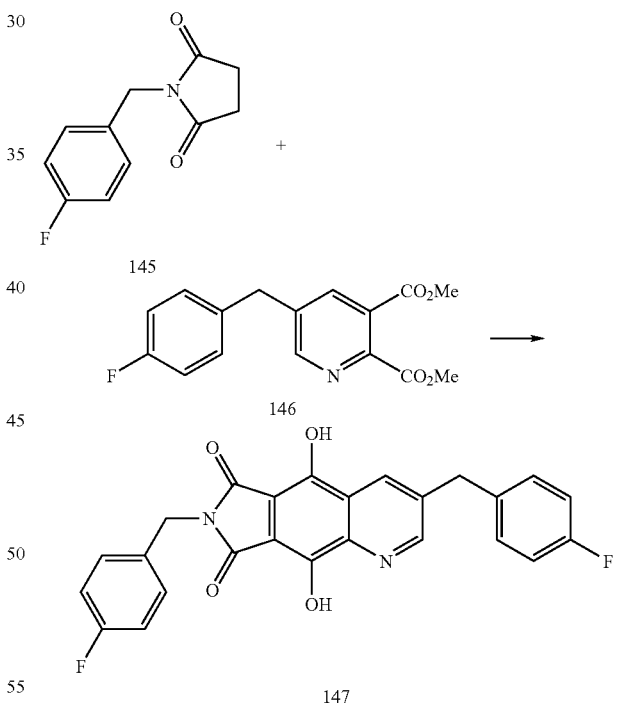

Dimethyl ester 146 (65 mg, 0.196 mmol, 1 equiv., its synthesis has previously been described in WO 2005/077050A2) and imide 145 (49 mg, 0.23 mmol, 1 equiv.) and were dissolved in dry THF (1 mL) and dry methanol (100 μL) under an atmosphere of nitrogen. To this was added NaH (20 mg, 0.49 mmol, 2.5 equiv, 60% in mineral oil). The mixture stirred until bubbling ceased, then refluxed for 24 hours. $HCl_{(aq)}$ (2 mL, 6 N) was added to the mixture while in an ice bath, stirring for 15 minutes. 10 mL diethyl ether was added, and the precipitate was filtered, and washed with diethyl ether and H₂O, then dried under vacuum at 100° C. with no further purification to afford the desired product 147 as a solid.

300 MHz ¹H NMR (CD₃SOCD₃) δ 10.68 (bs, 1H), 8.96 (d, J=2.1 Hz, 1H), 8.46 (d, J=2.1 Hz, 1H), 7.40-7.33 (m, 4H), 7.18-7.09 (m, 4H), 4.71 (s, 2H), 4.25 (s, 2H).

300 MHz ¹⁹F NMR (CDCl₃) δ (ppm) −115.90, −117.19.

MS: 447.24 (M+1).

Example 40

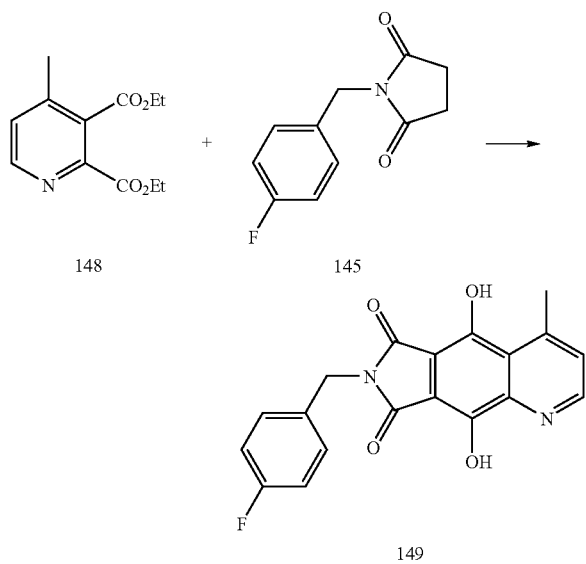

The synthesis of diethyl ester 148 (210 mg, 0.89 mmol, 1 equiv.) has previously been described in WO89/08103 is dissolved in dry THF (9 mL, 0.1 M). To this was added imide 145 (201 mg, 0.97 mmol, 2.2 equiv.) and cooled to −78° C. before LiHMDS (1.97 mL, 1.97 mmol, 2.2 equiv.) was added slowly over 15 min. The bath was removed and the reaction allowed to stir for 45 min. HCl$_{(aq)}$ (2 mL, 6 N) was added to the mixture while in an ice bath, stirring for 15 minutes and the mixture concentrated in vacuo. 30 mL diethyl ether was added, and the precipitate was filtered, and washed with diethyl ether and H₂O, then dried under vacuum at 100° C. with no further purification to afford the desired product 149 as a solid.

300 MHz ¹H NMR (CDCl₃) δ 8.95 (d, J=3.8 Hz, 1H), 8.72 (d, J=3.8 Hz, 1H), 7.47-7.38 (m, 2H), 7.12-6.98 (m, 2H), 4.84 (s, 2H), 2.99 (s, 3H).

MS: 353.18 (M+1).

Example 41

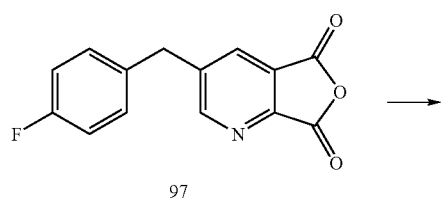

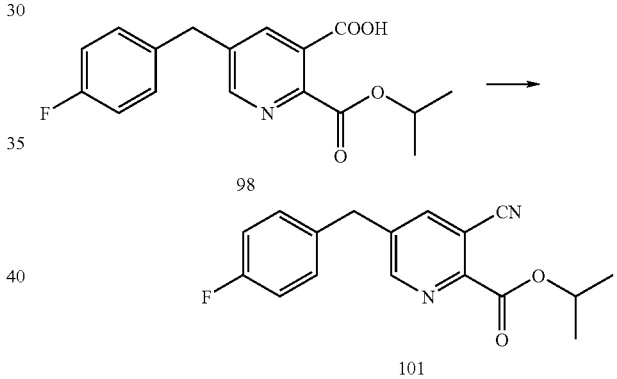

Into a flask containing anhydride 97 (synthesis previously detailed in WO2005/075475) (1000 mg, 3.89 mmol, 1 equiv.) was added THF (13 mL, 0.3 M) and the flask chilled to −10° C. before Mg(ClO₄)₂ (1042 mg, 4.67 mmol, 1.2 equiv.) was added under an inert atmosphere. The reaction was allowed to stir for 5 min. before isopropanol (13 mL, 0.3 M) was added and the reaction allowed to warm up to room temperature and stirred overnight. The reaction was concentrated in vacuo to a paste before being diluted with ethyl acetate (150 mL) and with water (20 mL). The organic layer was washed with saturated NH₄Cl and brine then dried over Na₂SO₄, filtered and concentrated in vacuo to yield a light brown solid as 98 (1.05 gm, y. 85%) as the only regioisomer.

300 MHz ¹H NMR (CDCl₃) δ (ppm) 8.69 (d, J=1.7 Hz, 1H), 8.05 (d, J=1.7 Hz, 1H), 7.27-7.13 (m, 2H), 7.05-7.00 (m, 2H), 5.34 (s, J=6.6 Hz, 1H), 4.06 (s, 2H), 1.40 (d, J=6 Hz, 6H).

300 MHz ¹⁹F NMR (CDCl₃) δ (ppm) −116.09

MS: 318.00 (M+1).

Into a flask containing acid 98 (285 mg, 0.89 mmol, 1 equiv.) was added pyridine (4 mL, 0.3 M) and chilled to 0° C. before methanesulfonyl chloride (140 μL, 1.79 mmol, 2 equiv.) was added under an inert atmosphere. The reaction was allowed to stir for 1 hr before ammonia was bubbled into the reaction for several minutes and then allowed to stir for 30 min. The flask was then placed onto a rotary evaporator to remove excess NH₃. The flask was cooled to 0° C. before methanesulfonyl chloride (560 μL, 7.16 mmol, 8 equiv.) was added slowly. The reaction was allowed to warm up to room temperature and stir overnight. The reaction was concentrated down to a paste and slowly quenched with saturated NaHCO₃ which was stirred for 1 hr. Ethyl acetate was added and the reaction extracted (3×). The organic layers were combined and washed with water (2×), saturated NaHCO₃, brine and dried over Na₂SO₄, filtered and concentrated in vacuo. The reaction was purified by ISCO silica gel chromatography to yield nitrile 101 (191 mg, yield of 71%).

300 MHz ¹H NMR (CDCl₃) δ (ppm) 8.77 (d, J=2.0 Hz, 1H), 7.85 (d, J=2.0 Hz, 1H), 7.27-7.13 (m, 2H), 7.11-7.02 (m, 2H), 5.34 (sp, J=6.3 Hz, 1H), 4.08 (s, 2H), 1.47 (d, J=6.3 Hz, 6H).

300 MHz $^{19}$F NMR (CDCl$_3$) δ (ppm) −115.38
MS: 299.00 (M+1).
R$_f$ 0.35 (7/3 Hexanes/EtOAc)

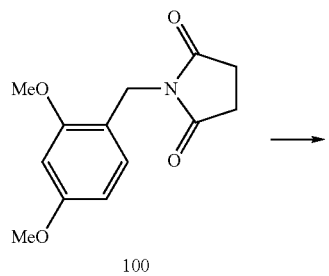

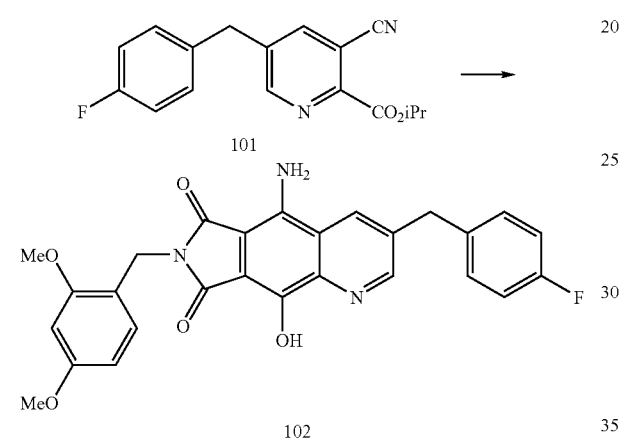

Compound 100 (3.69 g, 14.83 mmol, 1.15 equiv.) and nitrile 101 (3.84 g, 12.88 mmol, 1 equiv.) were dissolved in THF (65 mL) and cooled to 0° C. To this was added LiHMDS (30.91 mL, 30.91 mmol, 2.4 equiv., 1 M THF) drop wise over 10 min. After 1 hr, reaction was complete and was quenched with acid (10 mL, 6 M HCl) and rotavaped to a small volume. The paste was washed with a mixture of diethyl ether and hexanes along with water before being allowed to dry under vacuum at 100° C. A red solid was obtained of 102 (5.42 g, 86% yield).

300 MHz $^1$H NMR (DMSO-d$_6$) δ (ppm) 8.94 (s, 1H), 8.80 (d, 1H), 7.40-7.37 (m, 2H), 7.18-7.10 (m, 2H), 6.88 (d, J=8.4 Hz, 1H), 6.57 (d, J=2.1 Hz, 1H), 6.41 (d, J=8.1 Hz, 1H), 4.60 (s, 2H), 4.20 (s, 2H), 3.80 (s, 3H), 3.71 (s, 3H).

300 MHz $^{19}$F NMR (DMSO-d$_6$) δ (ppm) −117.138.
MS: 488.16 (M+1).

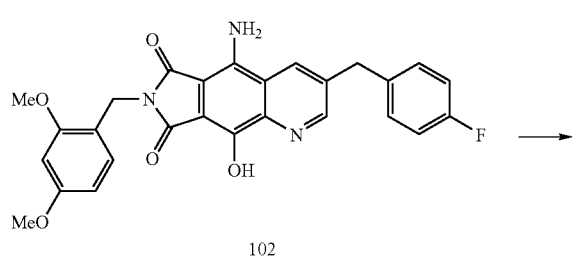

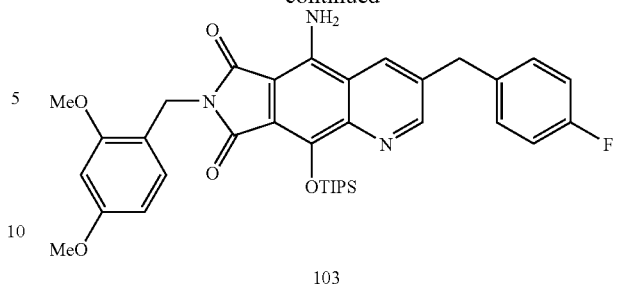

Phenol 102 (5.42 g, 11.13 mmol, 1 equiv.) in DMF (45 mL, 0.2 M) was treated with TEA (4.65 mL, 16.88 mmol, 1.5 equiv.) and DMAP (680 mg, 5.56 mmol, 0.5 equiv.). TIPSCl (3.54 g, 16.88 mmol, 1.5 equiv.) was slowly added and the reaction mixture was stirred at room temperature for 2 h under a nitrogen atmosphere. The reaction mixture was diluted with ethyl acetate (200 mL) and quenched with water (100 mL). The layers were separated and the aqueous layer was extracted with ethyl acetate (200 mL). The combined organic layers were washed with aqueous LiCl (twice), citric acid (5% solution) and brine then dried (over Na$_2$SO$_4$), filtered and concentrated in vacuo. The crude product was triturated in hexane and filtered to afford the desired product 103 (5.35 g, 75%) as a yellow solid.

300 MHz $^1$H NMR (CDCl$_3$) δ (ppm) 8.79 (s, 1H), 7.88 (d, 1H), 7.25-7.15 (m, 3H), 7.10-7.03 (m, 2H), 6.43-6.38 (m, 2H), 4.83 (s, 2H), 4.20 (s, 2H), 3.82 (s, 3H), 3.77 (s, 3H), 1.55-1.50 (m, 3H), 1.11 (d, J=7.5 Hz, 18H).

300 MHz $^{19}$F NMR (CDCl$_3$) δ (ppm) −116.16
MS: 644.30 (M+1).

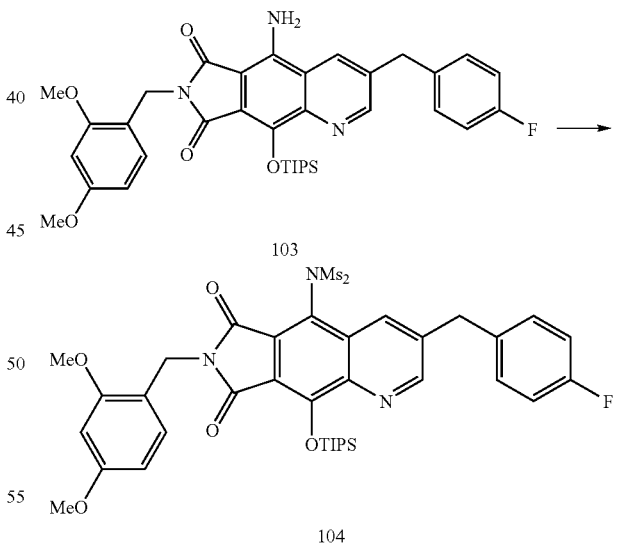

Aniline 103 (4.94 g, 7.68 mmol, 1 equiv.) in CH$_2$Cl$_2$ (40 mL) was treated with TEA (8.52 mL, 61.43 mmol, 8 equiv.) and stirred at −10° C. as a solution of methanesulfonyl chloride (2.4 mL, 30.71 mmol, 4 equiv.) in predissolved in CH$_2$Cl$_2$ (15 mL) was added drop wise over 45 min. After addition, the mixture was stirred for 3 h while warming to 0° C. The volatiles were removed in vacuo then the residue was redissolved in CH$_2$Cl$_2$ (300 mL) then quenched with H$_2$O (200 mL). The layers were separated and the aqueous layer was extracted with CH$_2$Cl$_2$ (100 mL). The combined organic layer was washed with H$_2$O (3×), citric acid (5% solution) and brine then dried (over Na$_2$SO$_4$), filtered and concentrated in vacuo with no further purification to yield the crude intermediate bis-mesylate 104 (5.69, 87% mass recovery).

300 MHz $^1$H NMR (CDCl$_3$) δ (ppm) 8.86 (d, J=2.1 Hz, 1H), 8.04 (s, 1H), 7.25-7.15 (m, 3H), 7.10-7.03 (m, 3H), 6.42-6.39 (m, 2H), 4.84 (s, 2H), 4.24 (s, 2H), 3.78 (s, 3H), 3.79 (s, 3H), 3.31 (s, 6H), 1.59-1.52 (m, 3H), 1.12 (d, J=7.8 Hz, 18H).

300 MHz $^{19}$F NMR (CDCl$_3$) δ (ppm) −115.66
MS: 644.30 (M+1).

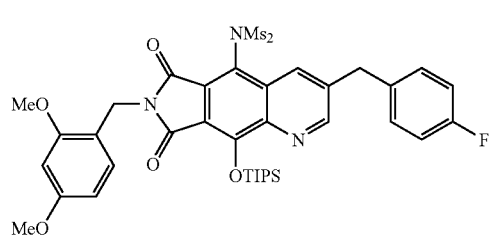

104

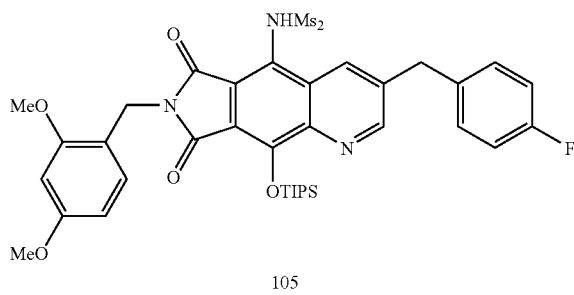

105

A solution of bis-mesylate 104 (6.09 g, 7.62 mmol, 1 equiv.) in THF (39 mL, 0.2 M) was stirred at −10° C. as potassium t-butoxide (7.6 mL, 7.62 mmol, 1 equiv., 1.0 M solution in THF) was added drop wise over 10 min. After 1 hr, the solution was diluted with ethyl acetate (200 mL) and quenched with H$_2$O (200 mL). The layers were separated and the aqueous layer was extracted with ethyl acetate (200 mL, 2×). The combined organic layers were washed with H$_2$O (3×), saturated NH$_4$Cl and brine then dried (over Na$_2$SO$_4$), filtered and concentrated in vacuo. The crude residue was dissolved in CH$_2$Cl$_2$ (30 mL) and passed through a SiO$_2$ plug, which was pre-washed with 9/1—ethyl acetate/hexane+ 0.05% TEA. The short column was eluted with 0.05% TEA+ 9/1—ethyl acetate/hexane then 0.05% TEA+2/1—ethyl acetate/hexane to afford the mono-mesylate 105 (5.08 g, 7.04 mmol) as a light brown solid.

300 MHz $^1$H NMR (CDCl$_3$) δ (ppm) 8.75 (d, J=2.1 Hz, 1H), 8.71 (s, 1H), 7.27-7.17 (m, 2H), 7.10-7.03 (m, 3H), 6.44-6.42 (m, 2H), 4.85 (s, 2H), 4.19 (s, 2H), 3.80 (s, 3H), 3.79 (s, 3H), 2.99 (s, 3H), 1.59-1.52 (m, 3H), 1.12 (d, J=7.8 Hz, 18H).

300 MHz $^{19}$F NMR (CDCl$_3$) δ (ppm) −116.47
MS: 745.43 (M+23).

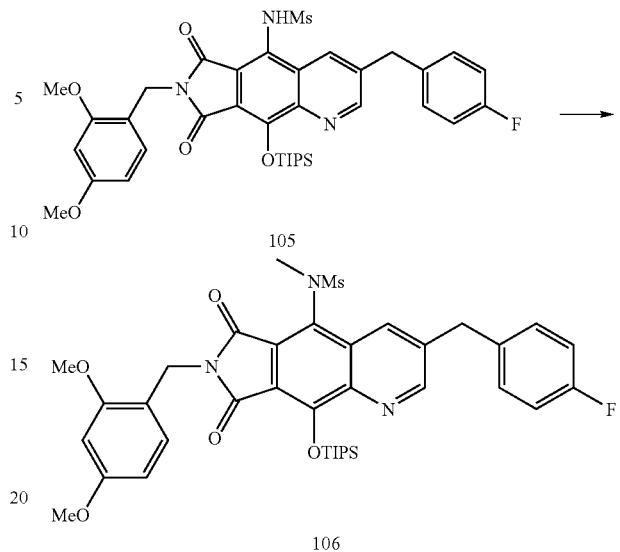

105

106

Imide 105 (5.08 g, 7.04 mmol, 1 equiv.) was stirred in DMF (70 ml, 0.1 M) and cooled to 0° C. before being treated with Cs$_2$CO$_3$ (3.4 g, 10.56 mmol, 1.5 equiv.). It was stirred for 5 min. before iodomethane (703 μl, 11.26 mmol, 1.6 equiv.) was added. The reaction mixture was diluted with ethyl acetate then quenched with water. The organic layer was washed with water, saturated NaHCO$_3$, and brine. The solution was dried over sodium sulfate, filtered and concentrated in vacuo with no further purification to afford the methylated crude product 106 (4.84 g, 94% mass recovery).

300 MHz $^1$H NMR (CDCl$_3$) δ (ppm) 8.73 (d, J=2.1 Hz, 1H), 8.46 (d, J=2.1 Hz, 1H), 7.27-7.19 (m, 3H), 7.10-7.10 (m, 1H), 7.02-7.09 (m, 1H), 6.44-6.42 (m, 2H), 4.86 (s, 2H), 4.22 (s, 2H), 3.81 (s, 3H), 3.79 (s, 3H), 3.41 (s, 3H), 3.11 (s, 3H), 1.59-1.52 (m, 3H), 1.12 (d, J=7.8 Hz, 18H).

300 MHz $^{19}$F NMR (CDCl$_3$) δ (ppm) −116.46
MS: 735.45 (M+1).

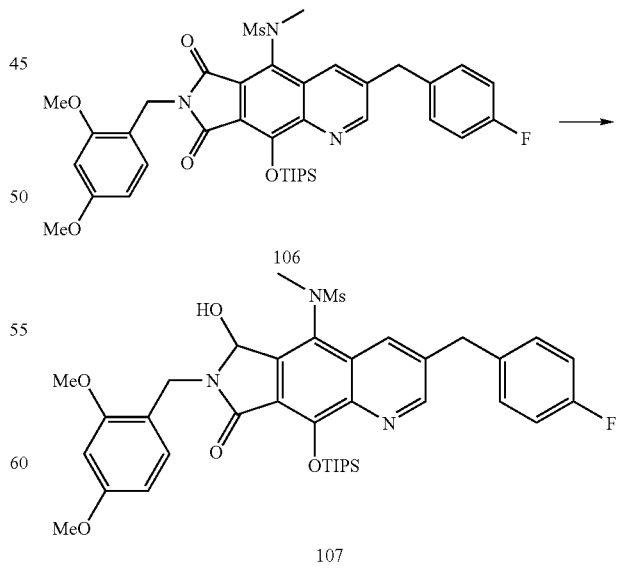

106

107

To imide 106 (2.02 g, 2.74 mmol, 1 equiv.) was added THF (30 ml, 0.1 M) and cooled to 0° C. before adding LiBH$_4$ (2.05 ml, 4.12 mmol, 1.5 equiv.) slowly over 5 min. MeOH (780 μl, 19.23 mmol, 7 equiv.) was added slowly. LiBH₄ was added until reaction was complete. The reaction was diluted with EtOAc, treated with citric acid (10% solution, 250 mL), filtered, and THF was removed in vacuo. The resulting solution was diluted with EtOAc (200 mL), washed with water followed by brine. The solution was dried (over Na₂SO₄), filtered and concentrated to afford crude aminal 107 (2.04 g, 97% mass recovery) as a light yellow solid. 300 MHz $^1$H NMR (CDCl₃) δ (ppm) 8.71 (d, J=1.8 Hz, 1H), 8.13 (s, 1H), 7.27-7.19 (m, 3H), 7.10-7.03 (m, 2H), 6.44-6.42 (m, 3H), 5.71 (d, J=9.3 Hz, 1H), 5.05 (d, J=14.7 Hz, 1H), 4.52 (d, J=15 Hz, 1H), 4.20 (s, 2H), 3.85 (s, 3H), 3.79 (s, 3H), 3.21 (s, 3H), 3.19 (s, 3H), 1.59-1.52 (m, 3H), 1.12 (d, J=7.8 Hz, 18H).
MS: 760.34 (M+23).

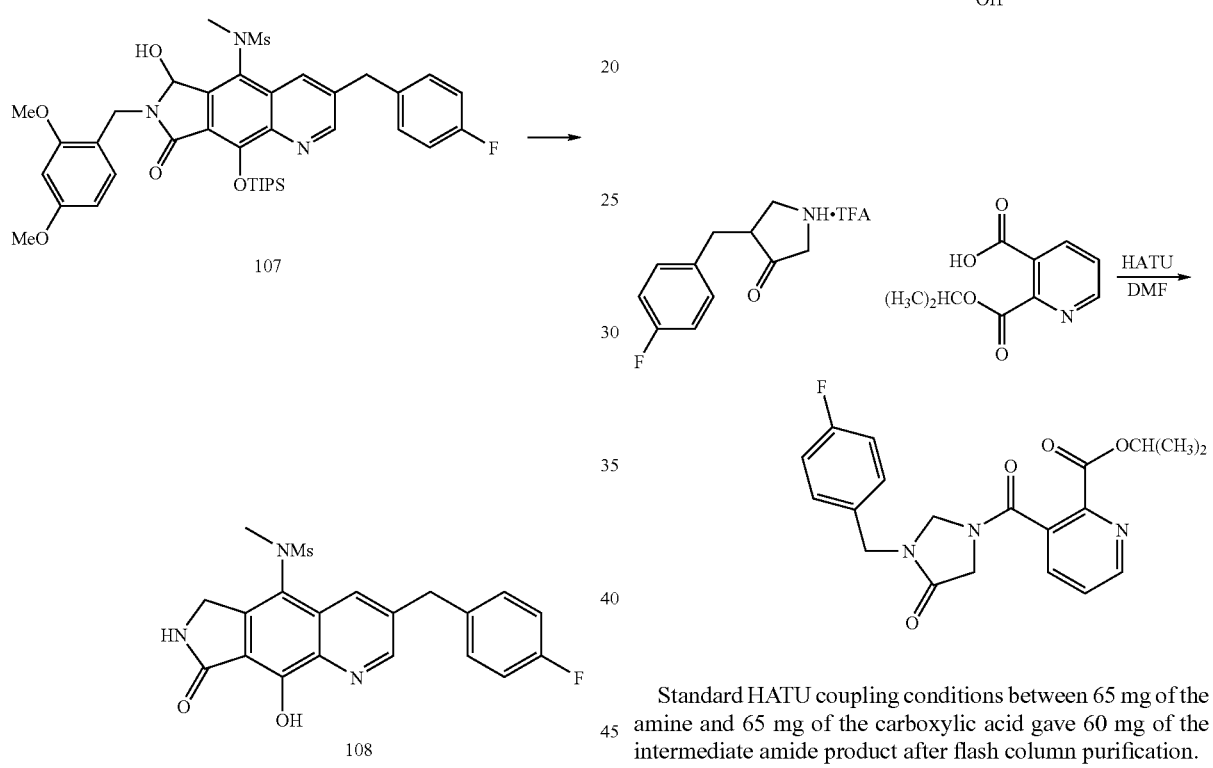

Aminal 107 (2.02 g, 2.74 mmol, 1 equiv.) in CH₂Cl₂ (30 mL, 0.1 M) was treated with triethylsilane (6.5 mL, 41.09 mmol, 15 equiv.) and trifluoroacetic acid (4.2 mL, 54.79 mmol, 20 equiv.). The reaction mixture was stirred at room temperature under an inert atmosphere for 24 hours. The volatiles were removed in vacuo and azeotroped with toluene (2×10 mL). This material was redissolved in trifluoroacetic acid (14 mL, 0.2 M) and heated to 85° C. overnight. The volatiles were removed in vacuo and azeotroped with toluene (2×10 mL). The crude residue was suspended in dichloromethane and washed thoroughly via trituration. Sonication was used to aid this washing. The solid was filtered on a sintered funnel and air dried thoroughly. An off-white brownish solid 108 (970 mg, 94%) was obtained as the TFA salt.

300 MHz $^1$H NMR (DMSO-d₆) δ (ppm) 8.84 (d, J=1.8 Hz, 1H), 8.50 (bs, 1H), 8.19 (s, 1H), 7.39-7.34 (m, 2H), 7.17-7.10 (m, 2H), 4.50 (s, 2H), 4.27 (s, 2H), 3.24 (s, 3H), 3.16 (s, 3H).
300 MHz $^{19}$F NMR (DMSO-d₆) δ (ppm) −117.15, −76.32
MS: 415.96 (M+1).

Example 42

2-(4-Fluoro-benzyl)-9-hydroxy-2,3-dihydro-2,3a,8-triaza-cyclopenta[b]naphthalene-1,4-dione 1013

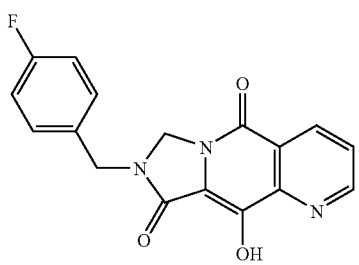

Standard HATU coupling conditions between 65 mg of the amine and 65 mg of the carboxylic acid gave 60 mg of the intermediate amide product after flash column purification.

Treatment of 60 mg of the cyclization precursor with 2 mL 25% NaOMe solution resulted in conversion to the desired product. Upon quenching with ammonium chloride and extraction of the aqueous layer with EtOAc., 20 mg of crude product was obtained after concentration of the organic layer. HPLC purification of this material gave 1 mg of the desired final product 1013, which was characterized by $^1$H and MS analysis.

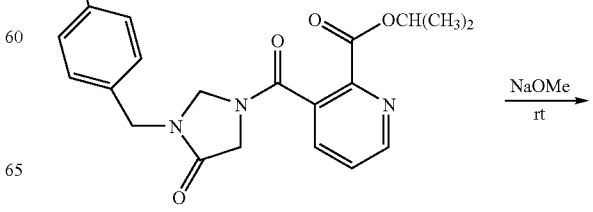

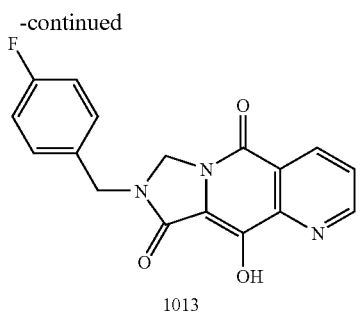

1013

¹H NMR (300 MHz, CD₃N) δ 9.05 (d, 1H), 8.75 (d, 1H) 5.20 (s, 2H), 4.75 (s, 2H). MS=326.1 (M+H).

Example 43

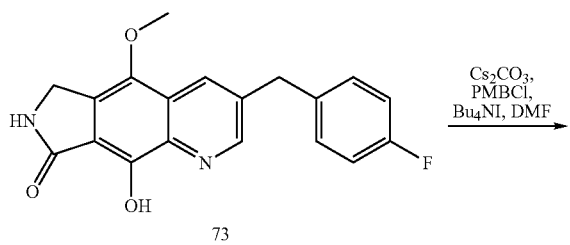

74: The lactam 73 (200 mg, 0.44 mmol) was dissolved in DMF (4.4 mL) and treated with Cs₂CO₃ (288 mg, 0.8 mmol), para-methoxybenzyl chloride (72 μL, 0.53 mmol) and tetrabutylammonium iodide (82 mg, 0.22 mmol). The reaction was stirred under nitrogen atmosphere at 55° C. for 2 hours, upon which the reaction was quenched with water and diluted with ethyl acetate. The organic layer was washed with water (twice), aqueous LiCl, and brine, then dried (over Na₂SO₄), filtered and concentrated in vacuo. The crude residue was purified by chromatography on silica gel (1/9—hexane/ethyl acetate) in order to obtain desired product 74 (120 mg, 60%): 300 MHz ¹H NMR (CDCl₃) δ (ppm) 8.88 (s, 1H), 8.21 (s, 1H), 7.6 (m, 1H), 7.19 (m, 2H), 7.03 (m, 2H), 6.83 (d, 2H), 5.6 (s, 2H), 4.61 (s, 2H), 4.19 (s, 2H), 3.99 (s, 3H), 3.77 (s, 3H); MS: 459 (M+1).

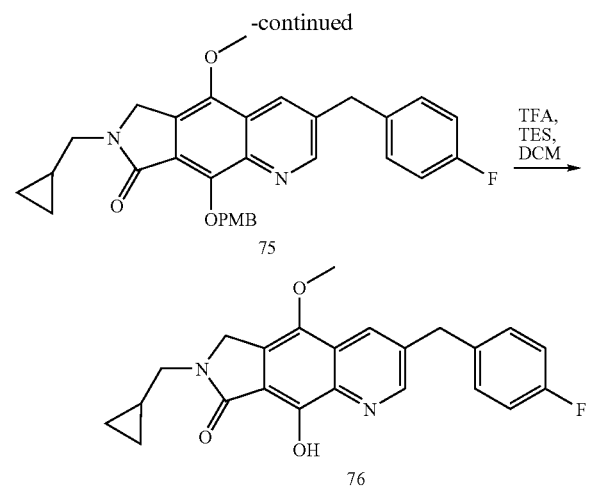

75: To a solution of lactam intermediate 74 (50 mg, 0.11 mmol) dissolved in DMF (1.1 ml) and cooled in an ice bath to 0° C. was added sodium hydride (6.5 mg, 0.16 mmol, 60% mineral oil) and stirred for 5 minutes under nitrogen atmosphere. Commercially available (Bromomethyl)cyclopropane (16 μL, 0.16 mmol) and tetrabutylammonium iodide (12.0 mg, 0.03 mmol) was added and the reaction was allowed to stir for 2 hours in an ice-bath warming to room temperature. The reaction was quenched with H₂O and diluted with ethyl acetate. The organic layer was washed with H₂O, aqueous LiCl (twice), and brine, then dried (over Na₂SO₄), filtered and concentrated in vacuo. The crude residue was purified by chromatography on silica gel (3/1—ethyl acetate/hexane) to afford the desired product 75 (25 mg, 45%): 300 MHz ¹H NMR (CDCl₃) δ (ppm) 8.87 (s, 1H), 8.20 (s, 1H), 7.65 (d, 2H), 7.23 (dd, 2H), 7.03 (dd, 2H), 6.86 (d, 2H), 5.55 (s, 2H), 4.67 (s, 2H), 4.19 (s, 2H), 4.02 (s, 3H), 3.79 (s, 3H), 3.52 (d, 2H), 1.11 (m, 1H), 0.62 (m, 2H), 0.38 (m, 2H); MS: 513 (M+1).

76: A solution of intermediate 75 (25 mg, 0.049 mmol) in dichloromethane (2 mL) was treated with trifluoroacetic acid (0.15 mL) and triethylsilane (0.10 mL). The reaction mixture was stirred at room temperature under an inert atmosphere overnight upon which the mixture was azeotroped with toluene/THF repeatedly. The solid was triturated in diethyl ether/hexane (1/1) to afford the desired product 76 (15 mg, 61%) as the TFA salt: 300 MHz ¹H NMR (CD₃OD) δ (ppm) 8.73 (s, 1H), 8.31 (s, 1H), 7.32 (dd, 2H), 7.06 (dd, 2H), 4.83 (s, 2H), 4.22 (s, 2H), 4.03 (s, 3H), 3.45 (d, 2H), 1.16 (m, 1H), 0.62 (m, 2H), 0.38 (m, 2H); 300 MHz ¹⁹F NMR (CD₃OD) δ (ppm) −77.47, −119.15; MS: 393 (M+1).

Example 44

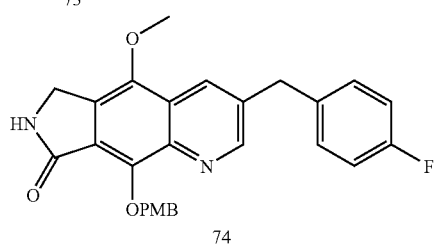

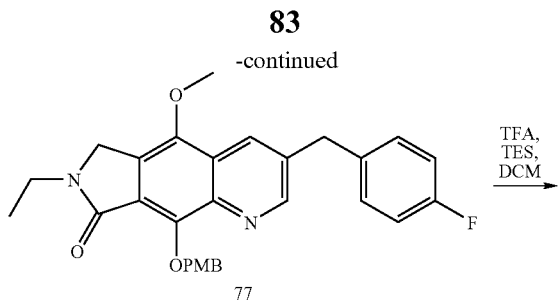

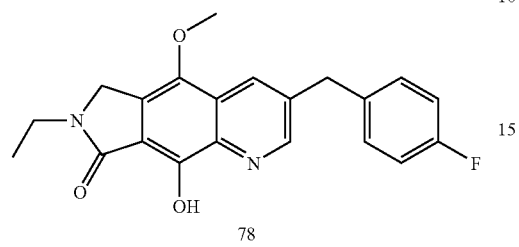

77: The compound was made in a similar fashion as compound 75 with the corresponding lactam 74 (30 mg, 0.059 mmol) and commercially available ethyl iodide to afford the desired product 77 (18 mg, 57%): 300 MHz $^1$H NMR (CDCl$_3$) δ (ppm) 8.87 (s, 1H), 8.20 (s, 1H), 7.66 (d, 2H), 7.21 (dd, 2H), 7.03 (dd, 2H), 6.86 (d, 2H), 5.55 (s, 2H), 4.57 (s, 2H), 4.19 (s, 2H), 4.02 (s, 3H), 3.79 (s, 3H), 3.72 (q, 2H), 1.31 (t, 3H); MS: 487 (M+1).

78: The compound was made in a similar fashion as compound 76 to afford the desired product 78 (10 mg, 56%) as the TFA salt: 300 MHz $^1$H NMR (CD$_3$OD) δ (ppm) 8.80 (s, 1H), 8.53 (s, 1H), 7.33 (dd, 2H), 7.08 (dd, 2H), 4.81 (s, 2H), 4.28 (s, 2H), 4.08 (s, 3H), 3.72 (q, 2H), 1.31 (t, 3H); 300 MHz $^{19}$F NMR (CD$_3$OD) δ (ppm) −77.80, −118.90; MS: 367 (M+1).

Example 45

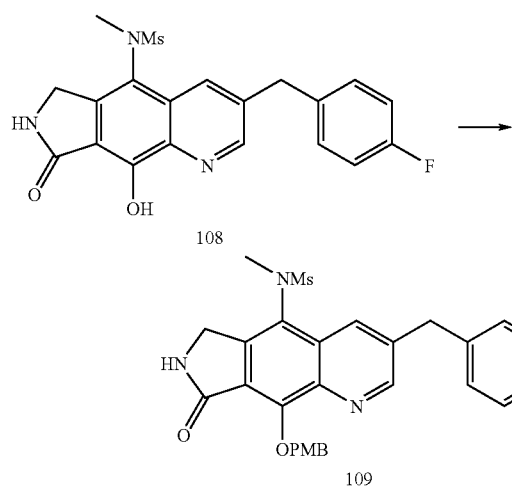

To phenol 108 (600 mg, 1.13 mmol, 1 equiv.) was added DMF (12 mL, 0.1 M) followed by Cs$_2$CO$_3$ (960 mg, 2.95 mmol, 2.6 equiv.) and tetra-butylammonium iodide (125 mg, 0.34 mmol, 0.3 equiv.) before adding p-methoxybenzyl chloride (230 μL, 1.70 mmol, 1.5 equiv.). The reaction was then heated to 65° C. It was cooled to room temperature before diluting with EtOAc (150 mL) and quenching with water. It was extracted with EtOAc and washed with water (2×100 mL), saturated NH$_4$Cl and brine. The organic layer was dried over sodium sulfate, filtered and concentrated in vacuo. ISCO flash column chromatography was carried out with 4/1 EtOAc/Hexanes to yield 109 (255 mg, 42%).

300 MHz $^1$H NMR (CDCl$_3$) δ (ppm) 8.93 (d, J=2.1 Hz, 1H), 7.79 (d, J=2.1 Hz, 1H), 7.59 (d, J=8.7 Hz, 2H), 7.28-7.20 (m, 2H), 7.09-7.04 (m, 2H), 6.85 (d, J=8.7 Hz, 2H), 6.26 (bs, 1H), 5.75 (d, J=6.3 Hz, 2H), 4.80 (d, J=16.5 Hz, 1H), 4.50 (d, J=16.6 hz, 1H), 4.23 (s, 2H), 3.78 (s, 3H), 3.26 (s, 3H), 2.87 (s, 2H).

300 MHz $^{19}$F NMR (CDCl$_3$) δ (ppm) −115.87, −76.83
MS: 558.09 (M+23).

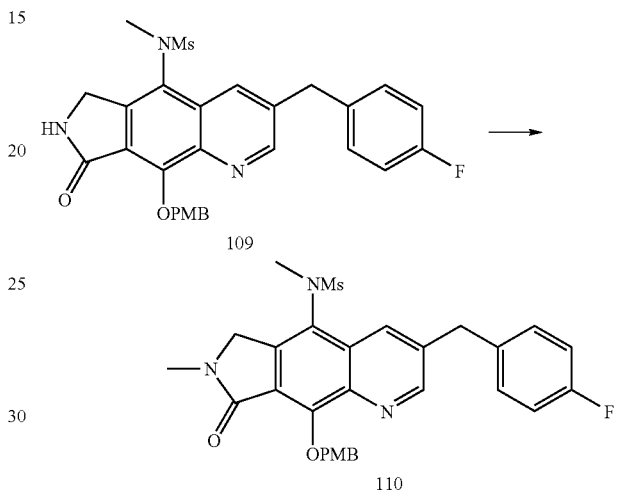

Lactam 109 (185 mg, 0.34 mmol, 1 equiv.) is dissolved in DMF (3.5 mL, 0.1 M) and cooled in an ice bath to 0° C. before sodium hydride (16.5 mg, 0.41 mmol, 1.3 equiv., 60% mineral oil) and stirred for 5 minutes under nitrogen atmosphere. Iodomethane (28 μL, 0.45 mmol, 1.3 equiv.) was added and the reaction was allowed to stir for 30 minutes at 0° C. The reaction was quenched with water and diluted with ethyl acetate. The organic layer was washed with water and brine before being dried over Na$_2$SO$_4$, filtered and concentrated in vacuo. The crude residue was purified by chromatography on silica gel (7/3—Ethyl acetate/Hexane) to afford the desired product 110 (110 mg, 70%).

300 MHz $^1$H NMR (CDCl$_3$) δ (ppm) 8.94 (d, J=2.1 Hz, 1H), 7.74 (s, 1H), 7.79 (d, J=8.7 Hz, 1H), 7.28-7.20 (m, 2H), 7.09-7.04 (m, 2H), 6.86 (d, J=8.7 Hz, 2H), 5.74 (d, J=10.8 Hz, 1H), 5.68 (d, J=10.8 Hz, 1H), 4.75 (d, J=17.1 Hz, 1H), 4.46 (d, J=17.1 Hz, 1H), 4.22 (s, 2H), 3.80 (s, 3H), 3.26 (s, 3H), 3.22 (s, 3H), 2.86 (s, 3H).

300 MHz $^{19}$F NMR (CDCl$_3$) δ (ppm) −115.90
MS: 572.07 (M+23).

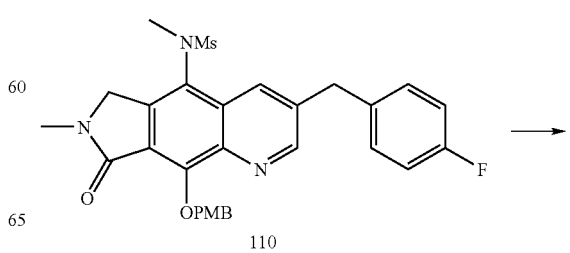

-continued

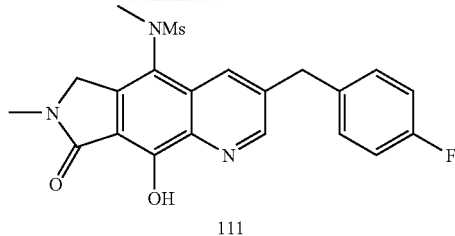

111

Compound 111 was made in a similar fashion as described above.

300 MHz $^1$H NMR (DMSO-d$_6$) δ (ppm) 8.84 (d, J=2.1 Hz, 1H), 7.78 (s, 1H), 7.20-7.19 (m, 2H), 7.09-7.04 (m, 2H), 4.81 (d, J=17.4 Hz, 1H), 4.48 (d, J=17.4 Hz, 1H), 4.24 (s, 2H), 3.26 (s, 3H), 3.21 (s, 3H).

MS: 430.07 (M+1).

Example 46

3-(4-Fluoro-benzyl)-9-hydroxy-7-methyl-6,7-dihydro-5H-1,7,10a-triaza-anthracene-8,10-dione 1014

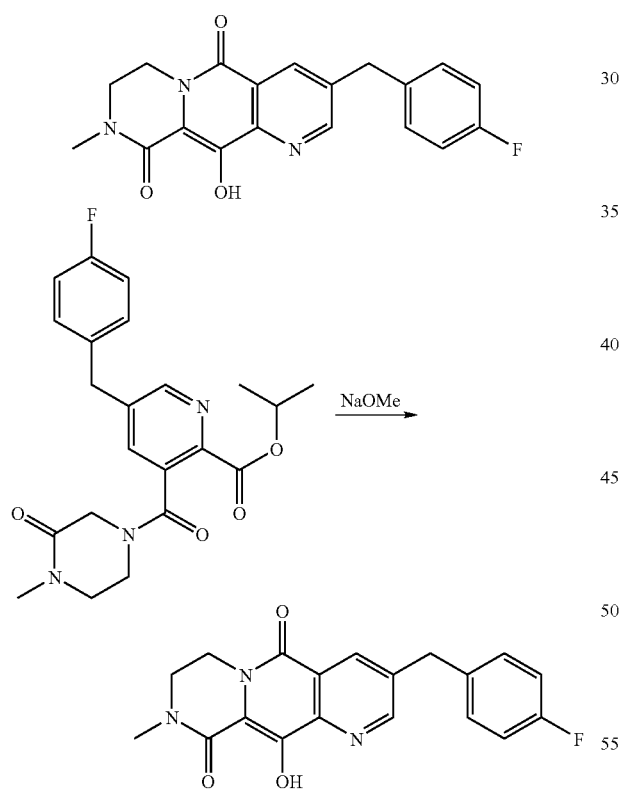

In a procedure analogous to the one reported above, 50 mg of the N-methyl piperazinone was reacted with 50 mg of the carboxylic acid B using standard HATU coupling conditions to give 30 mg of the pure intermediate amide after purification by flash column. NaOMe mediated ring closure was followed by quenching with ammonium chloride. Directly introducing this work-up mixture onto HPLC gave 2 mg of the pure tricyclic compound 1014, which was characterized by $^1$H and MS analysis. $^1$H NMR (300 MHz, CD$_3$OD) shows diagnostic peaks at δ 8.95 (s, 1H), 8.45 (s, 1H) 4.35 (m, 2H), 4.22 (s, 2H) and 3.75 (m, 2H). MS 354.3 (M+H).

Example 47

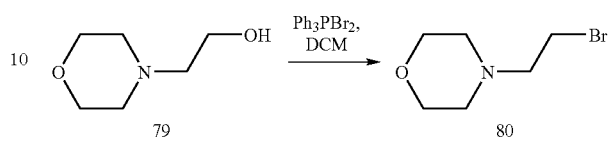

80: A solution of the alcohol 79 (1 g, 7.62 mmol) in dichloromethane (76 mL) cooled in an ice bath to 0° C. was treated with dibromotriphenyl phosphorane (3.86 g, 9.15 mmol). After being stirred at room temperature overnight, the solid desired product was filtered off to afford clean bromide 80 (1.4 g, quant); 300 MHz $^1$H NMR (CD$_3$OD) δ (ppm) 4.1 (m, 2H), 3.85 (m, 2H), 3.8 (t, 2H), 3.7 (t, 2H), 3.58 (m, 2H), 3.25 (m, 2H); MS: 194 (M+1).

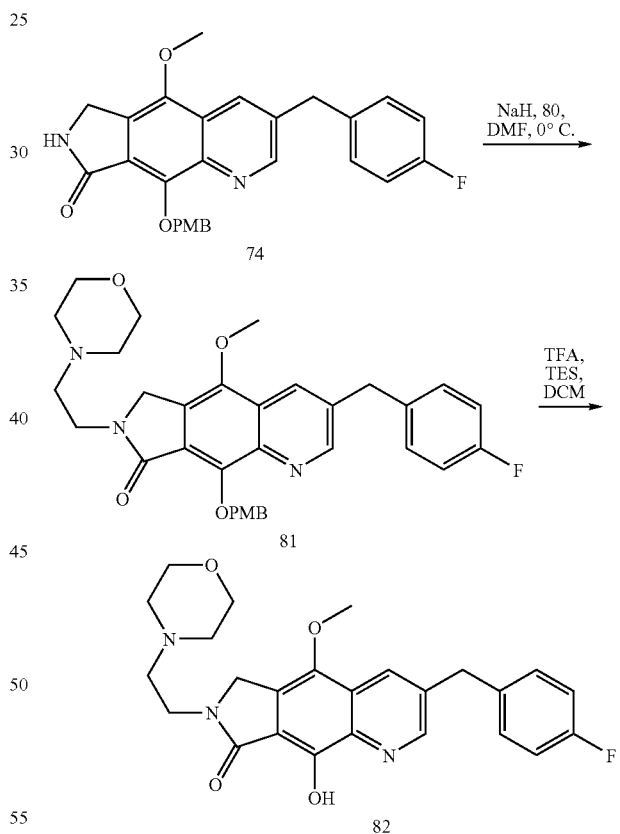

81: The compound was made in a similar fashion as described above for compound 75 with the corresponding lactam 74 (30 mg, 0.059 mmol) and bromide 80 to afford the desired crude product 81 (~35 mg) with no purification upon work-up nor further characterization: MS: 572 (M+1).

82: The compound was made in a similar fashion as described above for compound 76 to afford the desired product 82 (14 mg, 38%) as the TFA salt: 300 MHz $^1$H NMR (CD$_3$OD) δ (ppm) 8.82 (s, 1H), 7.98 (s, 1H), 7.32 (dd, 2H), 7.10 (dd, 2H), 4.67 (s, 2H), 4.21 (s, 2H), 4.1-3.5 (m, 15H); 300 MHz $^{19}$F NMR (CD$_3$OD) δ (ppm) −77.78, −118.85; MS: 452 (M+1).

Example 48

84: The compound was made in a similar fashion as compound 50 to afford the desired product 84 (1.41 g, from 1 g of starting alcohol 83): 300 MHz $^1$H NMR (CDCl$_3$) δ (ppm) 3.90 (t, 2H), 3.41 (t, 2H), 0.91 (s, 9H), 0.097 (s, 6H).

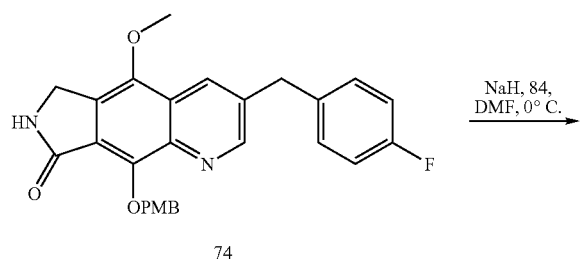

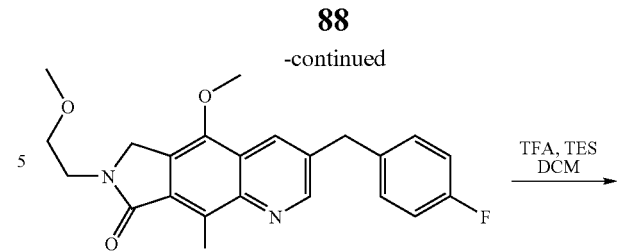

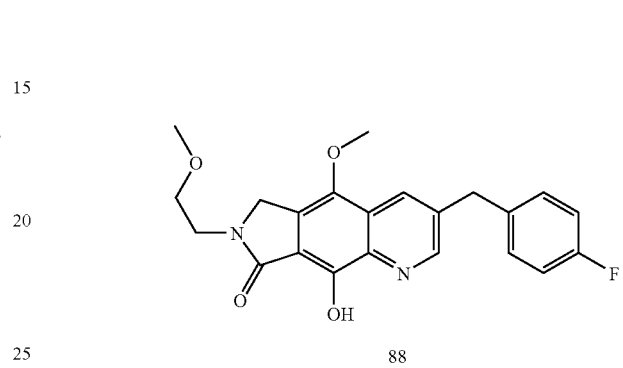

85: The compound was made in a similar fashion as described above for compound 75 with the corresponding lactam 74 (75 mg, 0.16 mmol) and bromide 84 (58 mg, 0.25 mmol) to afford the desired product 85 (20 mg, 20%): 300 MHz $^1$H NMR (CDCl$_3$) δ (ppm) 8.87 (s, 1H), 8.21 (s, 1H), 7.65 (d, 2H), 7.20 (dd, 2H), 7.02 (dd, 2H), 6.86 (d, 2H), 5.54 (s, 2H), 4.78 (s, 2H), 4.19 (s, 2H), 4.00 (s, 3H), 3.93 (t, 2H), 3.79 (s, 3H), 3.77 (t, 2H), 0.90 (s, 9H), 0.05 (s, 6H); MS: 617 (M+1).

86: To a solution of intermediate 85 (40 mg, 0.065 mmol) in THF (0.650 mL) was added tetrabutylammonium fluoride hydrate (34 mg, 0.13 mmol). The reaction mixture was stirred under nitrogen atmosphere at room temperature for 15 minutes upon which it was diluted with ethyl acetate, and quenched with H$_2$O. The organic layer was washed with 5% Citric Acid solution, H$_2$O and brine, then dried (over Na$_2$SO$_4$), filtered and concentrated in vacuo to afford the deprotected intermediate 86 (40 mg, crude) with no further purification nor characterization: MS: 503 (M+1).

87: To a solution of intermediate 86 (25 mg, 0.043 mmol) dissolved in DMF (0.500 ml) and cooled in an ice bath to 0° C. was added sodium hydride (2.0 mg, 0.052 mmol, 60% mineral oil) and stirred for 5 minutes under nitrogen atmosphere. Methyl iodide (3 μL, 0.052 mmol) was added and the reaction was allowed to stir for 1 hour at 0° C. The reaction was quenched with H$_2$O and diluted with ethyl acetate. The organic layer was washed with H$_2$O, aqueous LiCl, and brine, then dried (over Na$_2$SO$_4$), filtered and concentrated in vacuo to afford the crude desired product 87 (25 mg, crude): 300 MHz $^1$H NMR (CDCl$_3$) δ (ppm) 8.88 (s, 1H), 8.21 (s, 1H), 7.65 (d, 2H), 7.20 (dd, 2H), 7.02 (dd, 2H), 6.86 (d, 2H), 5.54 (s, 2H), 4.72 (s, 2H), 4.19 (s, 2H), 4.02 (s, 3H), 3.83 (t, 2H), 3.79 (s, 3H), 3.70 (t, 2H), 3.39 (s, 3H); MS: 517 (M+1).

88: The compound was made in a similar fashion as described above for compound 76 to afford the desired product 88 (9 mg, 51%—3 steps) as the TFA salt: 300 MHz $^1$H NMR (CD$_3$OD) δ (ppm) 8.78 (s, 1H), 8.45 (s, 1H), 7.32 (dd, 2H), 7.07 (dd, 2H), 4.84 (s, 2H), 4.27 (s, 2H), 4.04 (s, 3H),

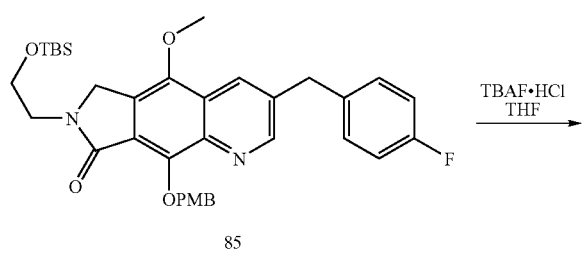

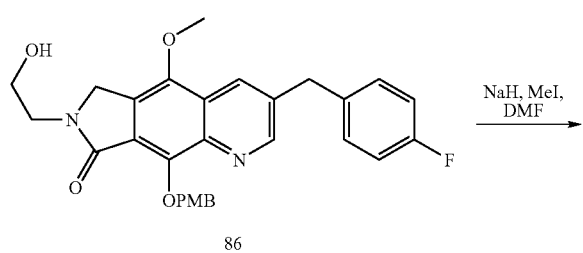

3.80 (t, 2H), 3.69 (t, 2H), 3.40 (s, 3H); 300 MHz $^{19}$F NMR (CD$_3$OD) δ (ppm) −77.70, −118.97; MS: 397 (M+1).

Example 49

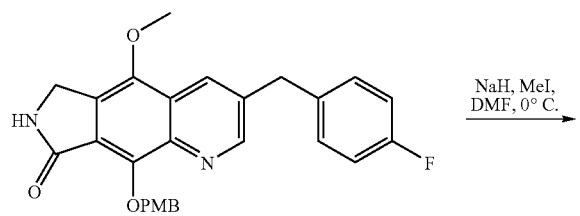

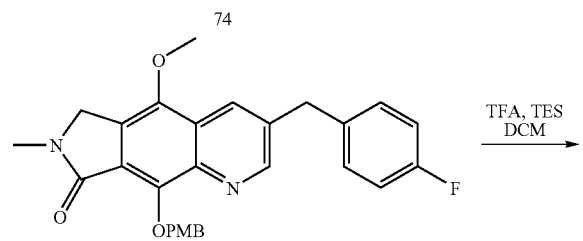

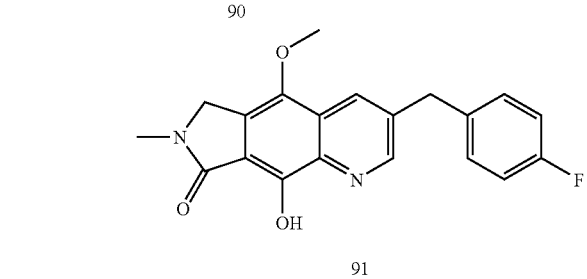

90: The compound was made in a similar fashion as described above for compound 75 with the corresponding lactam 74 (30 mg, 0.059 mmol) and methyl iodide to afford the desired crude product 81 (~35 mg) with no purification upon work-up nor further characterization: MS: 473 (M+1).

91: The compound was made in a similar fashion as described above for compound 76 to afford the desired product 91 (9 mg, 22%—2 steps) as the TFA salt: 300 MHz $^1$H NMR (CD$_3$OD) δ (ppm) 8.80 (s, 1H), 8.52 (s, 1H), 7.32 (dd, 2H), 7.08 (dd, 2H), 4.79 (s, 2H), 4.28 (s, 2H), 4.07 (s, 3H), 3.19 (s, 3H); 300 MHz $^{19}$F NMR (CD$_3$OD) δ (ppm) −77.81, −118.91; MS: 353 (M+1).

Example 50

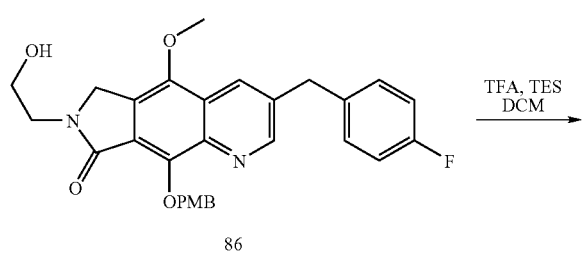

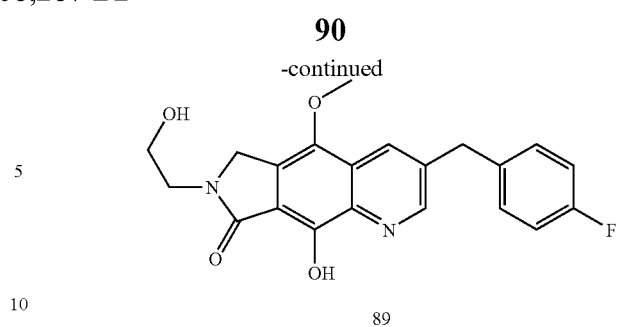

89: The compound was made in a similar fashion as described above for compound 76 to afford the desired product 89 (5 mg, 47%—2 steps) as the TFA salt: 300 MHz $^1$H NMR (CD$_3$OD) δ (ppm) 8.80 (s, 1H), 8.49 (s, 1H), 7.32 (dd, 2H), 7.07 (dd, 2H), 4.89 (s, 2H), 4.28 (s, 2H), 4.06 (s, 3H), 3.86 (t, 2H), 3.74 (t, 2H); 300 MHz $^{19}$F NMR (CD$_3$OD) δ (ppm) −77.75, −118.96; MS: 383 (M+1).

Example 51

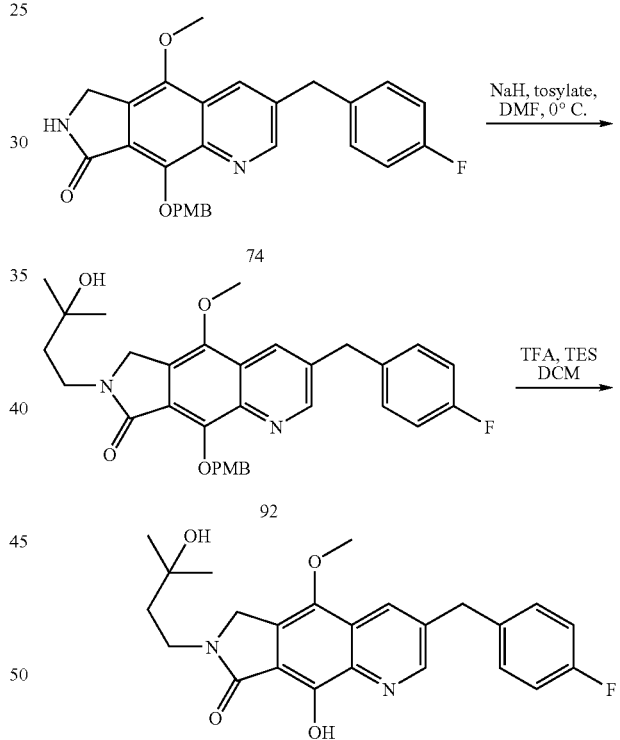

92: The compound was made in a similar fashion as described above for compound 75 with lactam 74 (50 mg, 0.11 mmol) and the corresponding tosylate (42 mg, 0.16 mmol) to afford the desired crude product 92 (~35 mg) with no purification upon work-up nor further characterization: MS: 545 (M+1).

93: The compound was made in a similar fashion as described above for compound 75 to afford the desired product 93 (10 mg, 17%—2 steps) as the TFA salt: 300 MHz $^1$H NMR (CD$_3$OD) δ (ppm) 8.81 (s, 1H), 8.56 (s, 1H), 7.33 (dd, 2H), 7.08 (dd, 2H), 4.82 (s, 2H), 4.29 (s, 2H), 4.08 (s, 3H), 3.75 (m, 2H), 1.89 (m, 2H), 1.30 (s, 3H); 300 MHz $^{19}$F NMR (CD$_3$OD) δ (ppm) −77.82, −118.83; MS: 425 (M+1).

Example 52

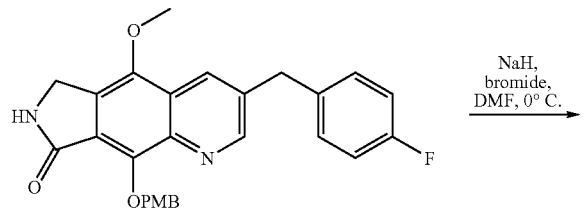

94: The compound was made in a similar fashion as described above for compound 75 with lactam 74 (40 mg, 0.087 mmol) and the corresponding benzyl bromide (12 μL, 0.096 mmol) to afford the desired crude product 94 (~35 mg) with no purification upon work-up nor further characterization: MS: 567 (M+1).

95: The compound was made in a similar fashion as described above for compound 76 to afford the desired product 95 (10 mg, 20%—2 steps) as the TFA salt: 300 MHz $^1$H NMR (CD$_3$OD) δ (ppm) 8.81 (s, 1H), 8.49 (s, 1H), 7.41 (dd, 2H), 7.32 (dd, 2H), 7.08 (m, 4H), 4.79 (s, 2H), 4.66 (s, 2H), 4.27 (s, 2H), 3.99 (s, 3H); 300 MHz $^{19}$F NMR (CD$_3$OD) δ (ppm) −77.84, −117.30, −118.91; MS: 447 (M+1).

Example 53

Synthesis of Compound 5020

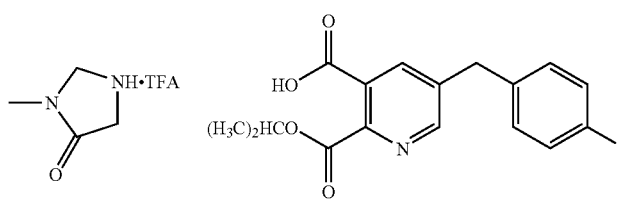

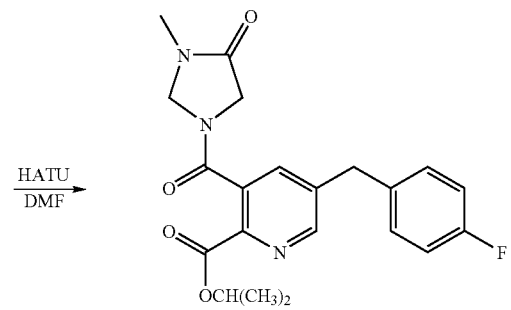

Standard HATU coupling conditions between 50 mg of the amine and 50 mg of the carboxylic acid gave 85 mg of the intermediate amide product 5019 as a crude mixture.

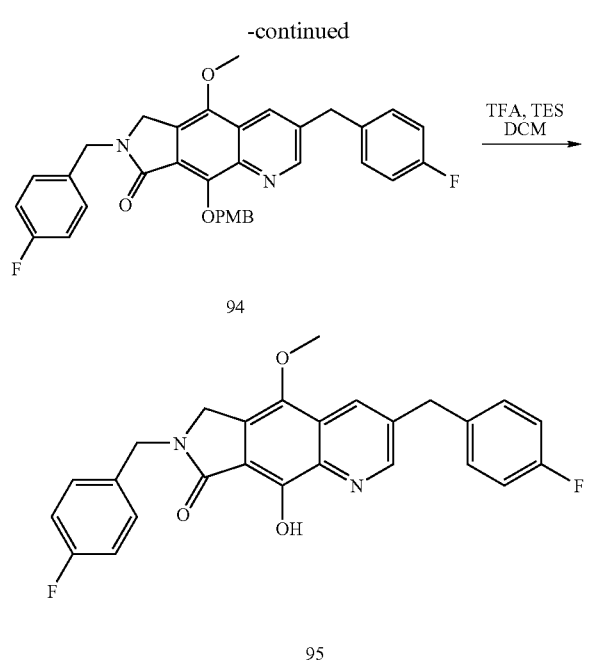

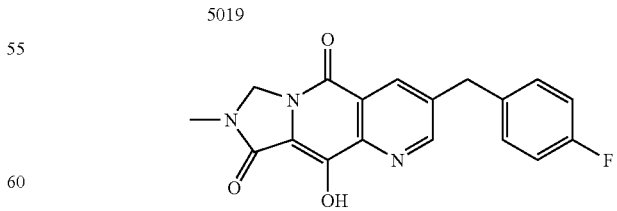

Treatment of 85 mg of the cyclization precursor 5019 with 2 mL NaHMDS (1.0M in THF) solution resulted in conversion to the desired product, as judged by LC/MS analysis.

Upon quenching with 4N HCl and extraction of the aqueous layer with EtOAc, 20 mg of crude product was obtained after concentration of the organic layer. HPLC purification of this material gave 2 mg of the desired final product 5020 (12% yield over 2 steps).

5020: 300 MHz $^1$H NMR (CD$_3$OD) δ (ppm): 9.0 (s, 1H), 8.5 (s, 1H) 5.2 (s, 2H), 4.8 (s, 2H), 3.3 (s, 3H). m/z 340 (M+H).

Example 54

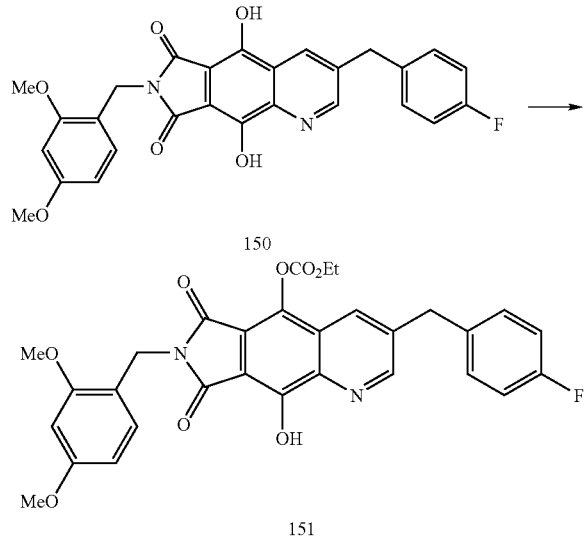

The synthesis of starting bisphenol 150 (also compound 564) is described elsewhere herein. Into a flask containing 150 (1.25 g, 2.56 mmol, 1 equiv.) was added dioxane (26 mL, 0.1 M). NaOH (102 mg, 2.56 mmol, 1 equiv.) dissolved in water (13 mL, 0.25 M) was added to the reaction mixture before ethyl chloroformate (295 µL, 3.07 mmol, 1 equiv.). The reaction was stirred for 16 hours before being quenched with HCl (30 mL, 1 N) and extracted with ethyl acetate (2×30 mL). The organic layer washed several times with water (4×30 mL), saturated NaHCO$_3$ (50 mL), brine solution (50 mL). It was dried over Na$_2$SO$_4$, filtered and concentrated in vacuo to yield 151 as a brown solid.

$^1$H NMR (300 MHz) CDCl$_3$ ∂: 8.94 (s, 1H), 8.27 (s, 1H), 7.21-7.15 (m, 3H), 7.06-7.00 (m, 2H), 6.43-6.41 (s, 2H), 4.83 (s, 2H), 4.43 (q, J=6.9 Hz, 2H), 4.21 (s, 2H), 3.79 (s, 3H), 3.75 (s, 3H), 1.46 (t, J=6.9 Hz, 3H).

MS: 561.07 (M+1).

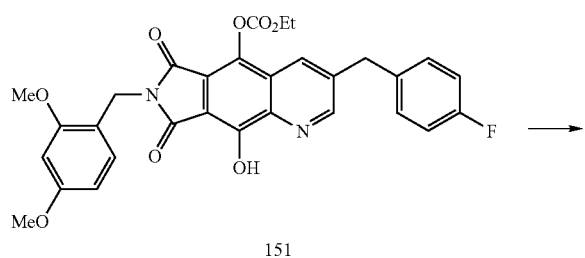

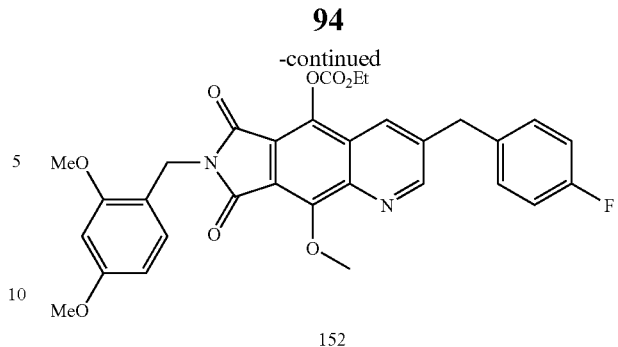

Into a flask containing phenol 151 (1.20 g, 2.21 mmol, 1 equiv.) was added DMF (20 mL) followed by Cs$_2$CO$_3$ (1.80 g, 5.53 mmol, 2.5 equiv.). To this was added MeI (690 µL, 11.07 mmol, 5 equiv.) under a nitrogen atmosphere and stirred for 16 hours. To the reaction was then added water (50 ml) and extracted with ethyl acetate (2×75 mL). The organic layer was washed several times with water (3×30 mL), saturated NaHCO$_3$ (40 mL), brine solution (30 mL). It was dried over Na$_2$SO$_4$, filtered and concentrated in vacuo before being purified by silica gel chromatography using 3/2 Hexanes/ethyl acetate to obtain 152 as an off-white solid.

$^1$H NMR (300 MHz) CDCl$_3$ ∂: 8.94 (d, J=2.1 Hz, 1H), 8.27 (s, 1H), 7.19-7.14 (m, 3H), 7.06-7.00 (m, 2H), 6.43-6.41 (s, 2H), 4.83 (s, 2H), 4.43 (q, J=7.2 Hz, 2H), 4.21 (s, 2H), 3.81 (s, 3H), 3.78 (s, 3H), 3.80 (s, 3H), 1.46 (t, J=7.2 Hz, 3H).

300 MHz $^{19}$F NMR (CDCl$_3$) δ (ppm) −116.02.

MS: 575.18 (M+1).

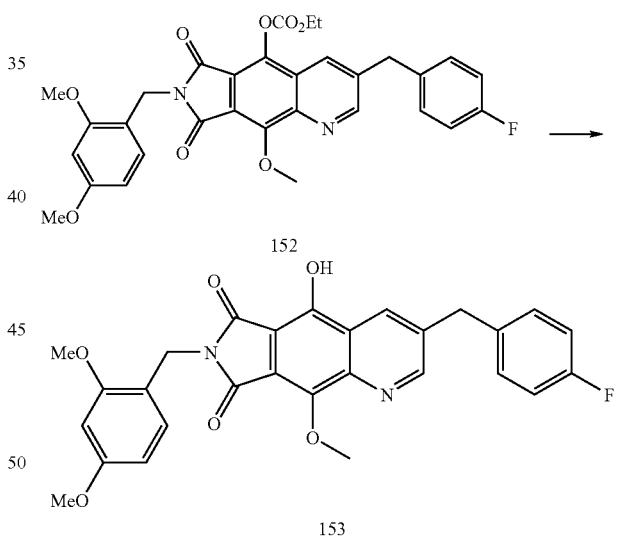

Compound 152 (420 mg, 0.73 mmol, 1 equiv.) was dissolved in THF (7 mL, 0.1 M). A solution of LiOH (92 mg, 2.19 mmol, 3 equiv.) was dissolved separately in H$_2$O (6 mL) before being transferred to the reaction mixture. The reaction was allowed to stir for 16 hours and quenched with HCl (20 mL, 1 N) and extracted with ethyl acetate (2×30 mL). The organic layer was washed with saturated NH$_4$Cl solution (25 mL), brine solution (25 mL) and dried over Na$_2$SO$_4$ and concentrated in vacuo to yield 153 (375 mg).

$^1$H NMR (300 MHz) CDCl$_3$ ∂: 8.80 (d, J=1.8 Hz, 1H), 8.27 (s, 1H), 7.19-7.14 (m, 3H), 7.06-7.00 (m, 2H), 6.43-6.41 (s, 2H), 4.83 (s, 2H), 4.21 (s, 2H), 3.83 (s, 3H), 3.82 (s, 3H), 3.80 (s, 3H).

300 MHz $^{19}$F NMR (CDCl$_3$) δ (ppm) −116.02.
MS: 503.12 (M+1).

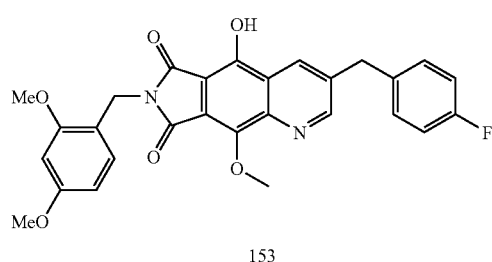
153

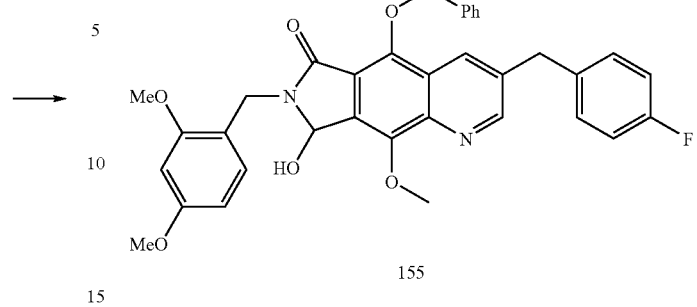
155

Imide 154 (120 mg, 0.18 mmol, 1 equiv.) was dissolved in THF (5 mL) and under a nitrogen atmosphere at 0° C. was added LiBH$_4$ (20 mg, 0.89 mmol, 5 equiv., 0.5 M). The reaction was allowed to stir for 1 hour and then quenched with water (5 mL) and extracted with ethyl acetate (2×5 mL). The organic layer was washed several times with water (2×10 mL), brine solution (10 mL). It was dried over Na$_2$SO$_4$, filtered and concentrated in vacuo to obtain crude 155 (90 mg).
MS: 671.18 (M+1).
R$_f$ 0.20 (9/1 Hex/EtOAc)

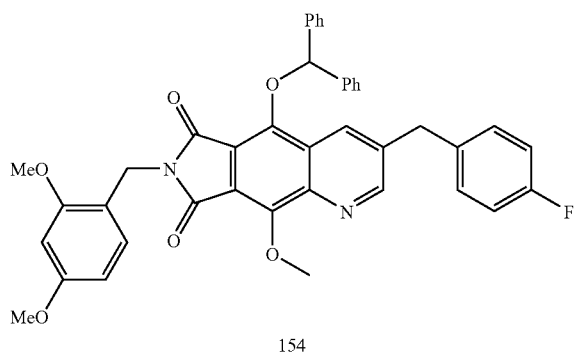
154

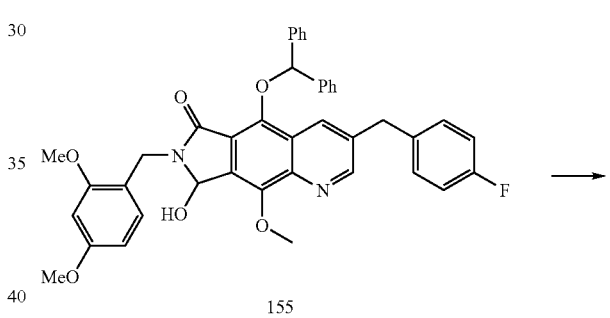
155

Phenol 153 (375 mg, 0.75 mmol, 1 equiv.) was dissolved in 1, 2 dichloroethane (7.5 mL, 0.1 M) and to this was added diphenyldiazomethane (290 mg, 1.50 mmol, 2 equiv.) and heated at 70° C. under a nitrogen atmosphere for 3 hours. The reaction was concentrated in vacuo and purified by silica gel chromatography using 4/1 Hexanes/Ethyl acetate to obtain compound 154.
300 MHz $^{19}$F NMR (CDCl$_3$) δ (ppm) −116.19.
MS: 695.05 (M+23).

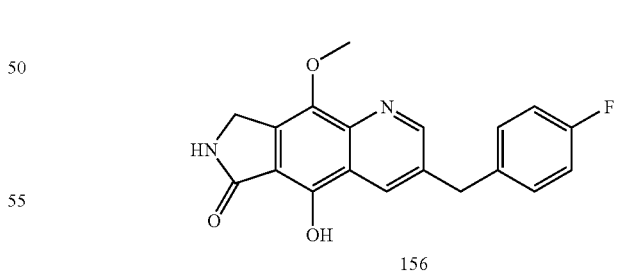
156

A procedure similar to the formation of 156 has been described above.
300 MHz $^1$H NMR (DMSO-d$_6$) δ (ppm) 9.93 (bs, 1H), 8.92 (d, J=2.1 Hz, 1H), 8.74 (s, 1H), 8.40 (s, 1H), 7.40-7.35 (m, 2H), 7.17-7.12 (m, 2H), 4.57 (s, 2H), 4.21 (s, 2H), 4.014 (s, 3H).
$^{19}$F NMR (DMSO) δ (ppm) −74.84, −117.22 (TFA salt).
MS: 339.26 (M+1).

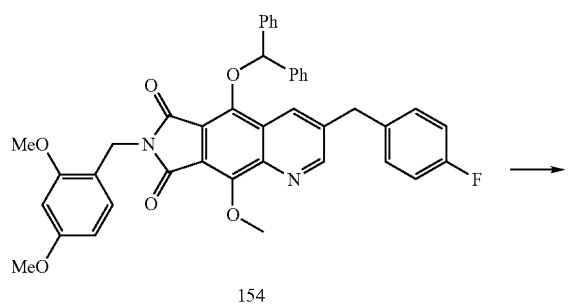
154

Example 55, 56

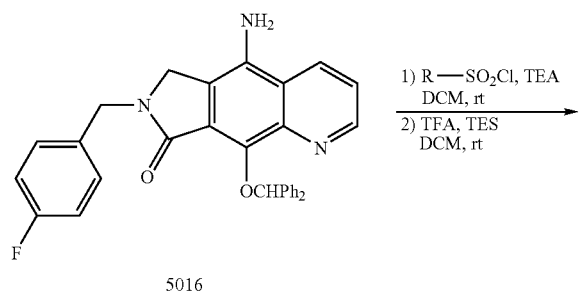

5016

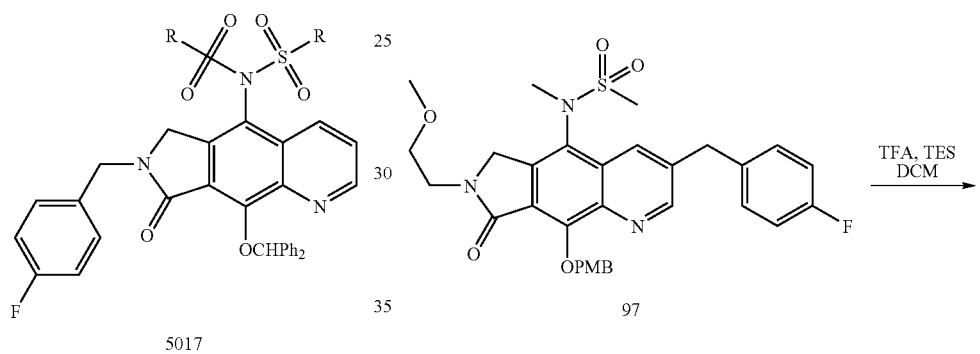

5017

| | R group | Example |
|---|---|---|
| 5017a) | CH$_3$ | 55 |
| 5017b) | CH$_2$CH$_3$ | 56 |

To 50 mg of aniline 5016 in 1 ml dichloromethane at rt was added 56 uL TEA, followed by 20 uL of methanesulfonyl chloride (0.2 mmol, 2 equiv). After 3 h the reaction was shown to be complete by LC/MS, and the reaction was diluted with 50 mL ethyl acetate. The organics were washed with 25 mL water and then 25 mL aq. brine solution. After drying over Na$_2$SO$_4$, solvent was removed by rotary evaporation to give 82 mg of the acylated aniline intermediate. Treatment of this product material with excess TFA and TES in a 1.0M solution of DCM resulted in deprotection of the DPM protecting group. 13 mg (31% yield over 2 steps) of the bis-acylated aniline product 5017a as the TFA salt after purification by reverse phase HPLC.

5017a—: 300 MHz $^1$H NMR (CD$_3$CN) δ (ppm): 8.9 (d, 1H), 8.4 (d, 1H), 7.8 (m, 1H), 7.4 (t, 2H), 7.1 (t, 2H), 4.7 (s, 2H), 4.6 (s, 2H), 3.4 (s, 3H). m/z=480 (M+H).

5017b—: 300 MHz $^1$H NMR (CDCl$_3$) δ (ppm): 9.0 (d, 1H), 8.4 (d, 1H), 7.7 (m, 1H), 7.3 (t, 2H), 7.0 (t, 2H), 5.8 (s, 1H), 4.8 (s, 2H), 4.5 (s, 2H), 3.6 (q, 4H), 1.4 (t, 6H). m/z=508 (M+H).

Example 57

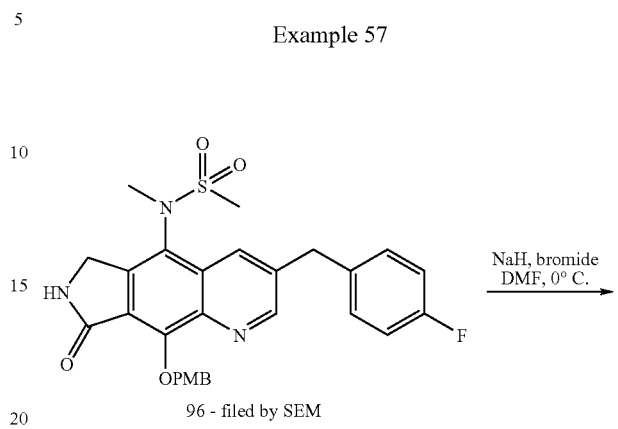

96 - filed by SEM

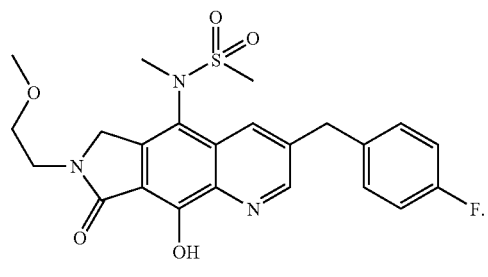

97

98

97: The compound was made in a similar fashion as described above for compound 75 with the corresponding lactam 96 (50 mg, 0.093 mmol) and bromide to afford the desired product 97 (24 mg, 43%): 300 MHz $^1$H NMR (CDCl$_3$) δ (ppm) 8.95 (s, 1H), 7.85 (s, 1H), 7.65 (d, 2H), 7.22 (dd, 2H), 7.07 (dd, 2H), 6.88 (d, 2H), 5.73 (m, 2H), 4.7 (m, 2H), 4.0-3.6 (m, 4H), 3.8 (s, 3H), 3.38 (s, 3H), 3.28 (s, 3H), 2.89 (s, 3H); MS: 594 (M+1).

98: The compound was made in a similar fashion as described above for compound 76 to afford the desired product 98 (15 mg, 78%) as the parent: 300 MHz $^1$H NMR (CDCl$_3$) δ (ppm) 8.88 (s, 1H), 7.87 (s, 1H), 7.25 (dd, 2H), 7.06 (dd, 2H), 4.75 (m, 2H), 4.24 (s, 2H), 4.0-3.6 (m, 4H), 3.38 (s, 3H), 3.27 (s, 3H), 2.86 (s, 3H); 300 MHz $^{19}$F NMR (CDCl$_3$) δ (ppm) −115.87; MS: 474 (M+1).

4H), 3.32 (s, 3H), 3.09 (s, 3H); 300 MHz $^{19}$F NMR (CD$_3$OD) δ (ppm) −77.68, −118.94; MS: 460 (M+1).

Example 58

Example 59

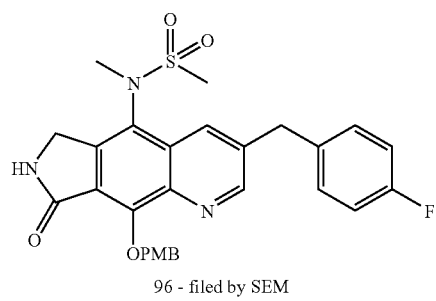

96 - filed by SEM

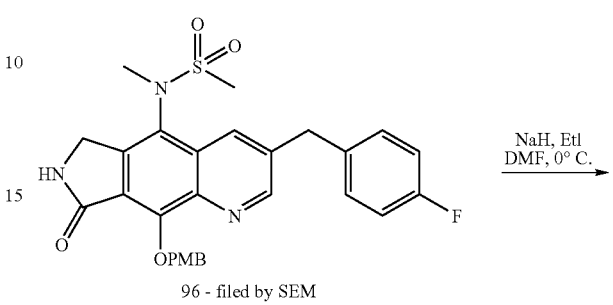

96 - filed by SEM

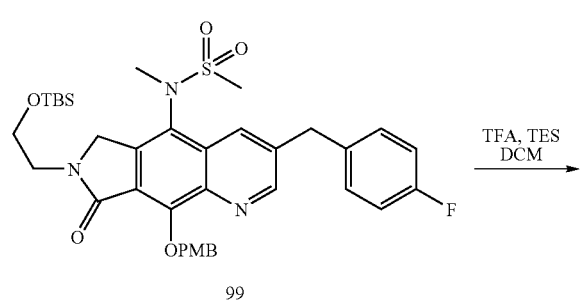

99

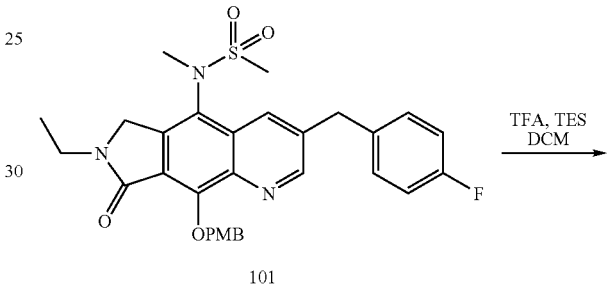

101

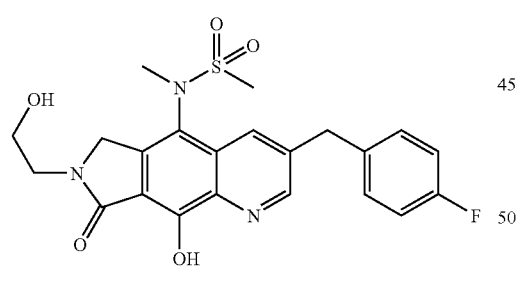

100

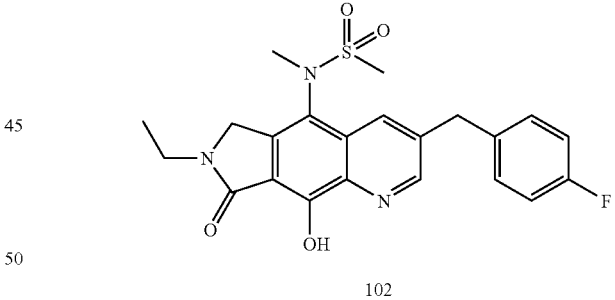

102

99: The compound was made in a similar fashion as described above for compound 75 with lactam 96 (16.5 mg, 0.031 mmol) and the bromide 84 (8 mg, 0.034 mmol) to afford the desired crude product 99 (~20 mg) with no purification upon work-up nor further characterization: MS: 694 (M+1).

100: The compound was made in a similar fashion as described above for compound 76 to afford the desired product 100 (10 mg, 20%—2 steps) as the TFA salt: 300 MHz $^1$H NMR (CD$_3$OD) δ (ppm) 8.83 (s, 1H), 8.20 (s, 1H), 7.35 (dd, 2H), 7.08 (dd, 2H), 4.83 (m, 2H), 4.29 (s, 2H), 3.9-3.6 (m, 101: The compound was made in a similar fashion as described above for compound 75 with the corresponding lactam 101 (35 mg, 0.065 mmol) and commercially available ethyl iodide to afford the desired product 77 (11 mg, 30%): 300 MHz $^1$H NMR (CDCl$_3$) δ (ppm) 8.93 (s, 1H), 7.74 (s, 1H), 7.65 (d, 2H), 7.23 (dd, 2H), 7.07 (dd, 2H), 6.88 (d, 2H), 5.70 (m, 2H), 4.6 (m, 2H), 4.23 (s, 2H), 3.8 (s, 3H), 3.70 (q, 2H), 3.27 (s, 3H), 2.86 (s, 3H), 1.31 (t, 3H); MS: 564 (M+1).

102: The compound was made in a similar fashion as described above for compound 76 to afford the desired product 102 (4 mg, 35%) as the TFA salt: 300 MHz $^1$H NMR (CDCl$_3$) δ (ppm) 8.96 (s, 1H), 7.85 (s, 1H), 7.25 (dd, 2H), 7.08 (dd, 2H), 4.65 (m, 2H), 4.26 (s, 2H), 3.69 (m, 2H), 3.26

(s, 3H), 2.84 (s, 3H), 1.33 (t, 3H); 300 MHz $^{19}$F NMR (CD$_3$OD) δ (ppm) −76.27, −115.60; MS: 444 (M+1).

Example 60

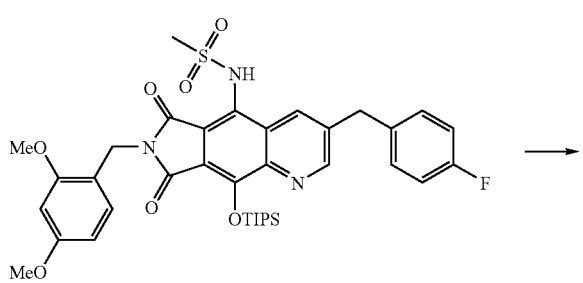

160

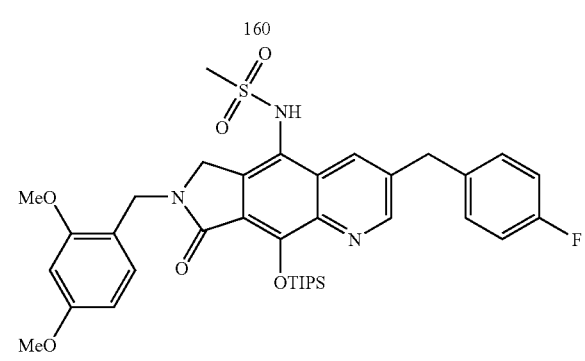

161

Imide 160 (5.50 g, 7.63 mmol, 1 equiv.) was dissolved in THF (25 mL, 0.3 M) and under a nitrogen atmosphere at 0° C. was slowly added LiBH4 (5.72 mL, 11.44 mmol, 1.5 equiv., 2 M in THF) over 15 min. The bath was removed and to the reaction was added anhydrous MeOH (620 μL, 15.25 mmol, 2 equiv.) before being heated to 80° C. The reaction was allowed to reflux for 1 hour and then cooled and quenched with water and extracted with ethyl acetate (2×100 mL). The combined organic layers were washed several times with water (2×50 mL), brine solution (10 mL). It was dried over Na$_2$SO$_4$, filtered and concentrated in vacuo to obtain lactam 161 (5.0 g, y. 93%).

300 MHz $^1$H NMR (CDCl$_3$) δ (ppm) 8.75 (d, J=1.8 Hz, 1H), 8.00 (s, 1H), 7.22-7.18 (m, 3H), 7.07-7.04 (m, 2H), 6.45-6.44 (m, 2H), 6.05 (bs, 1H), 4.76 (s, 2H), 4.45 (s, 2H), 4.20 (s, 2H), 3.83 (s, 3H), 3.80 (s, 3H), 2.80 (s, 3H), 1.54-1.53 (sp, J=7.6 Hz, 3H), 1.15 (d, J=7.6 Hz, 18H).

300 MHz $^{19}$F NMR (CDCl$_3$) δ (ppm) −116.10
MS: 707.99 (M+1).

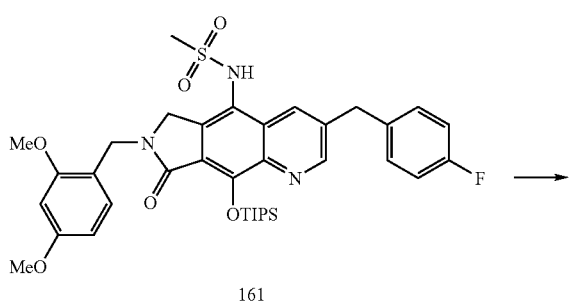

161

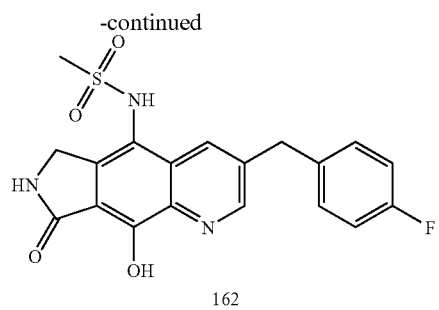

162

Lactam 161 (50 mg, 0.069 mmol, 1 equiv.) was dissolved in TFA (3 mL) and heated to 85° C. for an hour. The reaction mixture was then concentrated in vacuo and azeotroped with toluene (2×5 mL). The resulting compound, 162, was washed and sonicated with Ethyl ether/MeOH (3/1, 50 mL) before being filtered and dried.

300 MHz $^1$H NMR (DMSO-d$_6$) δ (ppm) 9.45 (s, 1H), 8.85 (bs, 1H), 8.43 (s, 1H), 8.38 (bs, 1H), 7.34-7.36 (m, 2H), 7.14-7.11 (m, 2H), 4.52 (s, 2H), 4.25 (s, 2H), 2.96 (s, 3H).

300 MHz $^{19}$F NMR (DMSO-d$_6$) δ (ppm) −73.92, −117.21
MS: 401.95 (M+1).

Example 61

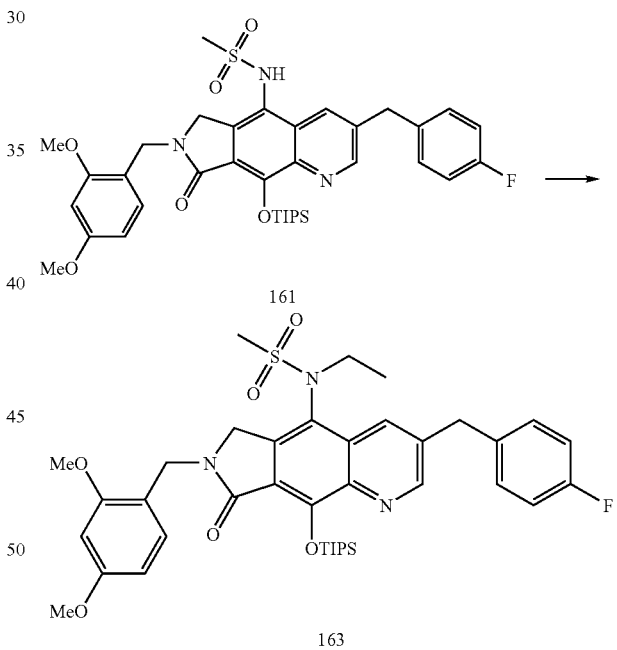

161

163

Lactam 161 (2.5 g, 3.53 mmol, 1 equiv) was stirred in DMF (24 mL, 0.15 M) and treated with Cs$_2$CO$_3$ (2.30 g, 7.07 mmol, 2 equiv.). It was stirred for 10 min. before ethyl iodide (430 μL, 5.30 mmol, 1.5 equiv.) was added and allowed to stir for an hour. The reaction mixture was diluted with ethyl acetate then quenched with water. The organic layer was washed with water, saturated NH$_4$Cl and brine. The solution was dried over sodium sulfate, filtered and concentrated in vacuo with no further purification to afford the product 163 (4.84 g, 94% mass recovery).

300 MHz $^1$H NMR (CDCl$_3$) δ (ppm) 8.75 (s, 1H), 7.73 (s, 1H), 7.25-7.19 (m, 3H), 7.10-7.04 (m, 2H), 6.47-6.44 (m, 2H), 4.77 (AB, J=14.4, 10.8 Hz, 2H), 4.62 (d, J=17.5 Hz, 1H), 4.30 (d, J=17.5 Hz, 1H), 4.20 (s, 2H), 3.81 (s, 3H), 3.79-3.64 (m, 1H), 3.55-3.48 (m, 1H), 2.76 (s, 3H), 1.59-1.52 (m, 3H), 1.12 (d, J=7.8 Hz, 18H), 1.03 (t, J=7.5 Hz, 1H).

300 MHz $^{19}$F NMR (CDCl$_3$) δ (ppm) −116.04

MS: 735.95 (M+1).

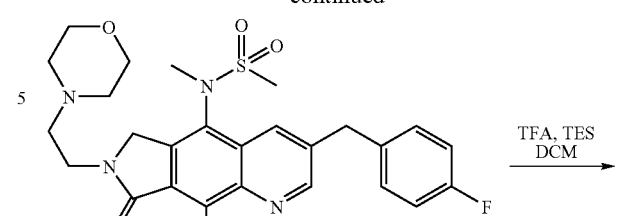

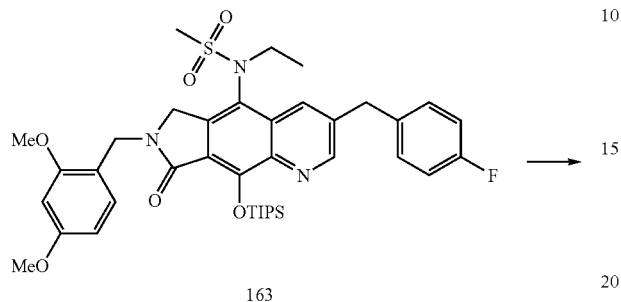

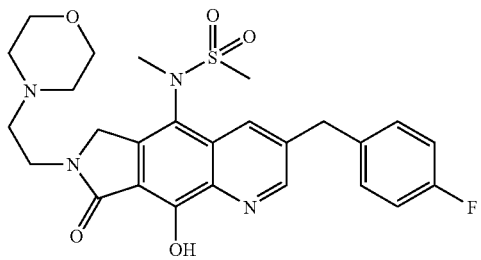

Lactam 164 is prepared in a manner similar to as described above.

300 MHz $^1$H NMR (DMSO-d$_6$) δ (ppm) 10.78 (bs, 1H), 8.86 (s, 1H), 8.49 (bs, 1H), 8.15 (s, 1H), 7.36-7.34 (m, 2H), 7.14-7.11 (m, 2H), 4.49 (s, 2H), 4.26 (s, 2H), 3.70 (q, J=6.9 Hz, 2H), 3.13 (s, 3H), 0.96 (t, J=6.9 Hz, 3H).

300 MHz $^{19}$F NMR (DMSO-d$_6$) δ (ppm) −117.13

MS: 430.20 (M+1).

103: The compound was made in a similar fashion as described above with lactam 96 (35 mg, 0.065 mmol) and the bromide 80 (16.5 mg, 0.085 mmol) to afford the desired crude product 103 (~50 mg) with no purification upon work-up nor further characterization: MS: 649 (M+1).

104: The compound was made in a similar fashion as described above to afford the desired product 104 (17.5 mg, 42%—2 steps) as the TFA salt: 300 MHz $^1$H NMR (DMSO) δ (ppm) 9.58 (bs, 1H), 8.88 (s, 1H), 8.20 (s, 1H), 7.39 (dd, 2H), 7.15 (dd, 2H), 4.65 (m, 2H), 4.28 (s, 2H), 4.1-3.4 (m, 10H), 3.27 (s, 3H), 3.20 (s, 3H), 3.6 (m, 2H); 300 MHz $^{19}$F NMR (DMSO) δ (ppm) −74.69, −117.05; MS: 529 (M+1).

Example 62

Example 63

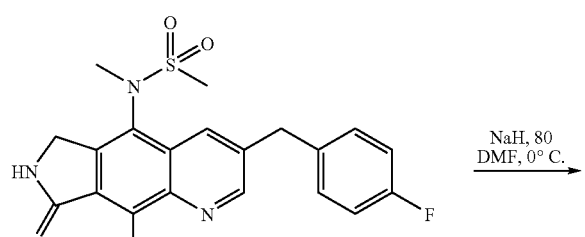

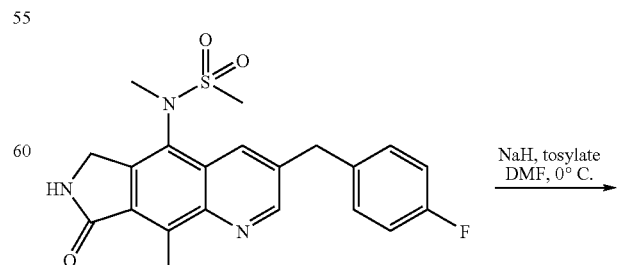

105

-continued

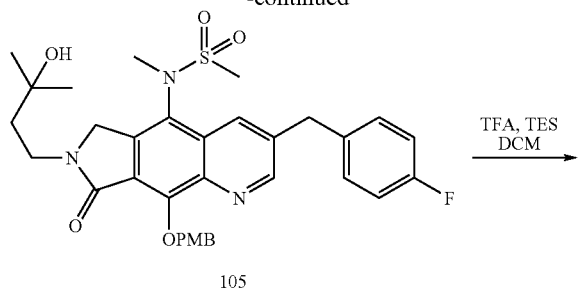

105

TFA, TES
DCM
→

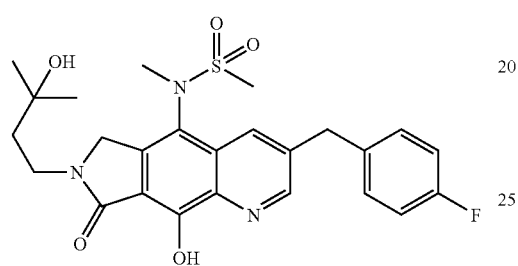

106

106

105: The compound was made in a similar fashion as described above with lactam 96 (35 mg, 0.065 mmol) and the tosylate (22 mg, 0.085 mmol) to afford the desired crude product 105 (~48 mg) with no purification upon work-up nor further characterization: MS: 622 (M+1).

106: The compound was made in a similar fashion as described above to afford the desired product 106 (16.5 mg, 41%—2 steps) as the TFA salt: 300 MHz $^1$H NMR (CD$_3$OD) δ (ppm) 8.84 (s, 1H), 8.26 (s, 1H), 7.34 (dd, 2H), 7.08 (dd, 2H), 4.74 (m, 2H), 4.31 (s, 2H), 3.75 (t, 2H), 3.33 (s, 3H), 3.09 (s, 3H), 1.88 (t, 2H), 1.29 (s, 6H); 300 MHz $^{19}$F NMR (CD$_3$OD) δ (ppm) −78.05, −118.81; MS: 502 (M+1).

Example 64

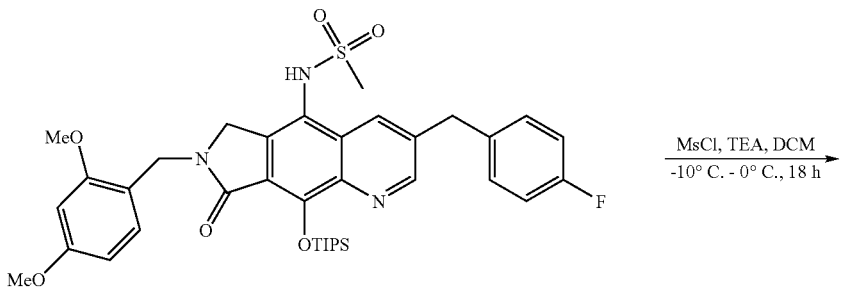

12

MsCl, TEA, DCM
-10° C. - 0° C., 18 h
→

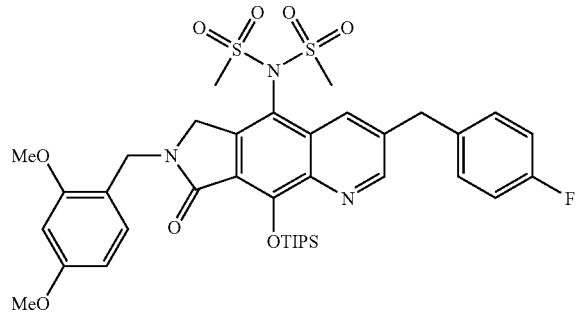

13

The common intermediate 12 (100 mg, 1.0 eq, 0.14 mmol) was dissolved in DCM (1.4 mL) and TEA (59 uL, 3.0 eq, 0.42 mmol) was added. The reaction mixture was cooled to −10° C. and mesyl chloride (11 uL, 1.0 eq, 0.14 mmol) was added via syringe. The reaction stirred at ambient temperature overnight and LC/MS showed the reaction to be complete. The reaction mixture was concentrated and the resulting residue was dissolved in EtOAc. The reaction was quenched with water and the layers separated. The organics were washed with saturated bicarbonate, water, and brine and dried over Na₂SO₄. The solvent was removed to yield a dark red film as compound 13 (160 mg).

13: 300 MHz $^1$H NMR (CDCl₃) δ (ppm): 8.8 (d, 1H), 7.7 (d, 1H), 7.2 (m, 4H), 7.0 (t, 2H), 6.4 (m, 3H), 4.7 (s, 2H), 4.4 (s, 2H), 4.2 (s, 2H), 3.8 (d, 6H), 3.2 (s, 6H), 1.5 (m, 3H), 1.0 (d, 18H).

MS: 787 (M+H).

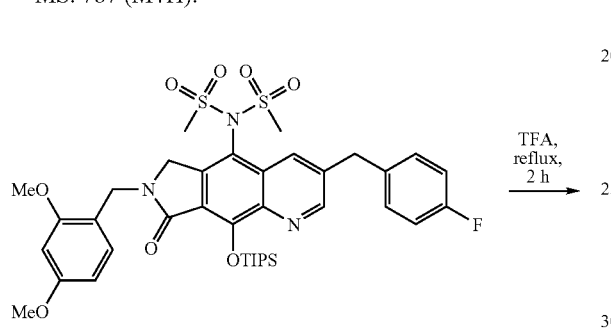

13

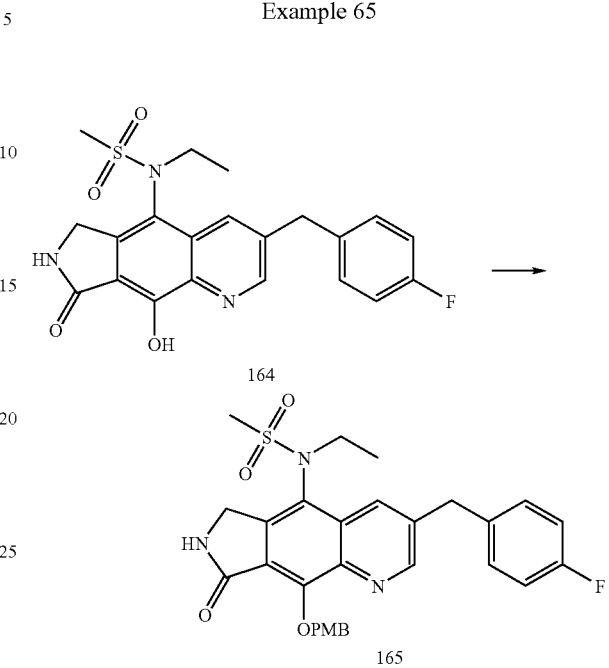

14

Intermediate 13 was dissolved in TFA (5 mL) and heated to reflux (75° C.) with condenser under nitrogen. After 2 h, LC/MS indicated that the reaction was complete, so the reaction mixture was cooled to room temperature. The reaction was diluted with toluene and concentrated to a residue. The resulting dark solid was then dissolved in DMSO and purified by rpHPLC to yield compound 14 (GS-337569, 5.1 mg).

14: 300 MHz $^1$H NMR (DMSO-d₆) δ (ppm): 8.9 (d, 1H), 8.5 (s, 1H), 7.9 (s, 1H), 7.3 (t, 2H), 7.1 (t, 2H), 4.5 (s, 2H), 4.3 (s, 2H), 3.5 (s, 6H). MS: 480 (M+H).

Example 65

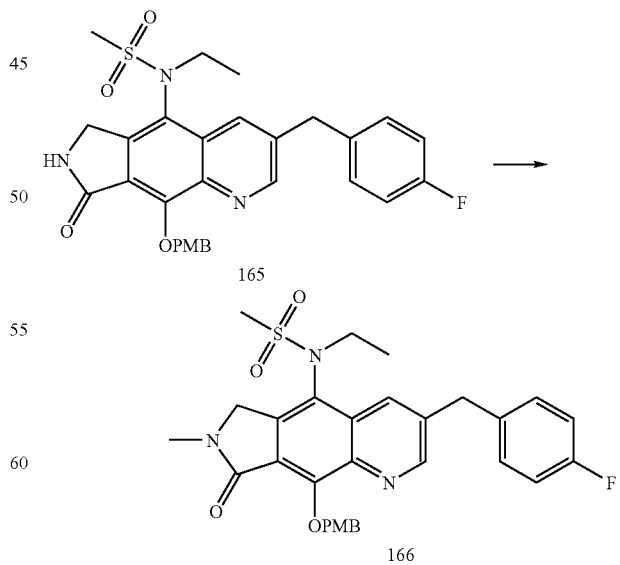

Lactam 165 is prepared in a manner similar as described above for compound 76.

300 MHz $^1$H NMR (CDCl₃) δ (ppm) 8.95 (d, J=1.5 Hz, 1H), 7.76 (s, 1H), 7.62 (d, J=8.6 Hz, 2H), 7.21-7.19 (m, 2H), 7.10-7.04 (m, 2H), 6.88 (d, J=8.6 Hz, 2H), 6.20 (bs, 1H), 5.76 (d, J=4.2 Hz, 2H), 4.84 (d, J=16.8 Hz, 1H), 4.53 (d, J=16.8 Hz, 1H), 4.23 (s, 2H), 3.80 (s, 3H), 3.59-3.47 (m, 2H), 2.82 (s, 3H), 1.13 (t, J=6.9 Hz, 1H).

300 MHz $^{19}$F NMR (CDCl₃) δ (ppm) −115.82

MS: 572.07 (M+23).

Lactam 166 is prepared in a manner as described above for compound 75.

300 MHz $^1$H NMR (CDCl$_3$) δ (ppm) 8.96 (s, 1H), 7.74 (s, 1H), 7.62 (d, J=8.4 Hz, 2H), 7.21-7.19 (m, 2H), 7.10-7.04 (m, 2H), 6.88 (d, J=8.6 Hz, 2H), 5.71 (d, J=8.1 Hz, 2H), 4.84 (d, J=17.4 Hz, 1H), 4.53 (d, J=17.4 Hz, 1H), 4.23 (s, 2H), 3.80 (s, 3H), 3.59-3.47 (m, 2H), 3.22 (s, 3H), 2.82 (s, 3H), 1.13 (t, J=6.4 Hz, 3H).

300 MHz $^{19}$F NMR (CDCl$_3$) δ (ppm) −115.77

MS: 586.13 (M+23).

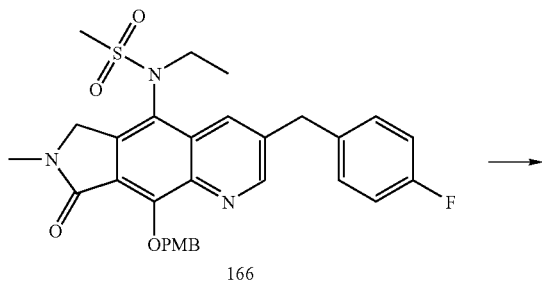
166

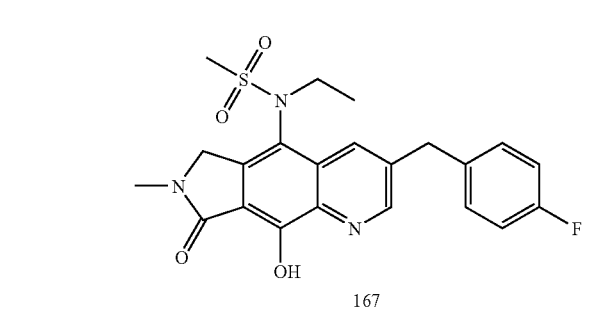
167

Phenol 167 is prepared in a manner as described above for compound 76.

300 MHz $^1$H NMR (CDCl$_3$) δ (ppm) 8.90 (s, 1H), 7.75 (s, 1H), 7.21-7.19 (m, 2H), 7.10-7.04 (m, 2H), 4.84 (d, J=17.3 Hz, 1H), 4.53 (d, J=17.3 Hz, 1H), 4.23 (s, 2H), 3.85-3.75 (m, 1H), 3.54-3.45 (m, 1H), 3.21 (s, 1H), 2.78 (s, 3H), 1.18 (t, J=6.6 Hz, 1H).

300 MHz $^{19}$F NMR (CDCl$_3$) δ (ppm) −115.73

MS: 444.13 (M+1).

Example 66

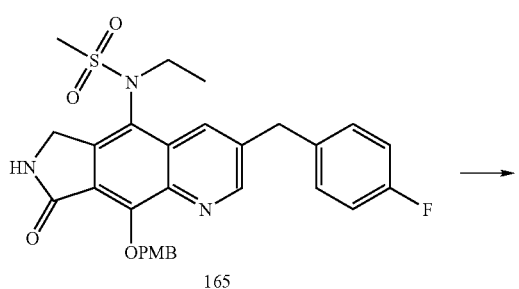
165

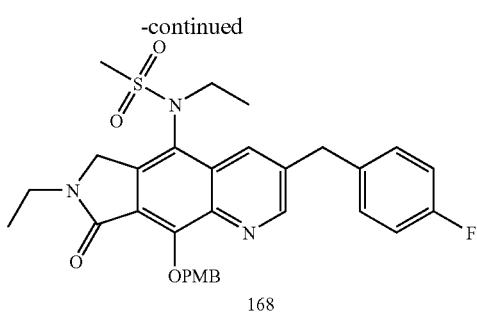
168

Lactam 168 is prepared in a manner as described above for compound 75.

300 MHz $^1$H NMR (CDCl$_3$) δ (ppm) 8.94 (d, J=1.8 Hz, 1H), 7.72 (s, 1H), 7.65 (d, J=8.4 Hz, 2H), 7.21-7.19 (m, 2H), 7.10-7.04 (m, 2H), 6.88 (d, J=8.4 Hz, 2H), 5.71 (d, J=10.5 Hz, 2H), 4.75 (d, J=17.2 Hz, 1H), 4.44 (d, J=17.2 Hz, 1H), 4.22 (s, 2H), 3.80 (s, 3H), 3.67-3.66 (m, 2H), 3.59-3.52 (m, 2H), 2.81 (s, 3H), 1.29 (t, J=7.5 Hz, 3H), 1.11 (t, J=7.2 Hz, 3H).

300 MHz $^{19}$F NMR (CDCl$_3$) δ (ppm) −115.83

MS: 586.13 (M+23).

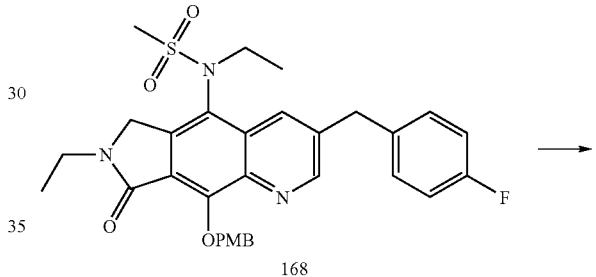
168

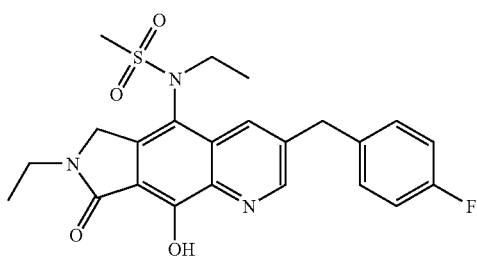
169

Phenol 169 is prepared in a manner as described above for compound 76.

300 MHz $^1$H NMR (CDCl$_3$) δ (ppm) 8.90 (s, 1H), 7.74 (s, 1H), 7.21-7.19 (m, 2H), 7.10-7.04 (m, 2H), 4.78 (d, J=16.3 Hz, 1H), 4.51 (d, J=16.3 Hz, 1H), 4.23 (s, 2H), 3.85-3.75 (m, 2H), 3.54-3.45 (m, 2H), 2.78 (s, 3H), 1.33-1.30 (m, 3H), 1.13-1.05 (m, 3H).

300 MHz $^{19}$F NMR (CDCl$_3$) δ (ppm) −115.73, −49.89

MS: 458.13 (M+1).

Example 67

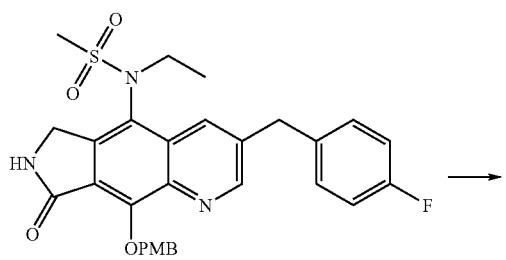

165

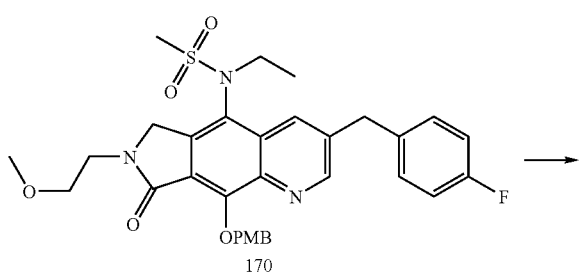

170

Lactam 170 is prepared in a manner as described above for compound 75.

300 MHz $^1$H NMR (CDCl$_3$) δ (ppm) 8.93 (d, J=2.1 Hz, 1H), 7.81 (s, 1H), 7.64 (d, J=8.6 Hz, 2H), 7.21-7.19 (m, 2H), 7.10-7.04 (m, 2H), 6.88 (d, J=8.6 Hz, 2H), 5.75 (d, J=7.2 Hz, 1H), 5.69 (d, J=7.2 Hz, 1H), 4.82 (d, J=17.4 Hz, 1H), 4.59 (d, J=17.4 Hz, 1H), 4.22 (s, 2H), 3.80 (s, 3H), 3.78-3.65 (m, 4H), 3.67-3.66 (m, 2H), 3.37 (s, 3H), 2.85 (s, 3H), 1.11 (t, J=6.9 Hz, 3H).

300 MHz $^{19}$F NMR (CDCl$_3$) δ (ppm) −115.95

MS: 630.13 (M+23).

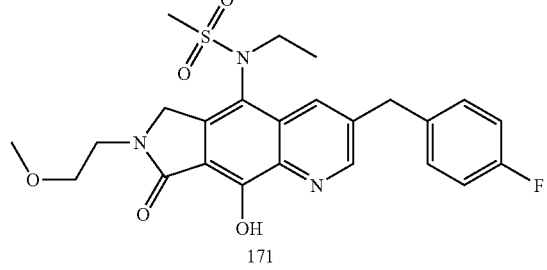

170

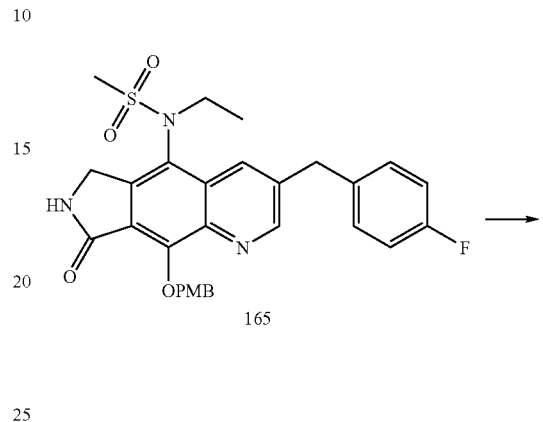

171

Lactam 171 is prepared in a manner as described above for compound 76.

300 MHz $^1$H NMR (CDCl$_3$) δ (ppm) 8.89 (s, 1H), 7.81 (s, 1H), 7.21-7.19 (m, 2H), 7.10-7.04 (m, 2H), 4.85 (d, J=16.1 Hz, 1H), 4.62 (d, J=16.1 Hz, 1H), 4.22 (s, 2H), 3.78-3.65 (m, 4H), 3.67-3.66 (m, 2H), 3.39 (s, 3H), 2.82 (s, 3H), 1.11 (t, 3H).

300 MHz $^{19}$F NMR (CDCl$_3$) δ (ppm) −115.84

MS: 510.13 (M+23).

Example 68

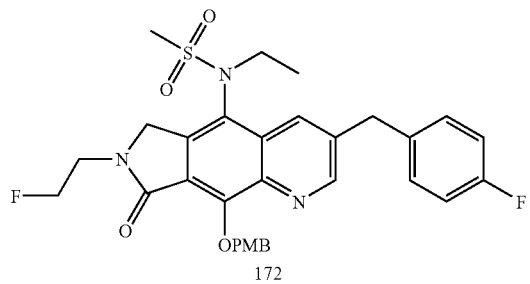

165

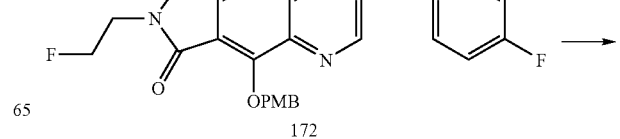

172

Lactam 172 is prepared in a manner as described above for compound 75.

300 MHz $^1$H NMR (CDCl$_3$) δ (ppm) 8.94 (d, J=2.1 Hz, 1H), 7.80 (s, 1H), 7.65 (d, J=8.7 Hz, 2H), 7.21-7.19 (m, 2H), 7.10-7.04 (m, 2H), 6.88 (d, J=8.7 Hz, 2H), 5.71 (d, J=4.2 Hz, 2H), 4.88 (d, J=17.1 Hz, 1H), 4.83-4.80 (m, 1H), 4.44 (d, J=17.1 Hz, 1H), 4.66-4.60 (m, 1H), 4.22 (s, 2H), 3.80 (s, 3H), 3.79-3.75 (m, 2H), 3.62-3.57 (m, 2H), 2.84 (s, 3H), 1.11 (t, J=6.9 Hz, 3H).

300 MHz $^{19}$F NMR (CDCl$_3$) δ (ppm) −115.87

MS: 6.18.07 (M+23).

172

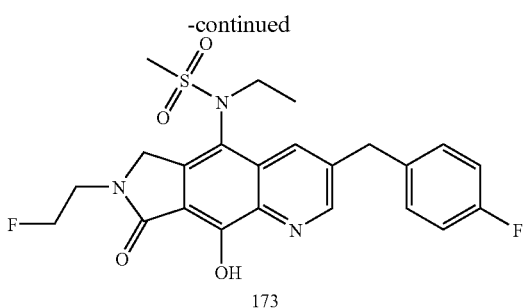

173

Phenol 169 is prepared in a manner as described above for compound 76.

300 MHz $^1$H NMR (CDCl$_3$) δ (ppm) 8.88 (d, J=2.1 Hz, 1H), 7.82 (s, 1H), 7.21-7.19 (m, 2H), 7.10-7.04 (m, 2H), 4.88 (d, J=17.1 Hz, 1H), 4.79-4.70 (m, 1H), 4.69 (d, J=17.1 Hz, 1H), 4.66-4.60 (m, 1H), 4.22 (s, 2H), 3.95-3.89 (m, 1H), 3.80-3.72 (m, 2H), 3.62-3.57 (m, 1H), 2.82 (s, 3H), 1.11 (t, J=6.9 Hz, 3H).

300 MHz $^{19}$F NMR (CDCl$_3$) δ (ppm) −115.77
MS: 498.13 (M+23).

Example 69

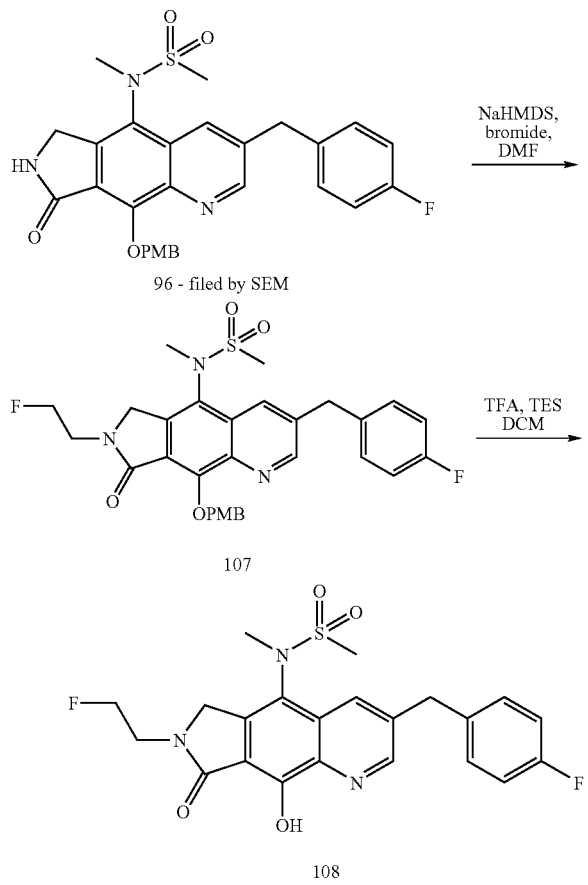

107: To a solution of lactam intermediate 96 (50 mg, 0.093 mmol) dissolved in DMF (0.93 ml) was added Sodium bis(trimethylsilyl)amide (NAHMDS) (0.121 mL, 0.12 mmol, 1M THF) and stirred for 5 minutes under nitrogen atmosphere. Commercially available 1-Bromo-2-fluoroethane (18 µL, 0.24 mmol) was added and the reaction was allowed to stir for 3 hours at room temperature. The reaction was quenched with H$_2$O and diluted with ethyl acetate. The organic layer was washed with H$_2$O, aqueous LiCl (twice), and brine, then dried (over Na$_2$SO$_4$), filtered and concentrated in vacuo. The crude residue was purified by chromatography on silica gel (3/1—ethyl acetate/hexane) to afford the desired product 107 (25 mg, 46%): 300 MHz $^1$H NMR (CDCl$_3$) δ (ppm) 8.94 (s, 1H), 7.82 (s, 1H), 7.63 (d, 2H), 7.21 (dd, 2H), 7.07 (dd, 2H), 6.88 (d, 2H), 5.72 (m, 2H), 4.9-4.6 (m, 4H), 4.24 (s, 3H), 4.2-3.7 (m, 2H), 3.8 (s, 3H), 3.28 (s, 3H), 2.89 (s, 3H); MS: 604 (M+23).

108: The compound was made in a similar fashion as described above to afford the desired product 108 (12 mg, 61%) as the free parent: 300 MHz $^1$H NMR (CDCl$_3$) δ (ppm) 8.87 (s, 1H), 7.85 (s, 1H), 7.22 (dd, 2H), 7.07 (dd, 2H), 4.9-4.6 (m, 4H), 4.25 (s, 2H), 4.0-3.6 (m, 2H), 3.28 (s, 3H), 2.87 (s, 3H); 300 MHz $^{19}$F NMR (CDCl$_3$) δ (ppm) −115.84; MS: 462 (M+1).

Example 70

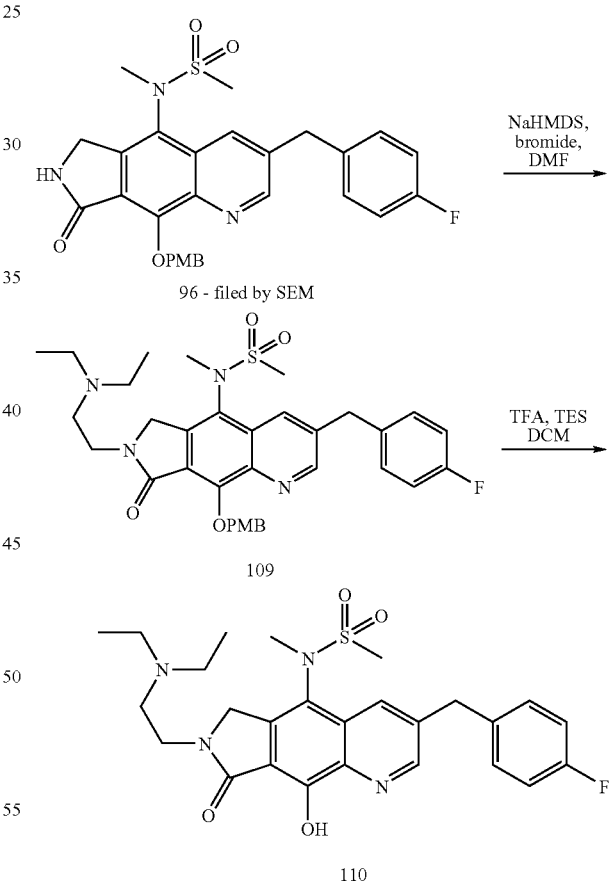

109: 2-Bromo-N,N-diethylethylamine hydrobromide is commercially available and the salt must be freed prior to addition by stirring the reagent in sat. Na$_2$CO$_3$ and EtOAc (1:1) and extracting the freed amine into the organic layer. Otherwise, the compound was made in a similar fashion as compound 107, however the desired product was not purified by silica gel chromatography, instead isolated as the crude product 109 (50 mg): MS: 635 (M+1).

110: The compound was made in a similar fashion as described above to afford the desired product 110 (26 mg, 44%—2 steps) as the TFA salt: 300 MHz $^1$H NMR (CD$_3$OD) δ (ppm) 8.85 (s, 1H), 8.13 (s, 1H), 7.34 (dd, 2H), 7.09 (dd, 2H), 4.78 (m, 2H), 4.30 (s, 2H), 4.02 (m, 2H), 3.54 (t, 2H), 3.40 (m, 4H), 3.30 (s, 3H), 3.07 (s, 3H), 1.37 (t, 6H); 300 MHz $^{19}$F NMR (CD$_3$OD) δ (ppm) −77.83, −118.83; MS: 515 (M+1).

Example 71

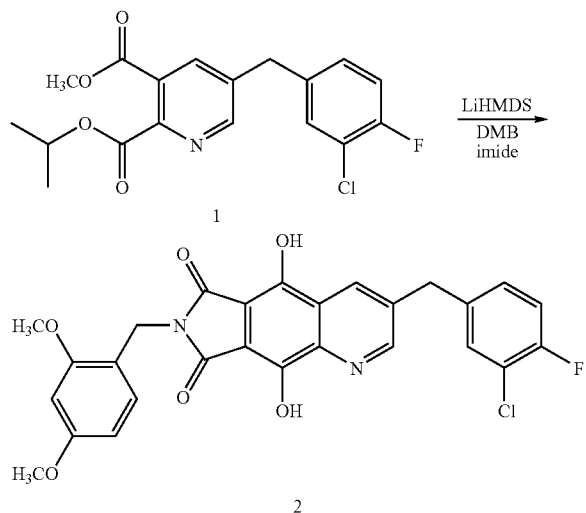

Synthesis of bis-phenol 2

The synthesis of compounds such similar to diester 1 have previously been described in WO89/08103. 3 g (9 mmol, 1 equiv) of diester 1 was dissolved in dry THF (50 mL, 0.18 M). DMB-protected succinimide (2.5 g, 9 mmol, 1 equiv) was added to this reaction solution, which was cooled to 0° C. before NaHMDS (18 mL, 18 mmol, 2 equiv) was added slowly over 15 min. The ice bath was removed and the reaction allowed to stir for 3 h. At that time, HCl$_{(aq)}$ (2 mL, 6 N) was added to the mixture. 300 mL diethyl ether was added, the precipitate was filtered, and then dried under vacuum at with no further purification to afford 4.2 g of the desired product as a dark yellow solid.

300 MHz $^1$H NMR (CD$_3$CN) shows diagnostic peaks at δ 8.95 (d, 1H), 8.78 (d, 1H), 7.47-7.38 (m, 2H), 7.12-6.98 (m, 2H), 4.76 (s, 2H), 4.32 (s, 2H), 3.85 (s, 3H), 3.76 (s, 3H).

MS: 522.9 (M+1).

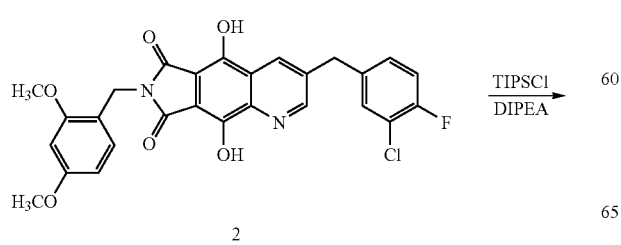

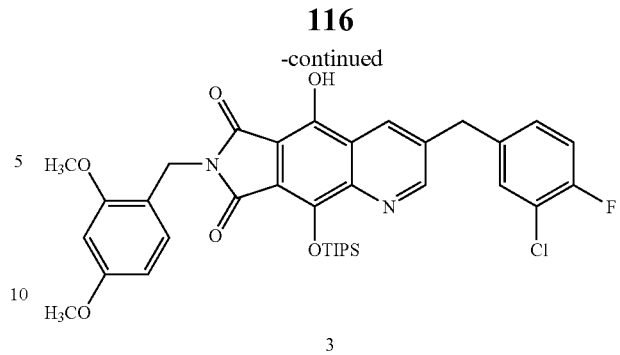

Synthesis of TIPS-ether 3

To 0.8 g (1.5 mmol) of bis-phenol. 2 in 30 ml DMF was added DIPEA (700 μL) and triisopropyl chlorosilane (0.3 mL, 1.5 mmol, 1 equiv). The reaction was heated to 70° C. for 1 h, and then allowed to stir at room temperature for 16 h. At this time, the reaction was diluted with ethyl acetate, washed with aq. citric acid solution and then brine, followed by drying of the organics over Na$_2$SO$_4$. Concentration of the organic layer gave 0.9 g of the desired TIPS ether 3 after combiflash purification.

300 MHz $^1$H NMR (CDCl$_3$) shows diagnostic peaks at δ 8.80 (d, 1H), 8.25 (d, 1H), 7.47-7.38 (m, 2H), 7.12-6.98 (m, 2H), 6.54-6.39 (m, 2H), 4.82 (s, 2H), 4.20 (s, 2H), 3.85 (s, 3H), 3.76 (s, 3H), 1.40 (m, 3H), 0.95 (d, 18H).

MS: 677.2 (M+1).

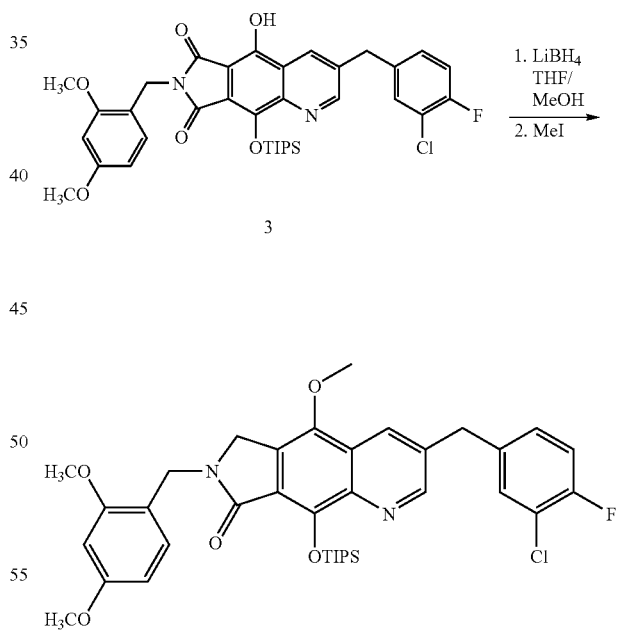

Synthesis of methyl-ether 4

Following the method for direct imide reduction reported above, to a solution of 0.2 g (0.3 mmol, 1 equiv) of the imide 3 in THF/methanol was added, dropwise, 0.15 mL (0.3 mmol, 1 equiv) of a 2M solution of LiBH$_4$ in THF. The reaction was then heated to 80° C. for 16 h. At this time, conversion to the corresponding lactam was observed to be complete as judged by LC/MS analysis. Quenching with aq. citric acid, followed by extraction of the product with EtOAc and drying the organic layer over $Na_2SO_4$ gave, upon concentration of volatiles, 200 mg of the product lactam. Combiflash purification on silica gel gave 50 mg of pure material that was submitted directly to phenol methylation.

The intermediate lactam, 50 mg (0.08 mmol, 1 equiv), was dissolved in 3 mL DMF, and $Cs_2CO_3$ (130 mg, 0.40 mmol, 5 equiv) followed by MeI (0.08 mmol, 5 μl, 1 equiv) was added. The reaction was stirred for 1 h at rt, by which time the reaction had gone to completion as judged by LC/MS analysis. The reaction was then filtered to remove solids and diluted with EtOAc, then washed 3× with water and dried over $Na_2SO_4$ to furnish 30 mg of methylated product 4 that required no additional purification.

300 MHz $^1$H NMR ($CDCl_3$) shows diagnostic peaks at δ 8.68 (d, J=3.8 Hz, 1H), 8.15 (d, J=3.8 Hz, 1H), 7.45-7.05 (m, 4H), 6.52-6.45 (m, 3H), 4.78 (s, 2H), 4.38 (s, 2H), 4.08 (s, 2H), 3.91 (s, 3H), 3.85 (s, 3H), 3.82 (s, 3H), 1.55 (m, 3H), 1.15 (d, 18 h). MS: 679.2 (M+1).

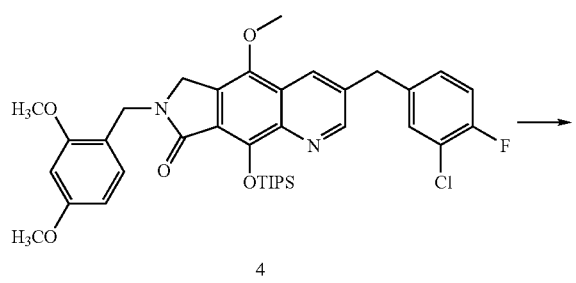

4

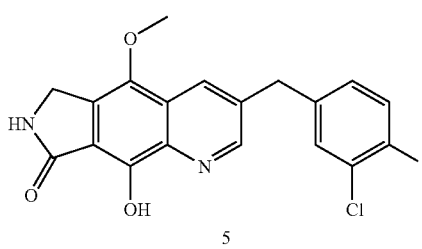

5

Synthesis of Final Product 5

To methyl ether 4 (30 mg, 0.044 mmol, 1 equiv) in TFA, 2 ml, is added 0.5 mL triethylsilane. The reaction is then heated to 80° C. and monitored by LC/MS. After 16 h, complete deprotection was observed to have taken place. The reaction was diluted with 25 mL toluene and the resulting solution concentrated to dryness by rotary evaporation followed by high vacuum. The crude product, 25 mg, was triturated with $Et_2O$/hexanes to give 9 mg of the final product 5 as the TFA salt. 300 MHz $^1$H NMR ($CDCl_3$) shows diagnostic peaks at δ 8.85 (d, J=3.8 Hz, 1H), 8.35 (d, J=3.8 Hz, 1H), 7.47-7.38 (m, 1H), 7.22-7.08 (m, 2H), 6.80 (bm, 1H), 4.64 (s, 2H), 4.22 (s, 2H), 4.02 (s, 3H).

MS: 373.2 (M+1).

Example 72

Synthesis of Compound 209

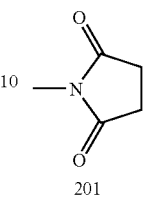

201

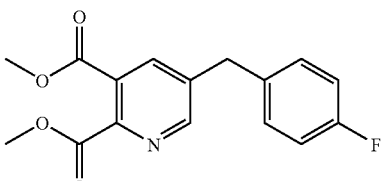

202

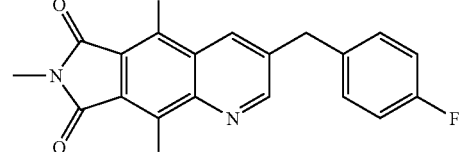

203

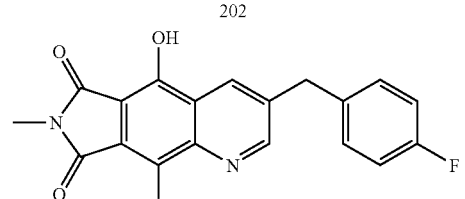

204

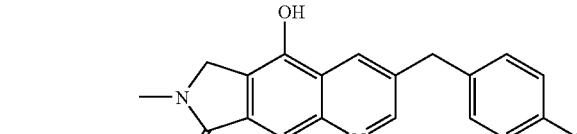

205

To 10 g (33 mmol, 1 equiv) of the dimethyl ester in 100 mL THF, cooled to 0° C., is added 3.7 g (33 mmol, 1 equiv) N-methyl succinimide. Then, 72 mL of a 1M THF solution of LiHMDS (72 mmol, 2.2 equiv) was added dropwise. The reaction was allowed to warm to rt, and an additional 15 mL LiHMDS solution was added. After 2 h of stirring, the reaction was re-cooled to ice-bath temperature and quenched by the addition of 30 mL 6M aq. HCl. The resulting solid was filtered and washed with cold diethyl ether. Oven drying of the precipitate gave 6.7 g of product 203 (58%) as a light yellow solid. ¹H NMR (300 MHz, d6-DMSO) shows diagnostic peaks at δ (ppm): 8.95 (s, 1H), 8.44 (s, 1H), 7.38 (m, 2H), 7.18 (m, 2H), 4.24 (s, 2H), and 2.95 (s, 3H). MS=353.2 (M+H).

Triethylamine (15 mL, 10.89 g, 107.6 mmol) was added to a suspension of 203 (9.16 g, 26 mmol) in 175 mL of anhydrous DMF, affecting dissolution. A single addition of TIPS-Cl caused the reaction to thicken significantly. Evaluation (LCMS) of the reaction after 5 min. indicated the complete absence of 203 and only a trace of 204. The in situ generated 5,8-bis TIPS protected 3 was hydrolyzed by the addition of DMF/Water 9:1 v/v (5 mL, 0.89 eq. based upon initial excess of TIPS-Cl). After stirring for 1 h 35 min at ambient temperature an additional aliquot of DMF/Water (0.62 mL, 0.11 eq—excess TIPS-Cl based) was added and hydrolysis continued 4 h 40 min before sealing and placing in a −10° C. freezer overnight. After warming to ambient temperature the reaction was diluted in to 600 mL of ethyl acetate, washed with 1 L of 5% (wt/vol) aqueous citric acid which was back extracted with ethyl acetate (2×200 mL). The pooled ethyl acetate extracts were washed successively with 5% (wt/vol) aqueous LiCl (2×250 mL), 500 mL water, and 300 mL of brine before drying (Na₂SO₄). The residue obtained after filtration and evaporation, in vacuo, was sonicated with 100 mL of heptane. The solid product produced was collected by filtration and washed twice with heptane before vacuum drying to afford 204, 11.88 g. ¹H NMR (300 MHz, CDCl₃) δ (ppm): 8.80 (s, 1H), 8.34 (s, 1H), 7.21 (m, 2H), 7.05 (m, 2H), 4.19 (s, 2H), 3.18 (s, 3H), 1.50 (m, 3H), 1.11 (d, 6H, J=7.4 Hz); LC/MS (m/z) 509.13 [M+H]⁺.

To a 0° C. suspension of 204 (11.71 g, 23.02 mmol) in 200 mL of THF was added LiBH₄ (2 M/THF, 46 mL, 92 mmol) drop-wise over a period of 8 min. After stirring for 5 min at 0° C. post LiBH₄ addition the reaction was placed in an 80° C. oil bath for 30 min. When the reaction had partially cooled methanol was added and it was then returned to the 80° C. bath for 2 h. Evaluation by LCMS indicated that the reduction to the lactam was complete. When cool the reaction was diluted into 800 mL of ethyl acetate, washed with 800 mL of water. Ethyl acetate (400 mL) was used to back extract the aqueous wash before the combined ethyl acetate extracts were washed with 2×350 mL of saturated aqueous ammonium chloride and 400 mL of brine. Drying, Na₂SO₄, filtration, and evaporation in vacuo afforded 205 after vacuum drying, 11.15 g. ¹H NMR (300 MHz, CDCl₃) δ 8.73 (s, 1H), 8.33 (s, 1H), 7.17 (m, 2H), 7.02 (m, 2H), 4.50 (s, 2H), 4.14 (s, 2H) 3.09 (s, 3H), 1.51 (m, 3H), 1.07 (d, 6H, J=7.3 Hz); LC/MS (m/z) 495.13 [M+H]⁺.

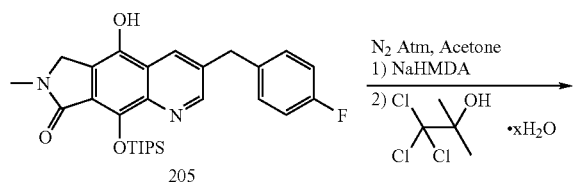

205

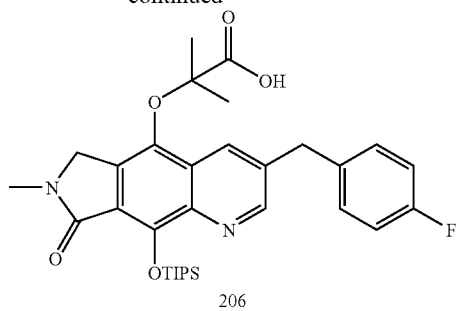

206

At ambient temperature, sodium bis(trimethylsilyl)amide (1M solution in THF, 1.15 mL, 1.15 mmol) was added to a solution of 205 (226.2 mg, 0.457 mmol) in 25 mL of acetone. The reaction was heated to 40° C. (oil bath) and treated, dropwise, with 1,1,1-trichloro-2-methyl-2-propanol hydrate (125.8 mg, dissolved in 2 mL of acetone). After 75 min. only traces of 205 remained. Evaporation, in vacuo at 30° C., dilution with brine, and pH adjustment to 8 with ~N HCl was followed by extraction with hexane containing traces of ethyl acetate (3×25 mL). The aqueous phase pH was adjusted to 5 with ~N HCl. Extraction with ethyl acetate, washing with brine, drying (Na₂SO₄) and evaporation afforded 39 mg of 206. Residual colored solids from the reaction were collected by dissolving in ethyl acetate, washing with brine, drying (Na₂SO₄) and evaporation to afford 126 mg of 6. LC/MS (m/z) 581.13 [M+H]⁺.

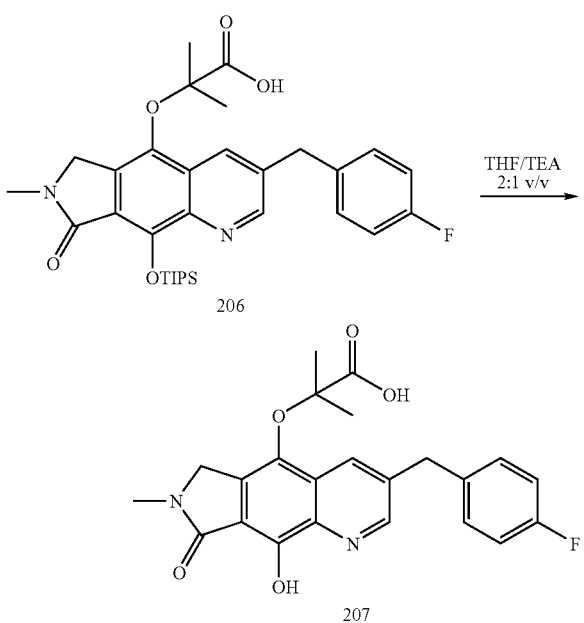

206

207

Compound 206 (126 mg, 0.217 mmol) was treated with 2 mL of THF/TFA 2:1. Deprotection of the phenol was complete after two hours. Evaporation, in vacuo, at 30° C. was followed by three co-evaporations with toluene. Purification of the residue obtained after sonication in heptane was accomplished by preparative reverse phase HPLC to afford 57.8 mg of 207. ¹H NMR (300 MHz, DMSO-d₆) δ 8.84 (d, 1H, J=1.9 Hz), 8.24 (d, 1H, J=1.9 Hz), 7.36 (m, 2H), 7.16 (m, 2H), 4.43 (s, 2H), 4.23 (s, 2H), 3.02 (s, 3H), 1.35 (s, 6H); ¹⁹F NMR (282 MHz, DMSO-d₆) δ −117.2 (m), −75.14 (s, TFA); LC/MS (m/z) 425.07 [M+H]⁺.

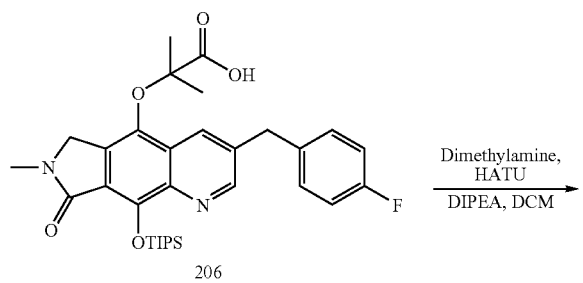

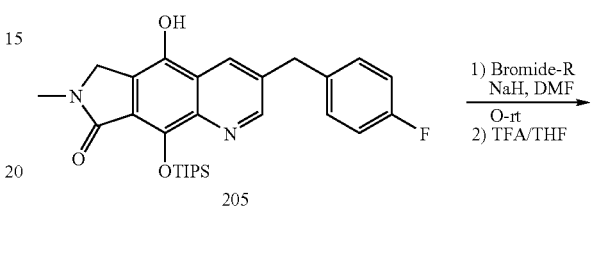

Into the solution of Compound 206 (150 mg, 0.26 mmol) in 10 ml of dichloromethane, was added 0.26 ml of 2N dimethylamine solution in THF, HATU (197.6 mg, 0.52 mmol) and DIPEA (134.2 mg, 1.04 mmol) at ambient temperature. After 2 h, the reaction was diluted with 150 ml ethyl acetate and washed with brine. The organic solution was dried with MgSO4. After removed the solvent, the residue was purified by combiflash yield 58 mg of 208. LC/MS (m/z): 608.2 [M+H$^+$]. $^1$H NMR (300 MHz, DMSO-d$_6$) δ (ppm) 8.71 (1H, s), 7.95 (1H, s), 7.24 (2H, m), 7.07 (2H, m), 5.3 (2H, s), 4.17 (3H, m), 3.48 (2H, s), 3.13 (3H, s), 2.81 (3H, s), 1.43 (3H, s), 1.26 (3H, s), 1.12 (18H, d, J=7.5 Hz), 0.88 (3H, m).

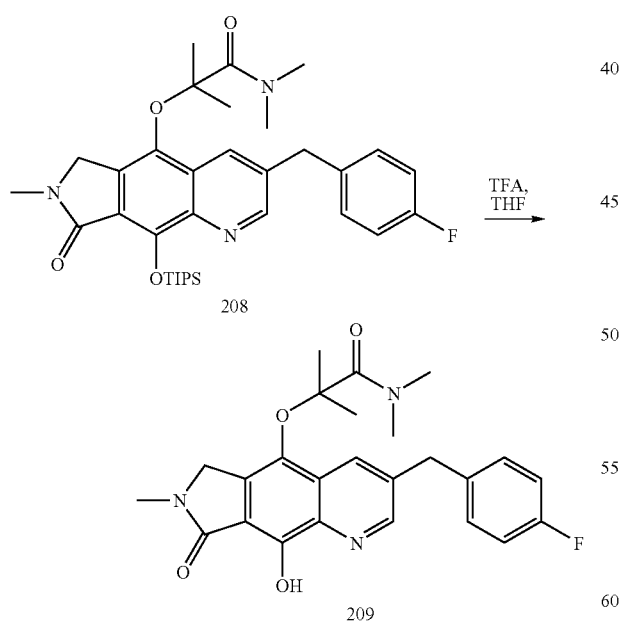

Compound 208 (58 mg, 0.095 mmol) was treated with 2 mL of THF/TFA 2:1. Deprotection of the phenol was complete after two hours. Evaporation, in vacuo, at 30° C. was followed by three co-evaporations with toluene. The residue was washed with ethyl ether, after dried yield 13.2 mg of 209.

LC/MS (m/z): 452.07 [M+H$^+$]. $^1$H NMR (300 MHz, DMSO-d$_6$) δ (ppm) 9 (1H, s), 8.24 (1H, s), 7.22 (2H, m), 7.08 (2H, m), 4.26 (3H, m), 3.47 (2H, s), 3.16 (6H, s), 3.22 (2H, s), 1.46 (6H, s). $^{19}$F NMR (300 MHz, DMSO-d$_6$) δ −115.8 (m), −76.3 (s, TFA).

Example 73

Synthesis of Compound 211-214

R =
211 Ethyl
212 N-(3-chloro-4,6-difluoro-benzyl)aminocarbonylmethyl
213 morpholinocarbonylmethyl
214 N,N-dimethylaminocarbonyl-methyl The free phenol 205 (0.54 mmol, 1 eq) was dissolved in DMF (0.1M) and cooled to 0° C. NaH (0.81 mmol, 1.1 eq) was added and the reaction stirred until gas evolution ceased. The ethyl bromide (0.59 mmol, 1.5 eq) was then added via syringe and the reaction proceeded at ambient temperature overnight. LC/MS after approximately 18 h showed the reaction to be complete. The reaction mixture was diluted with EtOAc (100 mL) and quenched with water. The organics were washed with water (3×50 mL) and brine (50 mL), then dried over Na$_2$SO$_4$. Solvent removed en vacuo and crude product taken forward to deprotection of the phenol. The crude residue was then dissolved in TFA/THF (1/1) and allowed to stir at room temperature for 1 h. LC/MS after 1 h showed complete deprotection of the phenol. Reaction mixture was concentrated en vacuo. The residue was redissolved in DMSO and purified by reverse phase HPLC. The purified product 211 was lyophilized to a powder and characterized by LC/MS and NMR.

211—(GS-339303): 300 MHz $^1$H NMR (DMSO-$d_6$) δ.((ppm): 8.8 (s, 1H), 8.5 (s, 1H), 8.2 (s, 1H), 7.3 (t, 2H), 7.41 (t, 2H), 4.4 (s, 2HO, 4.2 (s, 2H), 4.1 (q, 2H), 1.2 (t, 3H). m/z=353 (M+H).

212—(GS-340029): 300 MHz $^1$H NMR (DMSO-$d_6$) δ.((ppm): 8.9 (t, 1H), 8.8 (s, 1H), 7.6 (m, 2H), 7.4 (t, 2H), 7.1 (t, 2H), 4.7 (s, 2H), 4.6 (s, 2H), 4.4 (d, 2H), 4.2 (s, 2H), 3.0 (s, 3H). m/z=556 (M+H).

213—(GS-339874): 300 MHz $^1$H NMR (CDCl$_3$) δ.((ppm): 8.8 (s, 1H), 8.2 (s, 1H), 7.2 (t, 2H), 7.0 (t, 2H), 4.7 (s, 2H), 4.6 (s, 2H), 4.2 (s, 2H), 3.7 (m, 4H), 3.6 (m, 4H), 3.2 (s, 3H). m/z=466 (M+H).

214—(GS-341555): 300 MHz $^1$H NMR (DMSO-$d_6$) δ.((ppm): 8.8 (s, 1H), 8.5 (s, 1H), 7.3 (t, 2H), 7.1 (t, 2H), 4.7 (s, 2H), 4.6 (s, 2H), 4.2 (s, 2H), 3.0 (s, 3H). m/z=397 (M+H).

Example 74

Synthesis of Compound 217-227

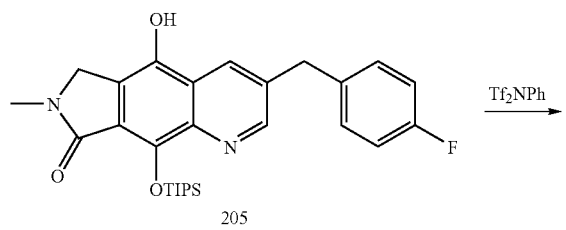

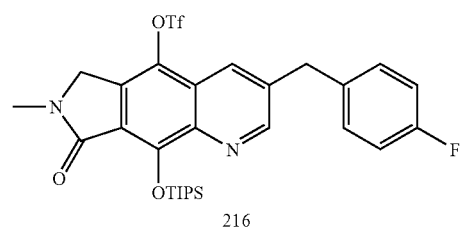

Cesium carbonate (5.2123 g, 15.997 mmol) was added to a 0° C. suspension of 205 (5.15 g, 10.41 mmol) in 100 mL acetonitrile. The reaction was stirred for 19 min. before adding N-phenyltrifluoromethanesulfonimide (4.4561 g, 12.47 mmol). After 1.5 h the ice bath was removed and the reaction was allowed to warm to ambient temperature. Evaluation by LC/MS indicated that the reaction was complete in 4.25 h. The reaction mixture was diluted into 400 mL of ethyl acetate, washed with 500 mL of water which was back extracted with 200 mL of ethyl acetate. The pooled ethyl acetate extracts were washed with water (3×400 mL), 400 mL of saturated NH$_4$Cl (aq) and 400 mL of brine before drying (Na$_2$SO$_4$), filtering and evaporating in vacuo at 30° C. Purification of the crude residue (7 g) was accomplished on silica gel (CombiFlash 330 g, hexane/ethyl acetate) to afford 216, 5.0 g. $^1$H NMR (300 MHz, CDCl$_3$) δ (ppm): 8.76 (s, 1H), 7.97 (s, 1H), 7.24 (m, 2H), 7.07 (m, 2H), 4.53 (s, 2H), 4.2 (s, 2H) 3.20 (s, 3H), 1.53 (m, 3H), 1.13 (d, 6H, J=7.6 Hz); LC/MS (m/z) 627.00 [M+H]$^+$.

Representative Procedure for Compounds 217-227

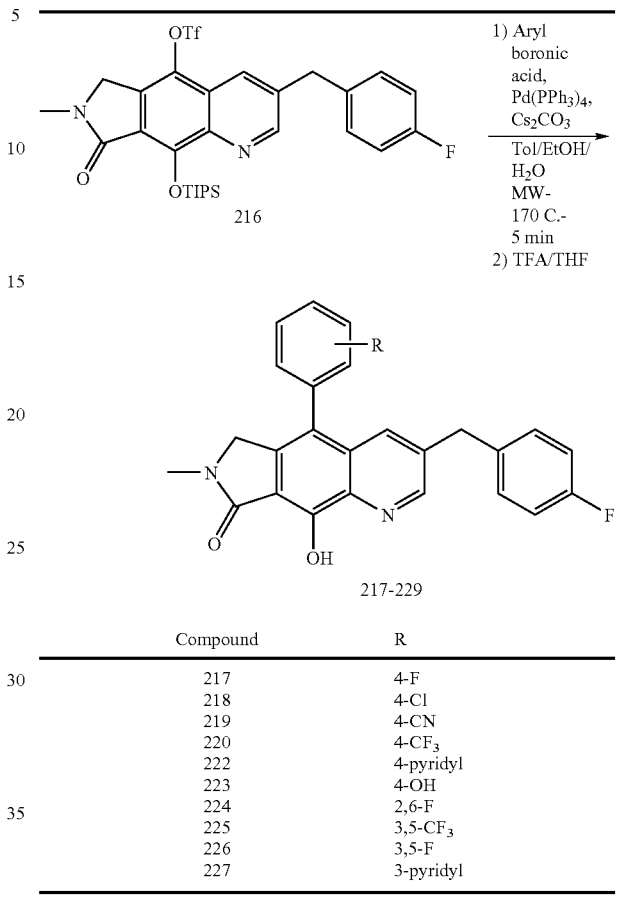

| Compound | R |
|---|---|
| 217 | 4-F |
| 218 | 4-Cl |
| 219 | 4-CN |
| 220 | 4-CF$_3$ |
| 222 | 4-pyridyl |
| 223 | 4-OH |
| 224 | 2,6-F |
| 225 | 3,5-CF$_3$ |
| 226 | 3,5-F |
| 227 | 3-pyridyl |

Triflate protected phenol 216 (0.1 mmol, 1 eq) dissolved in toluene/ethanol/water (2/1/0.5 mL, 0.3 M) in microwave vessel. Cs$_2$CO$_3$ (2.5 mmol, 2.5 eq) and Pd(PPh$_3$)$_4$ (0.015 mmol, 0.15 eq) were added followed by the 4-fluorophenyl boronic acid (0.15 mmol, 1.5 eq). Microwave vessel sealed with crimper and heated to 170° C. for 5 minutes under normal microwave intensity. After cooling to room temp, bilayer formed in reaction vessel. The top layer was analyzed by LC/MS and showed reaction to be complete. Reaction mixture diluted with EtOAc (50 mL) and quenched with 5% citric acid buffer (50 mL). Organics washed with water (50 mL) and brine (50 mL), the dried over Na$_2$SO$_4$. The solvent was concentrated en vacuo to a red-brown residue. The residue was dissolved in minimal dichloromethane and purified using ISCO Combiflash. The compound eluted with 80/20 EtOAc/Hexanes. The purified TIPS protected intermediate was dissolved in THF/TFA and stirred at room temperature to remove the TIPS protecting group. LC/MS after one hour showed complete deprotection of the phenol. Reaction mixture was concentrated en vacuo. The residue was redissolved in DMSO and purified by reverse phase HPLC. The purified product 217 was lyphilized to a powder and characterized by LC/MS and NMR.

217—(GS-340654): 300 MHz $^1$H NMR (Acetone-$d_6$) δ.((ppm): 8.9 (s, 1H), 8.0 (s, 1H), 7.5 (t, 2H), 7.3 (m, 4H), 7.0 (t, 2H), 5.8 (s, broad, 1H), 4.4 (s, 2H), 4.2 (s, 2H), 3.1 (s, 3H)). m/z=417 (M+H).

218—(GS-340746): 300 MHz $^1$H NMR (DMSO-$d_6$) δ.((ppm): 8.8 (s, 1H), 7.8 (s, 1H), 7.5 (d, 2H), 7.4 (d, 2H), 7.2 (t, 2H), 7.1 (t, 2H), 4.3 (s, 2H), 4.1 (s, 2H), 2.9 (s, 3H). m/z=433 (M+H).

219—(GS-340781): 300 MHz $^1$H NMR (DMSO-$d_6$) δ(ppm): 8.8 (s, 1H), 8.0 (d, 2H), 7.8 (s, 1H), 7.6 (d, 2H), 7.2 (t, 2H), 7.0 (t, 2H), 4.3 (s, 2H), 4.19 (s, 2H), 2.9 (s, 3H). m/z=424 (M+H).

220—(GS-340911): 300 MHz $^1$H NMR (CDCl$_3$) δ(ppm): 8.8 (s, 1H), 7.8 (s, 1H), 7.7 (d, 2H), 7.4 (d, 2H), 7.0 (t, 2H), 6.9 (t, 2H), 4.1 (s, 2H), 3.1 (s, 3H). m/z=481 (M+H).

222—(GS-341422): 300 MHz $^1$H NMR (DMSO-$d_6$) δ(ppm): 8.8 (s, 3H), 7.8 (s, 1H), 7.7 (d, 2H), 7.3 (t, 2H), 7.1 (t, 2H), 4.4 (s, 2H), 4.2 (s, 2H), 2.9 (s, 3H). m/z=400 (M+H).

223—(GS-341554): 300 MHz $^1$H NMR (DMSO-$d_6$) δ.(ppm): 8.8 (s, 1H), 7.9 (s, 1H), 7.3 (t, 2H), 7.2 (d, 2H), 7.1 (t, 2H), 6.9 (t, 2H), 4.3 (s, 2H), 4.1 (s, 2H) 2.9 (s, 3H). m/z=415 (M+H).

224—(GS-341051): 300 MHz $^1$H NMR (CDCl$_3$) δ (ppm): 9.1 (s, 1H), 7.7 (s, 1H), 7.5 (m, 1H), 7.1 (m, 5H), 7.0 (m, 2H), 6.1 (s-broad, 1H), 4.4 (s, 2H), 4.2 (s, 2H), 3.1 (s, 3H). m/z=435 (M+H).

225—(GS-340922): 300 MHz $^1$H NMR (DMSO-$d_6$) δ.(ppm): 8.8 (s, 1H), 8.2 (s, 1H), 8.1 (s, 2H), 7.6 (s, 1H), 7.3 (t, 2H), 7.0 (t, 2H), 4.4 (s, 2H), 4.1 (s, 2H), 3.0 (s, 3H). m/z=535 (M+H).

226—(GS-340686): 300 MHz $^1$H NMR (CDCl$_3$) δ (ppm): 8.7 (s, 1H), 7.7 (s, 1H), 7.1 (t, 2H), 7.0 (m, 3H), 6.8 (m, 2H), 4.39 s, 2H), 4.1 (s, 2H), 3.1 (s, 3H). m/z=435 (M+H).

227—(GS-341440): 300 MHz $^1$H NMR (DMSO-$d_6$) δ (ppm): 8.8 (s, 1H), 8.7 (m, 2H), 8.0 (d, 1H), 7.8 (s, 1H), 7.6 (t, 1H), 7.2 (t, 2H), 7.0 (t, 2H), 4.3 (s, 2H), 4.1 (s, 2H), 3.0 (s, 3H). m/z=400 (M+H).

Example 75 Synthesis of Compounds 235-239

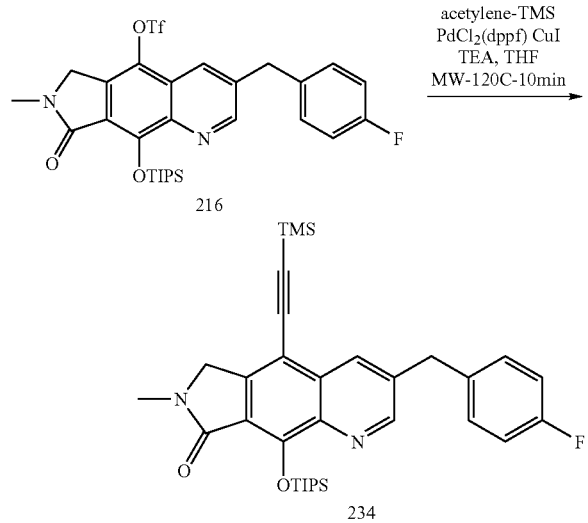

To a 5 mL microwave vial containing a solution of 2 g TIPS-protected aryl triflate 16 in THF (2 mL) was added 2 mL Et$_3$N. Then, 350 mg CuI and 250 mg PdCl$_2$(dppf) was added, followed by 1 mL TMS-acetylene. The reaction was heated at 110° C. for 15 minutes, at which time TLC and LC/MS analysis indicated the reaction was complete. Combiflash purification of the crude reaction product on MeOH-conditioned silica gel provided the pure 1.18 g of the TIPS protected TMS-acetylene product 234 in 64% yield. $^1$H NMR (300 MHz, CDCl$_3$) shows diagnostic peaks at δ (ppm): 8.72 (s, 1H), 8.15 (s, 1H), 4.45 (s, 2H) 4.21 (s, 2H), 3.20 (s, 3H), 1.55 (3H, m), 1.12 (12H, d), 0.32 (s, 9H). MS=365.1 (M+H).

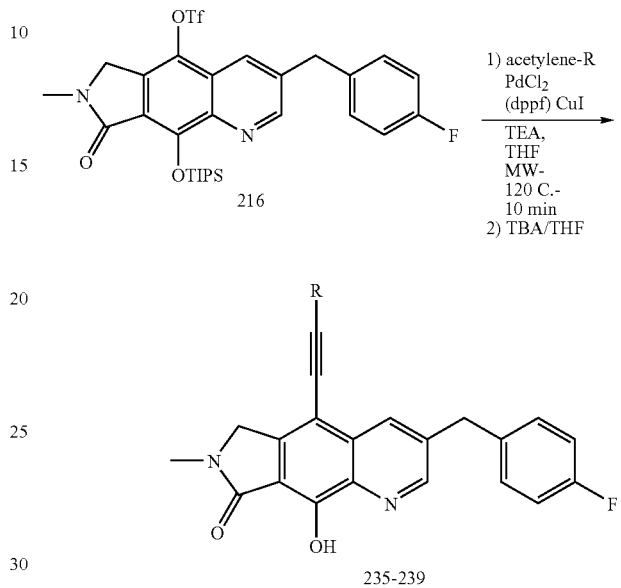

| Compound # | R |
|---|---|
| 235 | t-butyl |
| 236 | C(OH)(CH$_3$)$_2$ |
| 237 | phenyl |
| 238 | H |
| 239 | c-propyl |

235—(GS-341360): 300 MHz $^1$H NMR (CDCl$_3$) δ(ppm): 8.8 (s, 1H), 8.1 (s, 1H), 7.2 (t, 2H), 7.0 (t, 2H), 4.5 (s, 2H), 4.2 (s, 2H), 3.2 (s, 3H), 1.3 (s, 9H). m/z=403 (M+H).

236—(GS-341365): 300 MHz $^1$H NMR (CDCl$_3$) δ.((ppm): 8.8 (s, 1H), 8.1 (s, 1H), 7.2 (t, 2H), 7.0 (t, 2H), 4.5 (s, 2H), 4.2 (s, 2H), 3.2 (s, 3H), 1.8 (s-broad, 1H), 1.3 (s, 6H). m/z=405 (M+H).

237—(GS-341243): 300 MHz $^1$H NMR (CDCl$_3$) δ(ppm): 8.8 (s, 1H), 8.3 (s, 1H), 7.6 (d, 1H), 7.5 (m, 4H), 7.2 (t, 2H), 7.0 (t, 2H), 5.3 (s, 1H), 4.6 (s, 2H), 4.2 (s, 2H), 3.2 (s, 3H). m/z=423 (M+H).

238—To 1.01 g of the TMS-protected acetylene 234 in 10 mL THF was added ~2.5 equiv TBAF (2.5 g). The reaction was stirred at rt for 3 h, at which time LC/MS indicated both silyl groups had been cleaved from the starting material. HPLC purification of a 1 mL aliquot of the reaction provided acetylene product 238. $^1$H NMR (300 MHz, CDCl$_3$) shows diagnostic peaks at δ (ppm): 8.85 (s, 1H), 8.38 (s, 1H) 4.54 (s, 2H) 4.22 (s, 2H), 3.23 (s, 3H). MS=347.2 (M+H).

239—Application of the general procedure for the Sonagashira reaction utilizing cyclopropyl acetylene gave 5 mg 239 after deprotection with TBAT in THF and purification via neutral HPLC. $^1$H NMR (300 MHz, CDCl$_3$) shows diagnostic peaks at δ (ppm): 8.81 (s, 1H), 8.22 (s, 1H) 4.44 (s, 2H) 4.21 (s, 2H), 3.20 (s, 3H), 0.98 (2H, dd), 0.85 (2H, dd). MS=387.0 (M+H).

Example 76

Synthesis of Compound 240

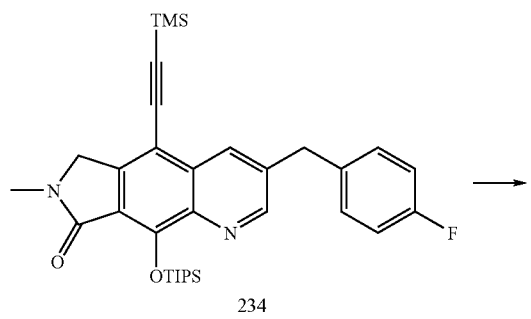

234

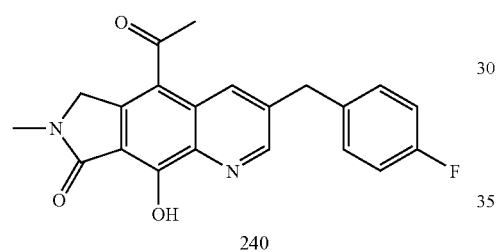

240

To 234 in THF 5 mL TFA and 0.25 mL water was added and stirring was continued overnight. After 16 h, LC/MS analysis showed that the conversion to the methyl ketone 240 was complete. The reaction was concentrated to a residue, which was then triturated with heptanes. An 300 mg aliquot of this crude material was purified via HPLC to afford the methyl ketone product 240. $^1$H-NMR (300 MHz, CDCl$_3$) shows diagnostic peaks at δ (ppm): 8.86 (s, 1H), 8.45 (s, 1H) 4.72 (s, 2H) 4.21 (s, 2H), 3.25 (s, 3H), 2.68 (2H, dd), 0.85 (2H, dd). MS=365.1 (M+H).

Example 77

Synthesis of Compound 242

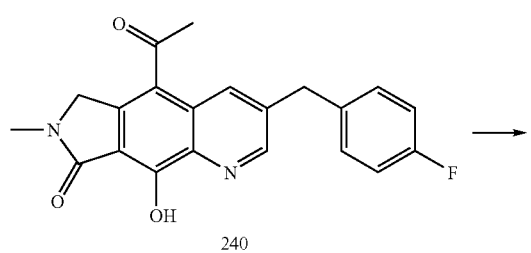

240

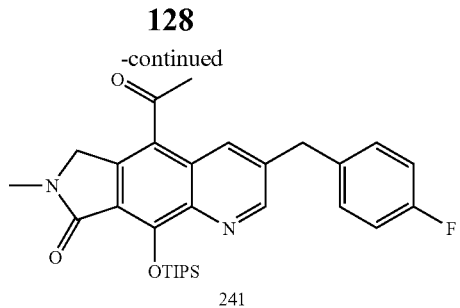

241

Compound 240 (~3 g of material) was TIPS protected by the standard method. The resulting C8-TIPS ether was purified by column chromatography on Davisil to give 380 mg of the TIPS-protected methyl ketone 241. $^1$H NMR (300 MHz, CDCl$_3$) shows diagnostic peaks at δ (ppm): 8.72 (s, 1H), 8.29 (s, 1H) 4.59 (s, 2H), 4.20 (s, 2H), 3.15 (s, 3H), 2.60 (3H, s), 1.55 (m, 3H), 1.10 (12H, d).

MS=521.4 (M+H).

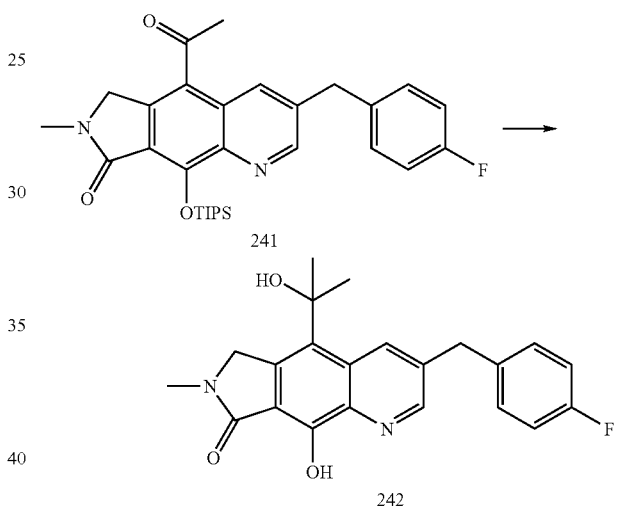

242

To a solution of 380 mg of the TIPS-protected methyl ketone 241 in THF at 0° C. is added a large excess (600 uL of a 1.6M solution in THF) of MeLi, dropwise. The mixture is stirred at low T for 30 min and quenched by the addition of saturated ammonium chloride solution. The mixture is then diluted with 100 mL ethyl acetate. The organic phase was dried over Na$_2$SO$_4$ and concentrated to give the resulting tertiary carbinol along with recovered, unreacted methyl ketone. Chromatography on Davisil-brand silica gel afforded 60 mg of the pure tertiary carbinol 242 along with 210 mg recovered ketone 241. $^1$H NMR (300 MHz, d$_6$-acetone) shows diagnostic peaks at δ (ppm): 8.80 (s, 1H), 8.70 (s, 1H) 4.92 (s, 2H) 4.33 (s, 2H), 3.15 (s, 3H) and 1.88 (s, 6H). MS=388.1 (M+H).

General Procedure for the Synthesis of Alkylhydrazone Analogs of Examples 78-80

To a microwave vial containing 25 mg of the methyl ketone 241 in 1 mL of ethyl alcohol was added 100 uL AcOH and 50 uL of the hydrazine. This mixture was heated to 150° C. for 10 minutes, after which time LC/MS shows that hydrazone formation as well as TIPS solvolysis had proceeded to completion. The resulting products were formed as isomer mixtures which were separable by HPLC. Purification by HPLC on C18 provided the final products as pure compounds.

Example 78

Synthesis of Compound 243

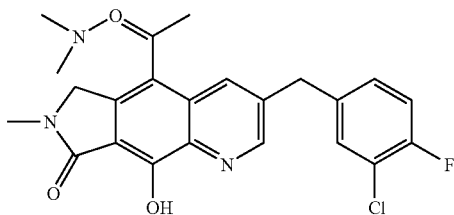

Use of dimethylhydrazine gave 8 mg hydrazone 243 after HPLC purification. Both stereoisomers were present after purification. $^1$H NMR (300 MHz, CD$_3$CN) shows diagnostic peaks at δ (ppm): 8.82 (s, 1H), 8.18 (s, 1H), 4.60 (s, 2H), 4.25 (s, 2H), 3.12 (s, 6H) and 2.62 (s, 3H). MS=407.3 (M+H).

Example 79

Synthesis of Compound 244

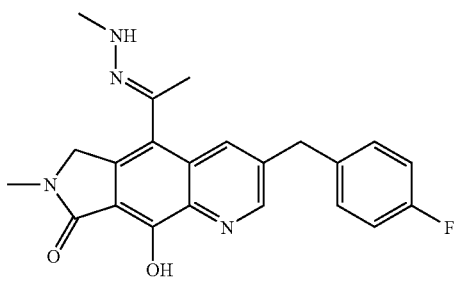

Use of methylhydrazine gave hydrazone 244 (3 mg) obtained pure after HPLC purification: $^1$H NMR (300 MHz, CD$_3$CN) shows diagnostic peaks at δ (ppm): 8.75 (s, 1H), 7.90 (s, 1H) 4.40 (dd, 2H) 4.21 (s, 2H) 3.04 (s, 3H), 2.72 (s, 3H) and 2.28 (s, 3H). MS=393.3 (M+H).

Example 80

Synthesis of Compound 245

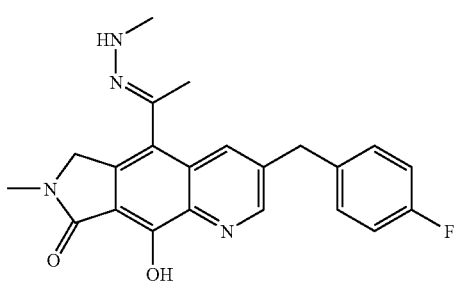

Use of methylhydrazine gave hydrazone 245 (4 mg) obtained pure after HPLC purification: $^1$H NMR (300 MHz, CD$_3$CN) shows diagnostic peaks at δ (ppm): 8.85 (s, 1H), 8.27 (s, 1H) 4.55 (dd, 2H) 4.21 (s, 2H) 3.15 (s, 3H), 2.88 (s, 3H) and 2.18 (s, 3H). MS 393.3 (M+H).

General Procedure for the Synthesis of Oxime Ether Analogs of Examples 81-82.

To a microwave vial containing 50 mg of the methyl ketone 241 in 2 mL of pyridine was added 100 mg of the hydroxylamine hydrochloride salt. This mixture was heated to 150° C. for 10 minutes, after which time LC/MS showed that oxime formation as well as TIPS solvolysis had proceeded to completion. The resulting products were formed as isomer mixtures (typically ~3:1 ratio) which were separable by HPLC. Purification by HPLC on a C18 column provided the final products as pure compounds. Characterization data for the major isomer is provided unless noted.

Example 81

Synthesis of Compound 246

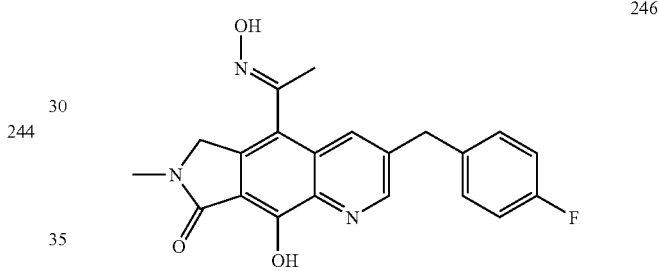

Use of hydroxylamine in the general procedure gave 4 mg oxime 246: $^1$H NMR (300 MHz, d$_6$-acetone) shows diagnostic peaks at δ (ppm): 8.86 (s, 1H), 8.20 (s, 1H) 4.56 (s, 2H) 4.28 (s, 2H), 3.15 (s, 3H) and 2.28 (s, 36H). MS 380.1 (M+H).

Example 82

Synthesis of Compound 247

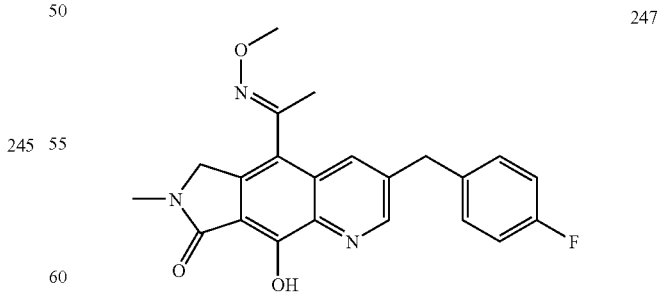

Use of methoxylamine hydrochloride in the general procedure gave 8 mg oxime 247: $^1$H NMR (300 MHz, CDCl$_3$) shows diagnostic peaks at δ (ppm): 9.15 (s, 1H), 8.38 (s, 1H) 4.60 (s, 2H) 4.30 (s, 2H) 4.04 (s, 3H), 3.25 (s, 3H) and 2.22 (s, 3H). MS=394.2 (M+H).

Procedure for Preparation of Olefin 250 Acetamide 251

To alcohol 242 in 1 mL dry acetonitrile is added 50 uL TFA. The reaction is sealed and allowed to stir until the reaction had reached completion. After 16 h, LC/MS showed that all starting material had been consumed, and that an approximate 1:1 ratio between the acetamide 251 and olefin 250 had been obtained. The crude reaction mixture was injected onto HPLC for purification, which furnished the pure products in 8 mg and 9 mg quantities, respectively.

Example 83

Synthesis of Compound 250

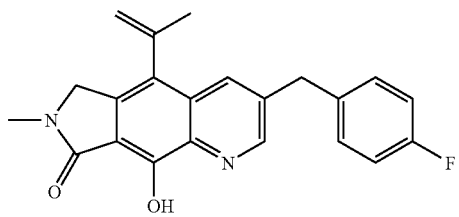

250

$^1$H NMR (300 MHz, CDCl$_3$) shows diagnostic peaks at δ (ppm): 9.18 (s, 1H), 8.38 (s, 1H) 5.60 (s, 1H) 5.08 (s, 1H), 4.54 (s, 2H), 3.25 (s, 3H) and 2.06 (s, 3H). MS=363.0 (M+H).

Example 84

Synthesis of Compound 251

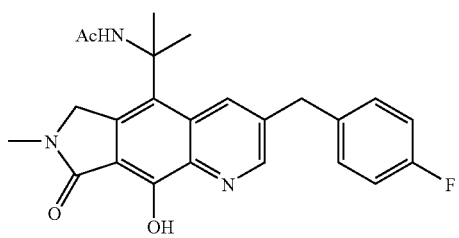

251

$^1$H NMR (300 MHz, CD$_3$CN) shows diagnostic peaks at δ (ppm): 9.05 (s, 1H), 8.84 (s, 1H) 4.82 (s, 2H) 3.18 (s, 3H), 1.85 (s, 6H) and 1.71 (s, 3H). MS 422.2 (M+H).

Example 85

Synthesis of Compound 277

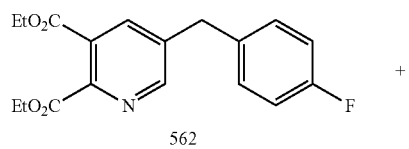

562

+

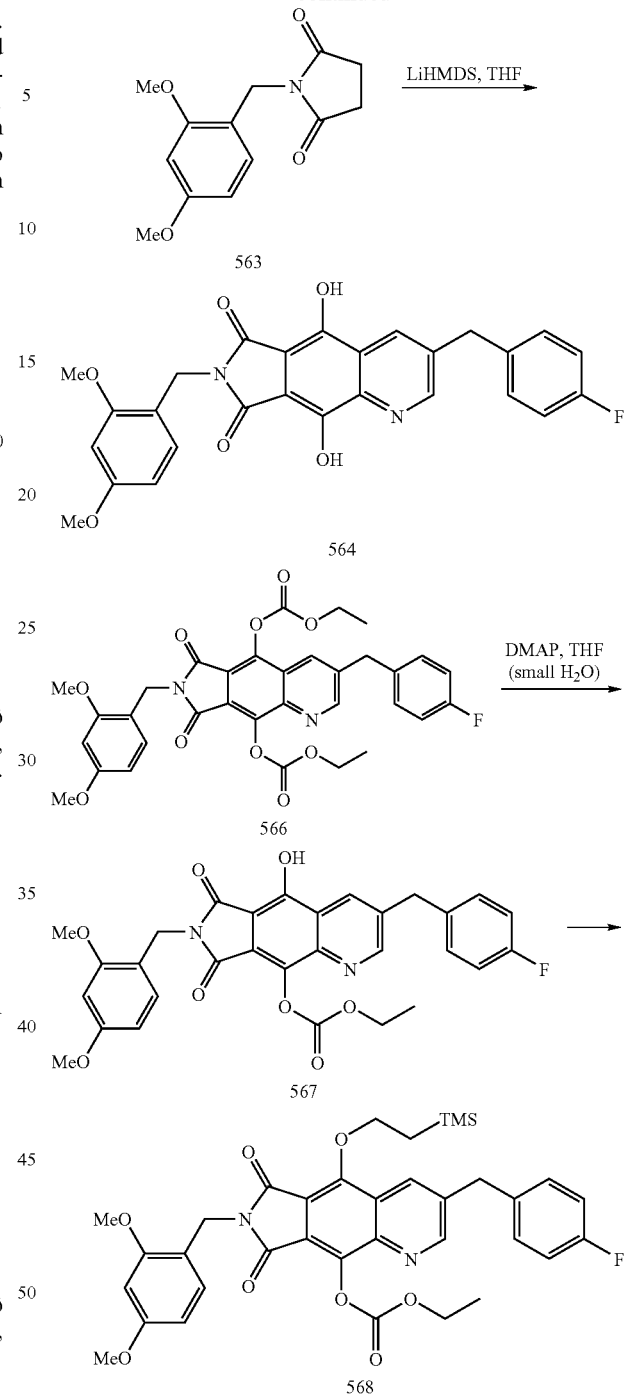

A solution of compound 562 (see WO2005/075475, 8.55 g, 25.8 mmol) and 563 (8.0 g, 32.1 mmol) in THF (75 mL) was cooled to 0° C. and treated with LiHMDS (64.6 mL, 64.6 mmol, 1.0 M in THF) prediluted in THF (45 mL) under Ar. The solution was gradually warmed to room temperature for 2 hours. The reaction mixture was cooled to 0° C. and 6N HCl (30 mL) was slowly added. THF was removed in vacuo the crude mixture was suspended in diethyl ether (150 mL) and H$_2$O (20 mL). The product was filtered and dried using an oven vacuum to afford 564 (16.65 g, crude, >100%) as a solid with no further purification; 300 MHz $^1$H NMR (DMSO) δ

(ppm) 10.6 (bs, 1H), 8.99 (s, 1H), 8.5 (s, 1H), 7.4-6.4 (m, 7H), 4.62 (s, 2H), 4.25 (s, 2H), 3.75 (s, 3H), 3.71 (s, 3H); MS: 489 (M+1).

To a solution of bisphenol 564 (16.65 g, crude) in DMF (250 mL) was added pyridine (8.3 mL, 102.4 mmol). To this was added ethyl chloroformate (6.9 mL, 85.3 mmol) carefully (exotherm) then the reaction was allowed to stir for 2 hours under a nitrogen atmosphere. The reaction mixture was diluted with ethyl acetate before being quenched with 6 N HCl (30 mL) and some H₂O. The organic layer was washed with H₂O, aqueous LiCl and brine, then dried (over Na₂SO₄), filtered and concentrated in vacuo. The crude residue was purified on silica gel (3/2—ethyl acetate/hexane) to afford the desired product 566 (8.5 g, 52%—2 steps); 300 MHz $^1$H NMR (CDCl₃) δ (ppm) 8.96 (s, 1H), 8.29 (s, 1H), 7.19 (m, 3H), 7.04 (dd, 2H), 6.42 (m, 2H), 4.83 (s, 2H), 4.42 (m, 4H), 4.21 (s, 2H), 3.79 (s, 3H), 3.78 (s, 3H), 1.46 (t, 6H); MS: 633 (M+1).

Into a flask containing the biscarbonate 566 (8.93 g, 14.1 mmol) was added THF (142 mL, 0.1 M). Under nitrogen atmosphere was added DMAP (1.9 g, 15.5 mmol) and the reaction stirred overnight upon which the reaction was found to be sluggish so DMAP (1.9 g) and H₂O (12 mL) was added and allowed to stir to completion for 1 hour. The reaction was quenched with water and 1N HCl (50 ml) and extracted with ethyl acetate (2×200 ml). The organic extracts were combined and washed with water (2 times) followed by brine. The organic layer was then dried (over Na₂SO₄), filtered and concentrated in vacuo to obtain the monocarbonate 567 (8.3 g, >100%) with no further purification; 300 MHz $^1$H NMR (CDCl₃) δ (ppm) 8.95 (s, 1H), 8.42 (s, 1H), 7.20 (m, 3H), 7.04 (dd, 2H), 6.44 (m, 2H), 4.83 (s, 2H), 4.42 (m, 2H), 4.20 (s, 2H), 3.81 (s, 3H), 3.79 (s, 3H), 1.46 (t, 3H); MS: 561 (M+1).

Into a flask containing phenol 567 (18.62 g, 33.2 mmol, 1 equiv.) was added THF (170 mL, 0.2 M) followed by 2-trimethylsilanyl-ethanol (14.3 mL, 99.7 mmol, 3 equiv.) and triphenylphosphine (17.3 g, 66.5 mmol, 2 equiv.) before adding DIAD (21.4 mL, 99.7 mmol, 3 equiv.) slowly over 10 min. The reaction was complete after several hours after which it was diluted with EtOAc and washed with water, saturated NH₄Cl and brine. After drying over Na₂SO₄, it was filtered and concentrated in vacuo and purified by flash column chromatography with Hexanes/EtOAc (7/3) to obtain compound 568 as a light brown oil. 300 MHz $^1$H NMR (CDCl₃) δ (ppm) 8.92 (s, 1H), 8.43 (s, 1H), 7.72-7.65 (m, 3H), 7.65-7.48 (m, 3H), 7.05-7.00 (m, 1H), 4.96 (s, 2H), 4.53 (t, J=8.7 Hz, 2H), 4.20 (s, 2H), 3.83 (s, 3H), 3.80 (s, 3H), 1.12-1.04 (m, 2H), 0.02 (s, 9H). MS: 660.76 (M+1).

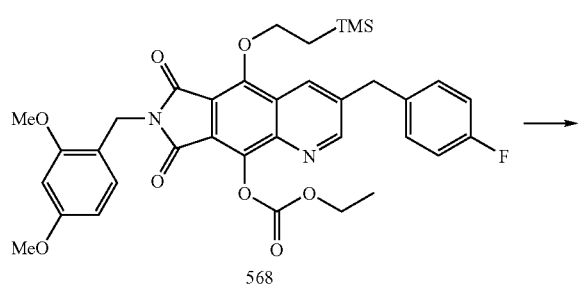

568

-continued

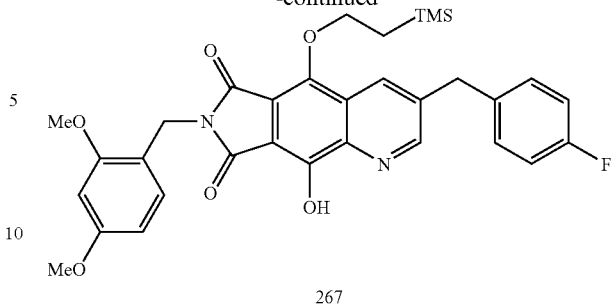

267

To flask containing compound 568 (15.96 g, 5.2 mmol 1 equiv.) was added THF (80 mL, 0.3 M) and DMAP (1.5 g, 2.6 mmol, 0.5 equiv.). Separately, K₂CO₃ (6.7 g, 48.4 mmol, 2 equiv.) was dissolved in H₂O (80 mL, 0.3 M) and transferred to the reaction. When the reaction was complete, it was diluted with ethyl acetate and quenched with water. The organic layer was washed with water and brine before being dried over Na₂SO₄, filtered and concentrated in vacuo. A brown solid was obtained as phenol 267 (15.4 g). $^1$H NMR (CDCl₃): δ 8.94 (d, J=1.8 Hz, 1H), 8.4 (s, 1H), 7.28-7.18 (m 3H), 7.16-7.00 (m, 2H), 6.45-6.40 (m, 3H), 4.86 (s, 2H), 4.53 (t, J=8.7 Hz, 2H), 4.02 (s, 2H), 3.83 (s, 3H), 3.80 (s, 3H), 1.12-1.04 (m, 2H), 0.02 (s, 9H). 300 MHz $^{19}$F NMR (CDCl₃) δ(ppm) −116.39. MS: 589 (M+1).

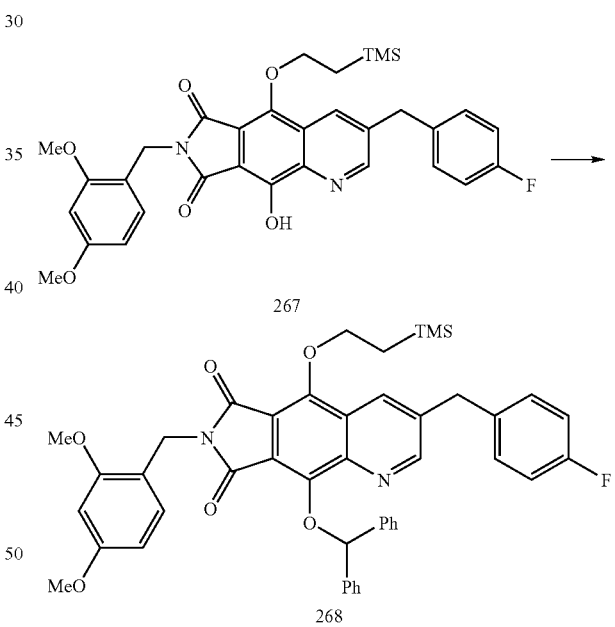

Phenol 267 (8.9 g, 21.7 mmol) was dissolved in 1,2-dichloroethane (130 mL, 0.2 M). Readily prepared Diphenylmethyl hydrozine (6.1 g, 31.5 mmol, 1.2 equiv.) was added in one portion. The mixture was stirred at 70° C. for 3 hours. The reaction was monitored by TLC (EtOAc/Hexane=3/7). After completion of the reaction, the solution was cooled down to room temperature. The solvent was evaporated. The crude product is purified by chromatography on a silica gel column, eluting with EtOAc/hexane to give the product 268 as a white solid (7.78 g, 40%). $^1$H NMR (CDCl₃): δ 8.94 (d, J=1.8 Hz, 1H), 8.4 (s, 1H), 7.62 (d, J=6.6 Hz, 2H), 7.41-7.23 (m, 10H), 7.16-7.00 (m, 2H), 6.45-6.40 (m, 3H), 4.86 (s, 2H), 4.53 (t, J=8.7 Hz, 2H), 4.02 (s, 2H), 3.83 (s, 3H), 3.80 (s, 3H), 1.12-

1.04 (m, 2H), 0.02 (s, 9H). 300 MHz $^{19}$F NMR (CDCl$_3$) δ(ppm) −116.39. MS: 755.07 (M+1).

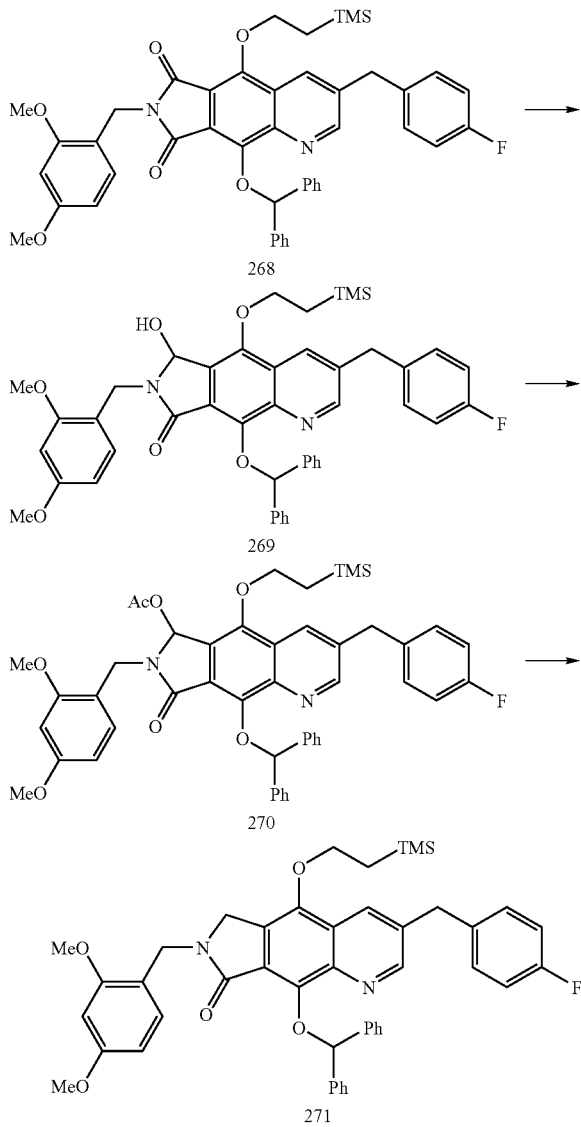

Imide 268 (6.18 g, 8.18 mmol) was dissolved in the mixture of THF (55 mL, 0.15 M), MeOH (1.6 mL, 41.0 mmol, 15 equiv.) and water (10 mL) and cooled to 0° C. in an ice-bath. To this was added LiBH$_4$ (12.3 mL, 24.6 mmol, 3 equiv., 2 M THF) dropwise. The mixture was stirred at 0° C. for 1 hour and at room temperature for 1 hour under nitrogen. TLC indicated the completion of the reaction. It was added saturated NH$_4$Cl (30 mL) and extracted with ethyl acetate (2×200 mL). The organic layer was washed with saturated NaHCO$_3$ and dried over MgSO$_4$. It was then evaporated to dryness to give an oily crude product of 269 (6.2 g).

The crude product 269 was dissolved in anhydrous dichloromethane (80 mL). To this solution was added N,N-dimethylaminopyridine (300 mg, 2.5 mmol, 0.3 equiv.), N,N-diisopropylethylamine (8.2 mL, 49.2 mmol, 6 equiv.) and acetic anhydride (3.1 mL, 32.8 mmol, 4 equiv.). The mixture was stirred at room temperature under nitrogen overnight. TLC indicated the completion of the reaction. It was quenched with 1N HCl (30 mL) and extracted with CH$_2$Cl$_2$ twice (2×100 mL). The organic layer was washed with saturated NaHCO$_3$, dried (Mg$_2$SO$_4$) and concentrated to give a crude product of 270 (6.45 g).

The crude product 270 was dissolved in anhydrous dichloromethane (80 mL, 0.1 M) under nitrogen. To this solution was added 2,6-lutidine (4.7 mL, 40.4 mmol, 5 equiv.), triethylsilane (19.4 mL, 121.2 mmol, 15 equiv.), then trimethylsilyl triflate (2.2 mL, 12.1 mmol, 1.5 equiv.) dropwise. The mixture was stirred at room temperature for 3 hours. TLC indicated the completion of the reaction. It was quenched with 1N HCl (30 mL) and extracted with CH$_2$Cl$_2$ twice (2×50 mL). The organic layer was washed with saturated NaHCO$_3$, dried (MgSO$_4$) and concentrated in vacuo. The residue was purified on a silica gel column, eluting with EtOAc/Hexane to afford the clean desired 71 (1.2 g in 3 steps).

$^1$H NMR (CDCl$_3$): δ (ppm): 8.86 (s, 1H), 8.01 (s, 1H), 7.94 (s, 1H), 7.70 (d, J=6.6 Hz, 4H), 7.41-7.23 (m, 10H), 7.16-7.00 (m, 2H), 6.45-6.40 (m, 2H), 4.80 (s, 2H), 4.30 (s, 2H), 4.53 (t, J=8.7 Hz, 2H), 4.16 (s, 2H), 4.00 (t, J=8.4 Hz, 2H), 3.83 (s, 3H), 3.80 (s, 3H), 1.05 (t, J=2H m, 2H), 0.02 (s, 9H). 300 MHz $^{19}$F NMR (CDCl$_3$) δ(ppm) −116.90. MS: 741.13 (M+1).

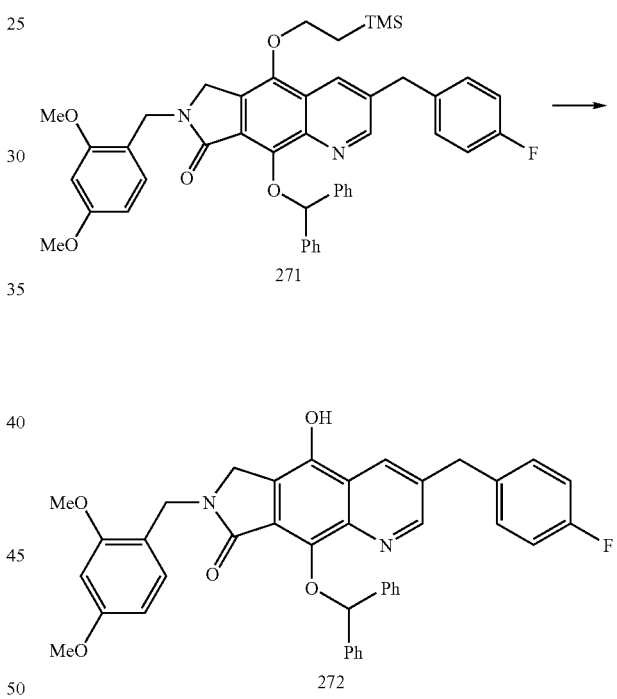

To flask containing compound 271 (1.1 g, 1.5 mmol, 1 equiv.) was added THF (15 mL, 0.1 M) and cooled to 0° C. before TBAF.xH$_2$O (760 mg, 2.9 mmol, 2 equiv.) was added. When the reaction was complete, it was diluted with ethyl acetate and quenched with water. The organic layer was washed with water and brine before being dried over Na$_2$SO$_4$, filtered and concentrated in vacuo. The solid was washed with hexanes, filtered and air dried. A red solid was obtained as phenol 272 (840 mg, 90% mass recovery). $^1$H NMR (CDCl$_3$): δ (ppm): 8.86 (s, 1H), 8.01 (s, 1H), 7.94 (s, 1H), 7.70 (d, J=6.6 Hz, 4H), 7.41-7.23 (m, 10H), 7.16-7.00 (m, 2H), 6.45-6.40 (m, 2H), 4.84 (s, 2H), 4.20 (s, 2H), 3.81 (s, 2H), 3.83 (s, 3H), 3.80 (s, 3H).

300 MHz $^{19}$F NMR (CDCl$_3$) δ (ppm): −112.43. MS: 640.93 (M+1).

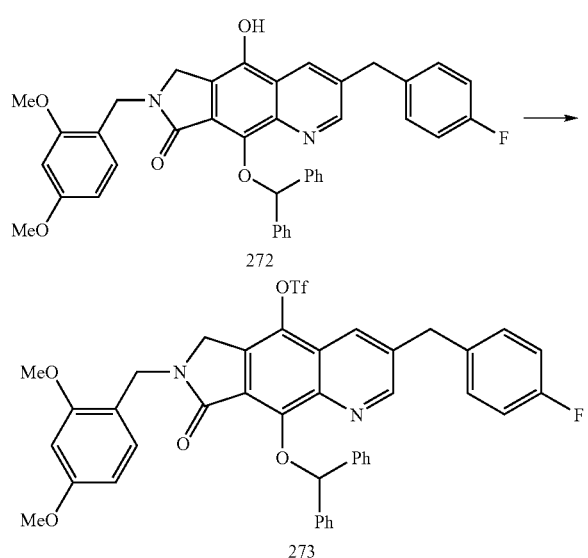

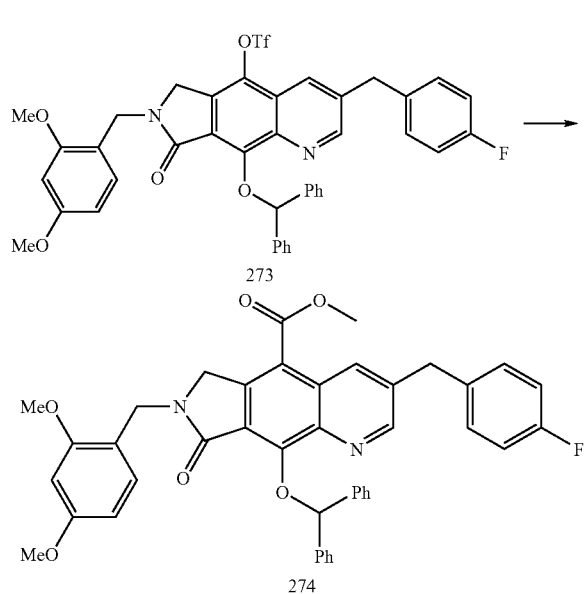

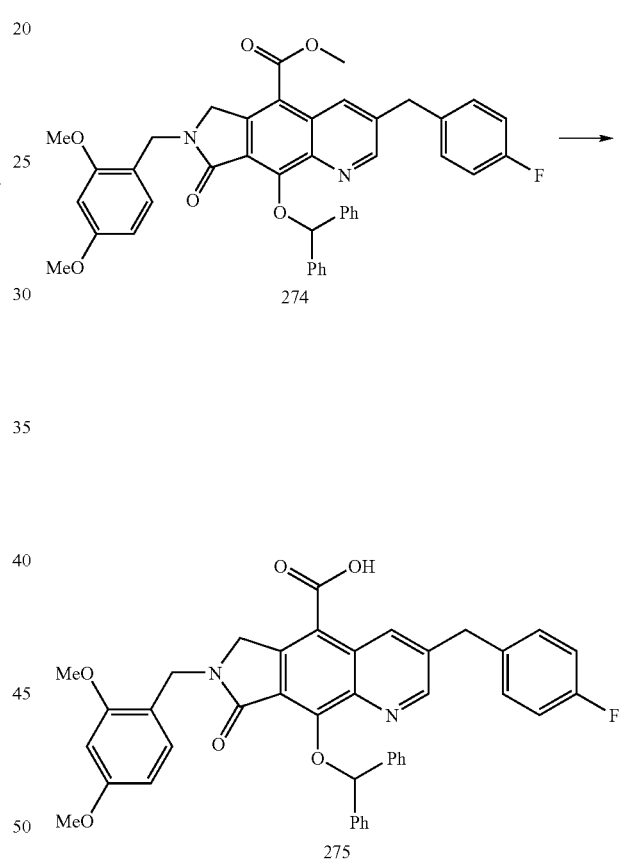

To flask containing compound 272 (840 mg, 1.3 mmol, 1 equiv.) was added CH₃CN (15 mL, 0.1 M) and Cs₂CO₃ (855 mg, 2.62 mmol, 1.2 equiv.). After allowing 5 minutes of stirring, Tf₂NPh (560 mg, 1.6 mmol, 1.3 equiv.) was added. When the reaction was complete, it was diluted with ethyl acetate and quenched with water. The organic layer was washed with water and brine before being dried over Na₂SO₄, filtered and concentrated in vacuo. A ISCO flash column chromatography was carried out with 2/3 EtOAc/Hexanes to yield 273 (530 mg, 50% mass recovery). $^1$H NMR (CDCl₃): δ 8.86 (d, J=1.8 Hz, 1H), 8.12 (s, 1H), 7.94 (s, 1H), 7.73-7.65 (m, 5H), 7.41-7.03 (m, 8H), 6.45-6.40 (m, 2H), 4.79 (s, 2H), 4.43 (s, 2H), 4.20 (s, 2H), 3.86 (s, 2H), 3.82 (s, 3H). 300 MHz $^{19}$F NMR (CDCl₃) δ (ppm) −73.39, −112.43. MS: 772.93 (M+1).

To the flask containing triflate 273 (282 mg, 0.37 mmol, 1 equiv.) was added DMF (3 mL, 0.12 M) and H₂O (0.5 mL) followed by Pd(OAc)₂ (16 mg, 0.07 mmol, 0.2 equiv.) and dppp (45 mg, 0.11 mmol, 0.3 equiv.) and TEA (120 µl, 0.8 mmol, 2.2 equiv.). The reaction vessel was connected with a 3-way valve and evacuating/flushing with CO several times. The reaction was then warmed to 60° C. and continued for several hours. The reaction was then cooled and flushed with inert atmosphere before adding Cs₂CO₃ (355 mg, 1.1 mmol, 3 equiv.) and iodomethane (110 µL, 1.8 mmol, 5 equiv.) and carried out for several hours before being diluted with ethyl acetate and water. The organic layer was washed with water and brine before being dried over Na₂SO₄, filtered and concentrated in vacuo. A ISCO flash column chromatography was carried out with 2/3 EtOAc/Hexanes to yield 274 as a brown solid (175 mg, 71% yield). $^1$H NMR (CDCl₃): δ (ppm) 8.97 (s, 1H), 8.88 (s, 1H), 8.25 (s, 1H), 7.73-7.65 (m, 5H), 7.41-7.03 (m, 8H), 6.45-6.40 (m, 2H), 4.83 (s, 2H), 4.54 (s, 2H), 4.19 (s, 2H), 3.87, (s, 3H), 3.86 (s, 2H), 3.82 (s, 3H). 300 MHz $^{19}$F NMR (CDCl₃) δ (ppm): −116.77. MS: 683.00 (M+1).

To a flask containing ester 274 (55 mg, 0.082 mmol, 1 equiv.) was added THF (10 mL, 0.5 M). A solution of LiOH (80 mg, 1.9 mmol, 4 equiv.) dissolved in H₂O (5 mL) was added and allowed to stir until reaction was complete. The reaction was diluted with EtOAc and the organic layer was washed with water and brine before being dried over Na₂SO₄, filtered and concentrated in vacuo and used as is. A light yellow solid was obtained of acid 275. $^1$H NMR (CDCl₃): δ (ppm) 9.15 (s, 1H), 8.88 (s, 1H), 8.30 (s, 1H), 7.73-7.65 (m, 5H), 7.41-7.03 (m, 8H), 6.45-6.40 (m, 2H), 4.83 (s, 2H), 4.54 (s, 2H), 4.19 (s, 2H), 3.80, (s, 3H), 3.78 (s, 2H). 300 MHz $^{19}$F NMR (CDCl₃) δ(ppm) −116.66. MS: 669.07 (M+1).

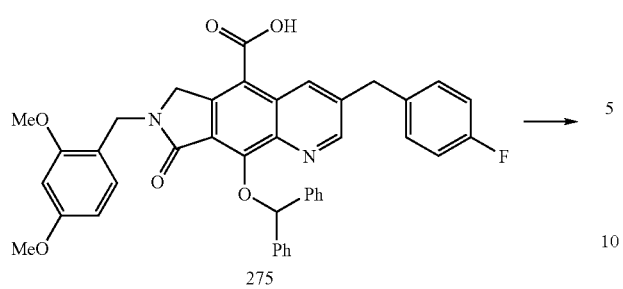

275

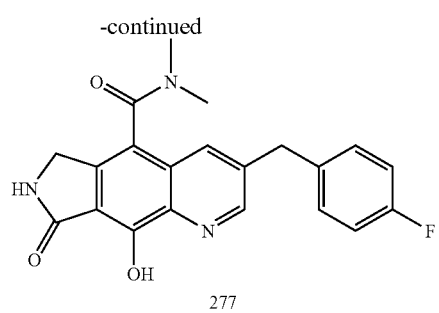

277

Deprotection of compound 276 provided compound 277: 300 MHz $^1$H NMR (DMSO-$d_6$) δ (ppm) 10.53 (bs, 1H), 8.84 (s, 1H), 8.42 (s, 1H), 7.83 (s, 1H), 7.35-7.20 (m, 2H), 7.19-7.04 (m, 2H), 6.53 (s, 1H), 4.29 (s, 2H), 4.23 (s, 2H), 3.07 (s, 3H), 2.66 (s, 3H). 300 MHz $^{19}$F NMR (CDCl$_3$) δ (ppm): −73.98. MS: 380.09 (M+1).

Example 86

Synthesis of Compound 280

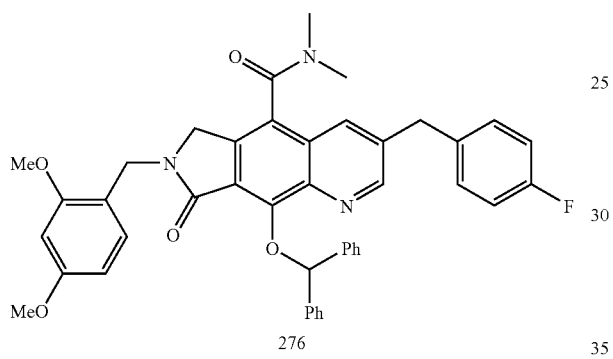

276

To acid 275 (295 mg, 0.44 mmol, 1 equiv.) was added DMF (5 mL) followed by DIPEA (230 µl, 1.3 mmol, 3 equiv.) and HATU (250 mg, 0.7 mmol, 1.5 equiv.). After 5 minutes, N,N dimethlyamine (1.1 mL, 0.45 mmol, 5 equiv., 2 M in THF) was added. When the reaction was complete it was quenched with water and diluted with Ethyl Acetate. The organic layer was washed with water and brine before being dried over Na$_2$SO$_4$, filtered and concentrated in vacuo. The crude residue was purified by chromatography on silica gel (4/1—Ethyl acetate/MeOH) to afford a white foam as the desired product 276 (210 mg, 69% yield). $^1$H NMR (CDCl$_3$): δ (ppm) 8.88 (s, 1H), 8.12 (s, 1H), 7.76-7.65 (m, 3H), 7.58 (s, 1H), 7.41-7.13 (m, 9H), 7.10-7.00 (s, 2H), 6.45-6.40 (m, 2H), 4.84 (s, J=14.4 Hz, 1H), 4.70 (d, J=14.4 Hz, 1H), 4.34 (d, J=17.4 Hz, 1H), 4.14 (s, 2H), 4.00 (d, J=17.4 Hz, 1H), 3.10 (s, 3H), 2.53 (s, 3H). 300 MHz $^{19}$F NMR (CDCl$_3$) δ(ppm) −116.52. MS: 696.00

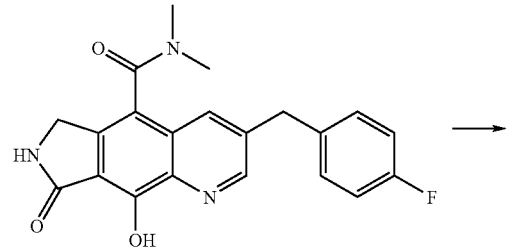

277

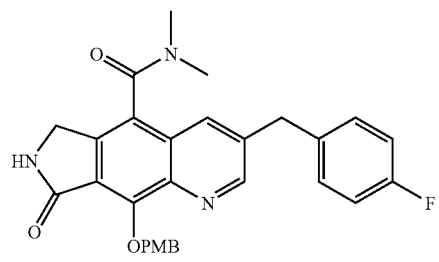

278

To phenol 277 (100 mg, 0.3 mmol, 1 equiv.) was added DMF (3 mL, 0.1 M) followed by Cs$_2$CO$_3$ (111 mg, 0.34 mmol, 1.3 equiv.). This was allowed to stir for 5 minutes before adding p-methoxybenzyl bromide (55 µL, 0.36 mmol, 1.4 equiv.). After completion, the reaction was cooled to room temperature before diluting with EtOAc (150 mL) and quenching with water. It was extracted with EtOAc and washed with water (2×100 mL), saturated NH$_4$Cl and brine. The organic layer was dried over sodium sulfate, filtered and concentrated in vacuo. The crude solid was washed with Hexanes/Ethyl Ether (1/1, v/v) and used as is. 300 MHz $^1$H NMR (CDCl$_3$) δ (ppm) 10.53 (bs, 1H), 8.85 (s, 1H), 8.43 (s, 1H), 7.83 (s, 2H), 7.28-7.20 (m, 2H), 7.09-7.04 (m, 2H), 4.29 (s, 2H), 4.23 (s, 2H), 3.06 (s, 3H), 2.66 (s, 3H), 6.85 (d, J=8.7 Hz, 2H), 6.26 (bs, 1H), 5.75 (d, J=6.3 Hz, 2H), 4.80 (d, J=16.5 Hz, 1H), 4.50 (d, J=16.6 Hz, 1H), 4.23 (s, 3H), 3.78 (s, 3H), 3.26 (s, 3H), 2.87 (s, 2H). 300 MHz $^{19}$F NMR (CDCl$_3$) δ (ppm): −115.87, −76.83. MS: 558.09 (M+23).

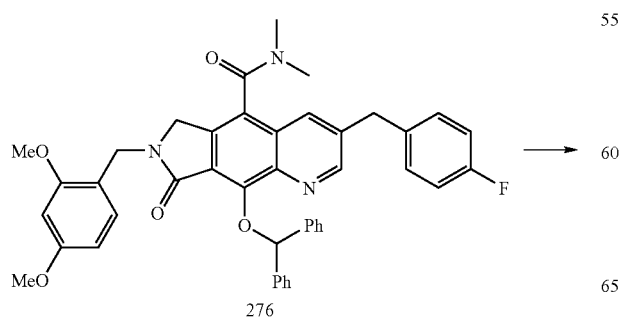

276

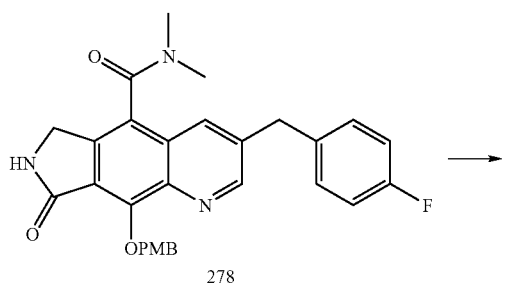

278

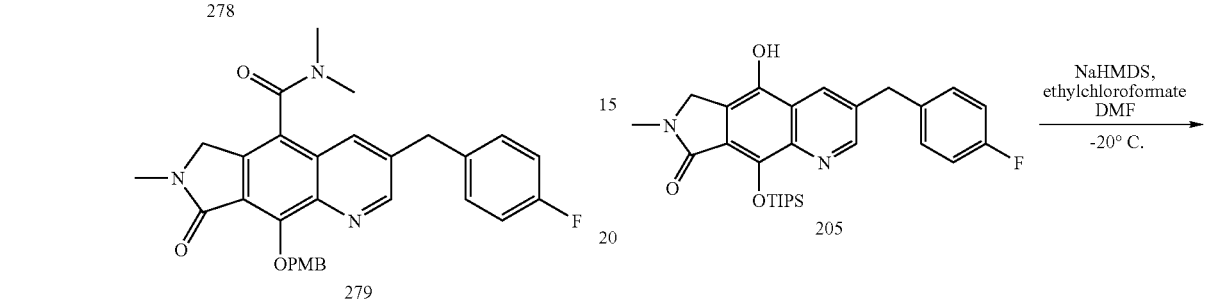

279

Lactam 278 (95 mg, 0.2 mmol, 1 equiv.) was stirred in DMF (2 mL, 0.1 M) and treated with NaHMDS (220 μL, 0.22 mmol, 1.2 equiv.). It was stirred for 5 min. before iodomethane (20 μL, 0.28 mmol, 1.5 equiv.) was added. The reaction mixture was diluted with ethyl acetate then quenched with water. The organic layer was washed with water, saturated NaHCO$_3$, and brine. The solution was dried over sodium sulfate, filtered and concentrated in vacuo. The crude residue was purified by chromatography on silica gel (1/3—Ethyl acetate/Hexane) to afford the desired product 279 (41 mg, 42%). 300 MHz $^1$H NMR (CDCl$_3$) δ (ppm) 8.87 (d, J=2.1 Hz, 1H), 7.78 (s, 1H), 7.65 (d, J=8.4 Hz, 2H), 7.17-7.09 (m, 2H), 7.10-7.00 (m, 1H), 7.02-7.09 (m, 2H), 6.44-6.42 (m, 2H), 5.73 (s, 2H), 4.57 (d, J=17.1 Hz, 1H), 4.23 (d, J=17.1 Hz, 1H), 4.16 (s, 2H), 3.81 (s, 3H), 3.21 (s, 3H), 3.17 (s, 3H), 2.71 (s, 3H). 300 MHz $^{19}$F NMR (CDCl$_3$) δ (ppm): −116.47. MS: 513.93 (M+1).

Deprotection of compound 279 provided compound 280. 300 MHz $^1$H NMR (CDCl$_3$) δ (ppm) 8.89 (s, 1H), 7.77 (s, 1H), 7.35-7.20 (m, 2H), 7.19-7.04 (m, 2H), 4.63 (d, J=17.7 Hz, 1H), 4.34 (d, J=17.7 Hz, 1H), 4.19 (s, 2H), 3.02 (s, 3H), 2.72 (s, 3H), 2.70 (s, 3H). 300 MHz $^{19}$F NMR (CDCl$_3$) δ (ppm): −76.51, −116.14 (TFA salt). MS: 394.10 (M+1).

Example 87

Synthesis of Compound 282

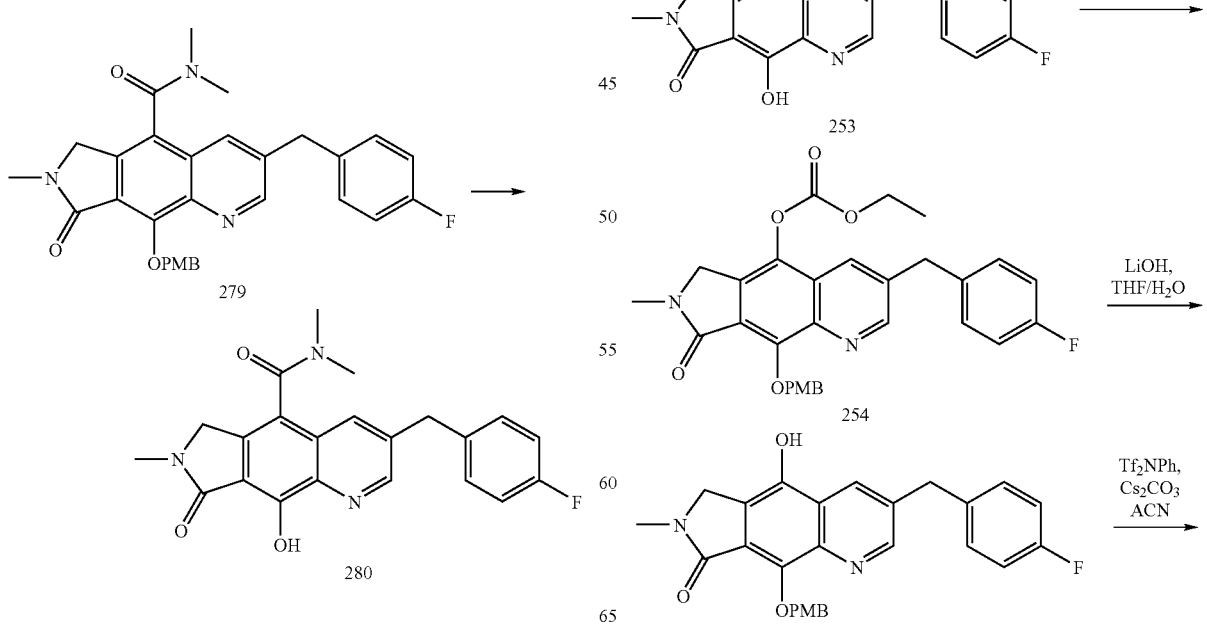

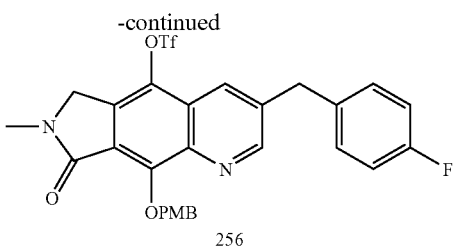

256

A solution of phenol 205 (7.43 g, 15.03 mmol) in DMF (150 mL, 0.1M) was cooled to approximately −20° C. then treated with NaHMDS (22.55 mL, 1M THF solution). Ethyl chloroformate (1.58 mL, 16.5 mmol) was added dropwise but also very quickly and the reaction was stirred at −20° C. for 10 minutes under nitrogen atmosphere. The reaction was quenched with $H_2O$ and diluted with ethyl acetate. The organic layer was washed with $H_2O$, sat. $NH_4Cl$, aqueous LiCl, and brine, then dried (over $Na_2SO_4$), filtered and concentrated in vacuo to afford the product 252 (8.5 g, quant) with no further purification: 300 MHz $^1H$ NMR ($CDCl_3$) δ(ppm): 8.69 (s, 1H), 7.85 (s, 1H), 7.19 (dd, 2H), 7.04 (dd, 2H), 4.37 (s, 2H), 4.36 (q, 2H), 4.175 (s, 2H), 3.175 (s, 3H), 1.52 (sep, 3H), 1.408 (t, 3H), 1.12 (d, 18H); MS: 567 (M+1).

To a solution of intermediate 252 (9.45 g, 16.69 mmol) in THF (167 mL, 0.1M) was added tetrabutylammonium fluoride hydrate (6.55 g, 25.03 mmol). The reaction mixture was stirred under nitrogen atmosphere at room temperature for 0.5 hours upon which it was diluted with ethyl acetate, and quenched with $H_2O$. The aqueous layer was acidified with 1N HCl (15 mL) and reextracted with ethyl acetate. The combined organic layer was washed with $H_2O$ (2×) and brine, then dried (over $Na_2SO_4$), filtered and concentrated in vacuo. The crude residue was triturated with hexane/diethyl ether (1/1) to afford clean solid phenol 253 (6.0 g, 88%): 300 MHz $^1H$ NMR ($CDCl_3$) δ(ppm): 8.81 (s, 1H), 7.96 (s, 1H), 7.19 (dd, 2H), 7.02 (dd, 2H), 4.48 (s, 2H), 4.36 (q, 2H), 4.194 (s, 2H), 3.199 (s, 3H), 1.418 (t, 3H); MS: 411 (M+1).

The phenol 253 (5.98 g, 14.58 mmol) was dissolved in DMF (146 mL, 0.1M) and treated with $Cs_2CO_3$ (11.84 g, 36.45 mmol) and stirred for 5 minutes before para-methoxybenzyl bromide (4.18 mL, 29.16 mmol) was added. The reaction was stirred under nitrogen atmosphere at room temperature for 2 hours, upon which the reaction was quenched with water and diluted with ethyl acetate. The organic layer was washed with sat $NH_4Cl$, aqueous LiCl, and brine, then dried (over $Na_2SO_4$), filtered and concentrated in vacuo. The crude residue was purified by chromatography on silica gel (3/7—hexane/ethyl acetate) in order to obtain desired product 254 (4.54 mg, 59%): 300 MHz $^1H$ NMR ($CDCl_3$) δ(ppm): 8.9 (s, 1H), 7.93 (s, 1H), 7.64 (d, 2H), 7.19 (m, 2H), 7.03 (m, 2H), 6.86 (d, 2H), 5.66 (s, 2H), 4.35 (s, 2H), 4.36 (q, 2H), 4.191 (s, 3H), 3.79 (s, 3H), 3.217 (s, 3H), 1.421 (t, 3H); MS: 531 (M+1).

To a solution of carbonate 254 (4.54 g, 8.56 mmol) dissolved in THF (85.6 mL, 0.1M) was added DMAP (0.523 g, 4.28 mmol) and a solution of LiOH*$H_2O$ (1.08 g, 25.7 mmol) in water (43 mL). The reaction was stirred at room temperature for 45 minutes upon which diluted with ethyl acetate and water. The mixture was acidified with 1N HCl (50 mL) and the product was extracted with ethyl acetate twice. The organic layer was washed with water (2×) and brine then dried (over $Na_2SO_4$), filtered and concentrated in vacuo to give clean product 255 (4.25 g, 100%) with no further purification: 300 MHz $^1H$ NMR ($CDCl_3$) δ(ppm): 8.65 (s, 1H), 8.38 (s, 1H), 7.42 (dd, 2H), 7.13 (dd, 2H), 6.95 (dd, 2H), 6.66 (d, 2H), 5.31 (s, 2H), 4.54 (s, 2H), 4.07 (s, 2H), 3.7 (s, 3H), 3.14 (s, 3H); MS: 459 (M+1).

The phenol 255 (4.25 g, 8.56 mmol) was dissolved in acetonitrile (130 mL) then cooled in an ice-bath. To this solution was added $Cs_2CO_3$ (4.19 g, 12.8 mmol) and the reaction was stirred for 5 minutes upon which N-phenyltrifluoromethansulfonimide (3.67 g, 10.3 mmol) was added. The reaction was stirred under nitrogen atmosphere for 3 hours while warming to room temperature. Upon completion, the mixture was diluted with ethyl acetate and quenched with $H_2O$. The organic layer was washed with sat $NH_4Cl_1$, $H_2O$ and brine, then dried (over $Na_2SO_4$), filtered and concentrated in vacuo. The crude residue was purified by chromatography on silica gel (2/3—hexane/ethyl acetate) to afford the desired triflate 256 (4.265 g, 84%): 300 MHz H NMR ($CDCl_3$) δ.((ppm): 8.96 (s, 1H), 8.02 (s, 1H), 7.6 (d, 2H), 7.20 (dd, 2H), 7.06 (dd, 2H), 6.86 (dd, 2H), 5.75 (s, 2H), 4.59 (s, 2H), 4.22 (s, 2H), 3.79 (s, 3H), 3.24 (s, 3H); 300 MHz $^{19}F$ NMR ($CDCl_3$) δ(ppm) −73.73, −116.225; MS: 591 (M+1).

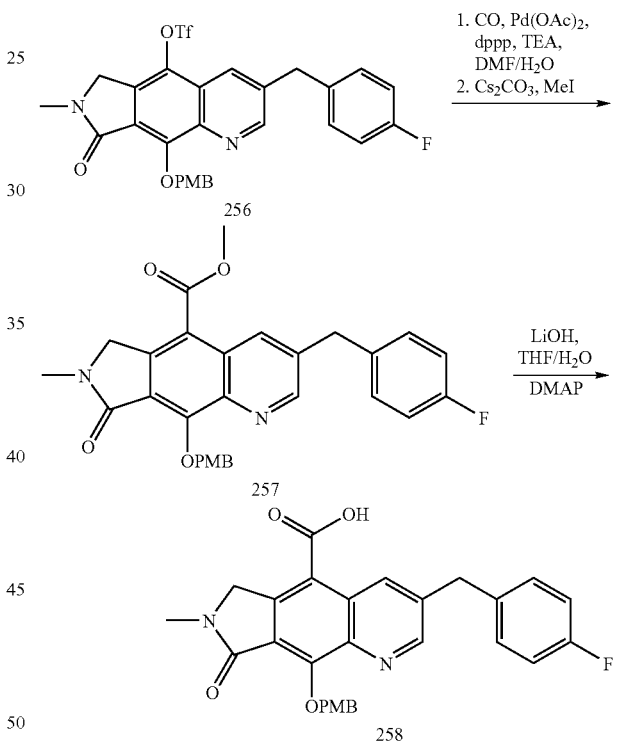

To a solution of triflate 256 (2.0 g, 3.39 mmol) and 1,3-bis (diphenyl-phosphino)propane (DPPP) (670 mg, 1.69 mmol) in DMF (56 mL) and water (5.6 mL) was added $Pd(OAc)_2$ (230 mg, 1.02 mmol). The solution was degassed under high vacuum (5 minutes) and flushed with carbon monoxide from a balloon. The flushing was repeated several times. TEA (1.13 mL, 8.14 mmol) was introduced. The mixture was heated at 65° C. under CO atmosphere for 2 hours then cooled down to the room temperature. $Cs_2CO_3$ (2.2 g, 6.78 mmol) and iodomethane (0.844 mL, 13.56 mmol) were added and the reaction mixture was stirred overnight at room temperature under nitrogen atmosphere. The mixture was diluted with ethyl acetate, washed with water, sat $NH_4Cl$, aq LiCl and brine, then dried (over $Na_2SO_4$), filtered and concentrated in vacuo. The crude product was purified by chromatography on silica gel column (4/1—hexane/ethyl acetate) to afford the methyl ester product 257 (1.29 g, 77%): 300 MHz $^1$H NMR (CDCl$_3$) δ (ppm): 9.08 (s, 1H), 8.8 (s, 1H), 7.58 (d, 2H), 7.2 (dd, 2H) 7.03 (dd, 2H), 6.82 (dd, 2H), 5.83 (s, 2H), 4.71 (s, 2H), 4.20 (s, 2H), 3.99 (s, 3H), 3.77 (s, 3H), 3.238 (s, 3H); MS: 501 (M+1).

To a solution of ester 257 (1.29 g, 2.58 mmol) dissolved in THF (25.8 mL, 0.1M) was added DMAP (95 mg, 0.774 mmol) and a solution of LiOH.H$_2$O (325 mg, 7.74 mmol) in water (12.9 mL). The reaction was stirred at room temperature for 4 hours upon which diluted with ethyl acetate and water. The mixture was acidified with 1N HCl (10 mL) and the product was extracted with ethyl acetate twice. The organic layer was washed with brine (2×) then dried (over Na$_2$SO$_4$), filtered and concentrated in vacuo to give clean product 258 (1.24 g, 100%) with no further purification: 300 MHz $^1$H NMR (CD$_3$OD) δ (ppm): 9.23 (s, 1H), 8.82 (s, 1H), 7.45 (d, 2H), 7.30 (dd, 2H) 7.06 (dd, 2H), 6.78 (dd, 2H), 5.69 (s, 2H), 4.805 (s, 2H), 4.23 (s, 2H), 3.73 (s, 3H), 3.21 (s, 3H); MS: 487 (M+1).

300 MHz $^1$H NMR (CDCl$_3$) δ (ppm): 8.91 (s, 1H), 7.71 (s, 1H), 7.58 (d, 2H), 7.19 (dd, 2H), 7.03 (dd, 2H), 6.83 (d, 2H), 5.72 (dd, 2H), 4.40 (dd, 2H), 4.16 (s, 2H), 4.018 (m, 1H), 3.78 (s, 3H), 3.511 (m, 1H), 3.20 (s, 3H), 2.98 (m, 2H), 2-1 (m, 6H); MS: 554 (M+1).

The compound was made in a similar fashion as before using TFA (no TES was added) to afford the desired product 282 (21.9 mg, 73%—2 steps) as the free parent: 300 MHz $^1$H NMR (CDCl$_3$) δ(ppm) 8.93 (s, 1H), 7.86 (s, 1H), 7.19 (dd, 2H), 7.05 (dd, 2H), 4.48 (dd, 2H), 4.21 (s, 2H), 3.96 (m, 1H), 3.52 (m, 1H), 3.195 (s, 3H), 3.009 (m, 2H), 1.8-1.4 (m, 4H), 1.3 (m, 1H), 1.08 (m, 1H); 300 MHz $^{19}$F NMR (CDCl$_3$) δ (ppm): −116.044; MS: 434 (M+1).

Example 88

Synthesis of Compound 284

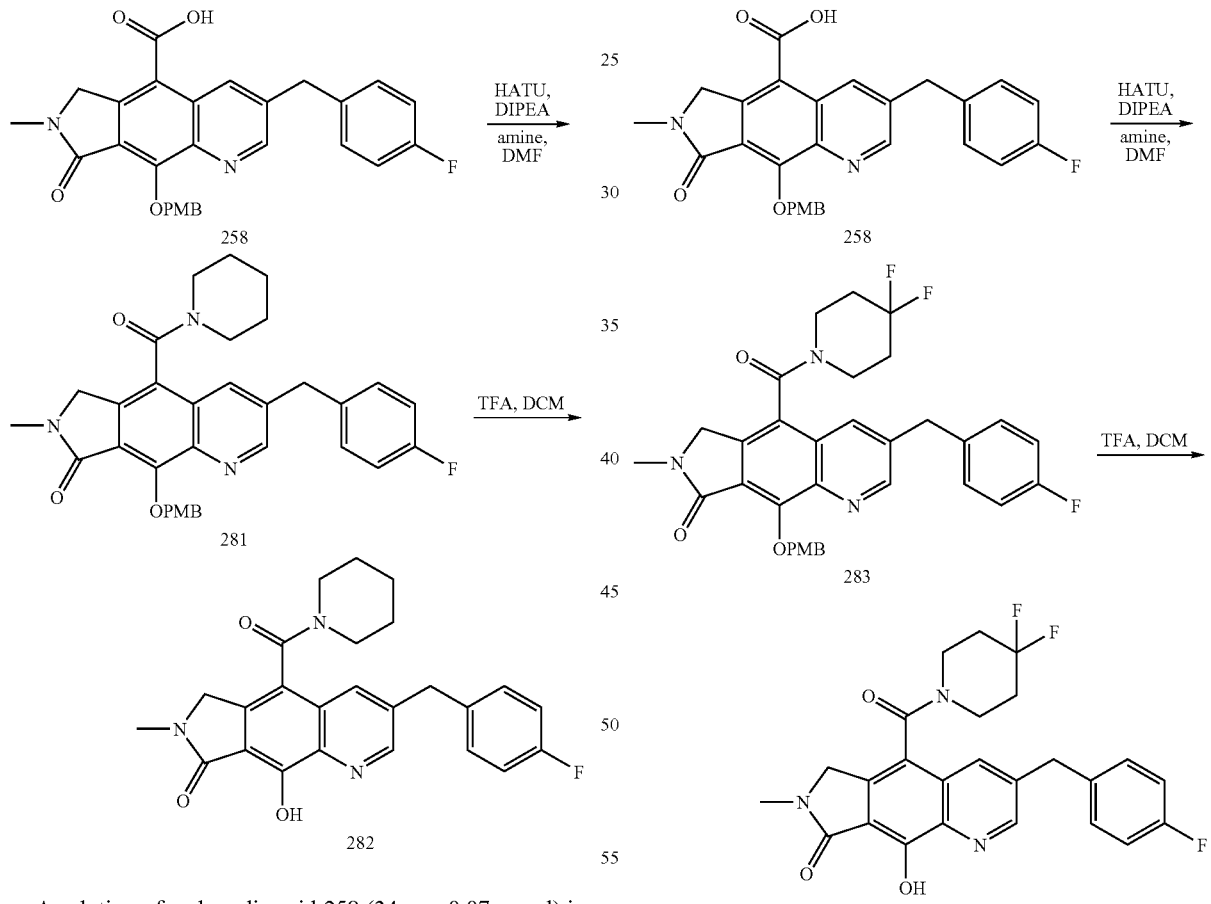

A solution of carboxylic acid 258 (34 mg, 0.07 mmol) in DMF (0.7 mL) that had been stirred with HATU (0.040 g, 0.105 mmol) and DIPEA (0.061 mL, 0.35 mmol) for 5 minutes was treated with piperidine (21 μL, 0.210 mmol). The reaction mixture was stirred for 1 hour at room temperature, under nitrogen atmosphere, upon which diluted with ethyl acetate and quenched with water. The organic layer saturated was washed with NH$_4$Cl, aqueous LiCl, and brine, then dried (NaSO$_4$), filtered and concentrated. The residue was purified by chromatography on silica gel (0-5%—methanol/ethyl acetate) to afford the desired product 281 (38.9 mg, qaunt):

The compound was made in a similar fashion as compound 281 to afford the desired product 284 (40 mg, quant): 300 MHz $^1$H NMR (CDCl$_3$) δ,((ppm) 8.94 (s, 1H), 7.57 (m, 2H), 7.18 (dd, 2H), 7.06 (dd, 2H), 6.83 (d, 2H), 5.765 (dd, 2H), 4.395 (dd, 2H), 4.17 (s, 2H), 4.16 (m, 1H), 3.78 (s, 3H), 3.69 (m, 1H), 3.21 (s, 3H), 3.147 (m, 2H), 2-1 (m, 4H); MS: 590 (M+1).

The compound was made in a similar fashion as compound 282 to afford the desired product 284 (25.3 mg, 77%—2 steps) as the free parent: 300 MHz $^1$H NMR (DMSO) δ(ppm) 8.89 (s, 1H), 7.89 (s, 1H), 7.36 (dd, 2H), 7.12 (dd, 2H), 4.42 (dd, 2H), 4.24 (s, 2H), 3.93 (m, 1H), 3.695 (m, 1H), 3.12 (m, 2H), 3.01 (s, 3H), 2.099 (m, 2H), 1.8 (m, 1H), 1.50 (m, 1H); 300 MHz $^{19}$F NMR (CDCl$_3$) δ (ppm): −95.348, −96.170, −97.60, −98.425, −117.054; MS: 470 (M+1).

4.59 (s, 2H), 4.10 (s, 2H), 3.03 (s, 3H); 300 MHz $^{19}$F NMR (CDCl$_3$) δ(ppm) −116.48; MS: 457 (M+1).

Example 89

Synthesis of Compound 286

Example 90

Synthesis of Compound 287

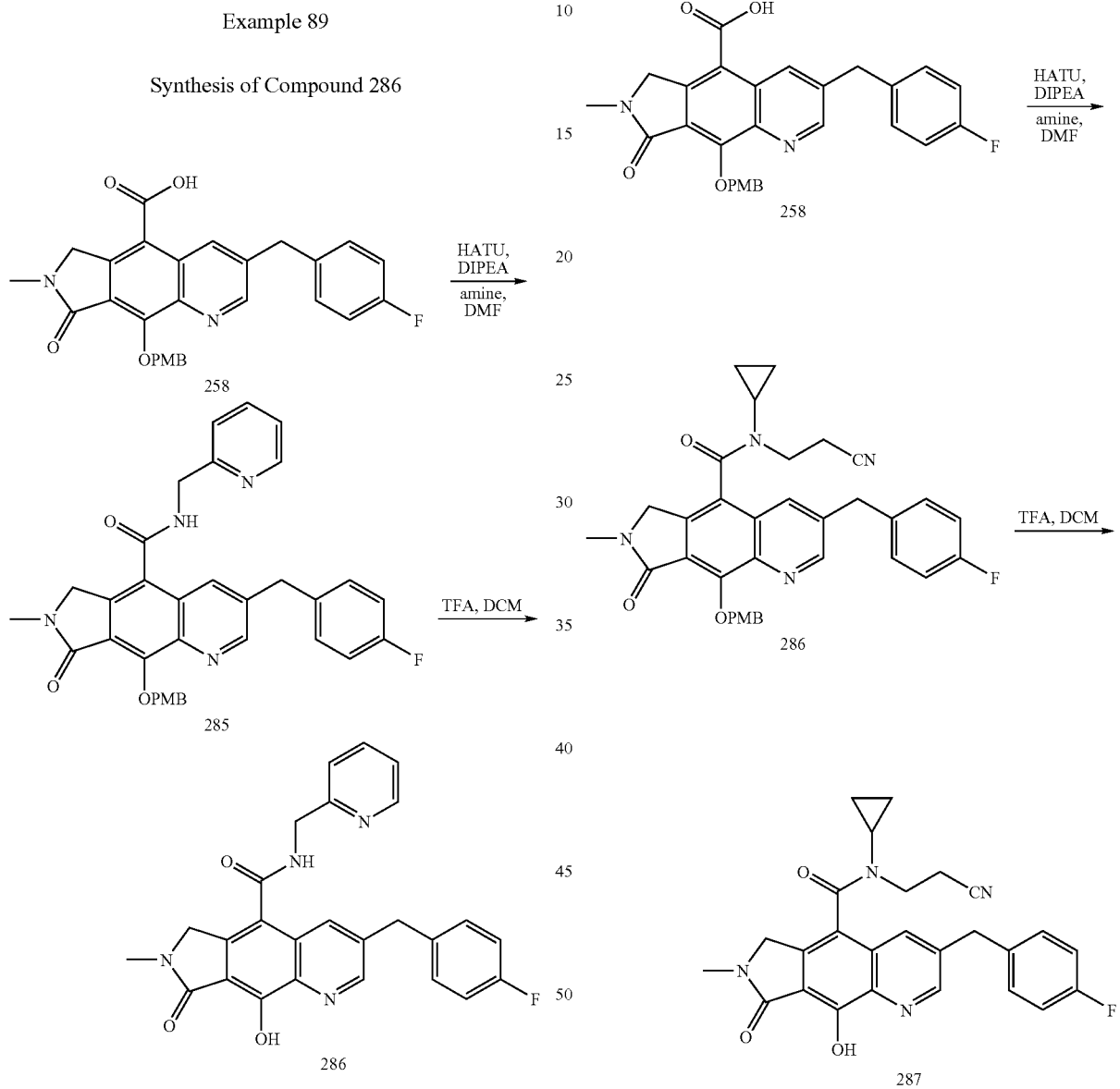

The compound was made in a similar fashion as compound 281 to afford the desired product 285 (30 mg): 300 MHz $^1$H NMR (CDCl$_3$) δ ((ppm) 8.67 (s, 1H), 8.57 (d, 1H), 8.325 (s, 1H), 8.086 (m, 1H), 7.81 (m, 1H), 7.8 (m, 1H), 7.55 (d, 2H), 7.45 (d, 1H), 7.3 (m, 1H), 7.18 (dd, 2H), 6.95 (dd, 2H), 6.78 (d, 2H), 5.45 (dd, 2H), 4.62 (d, 2H), 4.50 (s, 2H), 4.07 (s, 2H), 3.77 (s, 3H), 3.01 (s, 3H); MS: 577 (M+1).

The compound was made in a similar fashion as above to afford the desired product 285 (19.3 mg, 59%—2 steps) as the free parent: 300 MHz $^1$H NMR (CDCl$_3$) δ (ppm): 8.63 (s, 1H), 8.61 (d, 1H), 8.45 (s, 1H), 7.9 (m, 1H), 7.79 (m, 1H), 7.42 (m, 1H), 7.3 (m, 1H), 7.18 (dd, 2H), 6.94 (dd, 2H), 4.9 (d, 2H), Formation of the amide using procedures similar to those described above afforded the desired product 286 (26 mg): 300 MHz $^1$H NMR (CDCl$_3$) δ (ppm): 8.9 (s, 1H), 7.91 (s, 1H), 7.57 (d, 2H), 7.18 (dd, 2H), 7.02 (dd, 2H), 6.8 (d, 2H), 5.79 (dd, 2H), 4.45 (dd, 2H), 4.18 (s, 2H), 3.99 (m, 1H), 3.77 (m, 1H), 3.76 (s, 3H), 3.21 (s, 3H), 2.9 (m, 2H), 2.54 (m, 1H), 0.42 (m, 2H), 0.18 (m, 2H); MS: 579 (M+1).

The compound was made in a similar fashion as compound 265 to afford the desired product 271 (13.1 mg, 40%—2 steps) as the free parent: 300 MHz $^1$H NMR (CDCl$_3$) δ (ppm): 8.84 (s, 1H), 7.99 (s, 1H), 7.18 (dd, 2H), 7.01 (dd, 2H), 4.52 (dd, 2H), 4.19 (s, 2H), 3.99 (m, 1H), 3.79 (m, 1H), 3.201 (s, 3H), 2.90 (m, 2H), 2.61 (m, 1H), 0.483 (m, 2H), 0.28 (m, 2H); 300 MHz $^{19}$F NMR (CDCl$_3$) δ(ppm) −116.37; MS: 459 (M+1).

Example 91

Synthesis of Compound 289

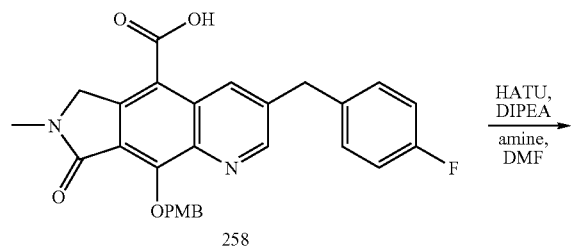

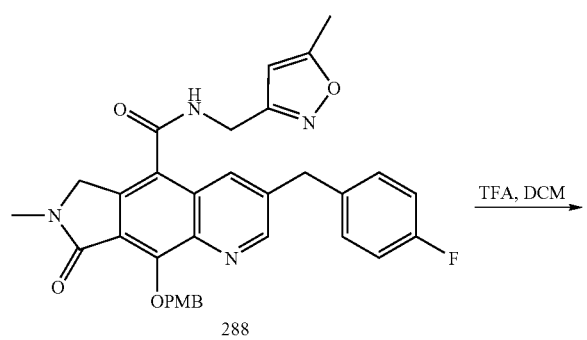

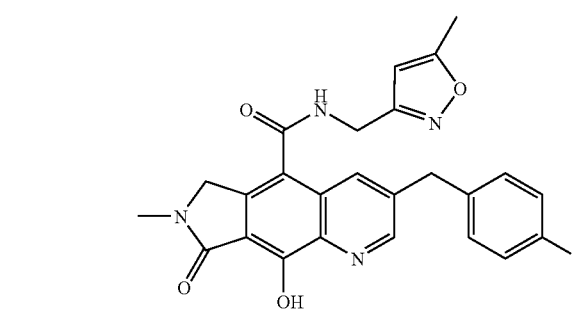

The compound was made in a similar fashion as above to afford the desired product 288 (24 mg): 300 MHz $^1$H NMR (CDCl$_3$) δ (ppm): 8.499 (s, 1H), 8.273 (bs, 2H), 7.55 (d, 2H), 7.26 (m, 2H), 7.02 (dd, 2H), 6.84 (d, 2H), 6.06 (s, 1H), 5.27 (s, 2H), 4.36 (s, 2H), 4.21 (m, 2H), 3.96 (m, 1H), 3.80 (s, 3H), 2.87 (s, 3H), 2.47 (s, 3H); MS: 581 (M+1).

The compound was made in a similar fashion as above to afford the desired product 289 (11 mg, 46%—2 steps) as the free parent: 300 MHz $^1$H NMR (CDCl$_3$) δ (ppm): 8.61 (s, 1H), 8.41 (s, 1H), 7.45 (m, 2H), 7.21 (m, 2H), 7.02 (dd, 2H), 6.1 (s, 1H), 4.8 (d, 2H), 4.49 (s, 2H), 4.1 (s, 2H), 2.94 (s, 3H), 2.48 (s, 3H); 300 MHz $^{19}$F NMR (CDCl$_3$) δ (ppm): −116.41; MS: 461 (M+1).

Example 92

Synthesis of Compound 291

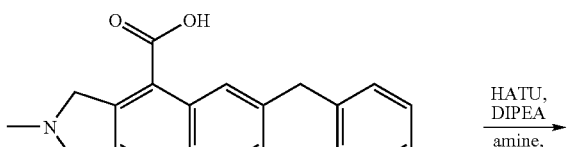

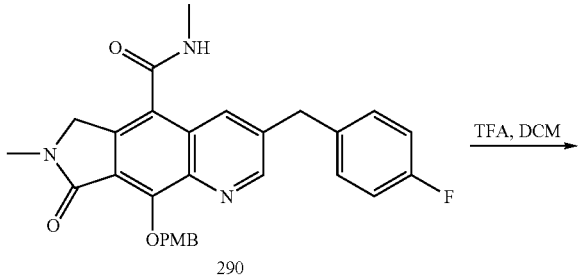

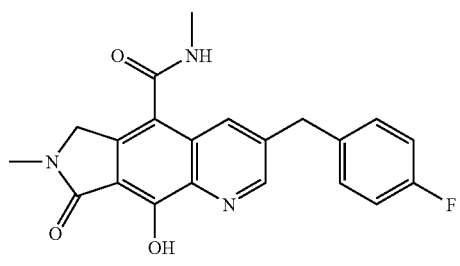

The compound was made in a similar fashion as above to afford the desired product 290 (20 mg): 300 MHz $^1$H NMR (CDCl$_3$) δ (ppm): 8.48 (s, 1H), 8.12 (s, 1H), 7.6 (d, 2H), 7.26 (m, 2H), 7.05 (dd, 2H), 6.9 (d, 2H), 5.27 (s, 2H), 4.32 (s, 2H), 4.05 (s, 2H), 3.82 (s, 3H), 2.82 (s, 3H), 2.66 (s, 3H); MS: 500 (M+1).

The compound was made in a similar fashion as above to afford the desired product 291 (12 mg, 64%—2 steps) as the free parent: 300 MHz $^1$H NMR (DMSO) δ (ppm): 8.2 (s, 1H), 8.376 (m, 1H), 8.275 (s, 1H), 7.34 (dd, 2H), 7.14 (dd, 2H), 4.55 (d, 2H), 4.21 (s, 2H), 3.03 (s, 3H), 2.83 (d, 3H); 300 MHz $^{19}$F NMR (CDCl$_3$) δ(ppm) −117.21; MS: 380 (M+1).

Example 93

Synthesis of Compound 292

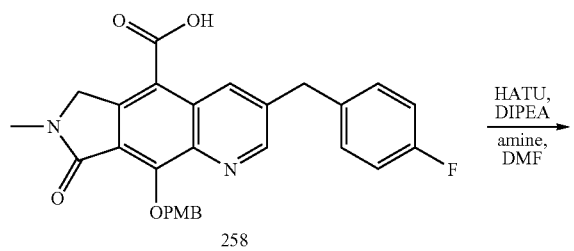

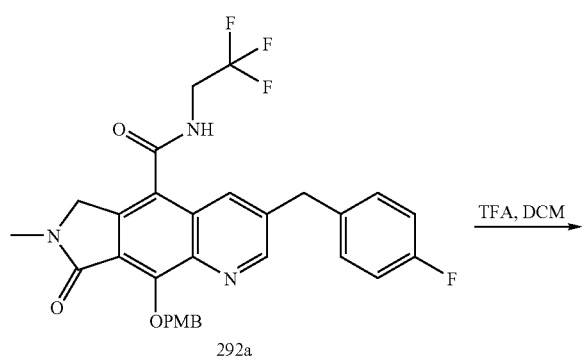

The compound was made in a similar fashion as above to afford the desired product 292a (25 mg): 300 MHz $^1$H NMR (CDCl$_3$) δ (ppm) 8.47 (s, 1H), 8.05 (s, 1H), 7.57 (d, 2H), 7.25 (m, 2H), 7.06 (dd, 2H), 6.92 (d, 2H), 5.26 (s, 2H), 4.32 (s, 2H), 3.974 (dd, 2H), 3.825 (s, 3H), 3.497 (m, 2H), 2.84 (m, 3H); MS: 568 (M+1).

The compound was made in a similar fashion as above to afford the desired product 292 (15.1 mg, 68%—2 steps) as the free parent: 300 MHz $^1$H NMR (CDCl$_3$) δ(ppm) 8.47 (s, 1H), 8.28 (s, 1H), 7.21 (dd, 2H), 7.05 (dd, 2H), 4.39 (s, 2H), 4.27 (dd, 2H), 4.067 (s, 3H), 2.86 (s, 3H); 300 MHz $^{19}$F NMR (CDCl$_3$) δ(ppm) −72.221, −115.87; MS: 448 (M+1).

Example 94

Synthesis of Compound 294

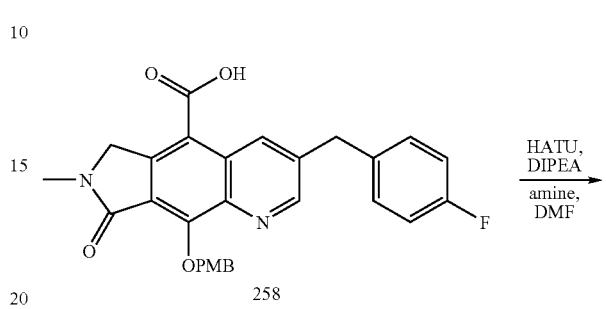

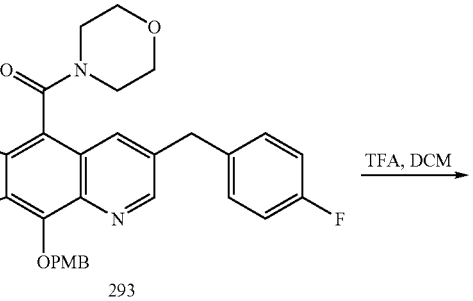

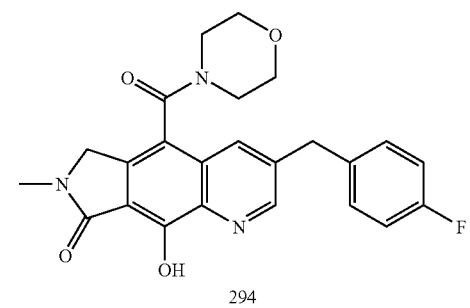

The compound was made in a similar fashion as above to afford the desired product 293 (20 mg): 300 MHz $^1$H NMR (CDCl$_3$) δ(ppm) 8.93 (s, 1H), 7.69 (s, 1H), 7.6 (d, 2H), 7.19 (dd, 2H), 7.06 (dd, 2H), 6.85 (d, 2H), 5.74 (s, 2H), 4.41 (dd, 2H), 4.12 (s, 2H), 3.91 (m, 1H), 3.78 (s, 3H), 3.77 (m, 2H), 3.62 (m, 1H), 3.42 (m, 1H), 3.20 (s, 3H), 3.20 (m, 1H), 3.2-3.0 (m, 3H); MS: 556 (M+1).

The compound was made in a similar fashion as above to afford the desired product 294 (9.7 mg, 66%—2 steps) as the free parent: 300 MHz $^1$H NMR (CDCl$_3$) δ(ppm) 8.88 (s, 1H), 7.79 (s, 1H), 7.2 (dd, 2H), 7.07 (dd, 2H), 4.49 (dd, 2H), 4.21

(s, 2H), 3.88 (m, 1H), 3.79 (m, 2H), 3.63 (m, 1H), 3.20 (s, 3H) 3.3-3.0 (m, 3H); 300 MHz $^{19}$F NMR (CDCl$_3$) δ(ppm) −115.84; MS: 436 (M+1).

Example 95

Synthesis of Compound 296

(s, 2H), 4.0 (m, 1H), 3.71 (m, 2H), 3.3 (d, 3H), 3.194 (s, 3H), 2.94 (d, 3H); 300 MHz $^{19}$F NMR (CDCl$_3$) δ(ppm) −116.47; MS: 438 (M+1).

Example 96

Synthesis of Compound 298

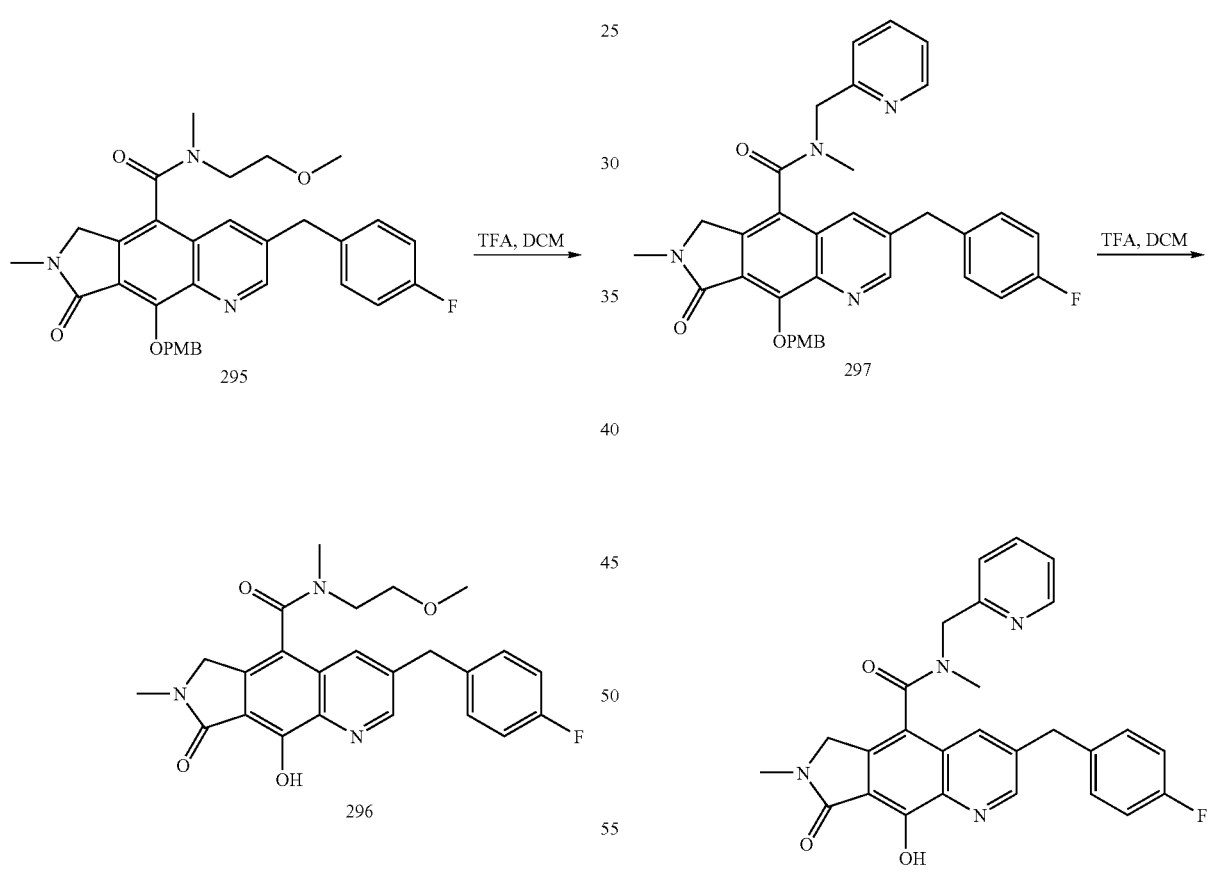

The compound was made in a similar fashion as above to afford the desired product 280 (27 mg): 300 MHz $^1$H NMR (CDCl$_3$) δ(ppm) 8.9 (s, 1H), 7.86 (d, 1H), 7.61 (d, 2H), 7.17 (dd, 2H), 7.02 (dd, 2H), 6.84 (d, 2H), 5.75 (dd, 2H), 4.4 (m, 2H), 4.16 (s, 2H), 3.79 (s, 3H), 3.72 (m, 1H), 3.3 (d, 3H), 3.25 (m, 1H), 3.22 (s, 3H), 2.91 (d, 2H); MS: 558 (M+1).

The compound was made in a similar fashion as above to afford the desired product 296 (15 mg, 73%—2 steps) as the free parent: 300 MHz $^1$H NMR (CDCl$_3$) δ(ppm) 8.80 (s, 1H), 7.86 (d, 1H), 7.17 (dd, 2H), 7.01 (dd, 2H), 4.45 (m, 2H), 4.16

The compound was made in a similar fashion above to afford the desired product 297 (26 mg) without full characterization by NMR; MS: 591 (M+1).

The compound was made in a similar fashion as above to afford the desired product 298 (13.6 mg, 50%—2 steps) as the free parent: 300 MHz $^1$H NMR (CD$_3$OD) δ(ppm) 8.82 (m, 1H), 8.55 (m, 1H), 8.2 (m, 2H), 7.72 (m, 1H), 7.63 (m, 1H), 7.29 (dd, 2H), 7.06 (dd, 2H), 5.03 (dd, 2H), 4.52 (m, 2H), 4.27

(s, 2H), 3.18 (s, 3H), 3.04 (m, 3H); 300 MHz $^{19}$F NMR (CDCl$_3$) δ (ppm)-78.07, -118.74; MS: 471 (M+1).

Example 97

Synthesis of Compound 301

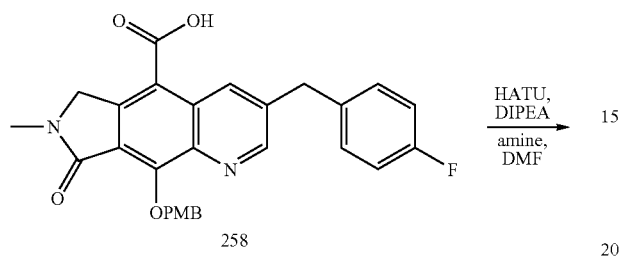

258

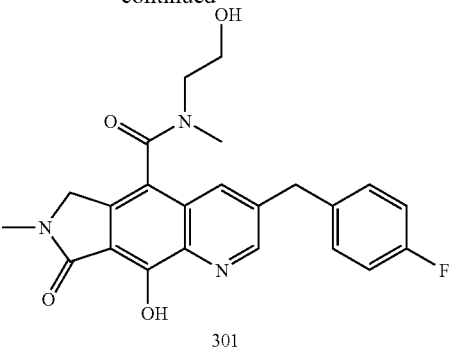

301

The compound was made in a similar fashion as above to afford the desired product 299 (45 mg) without full characterization by NMR; MS: 782 (M+1).

The compound was made in a similar fashion as above to afford the desired product 300 (45 mg) neither without any purification (trituration) nor without full characterization by NMR; MS: 662 (M+1).

To a solution of intermediate 300 (45 mg, 0.051 mmol) in THF (0.5 mL) was added tetrabutylammonium fluoride hydrate (27 mg, 0.103 mmol). The reaction mixture was stirred under nitrogen atmosphere at 65° C. for 2 days with multiple additions of TBAF upon which it was diluted with ethyl acetate, quenched with H$_2$O then acidified with 1N HCl (to pH 2). The desired product was extracted into the aqueous layer. Therefore, the water was removed in vacuo, and then the subsequent solid was suspended with methylene chloride. The solid salts were filtered off and the desired product had dissolved in the organics which was concentrated in vacuo to afford 301 (8.9 mg, 41%—3 steps) in high purity; 300 MHz $^1$H NMR (CD$_3$OD) δ(ppm) 8.86 (m, 1H), 8.23 (m, 1H), 7.32 (m, 2H), 7.08 (m, 2H), 4.57 (m, 2H), 4.28 (s, 2H), 3.8 (m, 1H), 3.6 (m, 1H), 3.25 (m, 2H), 3.16 (s, 3H), 2.95 (m, 3H); 300 MHz. $^{19}$F NMR (CDCl$_3$) δ(ppm) -78.18, -116.64; MS: 424 (M+1).

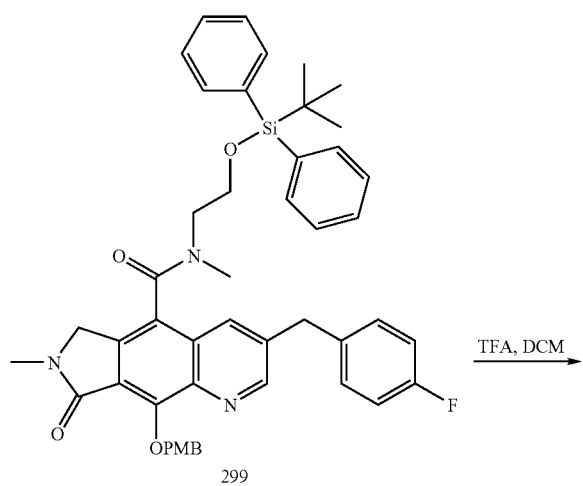

299

Example 98

Synthesis of Compound 303

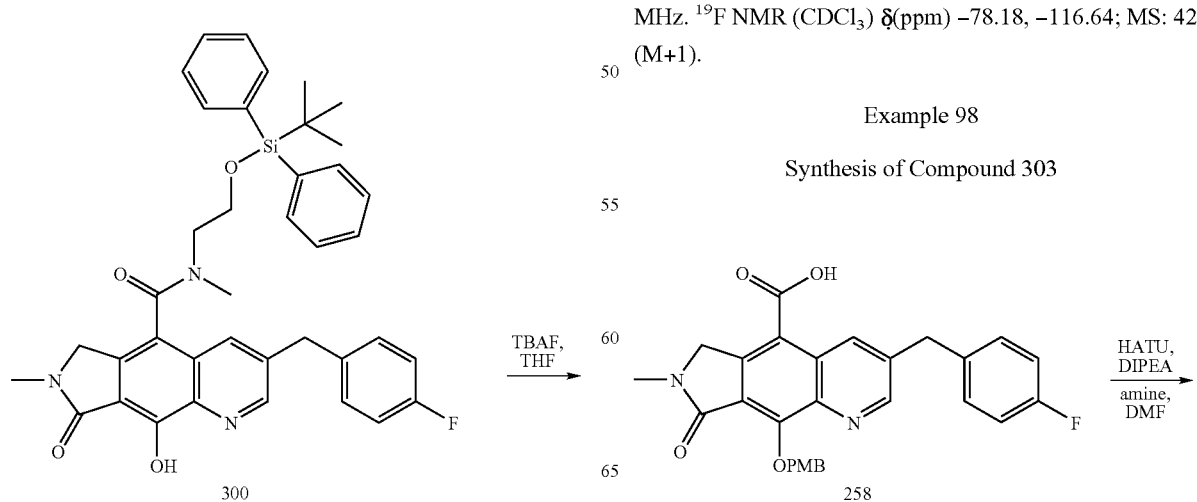

300      258

-continued

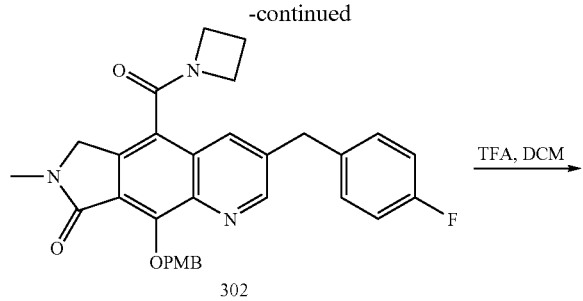
302

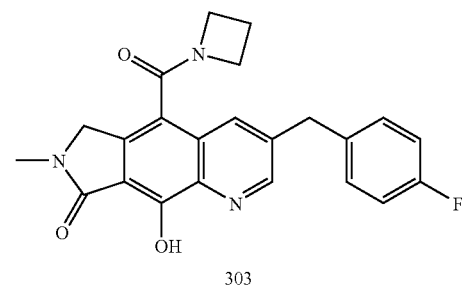
303

The compound was made in a similar fashion as above to afford the desired product 302 (22 mg): 300 MHz $^1$H NMR (CDCl$_3$) δ(ppm) 8.93 (s, 1H), 7.93 (s, 1H), 7.60 (d, 2H), 7.21 (m, 2H), 7.07 (dd, 2H), 6.83 (d, 2H), 5.78 (s, 2H), 4.55 (m, 2H), 4.25 (m, 2H), 4.20 (s, 2H), 3.78 (s, 3H), 3.57 (m, 2H), 3.22 (s, 3H), 2.26 (m, 2H); MS: 526 (M+1).

The compound was made in a similar fashion as above to afford the desired product 303 (14 mg, 67%—2 steps) as the free parent: 300 MHz $^1$H NMR (CDCl$_3$) δ(ppm) 8.84 (s, 1H), 7.97 (s, 1H), 7.21 (dd, 2H), 7.07 (dd, 2H), 4.62 (m, 2H), 4.21 (m, 4H), 3.57 (m, 2H), 3.21 (s, 3H), 2.24 (m, 2H); 300 MHz $^{19}$F NMR (CDCl$_3$) δ(ppm) −116.29; MS: 406 (M+1).

Example 99

Synthesis of Compound 305

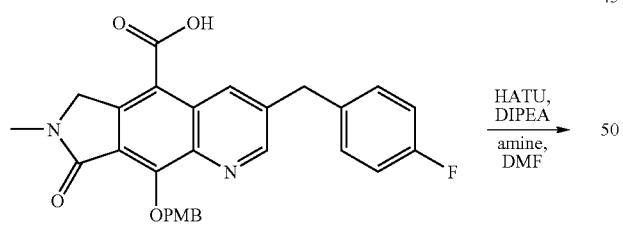
258

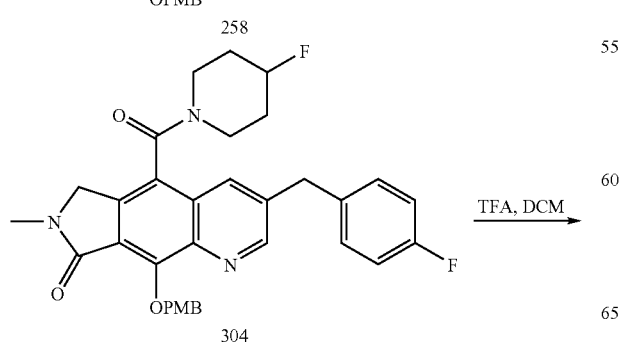
304

-continued

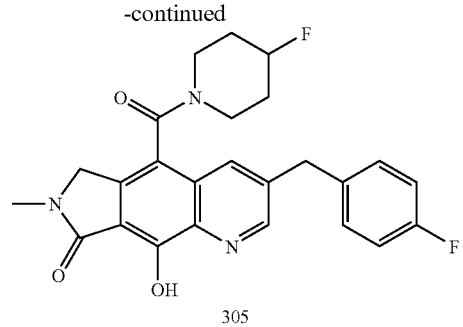
305

The compound was made in a similar fashion as above to afford the desired product 304 (22 mg): 300 MHz $^1$H NMR (CDCl$_3$) δ(ppm) 8.92 (m, 1H), 7.62 (m, 2H), 7.56 (s, 1H), 7.18 (m, 2H), 7.03 (m, 2H), 6.85 (d, 2H), 5.74 (dd, 2H), 5.0-4.5 (m, 2H), 4.4-3.8 (m, 5H), 3.78 (s, 3H), 3.5-2.8 (m, 2H), 3.20 (s, 3H), 2-1 (m, 4H); MS: 572 (M+1).

The compound was made in a similar fashion as above to afford the desired product 305 (13 mg, 56%—2 steps) as the free parent: 300 MHz $^1$H NMR (DMSO) δ(ppm) 8.89 (s, 1H), 7.80 (d, 1H), 7.36 (dd, 2H), 7.16 (m, 2H), 4.8 (m, 1H), 4.395 (s, 2H), 4.24 (s, 2H), 3.93 (m, 1H), 3.542 (m, 1H), 3.3-2.8 (m, 2H), 3.01 (s, 3H), 2-1 (m, 4H); 300 MHz $^{19}$F NMR (CDCl$_3$) δ(ppm) −117.095; MS: 452 (M+1).

Example 100

Synthesis of Compound 307

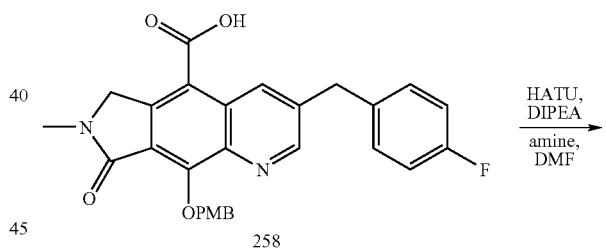
258

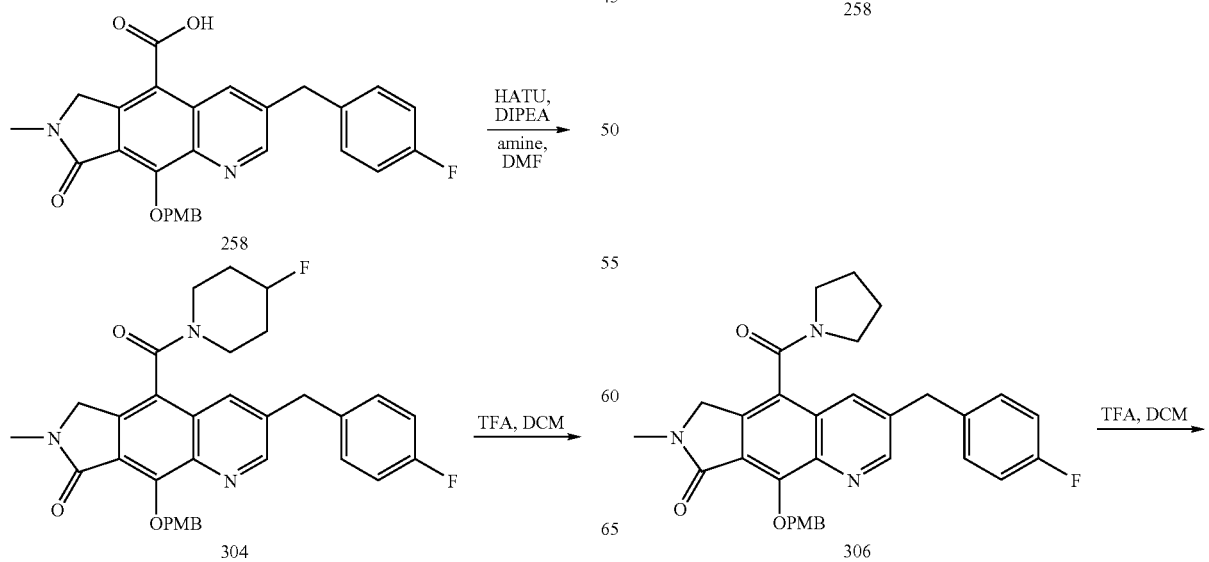
306

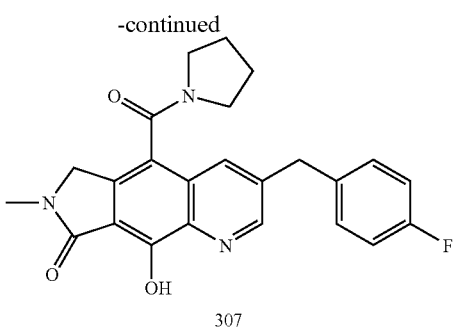

307

The compound was made in a similar fashion as above to afford the desired product 306 (22 mg): 300 MHz $^1$H NMR (CDCl$_3$) δ(ppm) 8.93 (s, 1H), 7.72 (s, 1H), 7.62 (d, 2H), 7.17 (dd, 2H), 7.03 (dd, 2H), 6.84 (d, 2H), 5.76 (dd, 2H), 4.45 (dd, 2H), 4.17 (s, 2H), 3.78 (s, 3H), 3.71 (m, 2H), 3.21 (s, 3H), 2.92 (m, 1H), 2.85 (m, 1H), 2.1-1.7 (m, 4H); MS: 540 (M+1).

The compound was made in a similar fashion as above to afford the desired product 307 (11.5 mg, 53%—2 steps) as the free parent: 300 MHz $^1$H NMR (CDCl$_3$) δ(ppm) 8.83 (s, 1H), 7.73 (d, 1H), 7.17 (dd, 2H), 7.03 (dd, 2H), 4.51 (m, 2H), 4.17 (s, 2H), 4.70 (m, 2H), 3.19 (s, 3H), 2.93 (m, 1H), 2.87 (m, 1H), 1.99 (m, 1H), 1.88 (m, 1H), 1.75 (m, 2H); MS: 420 (M+1).

Example 101

Synthesis of Compound 309

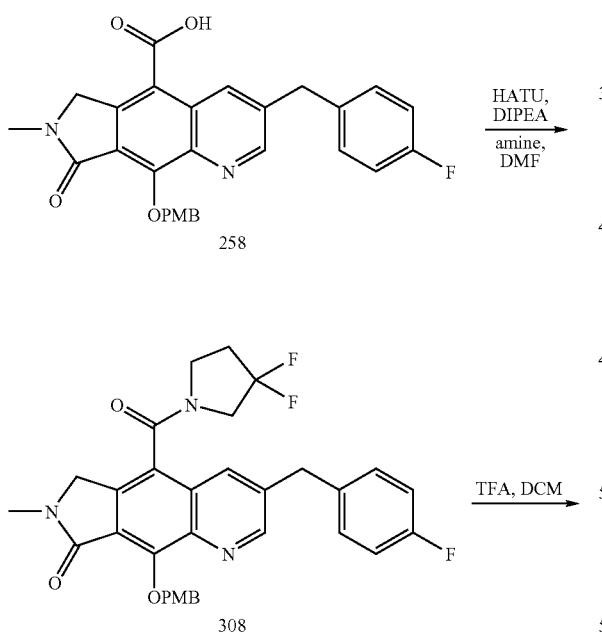

The compound was made in a similar fashion as above to afford the desired product 293 (24 mg): 300 MHz $^1$H NMR (CDCl$_3$) δ(ppm) 8.96 (s, 1H), 7.69 (d, 1H), 7.605 (d, 2H), 7.18 (dd, 2H), 7.05 (dd, 2H), 6.835 (d, 2H), 5.80 (dd, 2H), 4.46 (dd, 2H), 4.18 (s, 2H), 4.0 (m, 2H), 3.78 (s, 3H), 3.22 (s, 3H), 3.15 (m, 2H), 2.3 (m, 2H); MS: 576 (M+1).

The compound was made in a similar fashion as c above to afford the desired product 309 (14.1 mg, 53%—2 steps) as the free parent: 300 MHz $^1$H NMR (DMSO) δ(ppm) 8.85 (s, 1H), 7.95 (d, 1H), 7.35 (dd, 2H), 7.15 (dd, 2H), 4.45 (m, 2H), 4.22 (s, 2H), 4.0 (m, 1H), 3.8 (m, 1H), 3.6-3.15 (m, 2H), 3.05 (s, 3H), 2.5-2.2 (m, 2H); 300 MHz $^{19}$F NMR (CDCl$_3$) δ(ppm) −99.59, −100.17, 101.874, −117.138; MS: 456 (M+1).

Example 102

Synthesis of Compound 311

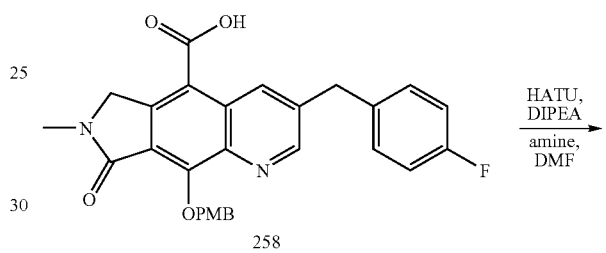

The compound was made in a similar fashion as above to afford the desired product 310 (20 mg): 300 MHz $^1$H NMR (CDCl$_3$) δ(ppm) 8.49 (s, 1H), 8.07 (m, 2H), 7.60 (d, 2H), 7.23 (m, 2H), 7.04 (m, 2H), 6.88 (m, 2H), 5.29 (m, 2H), 4.26 (m, 2H), 4.10 (s, 2H), 3.81 (s, 3H), 3.77 (m, 2H), 3.33 (m, 2H), 3.00 (s, 3H); MS: 530 (M+1).

The compound was made in a similar fashion as above to afford the desired product 311 (9.9 mg, 47%—2 steps) as the free parent: 300 MHz $^1$H NMR (DMSO) δ(ppm) 8.83 (s, 1H), 8.44 (m, 1H), 8.32 (s, 1H), 7.34 (dd, 2H), 7.14 (dd, 2H), 4.78

(bs, 1H), 4.55 (s, 2H), 4.20 (s, 2H), 3.56 (m, 2H), 3.38 (m, 2H), 3.03 (s, 3H); 300 MHz $^{19}$F NMR (CDCl$_3$) δ(ppm) −117.20; MS: 410 (M+1).

Example 103

Synthesis of Compound 313

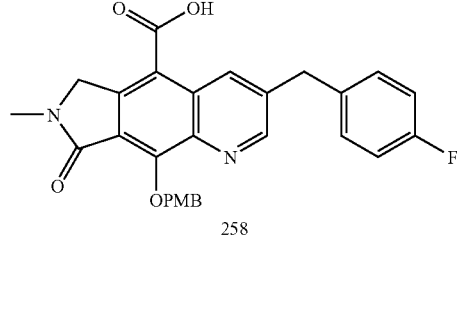

258

The compound was made in a similar fashion as above to afford the desired product 297 (26 mg, 91%): 300 MHz $^1$H NMR (CDCl$_3$) δ(ppm) 8.58 (s, 1H), 8.07 (m, 1H), 7.37 (d, 2H), 7.085 (m, 2H), 6.73 (d, 2H), 5.47 (s, 2H), 4.23 (m, 1H), 4.166 (s, 2H), 3.73 (s, 3H), 3.60 (s, 2H), 2.79 (m, 3H), 1.43 (s, 6H); MS: 558 (M+1).

The compound was made in a similar fashion as above to afford the desired product 313 (8.6 mg, 84% from 13 mg of 297) as the free parent: 300 MHz $^1$H NMR (CD$_3$OD) δ(ppm) 8.75 (s, 1H), 8.27 (s, 1H), 7.34 (dd, 2H), 7.07 (dd, 2H), 4.59 (s, 2H), 4.21 (s, 2H), 3.78 (s, 2H), 3.11 (s, 3H), 1.41 (s, 6H); 300 MHz $^{19}$F NMR (CDCl$_3$) δ(ppm) −119.122; MS: 438 (M+1).

Example 104

Synthesis of Compound 314

To a solution of 297 (8 mg, 0.0144 mmol) dissolved in methylene chloride (400 μL) was added SOCl$_2$ (2 μL, 0.0287 mmol). The reaction was stirred under nitrogen atmosphere at room temperature upon which the mixture was azeotroped with toluene/THF repeatedly. The crude residue was purified by reversed phase HPLC (with no buffers) to afford the oxazoline final product 314 (2.3 mg, 30%); 300 MHz $^1$H NMR (CDCl$_3$) δ(ppm) 9.28 (s, 1H), 8.82 (s, 1H), 7.22 (dd, 2H), 7.04 (dd, 2H), 4.72 (s, 2H), 4.22 (s, 2H), 4.08 (s, 2H), 3.21 (s, 3H), 1.39 (s, 6H); 300 MHz $^{19}$F NMR (CDCl$_3$) δ(ppm) −116.92; MS: 420 (M+1).

Example 105

Synthesis of Compound 316

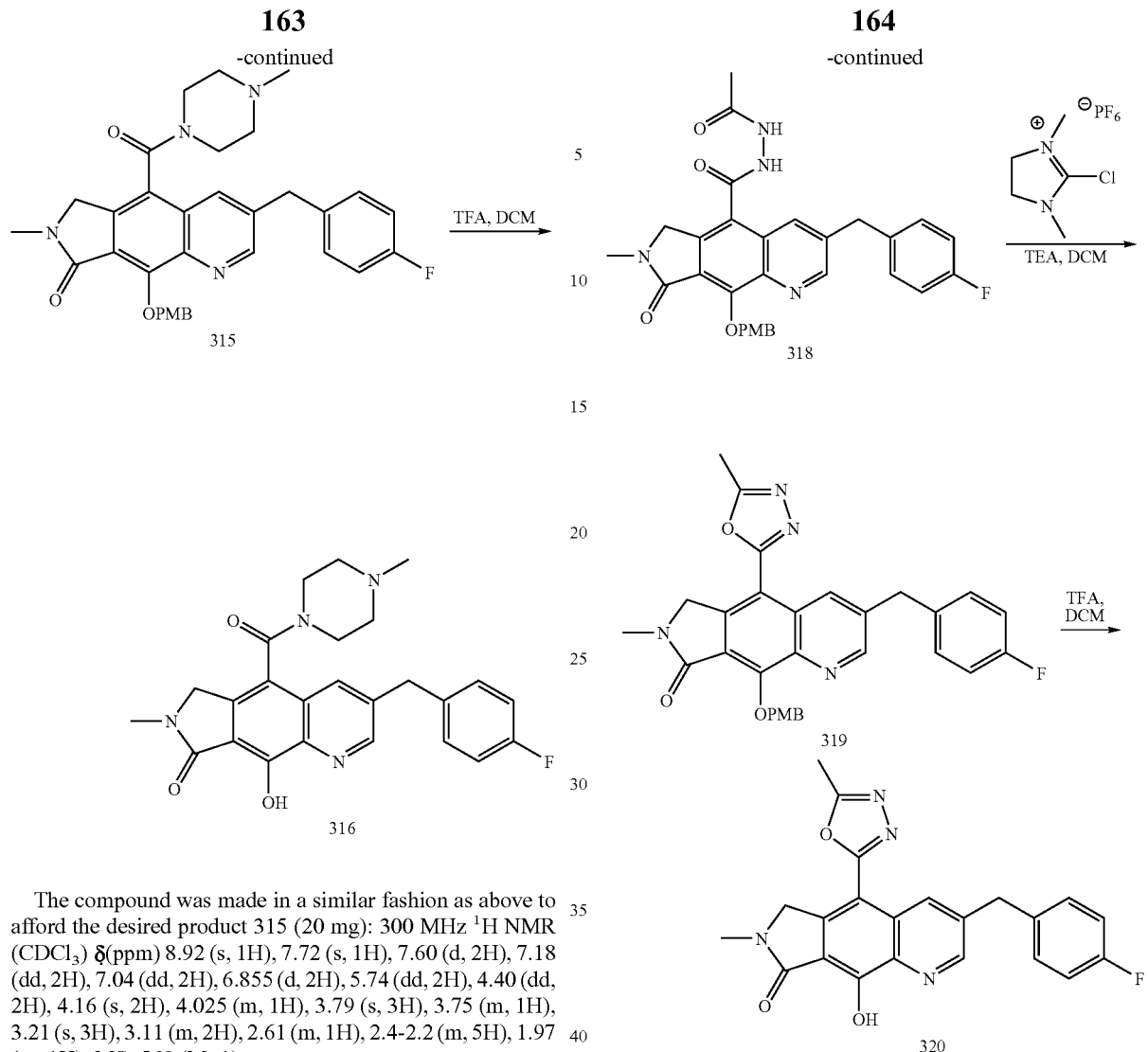

The compound was made in a similar fashion as above to afford the desired product 315 (20 mg): 300 MHz $^1$H NMR (CDCl$_3$) δ(ppm) 8.92 (s, 1H), 7.72 (s, 1H), 7.60 (d, 2H), 7.18 (dd, 2H), 7.04 (dd, 2H), 6.855 (d, 2H), 5.74 (dd, 2H), 4.40 (dd, 2H), 4.16 (s, 2H), 4.025 (m, 1H), 3.79 (s, 3H), 3.75 (m, 1H), 3.21 (s, 3H), 3.11 (m, 2H), 2.61 (m, 1H), 2.4-2.2 (m, 5H), 1.97 (m, 1H); MS: 569 (M+1).

The compound was made in a similar fashion as above to afford the desired product 316 (19 mg, 66%—2 steps) as the TFA salt: 300 MHz $^1$H NMR (CD$_3$OD) δ(ppm) 8.82 (s, 1H), 7.98 (d, 1H), 7.31 (dd, 2H), 7.09 (dd, 2H), 4.56 (s, 2H), 4.26 (s, 2H), 4.6-3.0 (m, 8H), 3.31 (s, 3H), 3.15 (s, 3H), 2.90 (s, 3H); 300 MHz $^{19}$F NMR (CDCl$_3$) δ(ppm) −77.47, −118.78; MS: 449 (M+1).

Example 106

Synthesis of Compound 320

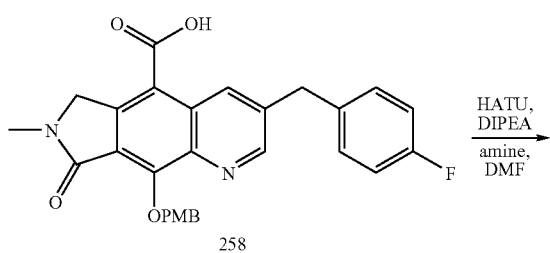

The compound was made in a similar fashion as above to afford the desired product 318 (23 mg): 300 MHz $^1$H NMR (CDCl$_3$) δ(ppm) 8.75 (s, 1H), 8.45 (s, 1H), 7.65 (m, 2H), 7.0 (m, 6H), 5.25 (m, 2H), 4.45 (m, 2H), 4.03 (s, 2H), 3.85 (s, 3H), 2.87 (m, 3H), 2.0 (s, 3H); MS: 543 (M+1).

To a solution of 318 (20 mg, 0.037 mmol) dissolved in methylene chloride (0.400 mL, 0.1M) was added 2-Chloro-1,3-dimethyl-2-imidazolinium hexafluorophosphate (15 mg, 0.055) and triethylamine (15 μL, 0.11 mmol). The reaction was stirred under nitrogen atmosphere for 1 day at room temperature then 2 days at 40° C. at which point the reaction was complete. The mixture was purified by chromatography on silica gel (9/1—ethyl acetate/hexane) to afford the desired 1,3,4-oxadiazole 319 (15 mg, 78%): 300 MHz $^1$H NMR (CDCl$_3$) δ(ppm) 9.09 (s, 1H), 8.93 (s, 1H), 7.575 (m, 2H), 7.23 (m, 2H), 7.04 (dd, 2H), 6.829 (d, 2H), 5.832 (s, 2H), 4.78 (s, 2H), 4.24 (s, 2H), 3.77 (s, 3H), 3.27 (s, 3H), 2.67 (s, 3H); MS: 525 (M+1).

The compound was made in a similar fashion as above then purified by reversed phase HPLC to afford the desired product 320 (6 mg, 33% from 15 mg of 319) as the TFA salt: 300 MHz $^1$H NMR (CD$_3$OD) δ(ppm) 9.28 (s, 1H), 8.80 (s, 1H), 7.32 (m, 2H), 7.06 (m, 2H), 4.8 (m, 2H), 4.20 (m, 2H), 3.19

(m, 3H), 2.69 (s, 3H); 300 MHz $^{19}$F NMR (CDCl$_3$) δ(ppm) −77.80, −118.928; MS: 405 (M+1).

Example 107

Synthesis of Compound 326

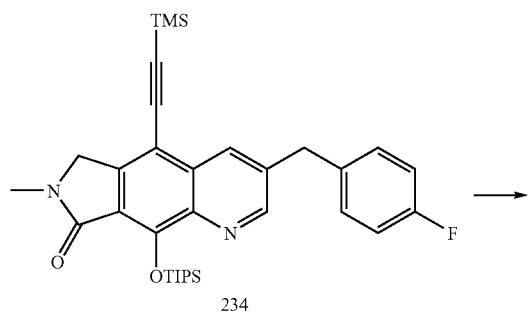
234

See *J. Org. Chem.*, 11, 56, 1991, 3549. Acetylene 234 (800 mg, 1.4 mmol, 1 equiv.) was stirred in THF (5 mL, 0.3 M) at 0° C. before freshly prepared dicyclohexylborane (10 mL, 8 equiv., see *Organic Synthesis. coll. vol.,* 10, 2004, p. 273. The reaction was allowed to stir overnight and when it was complete was stirred in 10% citric acid for 20 minutes along with ethyl acetate. The organic layer was washed with water, saturated NH$_4$Cl and brine. The solution was dried over sodium sulfate, filtered and concentrated in vacuo to yield acid 323. 300 MHz $^1$H NMR (DMSO$_6$) δ (ppm) 12.49 (bs, 1H), 8.79 (s, 1H), 8.35 (s, 1H), 7.41-7.30 (m, 2H), 7.16-7.01 (m, 2H), 4.47 (s, 2), 4.20 (s, 2H), 3.95 (s, 2H), 3.05 (s, 3H), 1.47-1.40 (m, 1H), 1.03 (d, J=7.5 Hz, 18H). 300 MHz $^{19}$F NMR (CDCl$_3$) δ (ppm) −117.24 MS: 537.28 (M+1).

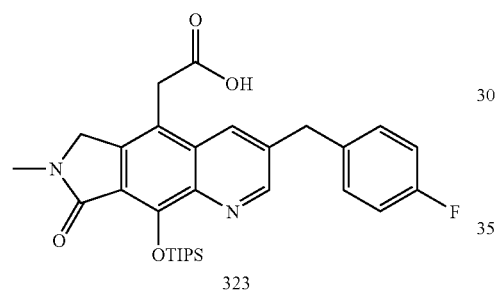
323

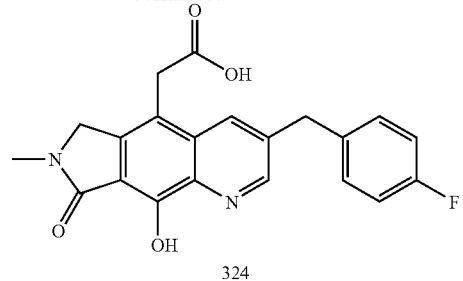
324

Compound 324 was made in a similar fashion as has been previously described for similar reactions. 300 MHz $^1$H NMR (DMSO-d$_6$) δ (ppm) 12.35 (bs, 1H), 8.80 (s, 1H), 8.36 (s, 1H), 7.20-7.19 (m, 2H), 7.09-7.04 (m, 2H), 4.49 (s, 2H), 4.21 (s, 2H), 3.93 (s, 2H), 3.05 (s, 3H). 300 MHz $^{19}$F NMR (CDCl$_3$) δ(ppm) −117.30. MS: 381.29 (M+1).

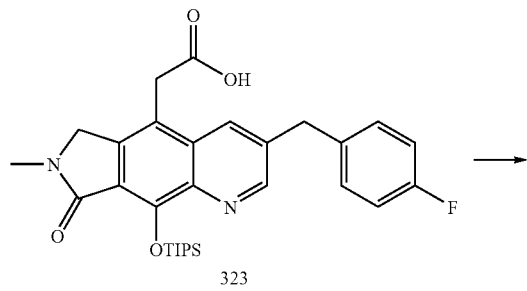
323

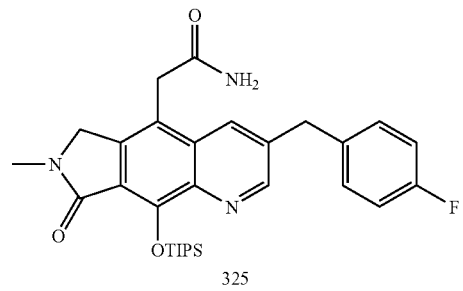
325

To acid 323 (150 mg, 0.3 mmol, 1 equiv.) was added DMF (3 mL, 0.1 M) followed by DIPEA (151 μL, 0.8 mmol, 3 equiv.) and HATU (160 mg, 0.4 mmol, 1.5 equiv.). After 5 minutes, NH$_3$ (2.8 mL, 1.4 mmol, 5 equiv., 0.5 M dioxane) was added. When the reaction was complete it was quenched with water and diluted with Ethyl Acetate. The organic layer was washed with water and brine before being dried over Na$_2$SO$_4$, filtered and concentrated in vacuo. The crude residue was purified by chromatography on silica gel (4/1—Ethyl acetate/MeOH) to afford a yellow solid am as the desired product 325. 300 MHz $^1$H NMR (DMSOd$_6$) δ (ppm) 8.77 (s, 1H), 8.44 (s, 1H), 7.60 (bs, 1H), 7.32-7.28 (m, 2H), 7.09-7.04 (m, 2H), 7.05 (bs, 1H), 4.50 (s, 2H), 4.20 (s, 2H), 3.78 (s, 2H), 3.06 (s, 3H), 1.53-1.48 (m, 1H), 1.14 (d, J=7.5 Hz, 9 Hz). 300 MHz $^{19}$F NMR (CDCl$_3$) δ (ppm): −117.26. MS: 536.18 (M+1).

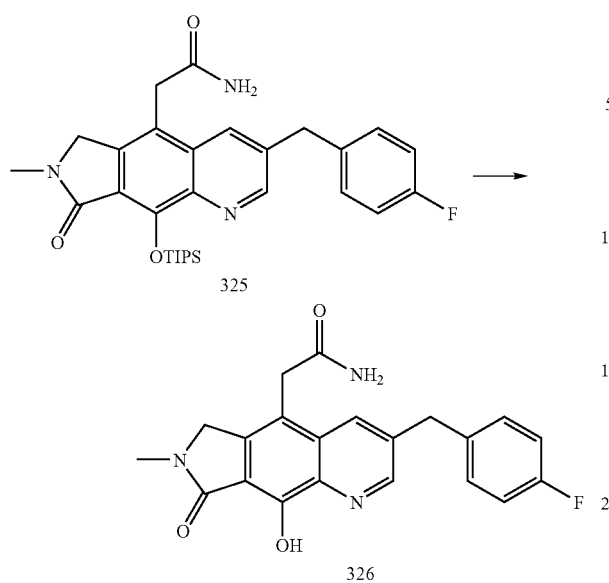

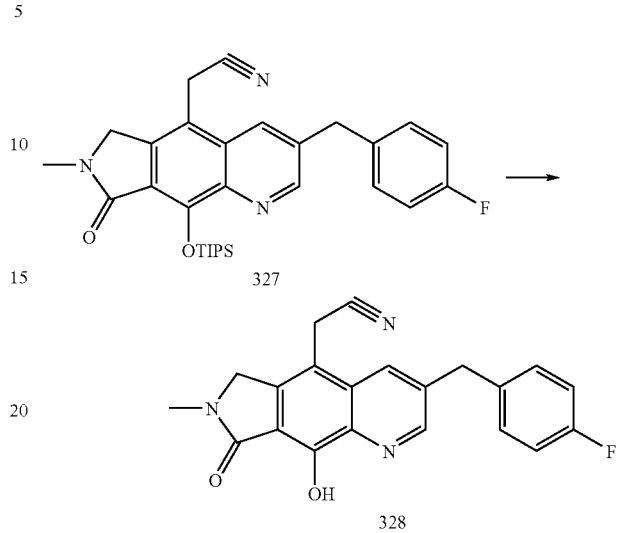

Compound 326 was made in a similar fashion as has been previously described for similar reactions. 300 MHz $^1$H NMR (CDCl$_3$) δ (ppm) 8.78 (s, 1H), 8.44 (s, 1H), 7.54 (bs, 1H), 7.32-7.28 (m, 2H), 7.09-7.04 (m, 2H), 7.03 (bs, 1H), 4.52 (s, 2H), 4.20 (s, 2H), 3.75 (s, 2H), 3.05 (s, 3H). 300 MHz $^{19}$F NMR (CDCl$_3$) δ (ppm): −74.17, −117.26 (TFA salt). MS: 536.18 (M+1).

Example 107

Synthesis of Compound 328 purified by chromatography on silica gel (3/2—Ethyl acetate/Hexanes) to afford a yellow solid am as the desired product 327.

MS: 518.15 (M+1).

Compound 328 was made in a similar fashion as has been previously described for similar reactions. 300 MHz $^1$H NMR (DMSO-d$_6$) δ (ppm) 8.86 (s, 1H), 8.53 (s, 1H), 7.20-7.19 (m, 2H), 7.09-7.04 (m, 2H), 4.58 (s, 1H), 4.31 (s, 2H), 4.24 (s, 2H), 3.06 (s, 3H). 300 MHz $^{19}$F NMR (CDCl$_3$) δ (ppm): −75.00, −117.21 (TFA salt). MS: 362.12 (M+1).

Example 108

Synthesis of Compound 330

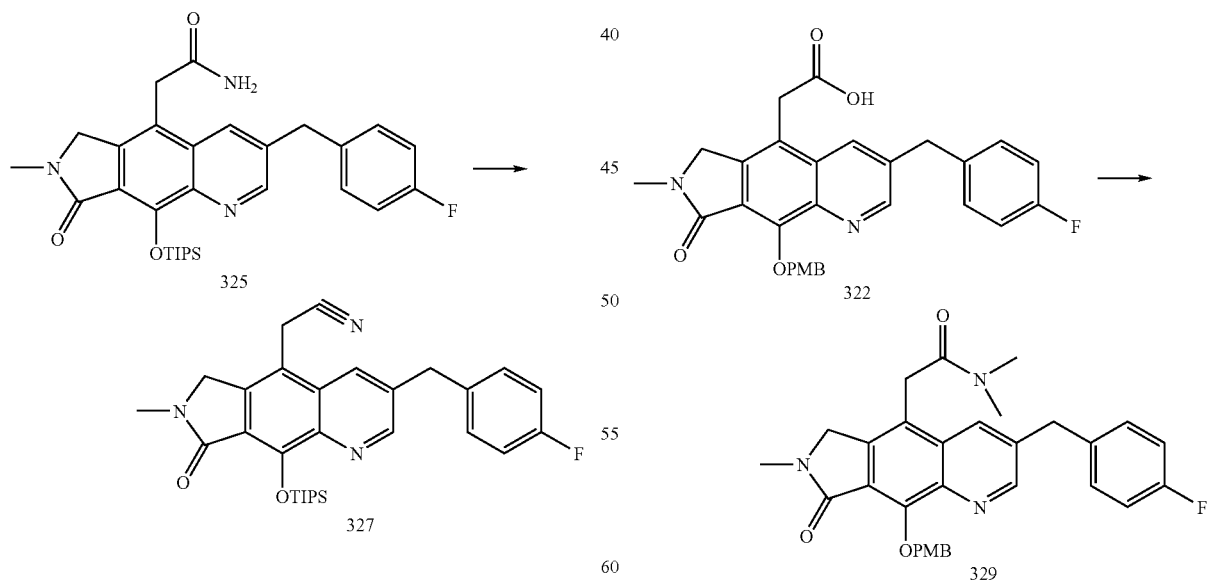

To amide 325 (50 mg, 0.09 mmol, 1 equiv.) was added pyridine (1 mL, 0.1 M) followed by methanesulfonyl chloride (30 μl, 0.38 mmol, 4 equiv.). The reaction was allowed to stir overnight and when it was complete it was quenched with water and diluted with Ethyl Acetate. The organic layer was washed with water and brine before being dried over Na$_2$SO$_4$, filtered and concentrated in vacuo. The crude residue was To acid 322 (30 mg, 0.06 mmol, 1 equiv.) was added DMF (1 mL, 0.05 M) followed by DIPEA (30 μl, 0.18 mmol, 3 equiv.) and HATU (35 mg, 0.08 mmol, 1.5 equiv.). After 5 minutes, NHMe$_2$ (90 μL, 0.2 mmol, 3 equiv., 2 M in THF) was added. When the reaction was complete it was quenched with water and diluted with Ethyl Acetate. The organic layer was washed with water and brine before being dried over Na₂SO₄, filtered and concentrated in vacuo. The crude residue was purified by chromatography on silica gel (4/1—Ethyl acetate/MeOH) to afford a white foam as the desired product 329 (210 mg, 69% yield). 300 MHz $^1$H NMR (CDCl₃) δ (ppm) 8.83 (s, 1H), 7.77-7.63 (m, 2H), 7.27-7.15 (m, 2H), 7.03-7.01 (m, 2H), 6.97-6.86 (m, 2H). 5.49 (s, 2H), 4.40 (s, 2H), 4.17 (s, 2H), 3.86 (s, 2H), 3.79 (s, 3H), 3.20 (s, 3H), 3.09 (s, 3H), 2.96 (s, 3H). 300 MHz $^{19}$F NMR (CDCl₃) δ(ppm) −116.76. MS: 528.09 (M+1).

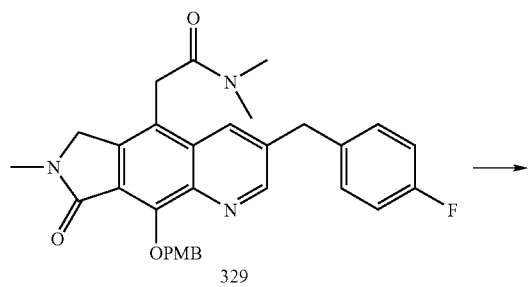
329

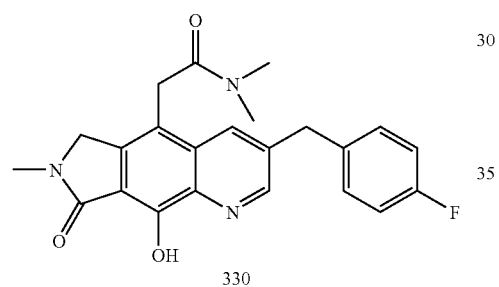
330

Compound 330 was made in a similar fashion as has been previously described for similar reactions. 300 MHz $^1$H NMR (CD₃OD) δ (ppm) 8.77 (s, 1H), 8.18 (s, 1H), 7.14-7.08 (m, 2H) 7.09-7.04 (m, 2H), 4.40 (s, 2H), 4.26 (s, 2H), 4.07 (s, 2H), 3.28 (s, 3H), 3.17 (s, 3H), 2.95 (s, 3H). 300 MHz $^{19}$F NMR (CDCl₃) δ(ppm) −77.71, −118.89. MS: 408.22 (M+1).

Example 109

Synthesis of Compound 332

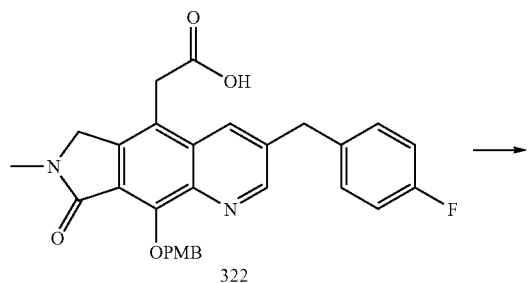
322

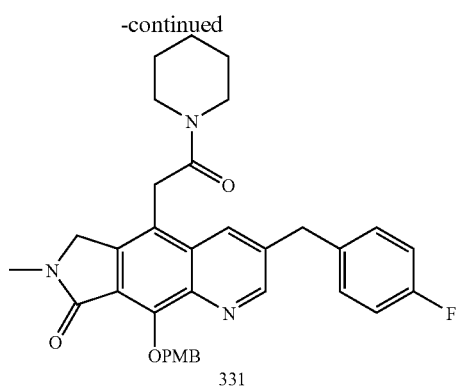
331

To acid 322 (45 mg, 0.09 mmol, 1 equiv.) was added DMF (2 mL, 0.05 M) followed by DIPEA (50 μL, 0.26 mmol, 3 equiv.) and HATU (51 mg, 0.13 mmol, 1.5 equiv.). After 5 minutes, peperidine (30 μL, 0.3 mmol, 3 equiv.) was added. When the reaction was complete it was quenched with water and diluted with Ethyl Acetate. The organic layer was washed with water and brine before being dried over Na₂SO₄, filtered and concentrated in vacuo. The crude residue was purified by chromatography on silica gel (4/1—Ethyl acetate/MeOH) to afford a yellow solid am as the desired product 331. 300 MHz $^1$H NMR (CDCl₃) δ (ppm) 8.83 (s, 1H), 7.83 (s, 1H), 7.77-7.63 (m, 2H), 7.27-7.15 (m, 2H), 7.03-7.01 (m, 2H), 6.97-6.86 (m, 2H). 5.56 (s, 2H), 4.39 (s, 2H), 4.16 (s, 2H), 3.84 (s, 2H), 3.79 (s, 3H), 3.55-3.50 (m, 2H), 3.50-4.35 (s, 2H), 3.18 (s, 3H), 1.65-1.55 (m, 4H), 1.50-1.45 (m, 2H). 300 MHz $^{19}$F NMR (CDCl₃) δ(ppm) −116.74. MS: 567.32 (M+1).

331

332

Compound 332 was made in a similar fashion as has been previously described for similar reactions. 300 MHz $^1$H NMR (CD₃OD) δ (ppm) 8.83 (s, 1H), 8.26 s, 1H), 7.35-7.30 (m, 2H) 7.09-7.04 (m, 2H), 4.52 (s, 2H), 4.30 (s, 2H), 4.10 (s, 2H), 3.66 (t, J=3.4 Hz, 1H), 3.51 (t, J=3.4 Hz, 1H), 3.17 (s, 3H), 1.75-1.68 (m, 2H), 1.67-1.60 (m, 2H), 1.54-1.48 (m, 2H). 300 MHz $^{19}$F NMR (CDCl$_3$) δ(ppm) −77.79, −118.60 (TFA salt). MS: 448.28 (M+1).

Example 110

Synthesis of Compound 336

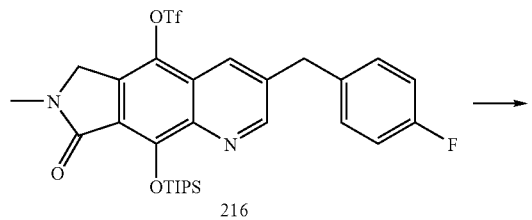
216

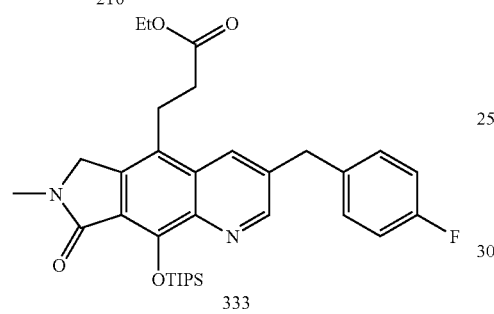
333

Into a microwave vial was added triflate 216 (55 mg, 0.09 mmol, 1 equiv.) in DMF (2 mL, 0.05 M) followed by LiCl (11 mg, 0.27 mmol, 3 equiv.) and P(o-tol)$_3$ (3 mg, 0.009 mmol, 0.1 equiv.) and PdCl$_2$(PPh$_3$)$_2$ (6 mg, 0.009 mmol, 0.1 equiv.) before 3-Ethoxy-3-oxopropylzinc bromide (260 μL, 0.13 mmol, 1.5 equiv.) was added. The vial was then placed into a microwave for 10 min at 120° C. After completion, the reaction was cooled and diluted with ethyl acetate and water. The organic layer was washed with water and brine before being dried over Na$_2$SO$_4$, filtered and concentrated in vacuo. A ISCO flash column chromatography was carried out with 2/3 EtOAc/Hexanes to yield 333 as a brown solid. 300 MHz $^1$H NMR (CDCl$_3$) δ (ppm) 8.69 (s, 1H), 7.95 (s, 1H), 7.32-7.28 (m, 2H), 7.09-7.04 (m, 2H), 4.44 (s, 2H), 4.19 (s, 2H), 4.09 (q, J=7.5 Hz, 2H), 3.20 (s, 3H), 2.57-2.50 (m, 4H), 1.53-1.48 (m, 1H), 1.25-1.17 (t, J=7.5 Hz, 3H), 1.14 (d, J=7.5 Hz, 9 Hz).

300 MHz $^{19}$F NMR (CDCl$_3$) δ (ppm): −116.78. MS: 579.2.7 (M+1).

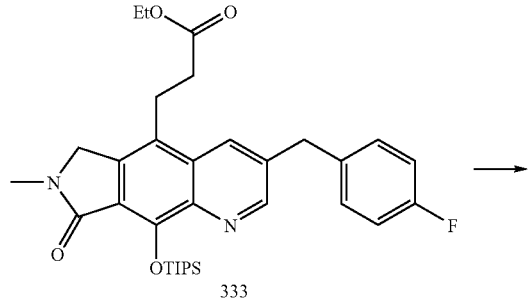
333

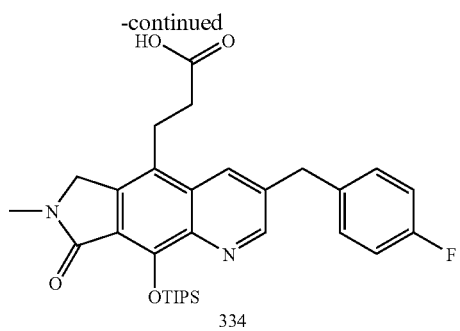
334

To a flask containing ester 333 (55 mg, 0.07 mmol, 1 equiv.) was added THF (10 mL, 0.05 M). A solution of LiOH (8 mg, 0.2 mmol, 2 equiv.) dissolved in H$_2$O (2 mL) was added and allowed to stir until reaction was complete. The reaction was diluted with EtOAc and the organic layer was washed with water and brine before being dried over Na$_2$SO$_4$, filtered and concentrated in vacuo and used as is. A light yellow solid was obtained of acid 334. 300 MHz $^1$H NMR (CDCl$_3$) δ (ppm) (partial) 4.42 (s, 2H), 4.16 (s, 2H), 3.15 (s, 3H), 2.63-2.55 (m, 2H), 2.53-2.40 (m, 2H), 1.53-1.48 (m, 1H), 1.25-1.17 (t, J=7.5 Hz, 3H). 300 MHz $^{19}$F NMR (CDCl$_3$) δ(ppm) −116.74. MS: 551.2 (M+1).

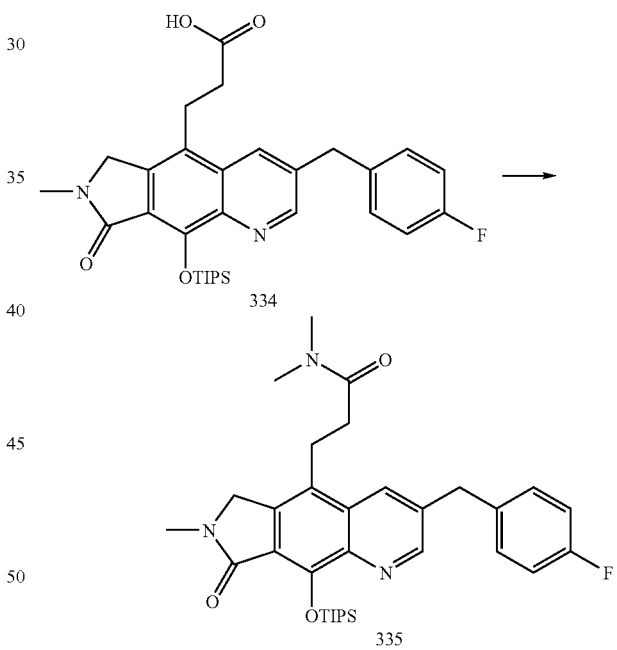
334

335

To acid 334 (25 mg, 0.05 mmol, 1 equiv.) was added DMF (1 mL, 0.05 M) followed by DIPEA (25 μl, 0.18 mmol, 3 equiv.) and HATU (25 mg, 0.07 mmol, 1.5 equiv.). After 5 minutes, NHMe$_2$ (90 μL, 0.2 mmol, 3 equiv., 2 M in THF) was added. When the reaction was complete it was quenched with water and diluted with Ethyl Acetate. The organic layer was washed with water and brine before being dried over Na$_2$SO$_4$, filtered and concentrated in vacuo. The crude residue was purified by chromatography on silica gel (9/1—Ethyl acetate/MeOH) to afford a white foam as the desired product 335 (15 mg, 60% yield). 300 MHz $^1$H NMR (CDCl$_3$) δ (ppm) 8.70 (s, 1H), 7.98 (s, 1H), 7.32-7.28 (m, 2H), 7.09-7.04 (m, 2H), 4.43 (s, 2H), 4.18 (s, 2H), 3.25 (t, J=8.1 Hz, 2H), 3.20 (s, 3H), 2.92

(s, 3H), 2.74 (s, 3H), 2.58 (t, J=8.1 Hz, 2H), 1.57-1.46 (m, 1H), 1.14 (d, J=7.5 Hz, 9 Hz).

300 MHz $^{19}$F NMR (CDCl$_3$) δ (ppm): −116.76. MS: 578.20 (M+1).

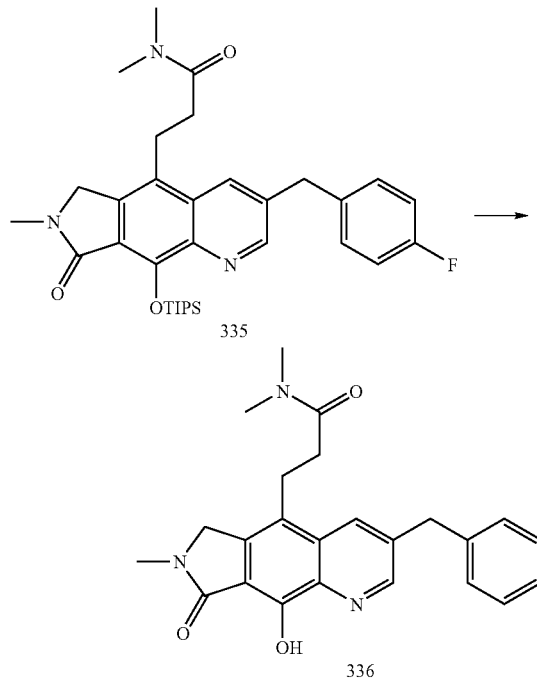

335

336

Compound 336 was made in a similar fashion as has been previously described for similar reactions. 300 MHz $^1$H NMR (CD$_3$OD) δ (ppm) 8.79 (s, 1H), 8.49 (s, 1H), 7.32-7.28 (m, 2H), 7.09-7.04 (m, 2H), 4.62 (s, 2H), 3.25-3.15 (m, 2H), 3.18 (s, 3H), 2.87 (s, 3H), 2.84 (s, 3H), 2.68-2.60 (m, 2H).

300 MHz $^{19}$F NMR (CDCl$_3$) δ (ppm): −77.73, −116.76 (TFA salt).

MS: 422.27 (M+1).

Example 111

Synthesis of Compound 461

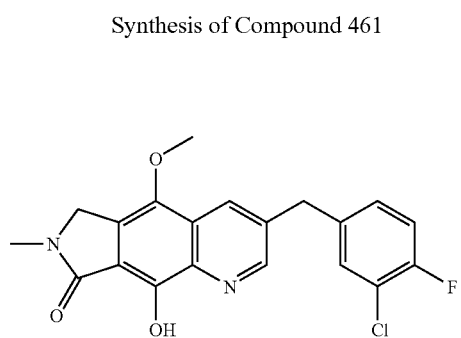

461

Beginning from the free-8-phenol C5-methyl ether (Example 71, compound 5), the standard sequence to carry out protection, lactam methylation, and deprotection to render the final product. After HPLC purification, 5 mg of the final product was isolated as the trifluoroacetate salt. 300 MHz $^1$H NMR (CDCl$_3$) shows diagnostic peaks at δ 8.85 (s, 1H), 8.34 (s, 1H), 7.21 (m, 1H), 7.08 (m, 2H), 4.64 (s, 2H), 4.18 (s, 2H), 3.97 (s, 3H), 3.18 (s, 3H). MS: 387.1 (M+H).

Example 112

Synthesis of Compound 339

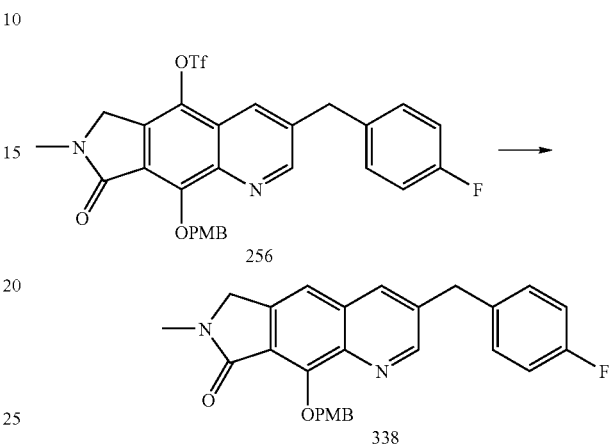

256

338

Into a microwave vial was added triflate 256 (75 mg, 0.13 mmol, 1 equiv.) was added DMSO (2 mL, 0.05 M) followed by TEA (51 μL, 0.24 mmol, 2 equiv.), formic acid (6 μL, 0.13 mmol, 1 equiv.) and PdCl$_2$(PPh$_3$)$_2$ (9 mg, 0.012 mmol, 0.1 equiv.). The vial was then placed in a microwave for 10 min at 130° C. After completion, the reaction was cooled and diluted with ethyl acetate and water. The organic layer was washed with water and brine before being dried over Na$_2$SO$_4$, filtered and concentrated in vacuo. A ISCO flash column chromatography was carried out with 2/3 EtOAc/Hexanes to yield 338 as a brown solid (48 mg, 88% yield). 300 MHz $^1$H NMR (CDCl$_3$) δ (ppm) 8.86 (s, 1H), 7.80 (s, 1H), 7.64 (d, J=8.7 Hz, 2H), 7.41 (s, 1H), 7.22-7.15 (m, 2H), 7.09-7.04 (m, 2H), 6.86 (d, J=8.4 Hz, 2H), 5.69 (s, 2H), 4.45 (s, 2H), 4.15 (s, 2H), 3.78 (s, 3H), 3.21 (s, 3H).

300 MHz $^{19}$F NMR (CDCl$_3$) δ (ppm): −115.83

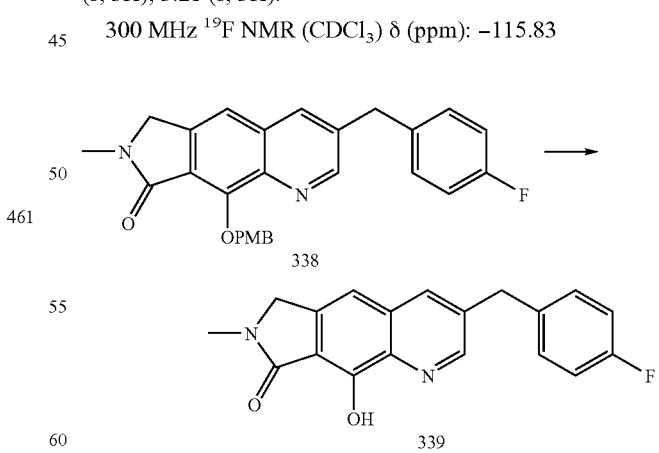

338

339

Compound 339 was made in a similar fashion as has been previously described for similar reactions. 300 MHz $^1$H NMR (CDCl$_3$) δ (ppm) 8.83 (s, 1H), 8.26 (s, 1H), 7.35-7.30 (m, 2H)

7.09-7.04 (m, 2H), 4.52 (s, 2H), 4.20 (s, 2H), 3.17 (s, 3H). 300 MHz $^{19}$F NMR (CDCl$_3$) δ(ppm) −76.12, −116.44 (TFA salt). MS: 579.13 (M+1).

Example 113

Synthesis of Compound 344

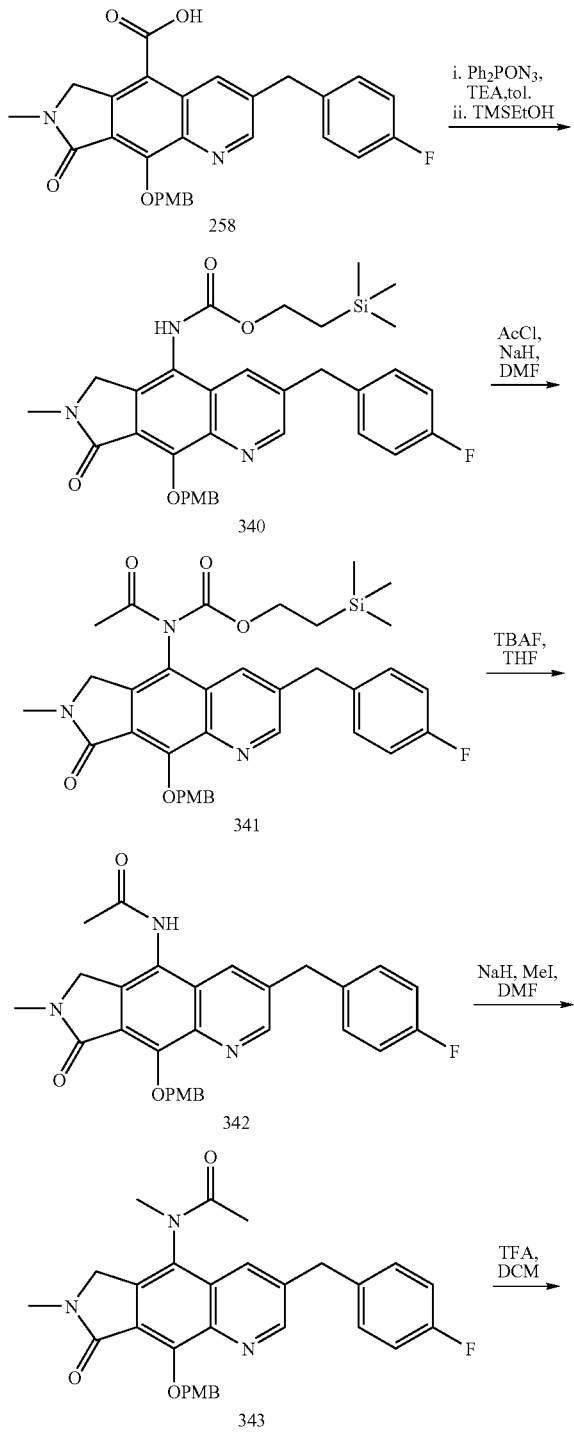

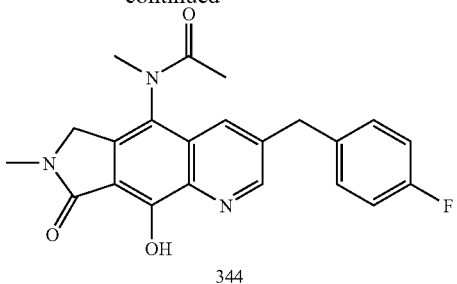

344

To a solution of carboxylic acid 258 (330 mg, 0.677 mmol) suspended in anhydrous toluene (3.4 mL) was added TEA (0.19 mL, 1.36 mmol) and Diphenylphosphorylazide (0.165 mL, 0.745 mmol). The reaction mixture was stirred at room temperature for 45 minutes under nitrogen atmosphere, upon which Trimethylsilylethanol (1.7 mL) was then added and the reaction was heated to 65° C. After stirring for 15 hours at 60° C. (2 portions of 0.05 mL of Diphenylphosphorylazide and TEA were added to the reaction during the course to speed it along to completion), the reaction was cooled to room temperature and concentrated in vacuo. The residue was then azeotroped with toluene repeatedly in order to remove trimethylsilylethanol. The resulting residue was diluted with ethyl acetate and washed once with saturated NH$_4$Cl, twice with water, and once with brine. The organic layer was then dried (over Na$_2$SO$_4$), filtered and concentrated in vacuo. The crude residue was purified by chromatography on silica gel (1/3—hexane/ethyl acetate) to afford the desired carbamate 340 (297 mg, 72%): 300 MHz $^1$H NMR (CDCl$_3$) δ(ppm) 8.78 (s, 1H), 8.02 (s, 1H), 7.63 (d, 2H), 7.18 (dd, 2H), 7.02 (dd, 2H), 6.855 (d, 2H), 5.62 (s, 2H), 4.43 (s, 2H), 4.26 (m, 2H), 4.122 (s, 2H), 3.79 (s, 3H), 3.19 (s, 3H), 1.05 (m, 2H); 0.078 (s, 9H); MS: 602 (M+1).

To a solution of carbamate 340 (80 mg, 0.133 mmol) dissolved in DMF (1.33 ml) and cooled in an ice bath to 0° C. was added sodium hydride (8 mg, 0.2 mmol, 60% mineral oil) and stirred for 5 minutes under nitrogen atmosphere. Acetyl chloride (14.3 μL, 0.2 mmol) was added and the reaction was allowed to stir for 2 hours. The reaction was diluted with ethyl acetate and quenched with H$_2$O/sat NH$_4$Cl. The organic layer was washed with aqueous LiCl (twice) and brine, then dried (over Na$_2$SO$_4$), filtered and concentrated in vacuo. No further purification was carried out to afford the desired product 341 (81 mg, 95% yield); MS: 644 (M+1).

To a solution of 341 (81 mg, 0.133 mmol) dissolved in THF (1.33 mL) cooled in an ice bath to 0° C. was added tetrabutylammonium fluoride hydrate (76.5 mg, 0.293 mmol). The reaction was allowed to stir under nitrogen atmosphere at 0° C. while warming up to room temperature overnight. The reaction mixture was diluted with ethyl acetate then quenched with saturated NH$_4$Cl. The organic layer was washed with brine (twice) then dried (over Na$_2$SO$_4$), filtered and concentrated in vacuo. The crude residue was purified by chromatography on silica gel (0-10%—methanol/ethyl acetate) to afford the desired product 342 (60 mg, 90%—2 steps) as a solid: 300 MHz $^1$H NMR (CDCl$_3$) δ(ppm) 8.56 (s, 1H), 7.96 (s, 1H), 7.68 (d, 2H), 7.21 (dd, 2H), 7.05 (dd, 2H), 6.895 (d, 2H), 5.47 (s, 2H), 4.29 (s, 2H), 4.012 (bs, 2H), 3.81 (s, 3H), 3.11 (s, 3H), 2.11 (s, 3H); MS: 500 (M+1).

To a solution of aniline 342 (30 mg, 0.06 mmol) dissolved in DMF (0.600 ml) and cooled in an ice bath to 0° C. was added sodium hydride (3 mg, 0.072 mmol, 60% mineral oil) and stirred for 5 minutes under nitrogen atmosphere. Iodomethane (5 µL, 0.075 mmol) was added and the reaction was allowed to stir for 30 minutes. The reaction was diluted with ethyl acetate and quenched with sat NH$_4$Cl. The organic layer was washed with aqueous LiCl (twice) and brine, then dried (over Na$_2$SO$_4$), filtered and concentrated in vacuo. The crude residue was purified by chromatography on silica gel (0-10%—methanol/ethyl acetate) to afford the desired product 343 (15.8 mg, 51%) as a solid: 300 MHz $^1$H NMR (CDCl$_3$) δ(ppm) 8.91 (s, 1H), 7.82 (s, 1H), 7.62 (d, 2H), 7.17 (dd, 2H), 7.02 (dd, 2H), 6.86 (d, 2H), 5.76 (s, 2H), 4.38 (dd, 2H), 4.19 (s, 2H), 3.79 (s, 3H), 3.28 (s, 3H), 3.24 (s, 3H), 1.71 (s, 3H); MS: 514 (M+1).

The compound was made in a similar fashion as above then purified by reversed phase HPLC to afford the desired product 344 (8.6 mg, 55% from 15.8 mg of 343) as the TFA salt: 300 MHz $^1$H NMR (CDCl$_3$) δ(ppm) 8.94 (s, 1H), 7.92 (s, 1H), 7.18 (m, 2H), 7.03 (m, 2H), 4.46 (dd, 2H), 4.23 (m, 2H), 3.29 (s, 3H), 3.24 (s, 3H), 1.77 (s, 3H); 300 MHz $^{19}$F NMR (CDCl$_3$) δ(ppm) −76.42, −115.84; MS: 394 (M+1).

Example 114

Synthesis of Compound 351

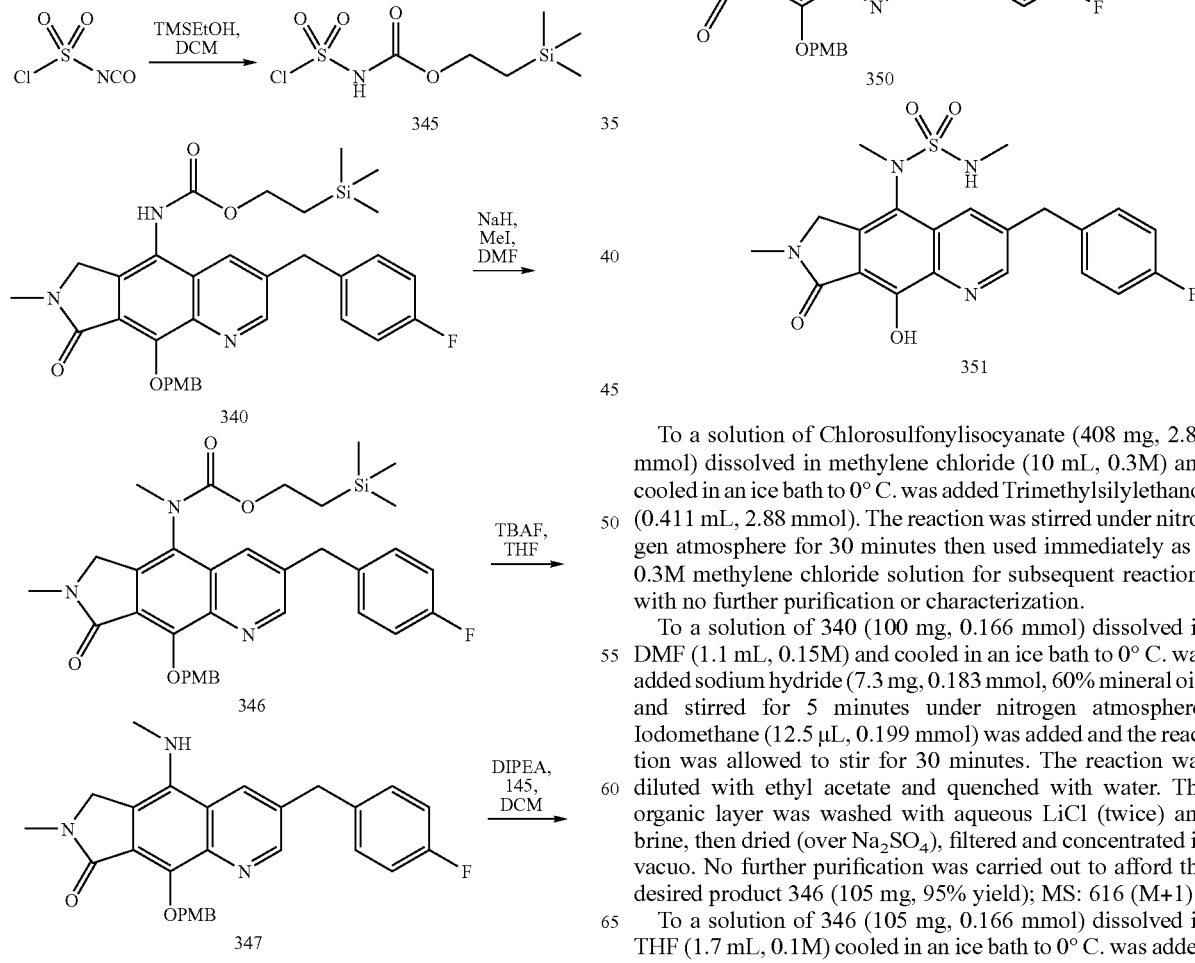

To a solution of Chlorosulfonylisocyanate (408 mg, 2.88 mmol) dissolved in methylene chloride (10 mL, 0.3M) and cooled in an ice bath to 0° C. was added Trimethylsilylethanol (0.411 mL, 2.88 mmol). The reaction was stirred under nitrogen atmosphere for 30 minutes then used immediately as a 0.3M methylene chloride solution for subsequent reactions with no further purification or characterization.

To a solution of 340 (100 mg, 0.166 mmol) dissolved in DMF (1.1 mL, 0.15M) and cooled in an ice bath to 0° C. was added sodium hydride (7.3 mg, 0.183 mmol, 60% mineral oil) and stirred for 5 minutes under nitrogen atmosphere. Iodomethane (12.5 µL, 0.199 mmol) was added and the reaction was allowed to stir for 30 minutes. The reaction was diluted with ethyl acetate and quenched with water. The organic layer was washed with aqueous LiCl (twice) and brine, then dried (over Na$_2$SO$_4$), filtered and concentrated in vacuo. No further purification was carried out to afford the desired product 346 (105 mg, 95% yield); MS: 616 (M+1).

To a solution of 346 (105 mg, 0.166 mmol) dissolved in THF (1.7 mL, 0.1M) cooled in an ice bath to 0° C. was added tetrabutylammonium fluoride hydrate (130 mg, 0.5 mmol).

The reaction was allowed to stir under nitrogen atmosphere at 0° C. while warming up to room temperature for 1.5 hours. The reaction mixture was diluted with ethyl acetate then quenched with saturated NH$_4$Cl. The organic layer was washed with water and brine, then dried (over Na$_2$SO$_4$), filtered and concentrated in vacuo. The crude residue was purified by chromatography on silica gel (1/9—hexane/ethyl acetate) to afford the desired product 347 (55 mg, 71%—2 steps) as a solid: 300 MHz $^1$H NMR (CDCl$_3$) δ(ppm) 8.70 (s, 1H), 8.26 (s, 1H), 7.64 (d, 2H), 7.19 (dd, 2H), 7.03 (dd, 2H), 6.82 (d, 2H), 5.39 (s, 2H), 4.64 (s, 2H), 4.06 (s, 2H), 3.76 (s, 3H), 3.24 (s, 3H), 3.07 (s, 3H); MS: 472 (M+1).

To a solution of aniline 347 (52 mg, 0.11 mmol) dissolved in methylene chloride (1.1 mL, 0.1M) was added diisopropylethylamine (0.100 mL, 0.55 mmol) and sulfamoyl chloride 345 (0.5 mL, 0.55 mm, freshly prepared 0.3M DCM solution). The reaction was stirred under nitrogen atmosphere at room temperature for 1 hour. The reaction mixture was diluted with ethyl acetate then quenched with saturated NH$_4$Cl. The organic layer was washed with brine (twice), then dried (over Na$_2$SO$_4$), filtered and concentrated in vacuo. No further purification or characterization was carried out to afford the desired product 348 (83 mg, >100% yield); MS: 695 (M+1).

To a solution of sulfonyl urea 348 (83 mg crude, ~0.11 mmol) dissolved in acetonitrile (2 ml) was added diisopropylethylamine (60 μL, 0.33 mmol) then Iodomethane (27.5 μL, 0.44 mmol) and the reaction was allowed to stir for 2 hours. At which point, the reaction had progressed to 50% conversion, so similar equivalents of MeI and DIPEA were added to coax the reaction to completion in 2 more hours. The reaction was diluted with ethyl acetate and quenched with sat NH$_4$Cl. The organic layer was washed with water, and brine, then dried (over Na$_2$SO$_4$), filtered and concentrated in vacuo. No further purification or characterization was carried out to afford the desired product 349 (85 mg, >100% yield); MS: 709 (M+1).

To a solution of 349 (85 mg crude, ~0.11 mmol) dissolved in THF (1.1 mL, 0.1M) was added tetrabutylammonium fluoride hydrate (87 mg, 0.33 mmol). The reaction was allowed to stir under nitrogen atmosphere to room temperature overnight. The reaction mixture was diluted with ethyl acetate then quenched with saturated NH$_4$Cl. The organic layer was washed with water and brine, then dried (over Na$_2$SO$_4$), filtered and concentrated in vacuo. The crude residue was purified by chromatography on silica gel (1/9—hexane/ethyl acetate) to afford the desired product 350 (50 mg, 80%—3 steps) as a solid: 300 MHz $^1$H NMR (CDCl$_3$) δ(ppm) 8.82 (s, 1H), 8.05 (s, 1H), 7.66 (m, 2H), 7.22 (m, 2H), 7.04 (m, 2H), 6.88 (m, 2H), 5.63 (s, 2H), 4.64 (dd, 2H), 4.14 (s, 2H), 3.80 (s, 3H), 3.205 (2 singlets coaleced, 6H), 2.60 (s, 3H); MS: 565 (M+1).

The compound was made in a similar fashion as above then purified by reversed phase HPLC (no buffers) to afford the desired product 351 (8 mg, 68% from 15 mg of 350) as the free parent: 300 MHz $^1$H NMR (CDCl$_3$) δ(ppm) 8.80 (s, 1H), 8.08 (s, 1H), 7.21 (dd, 2H), 7.04 (dd, 2H), 4.66 (dd, 2H), 4.197 (s, 2H), 3.19 (2 singlets coaleced, 6H), 2.64 (s, 3H); 300 MHz $^{19}$F NMR (CDCl$_3$) δ(ppm) −116.26; MS: 445 (M+1).

Example 115

Synthesis of Compound 353

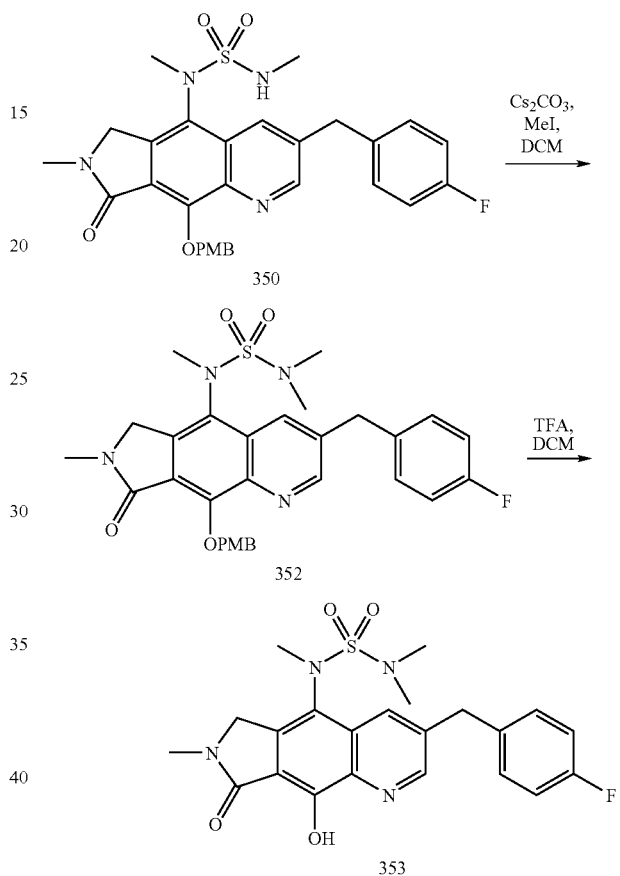

To a solution of sulfonyl urea 350 (35 mg, 0.062 mmol) dissolved in DMF (0.62 mL) was added Cesium carbonate (61 mg, 0.186 mmol) and allowed to stir for 2 minutes. Iodomethane (12 μL, 0.186 mmol) was added and the reaction was allowed to stir for 1 hour. The reaction was diluted with ethyl acetate and quenched with sat NH$_4$Cl. The organic layer was washed with aqueous LiCl, and brine, then dried (over Na$_2$SO$_4$), filtered and concentrated in vacuo. The crude residue was purified by chromatography on silica gel (3/7—hexane/ethyl acetate) to afford the desired product 352 (36 mg, quant) as a solid: 300 MHz $^1$H NMR (CDCl$_3$) δ(ppm) 8.95 (s, 1H), 8.12 (s, 1H), 7.65 (m, 2H), 7.25 (m, 2H), 7.06 (m, 2H), 6.88 (m, 2H), 5.72 (dd, 2H), 4.65 (dd, 2H), 4.23 (s, 2H), 3.79 (s, 3H), 3.23 (2s, 3H), 3.137 (s, 3H), 2.81 (s, 6H); MS: 579 (M+1).

The compound was made in a similar fashion as before then purified by reversed phase HPLC (no buffers) to afford the desired product 353 (25 mg, 88% from 36 mg of 352) as the free parent: 300 MHz $^1$H NMR (CDCl$_3$) δ(ppm) 8.86 (s, 1H), 8.07 (s, 1H), 7.22 (dd, 2H), 7.05 (dd, 2H), 4.68 (dd, 2H), 4.23 (s, 2H), 3.20 (2s, 3H), 2.12 (s, 3H), 2.78 (s, 6H); 300 MHz $^{19}$F NMR (CDCl$_3$) δ(ppm) −116.32; MS: 459 (M+1).

Example 116

Synthesis of Compound 354

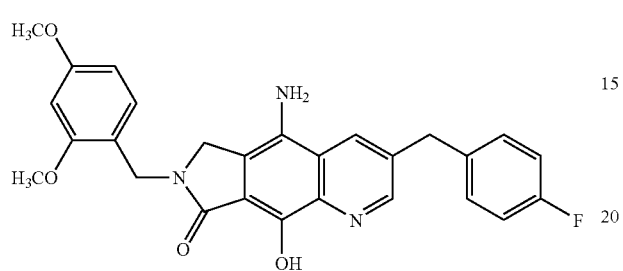

354

LiBH$_4$ reduction of compound 103 (Example 41, 500 mg) in THF/MeOH gave 330 mg of the intermediate aminal as the main product. Further reduction of the aminal with excess triethylsilane in TFA/DCM resulted in lactam 354. HPLC purification of this product resulted in isolation of 6 mg of the major reduction regioisomer. $^1$H NMR (300 MHz, CD$_3$OD) shows diagnostic peaks at δ (ppm): 8.80 (s, 1H), 7.95 (s, 1H) 4.35 (s, 2H) 4.25 (s, 2H), 3.90 (s, 3H) and 3.80 (s, 3H). MS=474.2 (M+H).

Example 117

Synthesis of Compound 355

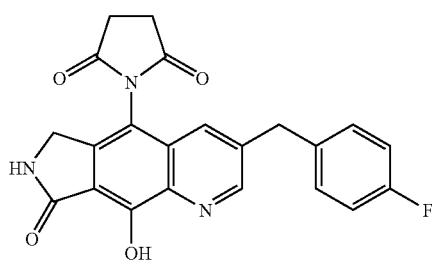

355

To 80 mg of the DMB lactam product 354 in 5 mL AcOH is added 200 mg succinic anhydride. The reaction is heated to 120° C. overnight. Volatiles are removed and 80 mg of the crude imide product is subjected to treatment with 1 mL TFA at 80° C. 60 mg of the crude product was purified on reverse phase HPLC to provide 1 mg of the cyclic imide 355. $^1$H NMR (300 MHz, CD$_3$OD) shows diagnostic peaks at δ (ppm): 8.62 (s, 1H), 7.83 (s, 1H), 7.24 (bm, 2H), 7.03 (m, 2H) 4.25 (s, 2H) 4.18 (s, 2H), and 3.05 (dd, 4H). MS=406.1 (M+H).

Example 118

Synthesis of Compound 359

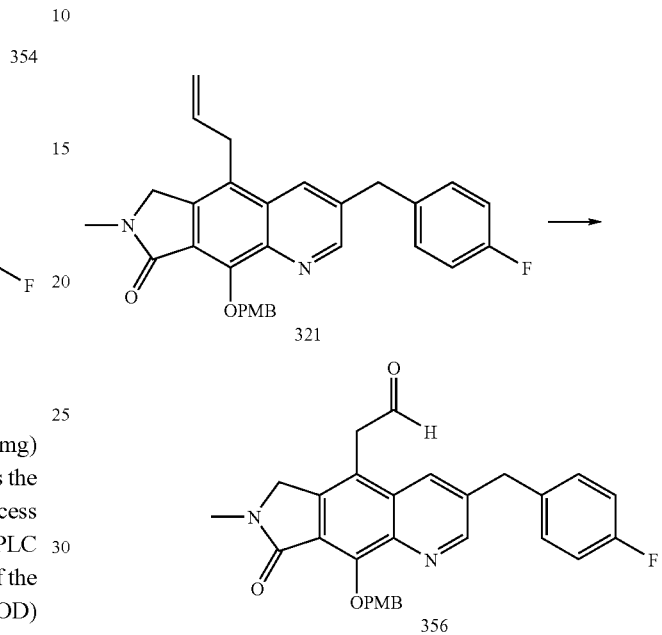

Olefin 321 (102 mg, 0.2 mmol, 1 equiv.) was stirred in CH$_2$Cl$_2$ (20 mL, 0.3 M) at 0° C. and MeOH (2 mL) before subjected to ozonolysis. After completion, to the reaction was added dimethyl sulfide (150 μL) and reaction was allowed to stir overnight before being diluted with ethyl acetate and water. The organic layer was washed with water, saturated NH$_4$Cl and brine. The solution was dried over sodium sulfate, filtered and concentrated in vacuo. The crude residue was purified by chromatography on silica gel (1/3—Ethyl acetate/Hexane) to afford the desired product 356 (95 mg, yield 95%). 300 MHz $^1$H NMR (CDCl$_3$) δ (ppm) 9.73 (s, 1H), 8.89 (s, 1H), 7.90 (s, 1H), 7.65 (d, J=8.7 Hz, 2H), 7.22-7.15 (m, 2H), 7.09-7.04 (m, 2H), 6.86 (d, J=8.7 Hz, 2H), 5.69 (s, 2H), 4.44 (s, 2H), 4.19 (s, 2H), 4.00 (s, 2H), 3.78 (s, 3H), 3.21 (s, 3H). 300 MHz $^{19}$F NMR (CDCl$_3$) δ (ppm): −116.47

MS: 485.07 (M+1).

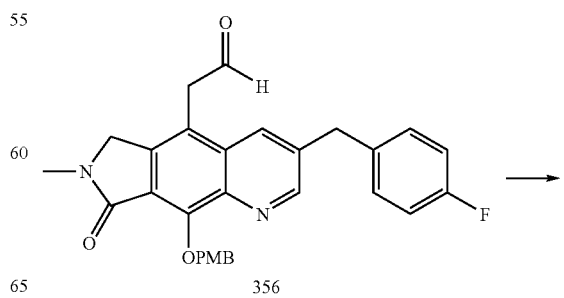

356

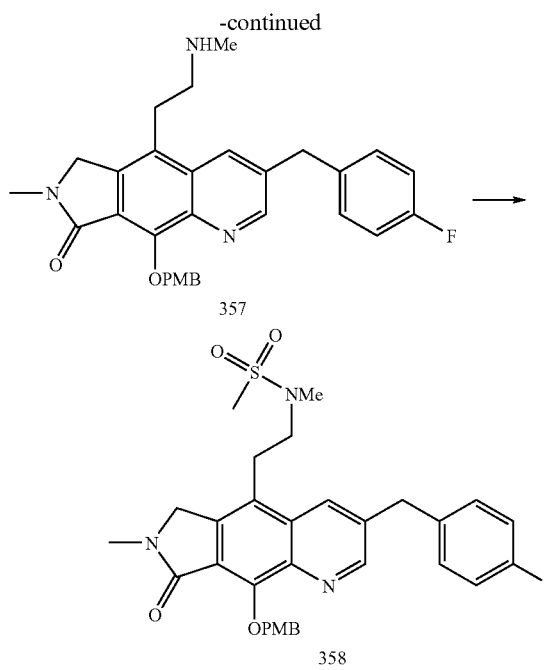

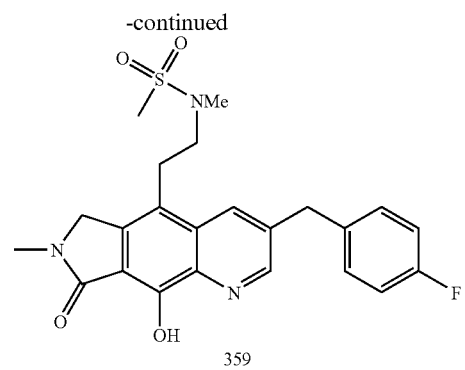

Compound 359 was made in a similar fashion as has been previously described for similar reactions. 300 MHz $^1$H NMR (DMSO-d$_6$) δ (ppm) 8.82 (s, 1H), 8.38 (s, 1H), 7.20-7.19 (m, 2H), 7.09-7.04 (m, 2H), 4.55 (d, 1H), 4.48 (d, 1H), 3.22-3.10 (m, 4H), 3.06 (s, 3H), 2.84 (s, 3H), 2.80 (s, 3H). 300 MHz $^{19}$F NMR (CDCl$_3$) δ (ppm): −74.78, −117.29. (TFA salt). MS: 458.20 (M+1).

Example 119

Synthesis of Compound 361

Aldehyde 356 (31 mg, 0.06 mmol, 1 equiv.) was stirred in CH$_2$Cl$_2$ (20 mL, 0.3 M) at 0° C. and methylamine (35 µL, 0.07 mmol, 1.1 equiv., 2 M THF) and acetic acid (2 µL, 0.03 mmol, 0.5 equiv.) along with NaCNBH$_3$ (5 mg, 0.08 mmol, 1.2 equiv.). The reaction was allowed to stir overnight before being diluted with ethyl acetate and water. The organic layer was washed with water, saturated NH$_4$Cl and brine. The solution was dried over sodium sulfate, filtered and concentrated in vacuo to yield crude amine 357. This was dissolved in CH$_2$Cl$_2$ (3 mL, 0.05 M) before adding TEA (30 µL, 0.21 mmol, 3 equiv.), DMAP (5 mg, 0.04 mmol, 0.5 equiv.,) and MsCl (8 µL, 0.11 mmol, 1.5 equiv.). After completion the reaction was diluted with ethyl acetate and water. The organic layer was washed with water, saturated NH$_4$Cl and brine. The solution was dried over sodium sulfate, filtered and concentrated in vacuo before being purified by chromatography on silica gel (Ethyl acetate) to afford the desired product 358. 300 MHz $^1$H NMR (CDCl$_3$) δ (ppm) 8.90 (s, 1H), 8.04 (s, 1H), 7.65 (d, J=8.7 Hz, 2H), 7.22-7.15 (m, 2H), 7.09-7.04 (m, 2H), 6.86 (d, J=8.7 Hz, 2H), 5.63 (s, 2H), 4.44 (s, 2H), 4.19 (s, 2H), 4.00 (s, 2H), 3.78 (s, 3H), 3.21 (s, 3H). (3.35-3.15 (m, 2H), 2.78-2.70 (s, 2H), 2.56 (s, 2H). 300 MHz $^{19}$F NMR (CDCl$_3$) δ (ppm): −116.70. MS: 578.13 (M+1).

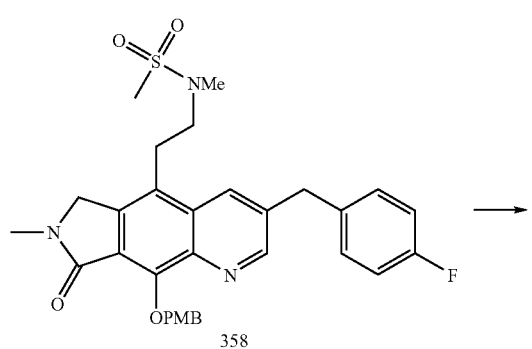

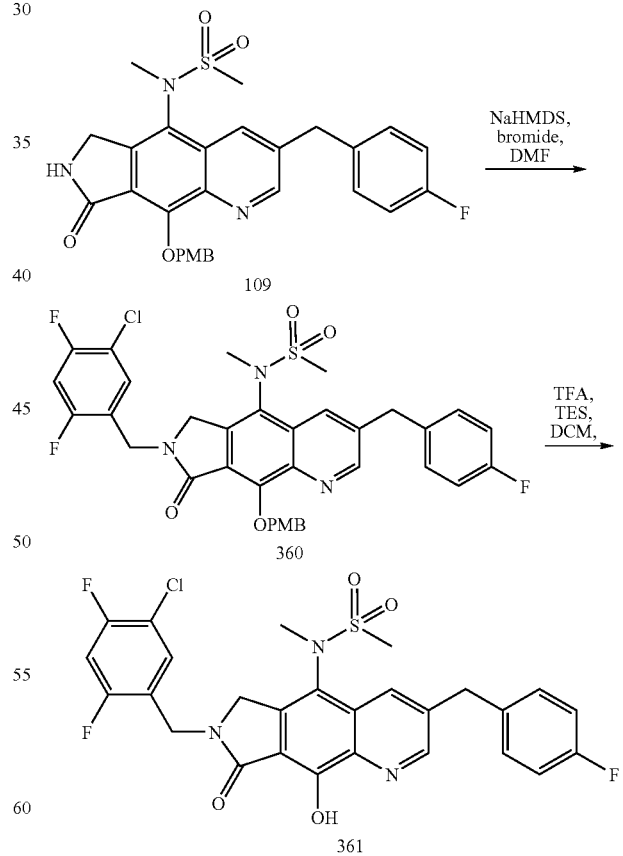

To a solution of compound 109 (Example 45, 50 mg, 0.093 mmol) dissolved in DMF (1 mL) was added Sodium bis(trimethylsilyl)amide (NaHMDS) (0.100 mL, 0.10 mmol, 1M THF) and stirred for 5 minutes under nitrogen atmosphere. The corresponding aryl bromide, also prepared previously in our 2006 filing, (25 mg, 0.10 mmol) was added and the reaction was allowed to stir for 1 hour at room temperature. The reaction was quenched with H$_2$O and diluted with ethyl acetate. The organic layer was washed with H$_2$O, aqueous LiCl, and brine, then dried (over Na$_2$SO$_4$), filtered and concentrated in vacuo. The crude residue was purified by chromatography on silica gel (1/1—ethyl acetate/hexane) to afford the desired product 360 (24 mg, 37%): 300 MHz $^1$H NMR (CDCl$_3$) δ(ppm) 8.95 (s, 1H), 7.74 (s, 1H), 7.632 (d, 2H), 7.50 (dd, 1H), 7.217 (dd, 2H), 7.07 (dd, 2H), 6.97 (dd, 1H), 6.89 (d, 2H), 5.79 (m, 2H), 5.0-4.34 (m, 4H), 4.23 (s, 3H), 3.8 (s, 3H), 3.23 (s, 3H), 2.83 (s, 3H); MS: 696 (M+1).

A solution of intermediate 360 (24 mg, 0.035 mmol) in dichloromethane (2 mL) was treated with trifluoroacetic acid (0.1 mL) and triethylsilane (0.1 mL). The reaction mixture was stirred at room temperature under an inert atmosphere overnight upon which the mixture was azeotroped with toluene/THF repeatedly. The solid was triturated in ether/methanol (3/1) to afford the desired product 361 (13.5 mg, 68%) as the parent (white) solid: 300 MHz $^1$H NMR (CDCl$_3$) δ(ppm) 8.88 (s, 1H), 7.78 (s, 1H), 7.50 (dd, 1H), 7.21 (dd, 2H), 7.07 (dd, 2H), 6.97 (dd, 1H), 4.92-4.4 (m, 4H), 4.24 (s, 3H), 3.24 (s, 3H), 2.81 (s, 3H); 300 MHz $^{19}$F NMR (CDCl$_3$) δ(ppm) −110.98, −115.66, −116.49; MS: 576 (M+1), 578 (3:1).

The compound was made in a similar fashion as before to afford the desired product 362 (12 mg, 21%): 300 MHz $^1$H NMR (CDCl$_3$) δ(ppm) 8.94 (s, 1H), 7.79 (s, 1H), 7.62 (d, 2H), 7.23 (dd, 2H), 7.08 (dd, 2H), 6.88 (d, 2H), 6.046 (m, 1H), 5.73 (m, 2H), 4.71 (dd, 2H), 4.24 (s, 3H), 4.12 (m, 2H), 3.8 (s, 3H), 3.27 (s, 3H), 2.88 (s, 3H); 300 MHz $^{19}$F NMR (CDCl$_3$) δ(ppm)-115.86, −120.46, −120.66, −120.84, −121.03; MS: 600 (M+1).

The compound was made in a similar fashion as before to afford the desired product 363 (8 mg, 83%) as the free parent: 300 MHz $^1$H NMR (CDCl$_3$) δ(ppm) 8.86 (s, 1H), 7.83 (s, 1H), 7.21 (dd, 2H), 7.07 (dd, 2H), 6.040 (m, 1H), 5.73 (m, 2H), 4.76 (dd, 2H), 4.25 (s, 3H), 4.12 (m, 1H), 3.82 (m, 1H), 3.28 (s, 3H), 2.87 (s, 3H); 300 MHz $^{19}$F NMR (CDCl$_3$) δ(ppm) −115.72, −120.49, −120.69, −120.80, −120.86, −121.05; MS: 480 (M+1).

Example 120

Synthesis of Compound 363

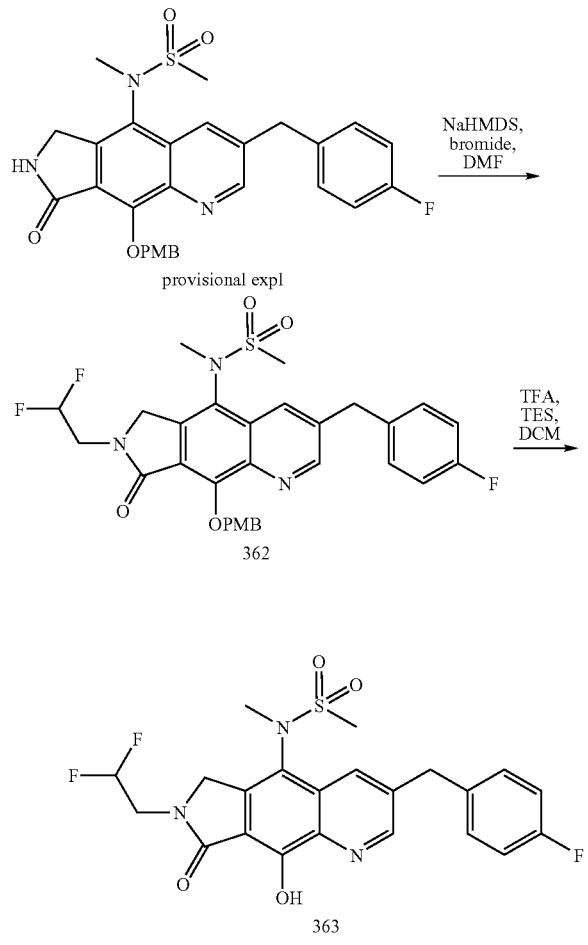

Example 121

Synthesis of Compound 367

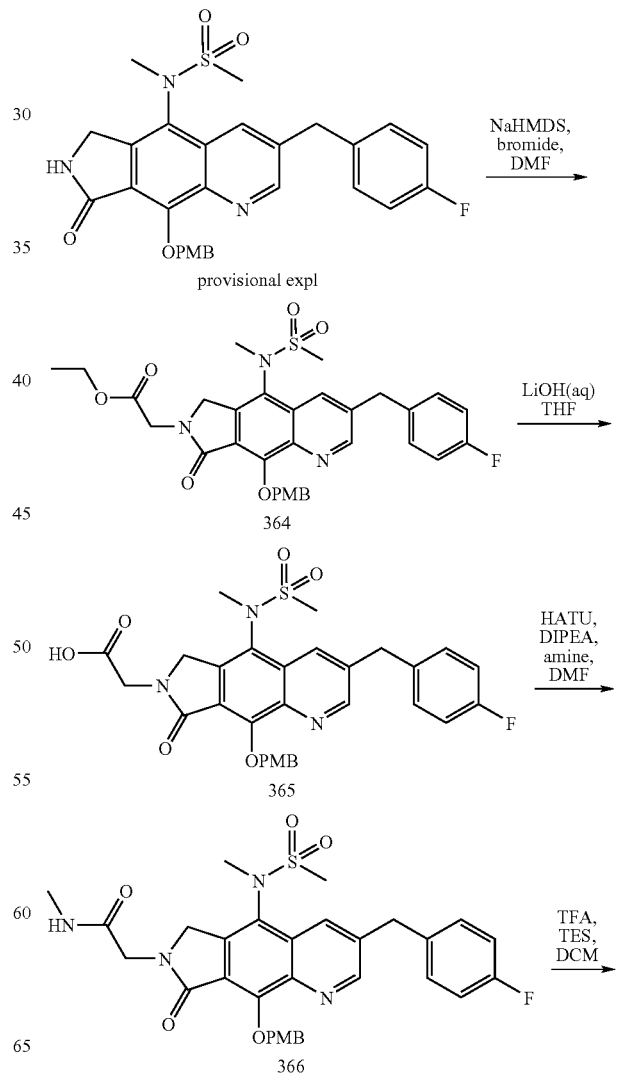

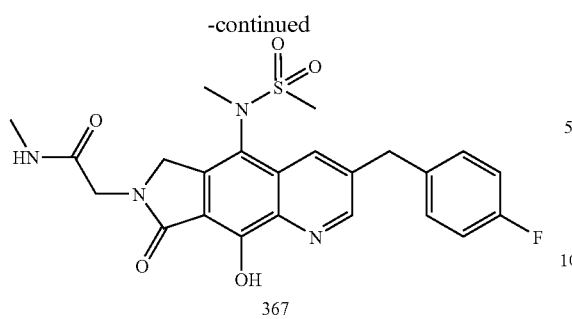

367

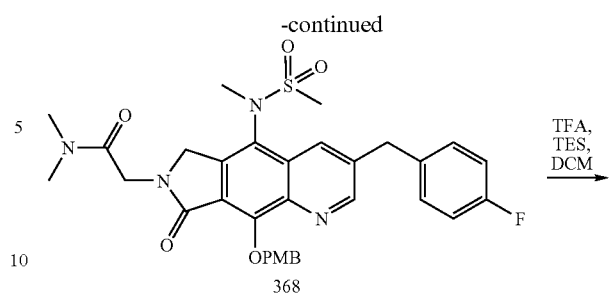

368

The compound was made in a similar fashion as before to afford the desired product 364 (20 mg, 57%): 300 MHz $^1$H NMR (CDCl$_3$) δ(ppm) 8.94 (s, 1H), 7.78 (s, 1H), 7.62 (d, 2H), 7.20 (dd, 2H), 7.07 (dd, 2H), 6.88 (d, 2H), 5.72 (dd, 2H), 4.83-4.14 (m, 4H), 4.23 (s, 3H), 3.8 (s, 3H), 3.27 (s, 3H), 2.87 (s, 3H), 1.29 (t, 3H); MS: 622 (M+1).

To a solution of ethyl ester 364 (20 mg, 0.032 mmol) dissolved in THF (0.600 mL) and water (0.200 mL) was added DMAP (catalytic) and LiOH*H$_2$O (6 mg, 0.129 mmol). The reaction was stirred at room temperature for 3 hours upon which diluted with ethyl acetate and water. The mixture was acidified with 1N HCl (until soln pH=3) and the product was extracted with ethyl acetate twice. The organic layer was washed with brine then dried (over Na$_2$SO$_4$), filtered and concentrated in vacuo to give clean product 365 (20 mg, 100%) with no further purification; MS: 594 (M+1).

A solution of carboxylic acid 365 (20 mg, 0.032 mmol) in DMF (0.320 mL) that had been stirred with HATU (0.024 g, 0.064 mmol) and DIPEA (0.017 mL, 0.097 mmol) for 5 minutes was treated with methylamine (81 μL, 0.161 mmol, 2M THF soln). The reaction mixture was stirred for 2 hours at room temperature, under nitrogen atmosphere, upon which diluted with ethyl acetate and quenched with saturated NH$_4$Cl. The organic layer was washed with water, aqueous LiCl, and brine, then dried (NaSO$_4$), filtered and concentrated. The residue was purified by chromatography on silica gel (0-10%—methanol/ethyl acetate) to afford the desired product 366 (16 mg, 82%): 300 MHz $^1$H NMR (CDCl$_3$) δ(ppm) 8.9 (s, 1H), 7.85 (s, 1H), 7.6 (d, 2H), 7.22 (dd, 2H), 7.06 (dd, 2H), 6.88 (d, 2H), 6.35 (bs, 1H), 5.68 (dd, 2H), 4.78 (dd, 2H), 4.24 (dd, 2H), 4.22 (s, 3H), 3.81 (s, 3H), 3.26 (s, 3H), 2.91 (s, 3H), 2.82 (d, 3H); MS: 607 (M+1).

The compound was made in a similar fashion before to afford the desired product 367 (8 mg, 83%) as the free parent: 300 MHz $^1$H NMR (CDCl$_3$) δ (ppm) 8.82 (s, 1H), 7.89 (s, 1H), 7.21 (dd, 2H), 7.06 (dd, 2H), 6.29 (bs, 1H), 4.78 (dd, 2H), 4.24 (dd, 2H), 4.239 (s, 3H), 3.27 (s, 3H), 2.91 (s, 3H), 2.84 (d, 3H); 300 MHz $^{19}$F NMR (CDCl$_3$) δ (ppm) -115.81; MS: 487 (M+1)Synthesis of Compound 369

Example 122

369

The compound was made in a similar fashion as before to afford the desired product 368 (20 mg, 77%): 300 MHz $^1$H NMR (CDCl$_3$) δ(ppm) 8.91 (s, 1H), 7.84 (s, 1H), 7.63 (d, 2H), 7.22 (dd, 2H), 7.057 (dd, 2H), 6.875 (d, 2H), 5.70 (dd, 2H), 4.80 (dd, 2H), 4.47 (dd, 2H), 4.219 (s, 3H), 3.80 (s, 3H), 3.26 (s, 3H), 3.12 (s, 3H), 2.99 (d, 3H), 2.89 (s, 3H); 300 MHz $^{19}$F NMR (CDCl$_3$) δ(ppm) -116.06; MS: 621 (M+1).

The compound was made in a similar fashion as before to afford the desired product 369 (15.5 mg, 96%) as the free parent: 300 MHz $^1$H NMR (CDCl$_3$) δ(ppm) 8.85 (s, 1H), 7.86 (s, 1H), 7.24 (dd, 2H), 7.058 (dd, 2H), 4.82 (dd, 2H), 4.45 (dd, 2H), 4.236 (s, 3H), 3.26 (s, 3H), 3.128 (s, 3H), 2.998 (d, 3H), 2.866 (s, 3H); 300 MHz $^{19}$F NMR (CDCl$_3$) δ(ppm) -115.985; MS: 501 (M+1).

Example 123

Synthesis of Compound 370

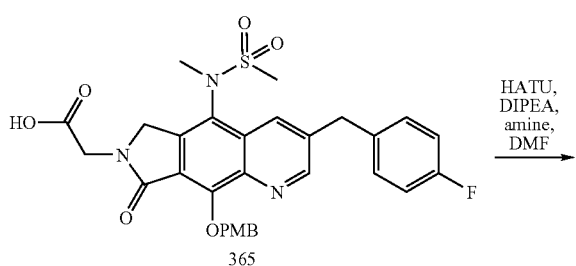

365

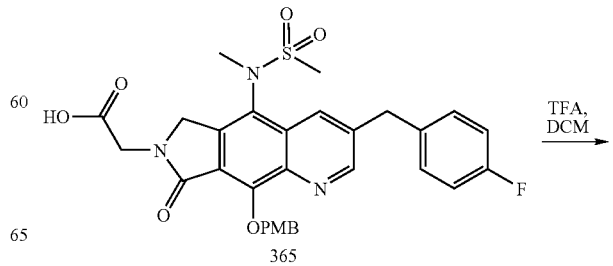

365

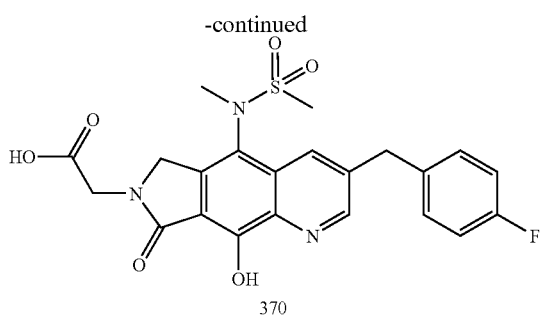

370

The compound was made in a similar fashion as before then purified by reversed phase HPLC to afford the desired product 370 (12.5 mg, 38%) as the TFA salt: 300 MHz $^1$H NMR (DMSO) δ(ppm) 8.87 (s, 1H), 8.19 (s, 1H), 7.385 (dd, 2H), 7.15 (dd, 2H), 4.64 (dd, 2H), 4.28 (s, 2H), 4.254 (s, 2H), 3.26 (s, 3H), 3.17 (s, 3H); 300 MHz $^{19}$F NMR (CDCl$_3$) δ(ppm) −74.89, −117.10; MS: 474 (M+1).

Example 124

Synthesis of Compound 372

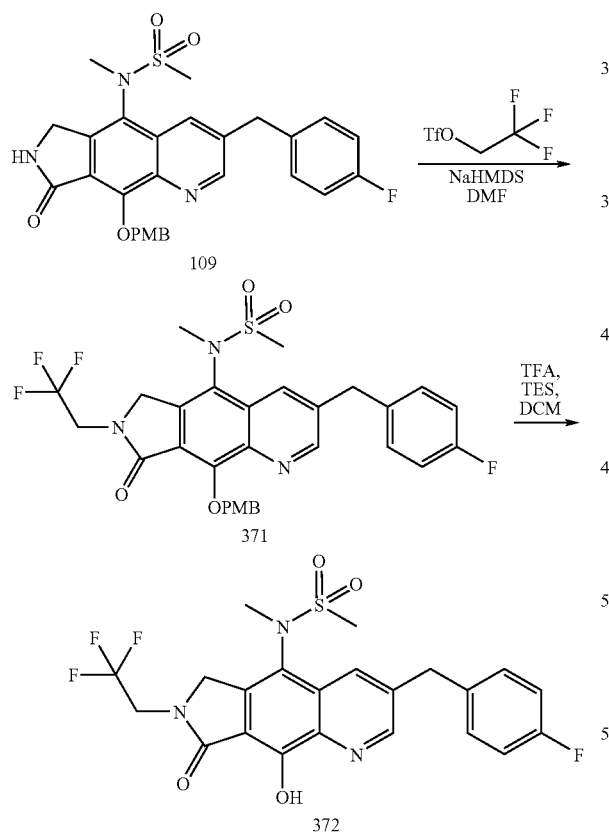

Compound 109 was alkylated with the trifluoroethyltriflate (see U.S. Pat. No. 5,922,737A1) for 1 day at room temperature to afford the desired product 371 (20 mg, 60% including 11 mg of recovered starting material): 300 MHz $^1$H NMR (CDCl$_3$) δ(ppm) 8.94 (s, 1H), 7.76 (s, 1H), 7.60 (d, 2H), 7.22 (dd, 2H), 7.075 (dd, 2H), 6.88 (d, 2H), 5.74 (m, 2H), 4.72 (dd, 2H), 4.47 (m, 1H), 4.23 (s, 3H), 3.99 (m, 1H), 3.8 (s, 3H), 3.26 (s, 3H), 2.85 (s, 3H); 300 MHz $^{19}$F NMR (CDCl$_3$) δ(ppm) −70.17, −115; MS: 618 (M+1).

The compound was made in a similar fashion as before to afford the desired product 372 (12.6 mg, 78%) as the free parent: 300 MHz $^1$H NMR (CDCl$_3$) δ(ppm) 8.87 (s, 1H), 7.81 (s, 1H), 7.21 (dd, 2H), 7.08 (dd, 2H), 4.78 (dd, 2H), 4.44 (m, 1H), 4.25 (s, 3H), 3.99 (m, 1H), 3.28 (s, 3H), 2.85 (s, 3H); 300 MHz $^{19}$F NMR (CDCl$_3$) δ(ppm) −70.28, −115.63; MS: 498 (M+1).

Example 125

Synthesis of Compound 374

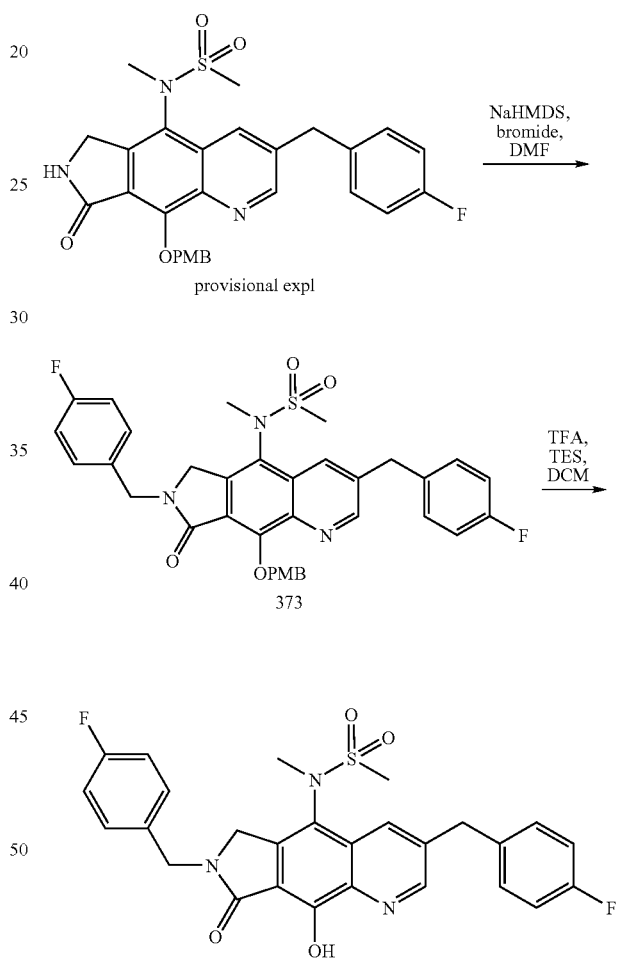

The compound was made in a similar fashion as before to afford the desired product 373 (45 mg, 64%): 300 MHz $^1$H NMR (CDCl$_3$) δ(ppm) 8.95 (s, 1H), 7.74 (s, 1H), 7.65 (d, 2H), 7.33 (dd, 1H), 7.21 (dd, 1H), 7.05 (m, 4H), 6.89 (d, 2H), 5.77 (m, 2H), 4.78 (dd, 2H), 4.46 (dd, 2H), 4.23 (s, 3H), 3.81 (s, 3H), 3.199 (s, 3H), 2.805 (s, 3H); MS: 644 (M+1).

The compound was made in a similar fashion as before to afford the desired product 374 (26 mg, 71%) as the free parent: 300 MHz $^1$H NMR (CDCl$_3$) δ(ppm) 8.80 (s, 1H), 7.77 (s, 1H), 7.65 (d, 2H), 7.33 (dd, 1H), 7.2 (dd, 1H), 7.06 (m, 4H), 4.75 (dd, 2H), 4.51 (dd, 2H), 4.238 (s, 3H), 3.20 (s, 3H), 2.79 (s, 3H); 300 MHz $^{19}$F NMR (CDCl$_3$) δ(ppm) −114.582, −115.703; MS: 524 (M+1).

Example 126

Synthesis of Compound 376

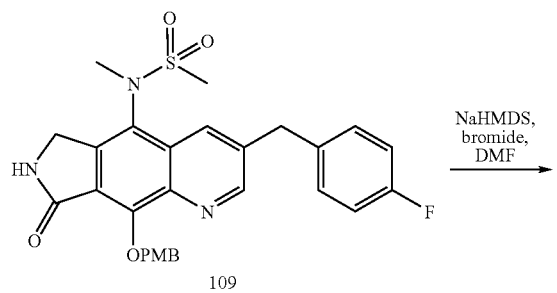

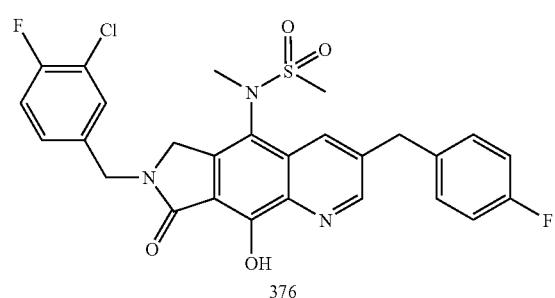

The compound was made in a similar fashion as before to afford the desired product 375 (22 mg, 43%): 300 MHz $^1$H NMR (CDCl$_3$) δ(ppm) 8.96 (s, 1H), 7.73 (s, 1H), 7.64 (d, 2H), 7.41 (dd, 1H), 7.2-7.04 (m, 6H), 6.89 (d, 2H), 5.78 (dd, 2H), 4.76 (dd, 2H), 4.47 (dd, 2H), 4.23 (s, 3H), 3.80 (s, 3H), 3.21 (s, 3H), 2.81 (s, 3H); MS: 678 (M+1).

The compound was made in a similar fashion as before to afford the desired product 376 (14 mg, 77%) as the free parent: 300 MHz $^1$H NMR (CDCl$_3$) δ(ppm) 8.88 (s, 1H), 7.76 (s, 1H), 7.65 (d, 2H), 7.41 (dd, 1H), 7.2-7.04 (m, 6H), 4.73 (dd, 2H), 4.52 (dd, 2H), 4.24 (s, 3H), 3.22 (s, 3H), 2.80 (s, 3H); 300 MHz $^{19}$F NMR (CDCl$_3$) δ(ppm) −115.69, −116.74; MS: 558 (M+1).

Example 127

Synthesis of Compound 378

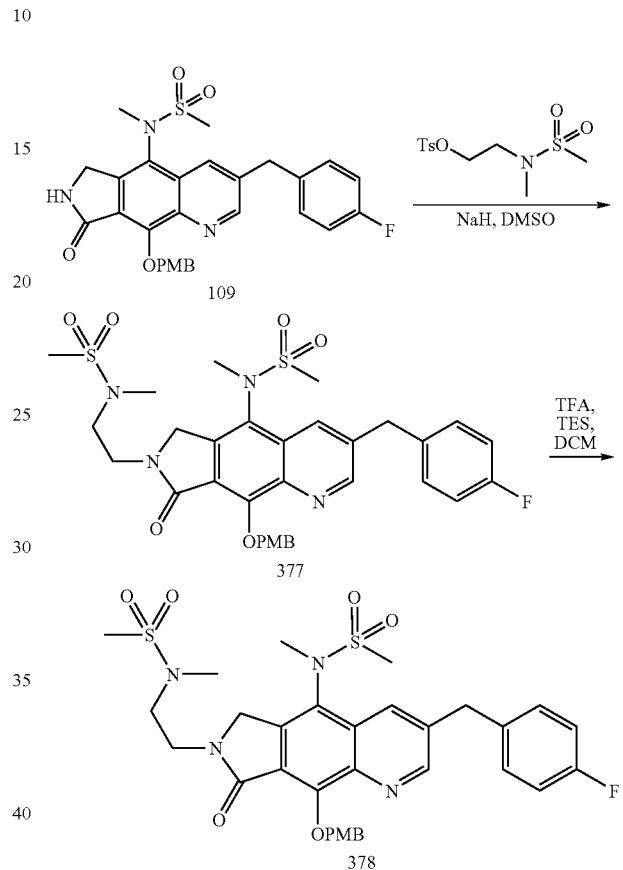

To a solution of compound 109 (Example 45, 45 mg, 0.084 mmol) dissolved in DMSO (1 mL) was added Sodium hydride (4.4 mg, 0.109 mmol, 60% disp oil) and stirred for 5 minutes under nitrogen atmosphere. The corresponding tosylate, as prepared by precedented literature, (52 mg, 0.168 mmol) was added and the reaction was allowed to stir for 30 min at room temperature. The reaction was quenched with H$_2$O and diluted with ethyl acetate. The organic layer was washed with aqueous LiCl (twice) and brine, then dried (over Na$_2$SO$_4$), filtered and concentrated in vacuo. The crude residue was purified by chromatography on silica gel (1-5%—methanol/ethyl acetate) to afford the desired product 377 (32 mg, 57%): 300 MHz $^1$H NMR (CDCl$_3$) δ(ppm) 8.91 (s, 1H), 7.89 (s, 1H), 7.61 (d, 2H), 7.22 (dd, 2H), 7.05 (dd, 2H), 6.87 (d, 2H), 5.72 (dd, 2H), 4.7 (dd, 2H), 4.22 (s, 3H), 4.05 (m, 1H), 3.79 (s, 3H), 3.75-3.3 (m, 3H), 3.28 (s, 3H), 2.96 (s, 3H), 2.92 (s, 3H), 2.77 (s, 3H); MS: 671 (M+1).

The compound was made in a similar fashion as before then purified by reversed phase HPLC to afford the desired product 378 (14.6 mg, 46%) as the TFA salt: 300 MHz $^1$H NMR (CDCl$_3$) δ(ppm) 8.96 (s, 1H), 8.042 (s, 1H), 7.21 (dd, 2H), 7.06 (dd, 2H), 4.77 (dd, 2H), 4.26 (s, 3H), 4.00 (m, 1H), 3.75-3.5 (m, 2H), 3.4 (m, 1H), 3.28 (s, 3H), 2.96 (s, 3H), 2.91

(s, 3H), 2.78 (s, 3H); 300 MHz $^{19}$F NMR (CDCl$_3$) δ(ppm) −76.25, −115.76; MS: 551 (M+1).

Example 128

Synthesis of Compound 380

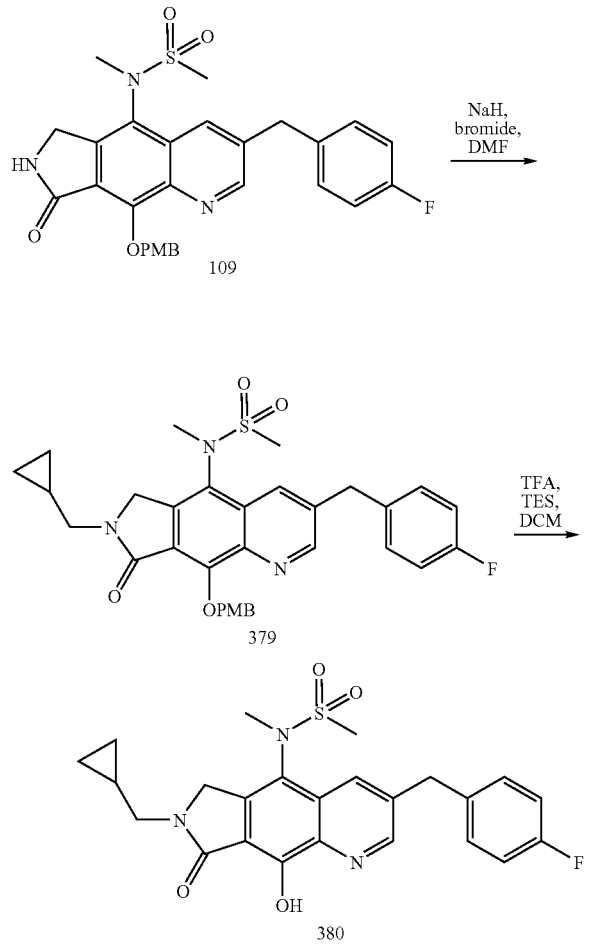

To a solution of compound 109 (50 mg, 0.098 mmol) dissolved in DMF (1 ml) and cooled in an ice bath to 0° C. was added sodium hydride (5.0 mg, 0.121 mmol, 60% mineral oil) and stirred for 5 minutes under nitrogen atmosphere. Bromomethylcyclopropane (18 μL, 0.187 mmol) and tetrabutylammonium iodide (10.0 mg) was added and the reaction was allowed to stir for 1 h at RT. The reaction was quenched with H$_2$O and diluted with ethyl acetate. The organic layer was washed with aqueous LiCl (twice) and brine, then dried (over Na$_2$SO$_4$), filtered and concentrated in vacuo. The crude residue was purified by chromatography on silica gel (3/2—ethyl acetate/hexane) to afford the desired product 379 (28 mg, 51%) with no further characterization: MS: 590 (M+1).

The compound was made in a similar fashion as before to afford the desired product 380 (13 mg, 58%) as the free parent: 300 MHz $^1$H NMR (CDCl$_3$) δ(ppm) 8.88 (s, 1H), 7.80 (s, 1H), 7.21 (dd, 2H), 7.07 (dd, 2H), 4.73 (dd, 2H), 4.24 (s, 3H), 3.52 (m, 1H), 3.4 (m, 1H), 3.28 (s, 3H), 2.84 (s, 3H), 1.09 (m, 1H), 0.62 (m, 2H), 0.374 (m, 2H); 300 MHz $^{19}$F NMR (CDCl$_3$) δ(ppm) −115.79; MS: 470 (M+1).

Example 129

Synthesis of Compound 382

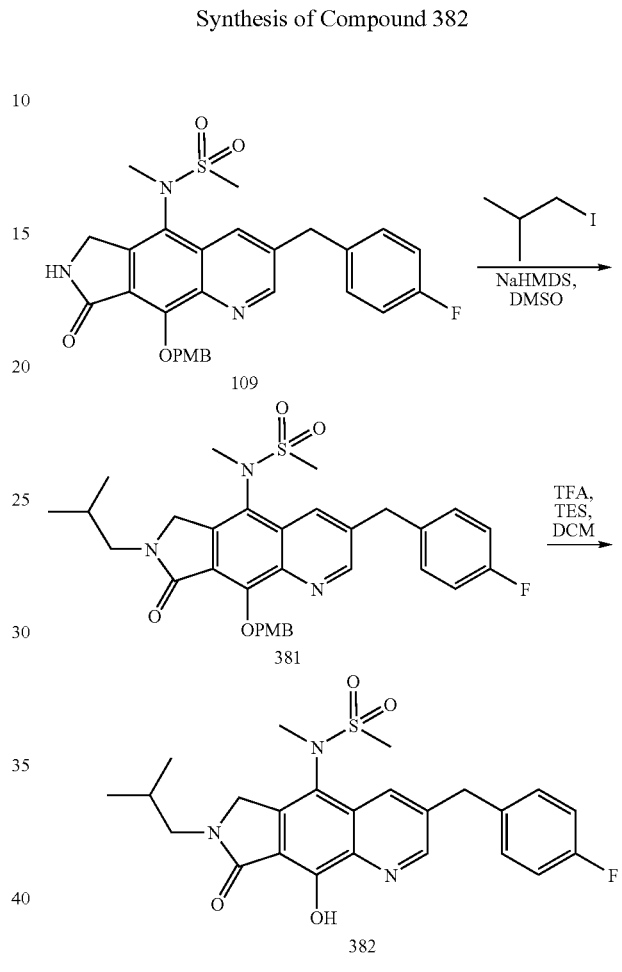

To a solution of compound 109 (100 mg, 0.187 mmol) dissolved in DMSO (1.87 mL) was added Sodium bis(trimethylsilyl)amide (NaHMDS) (0.243 mL, 0.243 mmol, 1M THF) and stirred for 5 minutes under nitrogen atmosphere. Commercially available 1-iodo-2-methylpropane (43 μL, 0.373 mmol) was added and the reaction was allowed to stir for 2 hours at room temperature at which point there was approximately 33% alkylated product. The reaction was quenched with H$_2$O and diluted with ethyl acetate. The organic layer was washed with aqueous LiCl (twice) and brine, then dried (over Na$_2$SO$_4$), filtered and concentrated in vacuo. The crude residue was purified by chromatography on silica gel (4/1—ethyl acetate/hexane) to afford the desired product 381 (33 mg, 62% including 52 mg of recovered starting material): 300 MHz $^1$H NMR (CDCl$_3$) δ(ppm) 8.95 (s, 1H), 7.76 (s, 1H), 7.63 (d, 2H), 7.22 (dd, 2H), 7.07 (dd, 2H), 6.75 (d, 2H), 5.74 (m, 2H), 4.57 (dd, 2H), 4.23 (s, 3H), 3.79 (s, 3H), 3.5 (m, 1H), 3.40 (m, 1H), 3.27 (s, 3H), 2.85 (s, 3H), 2.1 (m, 1H), 0.99 (m, 6H); MS: 592 (M+1).

The compound was made in a similar fashion as before to afford the desired product 382 (28 mg, 73%) as the free parent: 300 MHz $^1$H NMR (CDCl$_3$) δ(ppm) 8.89 (s, 1H), 7.77 (s, 1H), 7.21 (dd, 2H), 7.07 (dd, 2H), 4.63 (dd, 2H), 4.24 (s, 3H), 3.79 (s, 3H), 3.42 (m, 2H), 3.27 (s, 3H), 2.82 (s, 3H), 2.09 (m, 1H), 0.99 (m, 6H); 300 MHz $^{19}$F NMR (CDCl$_3$) δ(ppm) −115.82; MS: 472 (M+1).

Example 130

Synthesis of Compound 386

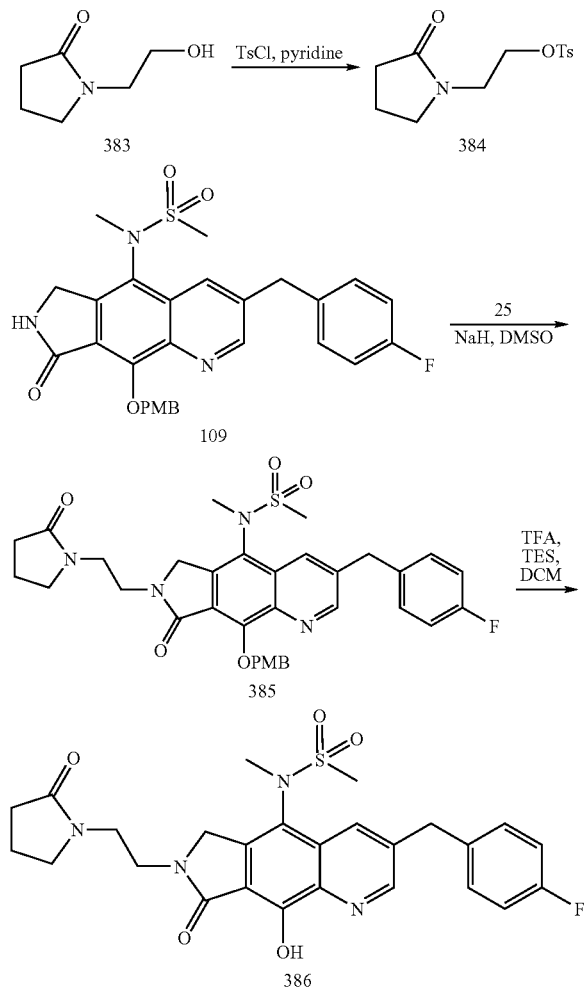

To a solution of the alcohol 383 (1 g, 7.74 mmol) dissolved in pyridine (1 mL) and cooled in an ice bath to 0° C. was added a premixed solution of tosyl chloride (2.21 g, 11.6 mmol) in dichloromethane (2 mL) and pyridine (1 mL). The reaction was stirred in the ice bath for 30 minutes then allowed to stir overnight at room temperature under nitrogen atmosphere. At which point, the reaction was quenched with ice-cooled H$_2$O and diluted with ethyl acetate. The organic layer was washed with 1N HCl, sat NaHCO$_3$ and brine (twice), then dried (over Na$_2$SO$_4$), filtered and concentrated in vacuo. The crude residue was purified by chromatography on silica gel (7/3—ethyl acetate/hexane) to afford the desired product 384 (800 mg, 37%): 300 MHz $^1$H NMR (CDCl$_3$) δ(ppm) 7.8 (d, 2H), 7.35 (d, 2H), 4.17 (t, 2H), 3.57 (t, 2H), 3.47 (t, 2H), 2.45 (s, 3H), 2.35 (t, 2H), 2.0 (m, 2H).

The compound was made in a similar fashion as before to afford the desired product 385 (59 mg, crude—the reaction went to ~66% completion to DP) with no further purification or characterization; MS: 647 (M+1).

The compound was made in a similar fashion as before then purified by reversed phase HPLC to afford the desired product 386 (5 mg) as the TFA salt: 300 MHz $^1$H NMR (CDCl$_3$) δ(ppm) 8.88 (s, 1H), 7.97 (s, 1H), 7.2 (dd, 2H), 7.05 (dd, 2H), 4.755 (dd, 2H), 4.24 (s, 3H), 4.1-3.3 (m, 6H), 3.4 (m, 1H), 3.30 (s, 3H), 2.92 (s, 3H), 2.26 (m, 2H), 2.03 (m, 2H); 300 MHz $^{19}$F NMR (CDCl$_3$) δ(ppm) −76.55, −115.95; MS: 527 (M+1).

Example 131

Synthesis of Compound 390

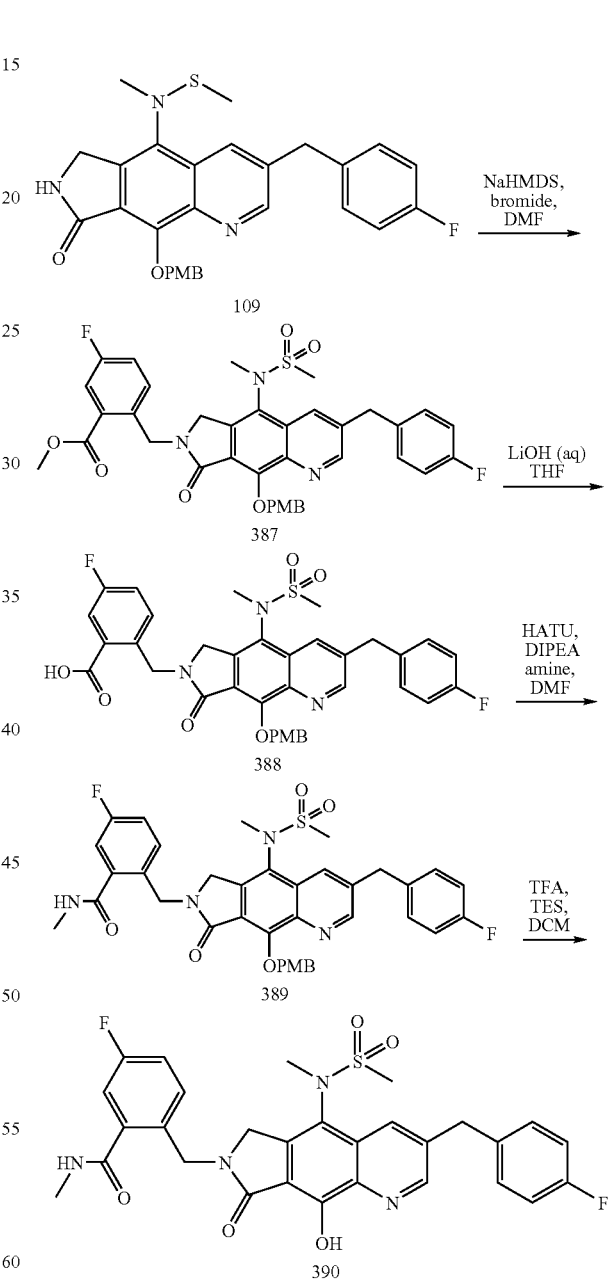

The compound was made in a similar fashion as before to afford the desired product 387 (100 mg, 64% from 120 mg of lactam): 300 MHz $^1$H NMR (CDCl$_3$), δ(ppm) 8.96 (s, 1H), 7.83 (s, 1H), 7.67 (m, 1H), 7.64 (d, 2H), 7.43 (m, 1H), 7.21 (dd, 2H), 7.06 (dd, 2H), 6.87 (d, 2H), 5.78 (dd, 2H), 5.2 (dd, 2H), 4.55 (dd, 2H), 4.24 (s, 3H), 3.97 (s, 3H), 3.8 (s, 3H), 3.22 (s, 3H), 2.86 (s, 3H); MS: 702 (M+1).

The compound was made in a similar fashion as before to afford the desired product 388 (90 mg, quant recovery crude); MS: 688 (M+1).

The compound was made in a similar fashion as before to afford the desired product 389 (44 mg, quant): 300 MHz $^1$H NMR (CDCl$_3$) δ(ppm) 8.93 (s, 1H), 7.87 (s, 1H), 7.6 (d, 2H), 7.44 (m, 1H), 7.24-7.06 (m, 6H), 6.86 (d, 2H), 6.515 (bs, 1H), 5.75 (dd, 2H), 4.91 (dd, 2H), 4.61 (dd, 2H), 4.23 (s, 3H), 3.8 (s, 3H), 3.24 (s, 3H), 2.98 (d, 3H), 2.91 (s, 3H); MS: 701 (M+1).

The compound was made in a similar fashion as before then purified by reversed phase HPLC to afford the desired product 390 (21 mg, 48%) as the TFA salt: 300 MHz $^1$H NMR (CDCl$_3$) δ (ppm) 8.96 (s, 1H), 7.998 (s, 1H), 7.45 (m, 1H), 7.24-7.036 (m, 6H), 4.89 (dd, 2H), 4.69 (d, 2H), 4.26 (s, 3H), 3.24 (s, 3H), 3.0 (d, 3H), 2.89 (s, 3H); 300 MHz $^{19}$F NMR (CDCl$_3$) δ(ppm) −76.31, −112.90, −115.62; MS: 581 (M+1).

Example 132

Synthesis of Compound 392

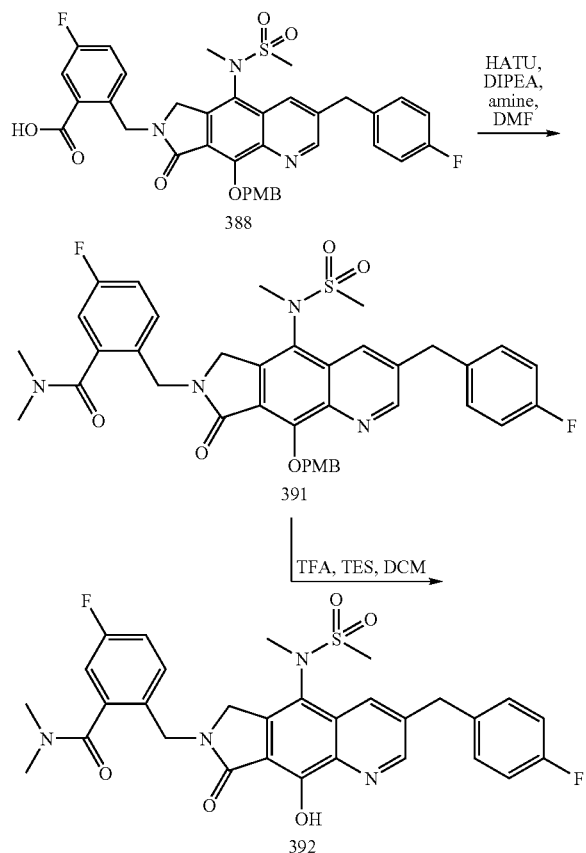

The compound was made in a similar fashion as before to afford the desired product 391 (41 mg, quant): 300 MHz $^1$H NMR (CDCl$_3$) δ(ppm) 8.93 (s, 1H), 7.94 (s, 1H), 7.65 (d, 2H), 7.44 (m, 1H), 7.24-6.94 (m, 6H), 6.88 (d, 2H), 5.765 (dd, 2H), 4.8 (dd, 2H), 4.45 (dd, 2H), 4.22 (s, 3H), 3.798 (s, 3H), 3.23 (s, 3H), 3.04 (s, 3H), 2.935 (s, 3H), 2.90 (s, 3H); MS: 715 (M+1).

The compound was made in a similar fashion as before to afford the desired product 392 (25 mg, 73%) as the free parent: 300 MHz $^1$H NMR (CDCl$_3$) δ(ppm) 8.84 (s, 1H), 7.95 (s, 1H), 7.44 (m, 1H), 7.22-6.95 (m, 5H), 4.77 (dd, 2H), 4.5 (dd, 2H), 4.23 (s, 3H), 3.23 (s, 3H), 3.033 (s, 3H), 2.90 (s, 6H); 300 MHz $^{19}$F NMR (CDCl$_3$) δ(ppm) −113.23, −116.01; MS: 595 (M+1).

Example 133

Synthesis of Compound 394

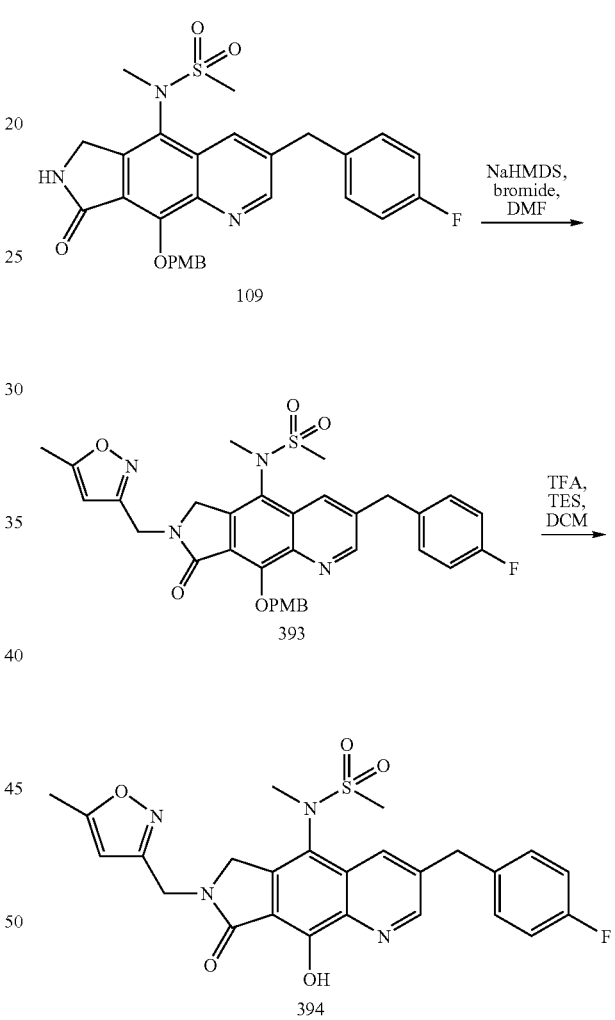

The compound was made in a similar fashion as before to afford the desired product 393 (33.5 mg, 63%): 300 MHz $^1$H NMR (CDCl$_3$) δ(ppm) 8.95 (s, 1H), 7.86 (s, 1H), 7.63 (d, 2H), 7.21 (m, 2H), 7.06 (m, 2H), 6.88 (d, 2H), 6.064 (s, 1H), 5.76 (dd, 2H), 4.84 (dd, 2H), 4.58 (dd, 2H), 4.23 (s, 3H), 3.8 (s, 3H), 3.24 (s, 3H), 2.89 (s, 3H), 2.41 (s, 3H); MS: 631 (M+1).

The compound was made in a similar fashion as before to afford the desired product 394 (19 mg, 70%) as the free parent: 300 MHz $^1$H NMR (CDCl$_3$) δ(ppm) 8.85 (s, 1H), 7.89 (s, 1H), 7.20 (dd, 2H), 7.06 (dd, 2H), 6.061 (s, 1H), 4.81 (dd, 2H), 4.63 (dd, 2H), 4.24 (s, 3H), 3.24 (s, 3H), 2.87 (s, 3H), 2.41 (s, 3H); 300 MHz $^{19}$F NMR (CDCl$_3$) δ(ppm) −115.85; MS: 511 (M+1).

Example 134

Synthesis of Compound 398

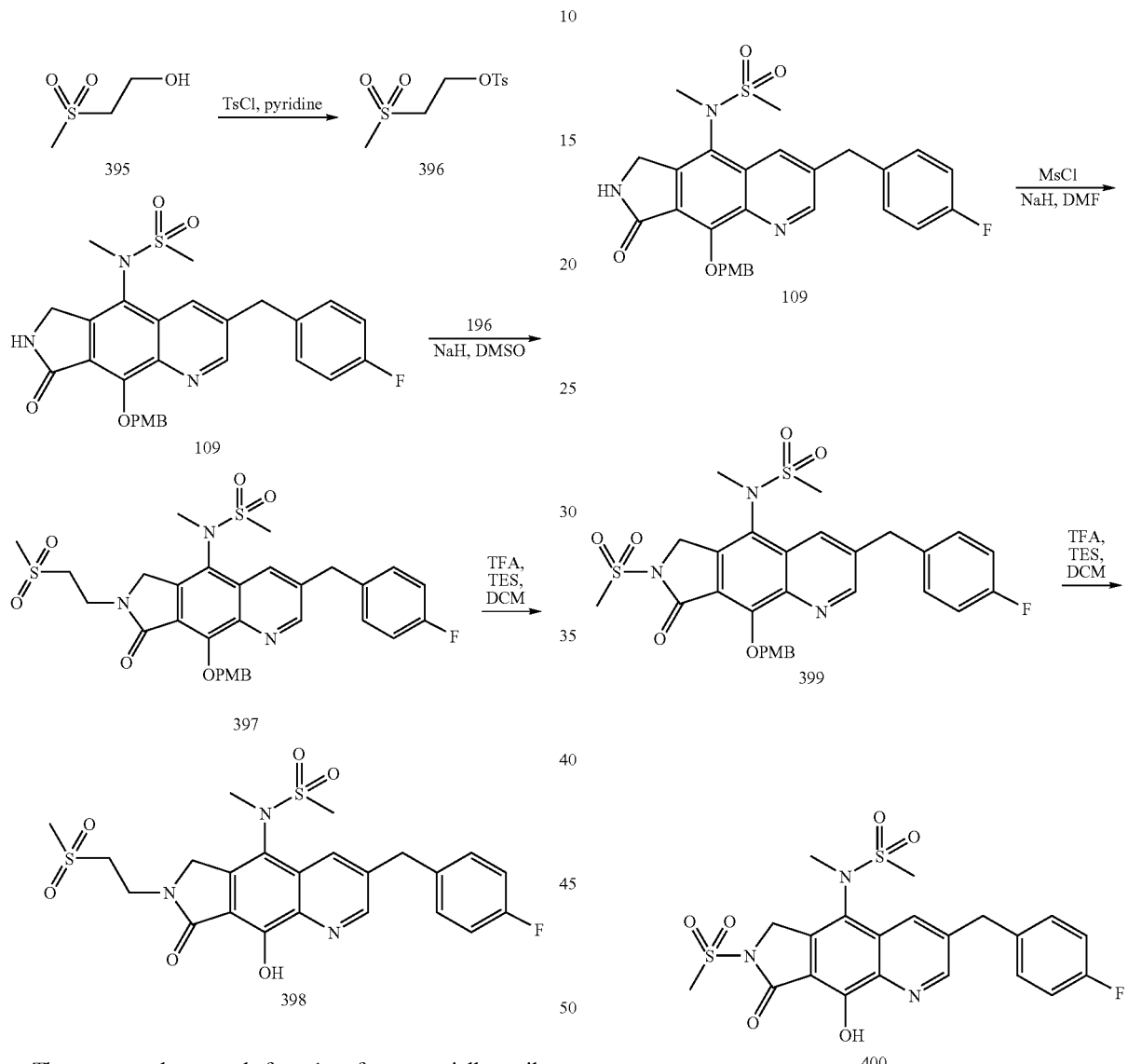

The compound was made from 1 g of commercially available alcohol 395 to afford the desired product 396 (1.46 mg, 65%): 300 MHz $^1$H NMR (CDCl$_3$) δ(ppm) 7.8 (d, 2H), 7.4 (d, 2H), 4.45 (t, 2H), 3.36 (t, 2H), 2.985 (s, 3H), 2.48 (s, 3H).

The compound was made in a similar fashion as before to afford the desired product 397 (59 mg, crude—the reaction went to ~66% completion to DP) with no further purification or characterization; MS: 642 (M+1).

The compound was made in a similar fashion as before then purified by reversed phase HPLC to afford the desired product 398 (7.2 mg) as the free parent: 300 MHz $^1$H NMR (CDCl$_3$) δ(ppm) 8.84 (s, 1H), 7.92 (s, 1H), 7.21 (m, 2H), 7.06 (m, 2H), 4.79 (dd, 2H), 4.24 (s, 2H), 4.2-4.0 (m, 2H), 3.6-3.4 (m, 2H), 3.28 (s, 3H), 3.01 (s, 3H), 2.90 (s, 3H); 300 MHz $^{19}$F NMR (CDCl$_3$) δ(ppm) −115.88; MS: 522 (M+1).

Example 135

Synthesis of Compound 400

The compound was made in a similar fashion as before to afford the desired product 399 (29 mg, 100% recovery—considering the reaction went to 50% completion to product with 30 mg recovered lactam after silica gel chromatography): 300 MHz $^1$H NMR (CDCl$_3$) δ(ppm) 8.95 (s, 1H), 7.88 (s, 1H), 7.58 (d, 2H), 7.26 (m, 2H), 7.08 (m, 2H), 6.88 (d, 2H), 5.79 (dd, 2H), 5.01 (dd, 2H), 4.25 (s, 3H), 3.81 (s, 3H), 3.47 (s, 3H), 3.26 (s, 3H), 2.93 (s, 3H); MS: 614 (M+1).

The compound was made in a similar fashion as before to afford the desired product 400 (18 mg, 78%) as the free parent: 300 MHz $^1$H NMR (DMSO) δ(ppm) 8.9 (s, 1H), 8.22 (s, 1H), 7.38 (dd, 2H), 7.15 (dd, 2H), 4.99 (dd, 2H), 4.29 (s, 3H), 3.45 (s, 3H), 3.27 (s, 3H), 3.20 (s, 3H); 300 MHz $^{19}$F NMR (CDCl$_3$) δ(ppm) −117.02; MS: 494 (M+1).

Example 136

Synthesis of Compounds 403 and 404

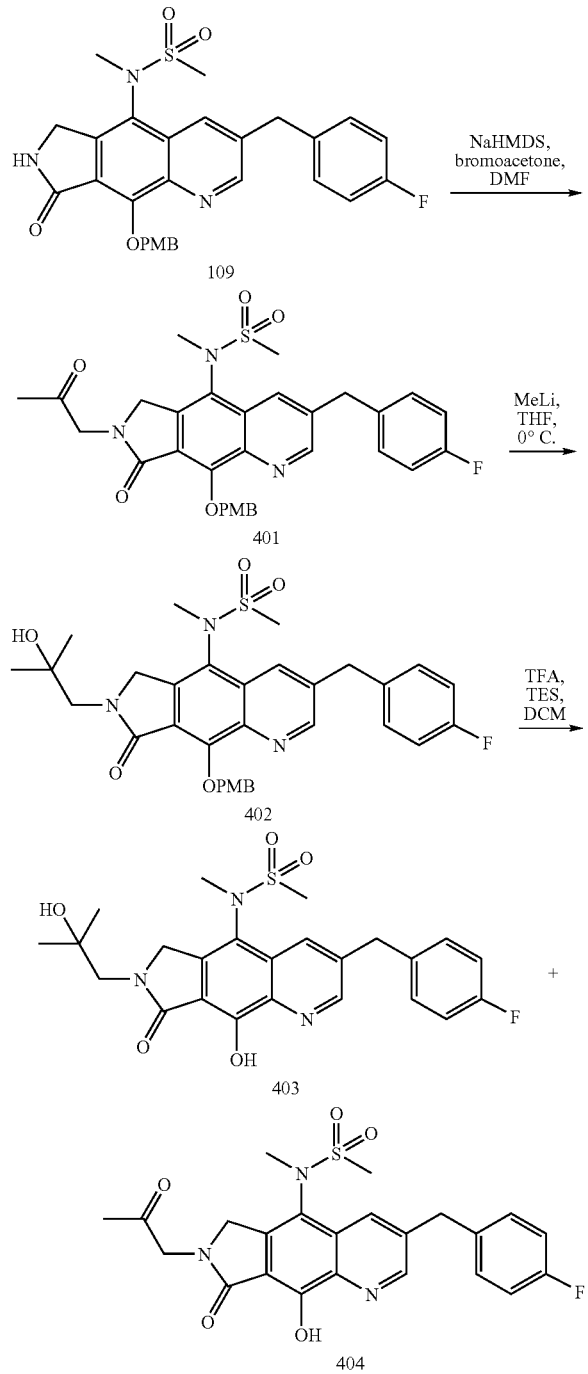

The compound was made in a similar fashion as before to afford the desired product 401 (25 mg): 300 MHz $^1$H NMR (CDCl$_3$) δ(ppm) 8.91 (s, 1H), 7.78 (s, 1H), 1.62 (d, 2H), 7.22 (dd, 2H), 7.03 (dd, 2H), 6.87 (d, 2H), 5.69 (dd, 2H), 4.66 (dd, 2H), 4.48 (dd, 2H), 4.22 (s, 3H), 3.79 (s, 3H), 3.26 (s, 3H), 2.85 (s, 3H), 2.26 (s, 3H); MS: 592 (M+1).

To a solution of 401 (25 mg, 0.04 mmol) dissolved in THF (2 mL) and cooled to −20° C. was added MeLi (50 μL, 0.08 mmol, 1.6M diethyl ether solution). The reaction was stirred for 2 days under nitrogen atmosphere and was allowed to warm to 0° C. while requiring multiple additions of MeLi to coax the reaction to ~66% completion. At which point, the reaction was quenched with sat NH$_4$Cl and diluted with ethyl acetate. The organic layer was washed with H$_2$O and brine, then dried (over Na$_2$SO$_4$), filtered and concentrated in vacuo to afford the crude mixture of 402 and starting material with no further purification nor characterization; MS: 608 (M+1).

403/404: The crude mixture from the synthesis of 402 (28 mg) was treated in similar fashion as before then purified by reversed phase HPLC to afford the desired product 403 (2 mg) and by-product 404 (1 mg) as the TFA salts:

403: 300 MHz $^1$H NMR (CDCl$_3$) δ(ppm) 8.92 (s, 1H), 7.85 (s, 1H), 7.22 (dd, 2H), 7.07 (dd, 2H), 4.85 (dd, 2H), 4.23 (s, 3H), 3.62 (dd, 2H), 3.25 (s, 3H), 2.85 (s, 3H), 1.32 (d, 6H); 300 MHz $^{19}$F NMR (CDCl$_3$) δ(ppm) −76.33, −115.79; MS: 488 (M+1).

404: 300 MHz $^1$H NMR (CDCl$_3$) δ(ppm) 8.9 (s, 1H), 7.85 (s, 1H), 7.23 (dd, 2H), 7.07 (dd, 2H), 4.7 (dd, 2H), 4.5 (dd, 2H), 4.23 (s, 3H), 3.25 (s, 3H), 2.85 (s, 3H), 2.27 (s, 3H); 300 MHz $^{19}$F NMR (CDCl$_3$) δ(ppm) −76.26, −115.73; MS: 472 (M+1).

Example 137

Synthesis of Compound 408

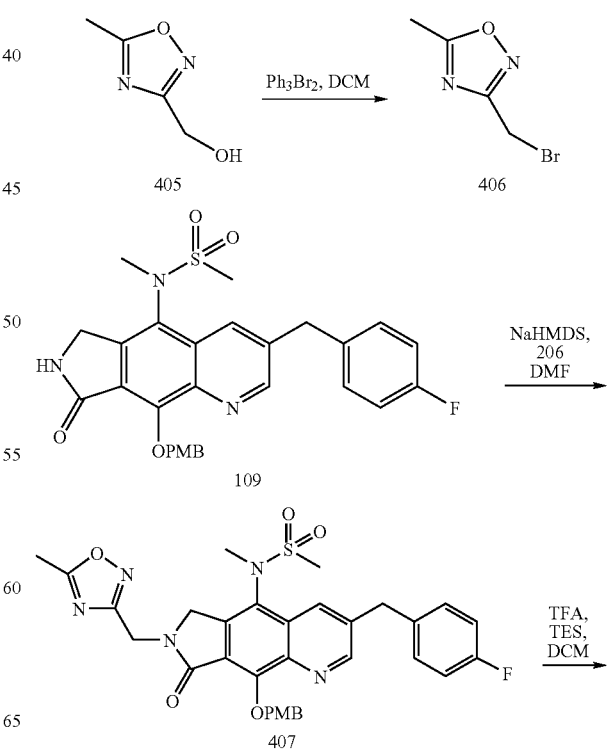

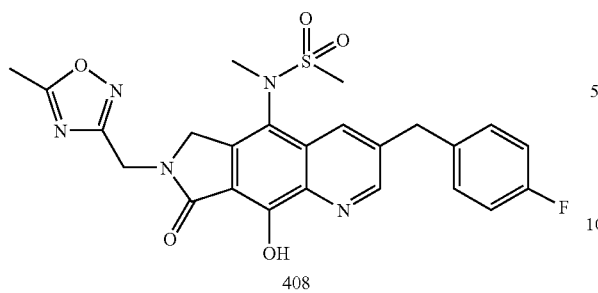

408

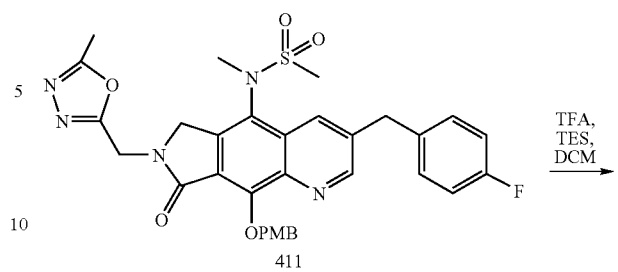

411

A solution of commercially available (5-methyl 1,2,4-oxadiazol-3-yl)methanol 405 (400 mg, 3.51 mmol) in dichloromethane (35 mL) cooled in an ice bath to 0° C. was treated with dibromotriphenyl phosphorane (1.92 g, 4.56 mmol)—slowly added in 2 portions. After being stirred at room temperature, under nitrogen atmosphere, overnight, the reaction mixture was concentrated down in vacuo. Then, the crude residue was purified by chromatography on silica gel (2/8—ethyl acetate/hexane) to afford the desired bromide 406 (472 mg, 76%): 300 MHz $^1$H NMR (CDCl$_3$) δ(ppm) 4.404 (s, 2H), 2.619 (s, 3H).

The compound was made in a similar fashion as before using 406 as the alkylating agent to afford the desired product 407 (52 mg, 88%): 300 MHz $^1$H NMR (CDCl$_3$) δ(ppm) 8.96 (s, 1H), 7.82 (s, 1H), 7.655 (d, 2H), 7.22 (dd, 2H), 7.07 (dd, 2H), 6.87 (d, 2H), 5.76 (dd, 2H), 4.89 (dd, 2H), 4.79 (dd, 2H), 4.24 (s, 3H), 3.8 (s, 3H), 3.26 (s, 3H), 2.87 (s, 3H), 2.60 (s, 3H); MS: 632 (M+1).

The compound was made in a similar fashion as before to afford the desired product 408 (35.6 mg, 85%) as the free parent: 300 MHz $^1$H NMR (DMSO) δ(ppm) 8.87 (s, 1H), 8.18 (s, 1H), 7.38 (dd, 2H), 7.14 (dd, 2H), 4.83 (dd, 2H), 4.66 (dd, 2H), 4.27 (s, 3H), 3.24 (s, 3H), 3.16 (s, 3H), 2.56 (s, 3H); 300 MHz $^{19}$F NMR (CDCl$_3$) δ(ppm) −117.095; MS: 512 (M+1).

Example 138

Synthesis of Compound 412

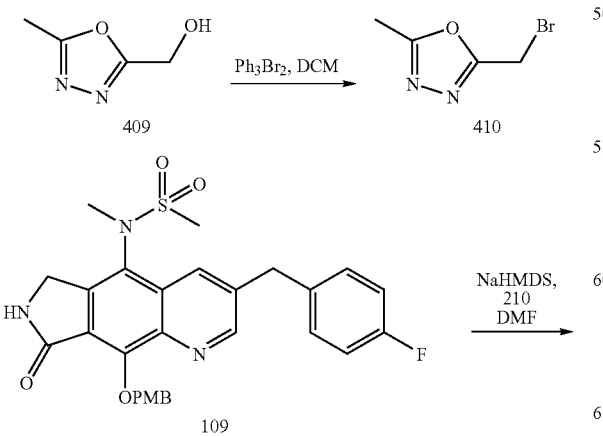

412

Starting with commercially available (5-methyl 1,2,4-oxadiazol-3-yl)methanol 409 (400 mg, 3.51 mmol), the compound was made in a similar fashion as before to afford the desired product 410: 300 MHz $^1$H NMR (CDCl$_3$) δ(ppm) 4.489 (s, 2H), 2.567 (s, 3H).

The compound was made in a similar fashion as before to afford the desired product 411 (48 mg, 81%): 300 MHz $^1$H NMR (CDCl$_3$) δ(ppm) 8.95 (s, 1H), 7.83 (s, 1H), 7.63 (d, 2H), 7.23 (dd, 2H), 7.07 (dd, 2H), 6.87 (d, 2H), 5.75 (dd, 2H), 5.03 (dd, 2H), 4.72 (dd, 2H), 4.235 (s, 3H), 3.8 (s, 3H), 3.25 (s, 3H), 2.88 (s, 3H), 2.547 (s, 3H); MS: 632 (M+1).

The compound was made in a similar fashion as before then purified by reversed phase HPLC (not buffered/neutral solvents) to afford the desired product 412 (19 mg, 52%) as the free parent: 300 MHz $^1$H NMR (DMSO) δ (ppm) 8.87 (s, 1H), 8.18 (s, 1H), 7.38 (dd, 2H), 7.14 (dd, 2H), 4.95 (dd, 2H), 4.67 (dd, 2H), 4.28 (s, 3H), 3.24 (s, 3H), 3.16 (s, 3H), 2.467 (s, 3H); 300 MHz $^{19}$F NMR (CDCl$_3$) δ(ppm) −117.092; MS: 512 (M+1).

Example 139

Synthesis of Compound 423

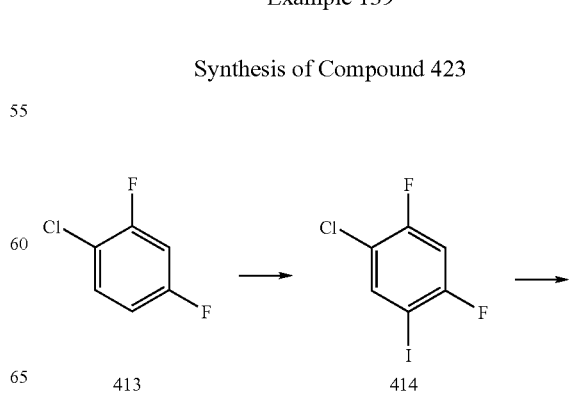

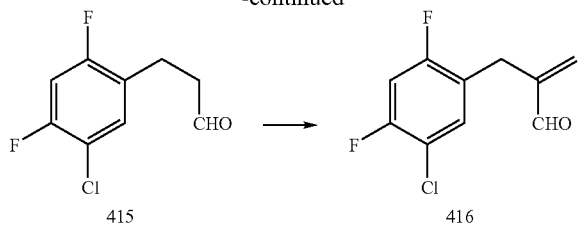

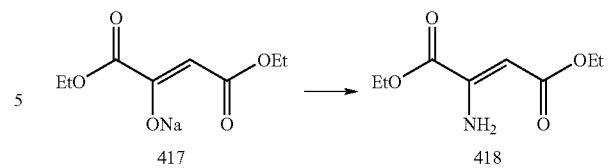

See *Nucs., Nuct., Nuc. Acids*, 20(1&2), 11-140. Into a flask containing 1-Chloro-2,4-difluoro-benzene 413 is added methanesulphonic acid (30 mL, 336 mol, 3.35 equiv.) and cooled to 0° C. before adding N-iodosuccinimide (39.7 gm, 176 mmol, 1.05 equiv) which is added slowly in 4 portions over 30 minutes. The reaction was allowed to warm up to room temperature and stir for 90 minutes. The reaction was quenched by slowly adding ice-water while it is stirring vigorously. Hexanes were added and the reaction mixture extracted (2×). The organic layers were washed with saturated $NaHSO_3$ (3×). This was followed by washing with water (2×) and brine. The organic layer was dried over $Na_2SO_4$, filtered and concentrated in vacuo. A silica gel plug (2 inch long) was used to purify the product using Hexanes (100%) as eluent. A clear oil of 414 (43.3 g, 94%) was obtained. $^1H$ NMR (300 MHz) $CDCl_3$ δ (ppm): 7.79 (dd, $J_1$=7.8, $J_2$=6.6 Hz, 1H), 6.95 (t, J=8.1 Hz, 1H). $^{19}F$ NMR (300 MHz) $CDCl_3$ δ (ppm): −91.76, −110.77.

Into a flask containing 1-Fluoro-4-iodobenzene 414 (46.7 gm, 170.6 mmol, 1 equiv) was added DMF (50 mL, 2 M) along with $NaHCO_3$ (57.3 gm, 682.5 mmol, 4 equiv.), $Pd(OAc)_2$ (1.53 g, 6.8 mmol, 0.04 equiv.), allyl alcohol (34.9 mL, 511.9 mol, 3 equiv.) and tri-ethylammonium benzyl chloride (46.6 gm, 204.7 mmol, 1.2 equiv.) was added lastly. The reaction was warmed to 50° C. under an inert atmosphere. After three hours, TLC indicated the reaction was complete and it was cooled down to room temp and added ethyl ether (500 mL) and water (300 mL). The reaction mixture was separated and the organic layer washed with water (2×200 mL), brine (100 mL) before being dried over $Na_2SO_4$, filtered and concentrated in vacuo. ISCO flash column chromatography was carried out using Hexanes-EtOAc (7/3) to obtain 27.9 g (80%) of the desired aldehyde 415. 300 MHz $^1H$ NMR ($CDCl_3$) δ (ppm) 9.81 (s, 1H), 7.26 (t, J=8.1 Hz, 1H), 6.86 (t, J=9 Hz, 1H), 2.90 (t J=7.2 Hz, 2H), 2.81 (t, J=7.2 Hz, 2H). 300 MHz $^{19}F$ NMR ($CDCl_3$) δ(ppm) −114.20, −116.81

Into a flask containing aldehyde 415 (27.9 g, 0.2 mmol, 1 equiv.) was added formaldehyde (14.8 mL, 0.2 mmol, 1:2 equiv., 37% in water) followed by diethylamine HCl salt (20.0 g, 0.2 mmol, 1.2 equiv.) and the reaction was heated to 110° C. for an hour before being cooled down and diluted with EtOAc and water. The reaction mixture was separated and the organic layer washed with water (2×200 mL), brine (100 mL) before being dried over $Na_2SO_4$, filtered and concentrated in vacuo to produce a dark brown oil which was passed over a 2 inch silica plug to furnish 416 (26.9 g). 300 MHz $^1H$ NMR ($CDCl_3$) δ (ppm) 9.60 (s, 1H), 7.27 (s, 1H), 6.86 (t, J=8.7 Hz, 1H), 6.13 (d, J=14.4 Hz, 2H), 3.55 (s, 2H). 300 MHz $^{19}F$ NMR ($CDCl_3$) δ(ppm) −114.20, −116.81.

Diethyl 2-hydroxyfumarate 417 (50 g, 0.24 mol, 1 equiv.) was stirred in EtOH (240 mL, 1 M) and $NH_4OAc$ (36.7 g, 0.48 mol, 2 equiv.) before acetic acid (13.6 mL, 0.24 mmol, 1 equiv.) was added and warmed to 90° C. The reaction was allowed to stir for 1 hr, before being cooled down and concentrated in vacuo to an oil. Water (200 mL) along with $NH_4OH$ was added to bring the pH to around 8 which was extracted with $CH_2Cl_2$ (2×100 mL). The organic layer was washed with water (3×200 mL), brine (100 mL) before being dried over $Na_2SO_4$, filtered and concentrated in vacuo. The mixture was then placed on a 2 inch silica plug and eluted with 7/3 Hex/EtOAc to yield a light brown oil to yield 34.5 gm of 418 (yield of 77%) of desired product.

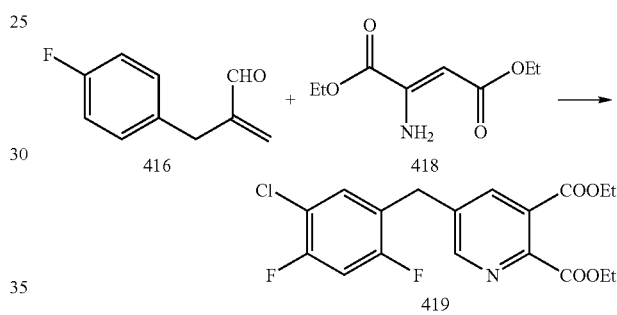

Into a flask containing olefin 416 (26.9 g, 0.12 mol, 1 equiv.) was stirred in n-Butanol (55 mL, 2.25 M) and to it added di-ester 418 (28.0 g, 0.14 mmol, 1.2 equiv.) and pTSA (475 mg, 0.44 mmol, 0.02 equiv.). The reaction was heated to 120° C. and allowed to stir overnight. It was concentrated in vacuo and purified by ISCO flash column chromatography using Hexanes/Ethyl acetate (4/1). 30.5 gm (yield is 64%) of 419 was obtained as a brown oil. (This product includes impurities that move very closely with the desired product. They are however mostly hydrolyzed in the ensuing reaction). 300 MHz $^1H$ NMR ($CDCl_3$) δ (ppm) 8.63 (s, 1H), 7.94 (s, 1H), 7.20 (t, J=7.5 Hz, 1H), 6.98 (t, J=9.0 Hz, 1H), 4.47 (q, J=7.2 Hz, 2H), 4.32 (q, J=7.2 Hz, 2H), 4.02 (s, 2H), 1.45-1.35 (m, 6H). 300 MHz $^{19}F$ NMR ($CDCl_3$) δ(ppm) −112.40, −114.79. MS: 383.93 (M+1).

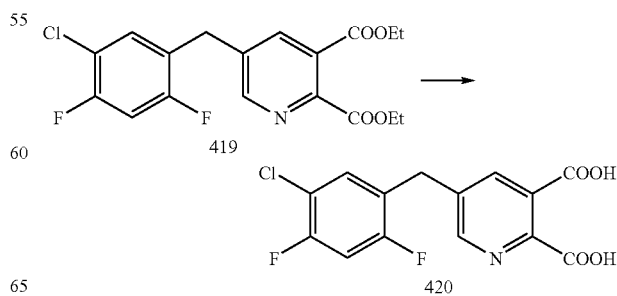

Into a flask containing the di-ester 419 (30.46 gm, 79.5 mmol, 1 equiv.) was added EtOH (200 mL, 0.4 M). Separately a solution of NaOH (12.7 g, 318.1 mmol, 4 equiv.) was dissolved in water (200 mL, 0.4 M) and added to the reaction solution. After an hour, TLC indicated the reaction was complete. It was concentrated in vacuo and treated with HCl$_{(aq)}$ (6 N) to a pH of 2. Extraction was carried out with EtOAc (2×200 mL) and the organic layer washed with water (2×200 mL), brine before being dried over Na$_2$SO$_4$, filtered and concentrated in vacuo to produce an orange yellow solid 420 (23.5 gm, 90%). 300 MHz $^1$H NMR (CDCl$_3$) δ (ppm) 8.64 (s, 1H), 8.03 (s, 1H), 7.76 (t, J=8.4 Hz, 1H), 7.55 (t, J=9.3 Hz, 1H), 4.01 (s, 2H). 300 MHz $^{19}$F NMR (CDCl$_3$) δ(ppm) −114.23, −114.42. MS: 328.00 (M+1).

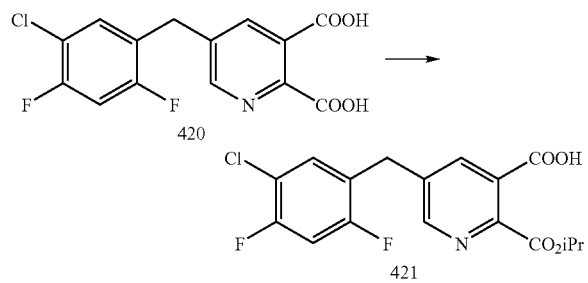

Into a flask containing diacid 420 (23.5 gm, 71.9 mmol, 1 equiv.) was added Ac$_2$O (70 mL, 1 M) and refluxed for 2 hr. The reaction was then cooled and concentrated in vacuo. It was azeotroped with toluene (2×10 mL) and used directly in the next reaction. It was dissolved in THF (240 mL, 0.3 M) and the flask chilled to −10° C. before Mg (ClO$_4$)$_2$ (19.3 g, 86.3 mmol, 1.2 equiv.) was added under an inert atmosphere. The reaction was allowed to stir for 5 min. before isopropanol (240 mL, 0.3 M) was added and the reaction allowed to warm up to room temperature and stirred overnight. The reaction was concentrated in vacuo to a paste before being diluted with ethyl acetate (500 mL) and with water (200 mL). The organic layer was washed with saturated NH$_4$Cl and brine then dried over Na$_2$SO$_4$, filtered and concentrated in vacuo to yield a light brown solid as 421 (25.3 gm, y. 96%). Small amount (less than 10%) of regioisomer is also obtained. 300 MHz $^1$H NMR (CDCl$_3$) δ (ppm) 8.70 (d, J=7.5 Hz, 1H), 8.08 (d, J=5.4 Hz, 1 Hz, 1H), 7.22 (t, J=7.2 Hz, 1H), 6.98 (t, J=8.7 Hz, 1H), 5.33 (st, 1H), 4.02 (s, 2H), 1.04 (d, J=6.3 Hz, 6H).

300 MHz $^{19}$F NMR (CDCl$_3$) δ(ppm) −112.30, −114.75. MS: 369.93 (M+1).

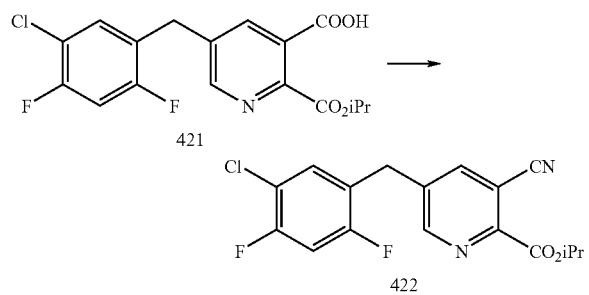

Into a flask containing acid 421 (3.2 g, 8.7 mmol, 1 equiv.) was added pyridine (30 mL, 0.3 M) and chilled to 0° C. before methanesulfonyl chloride (1.1 mL, 14.0 mmol, 1.6 equiv.) was added under an inert atmosphere. The reaction was allowed to stir for 1 hr before ammonia was bubbled into the reaction for several minutes and then allowed to stir for 30 min. The flask was then placed onto a rotary evaporator to remove excess NH$_3$. The flask was cooled to 0° C. before methanesulfonyl chloride (5.4 mL, 70.0 mmol, 8 equiv.) was added slowly. The reaction was allowed to warm up to room temperature and stir overnight. The reaction was concentrated down to a paste and slowly quenched with saturated NaHCO$_3$ which was stirred for 1 hr. Ethyl acetate was added and the reaction extracted (3×). The organic layers were combined and washed with water (2×), saturated NaHCO$_3$, brine and dried over Na$_2$SO$_4$, filtered and concentrated in vacuo. The reaction was purified by ISCO silica gel chromatography to yield nitrile 422 (1.9 g, yield of 64%). 300 MHz $^1$H NMR (CDCl$_3$) δ (ppm) 8.80 (s, 1H), 7.89 (s, 1 Hz, 1H), 7.22 (t, J=7.8 Hz, 1H), 7.00 (t, J=8.7 Hz, 1H), 5.40 (septet, 1H), 4.06 (s, 2H), 1.04 (d, J=6.6 Hz, 6H). 300 MHz $^{19}$F NMR (CDCl$_3$) δ(ppm) −111.38, −114.61

MS: 369.93 (M+1). R$_f$ 0.35 (7/3 Hexanes/EtOAc)

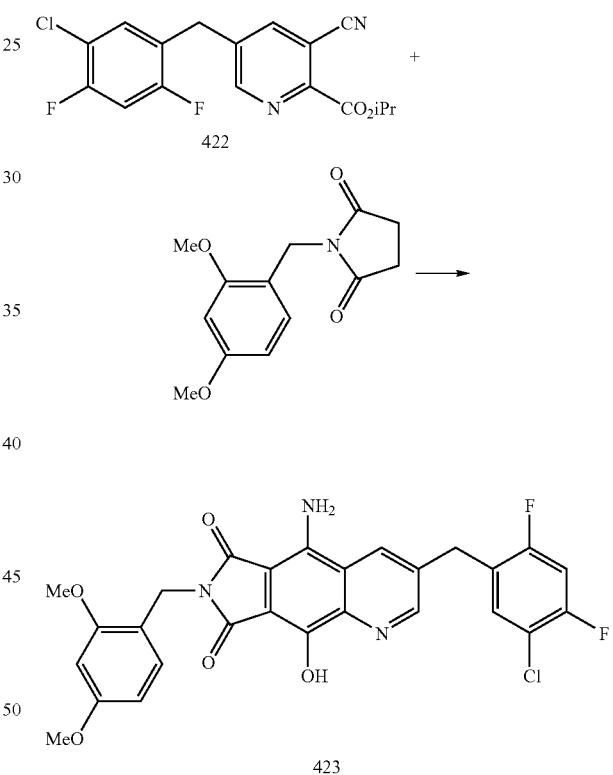

Succinimide (1.6 g, 6.6 mmol, 1.2 equiv.) and nitrile 422 (1.9 g, 5.51 mmol, 1 equiv.) were dissolved in THF (27 mL, 0.2 M) and cooled to 0° C. To this was added LiHMDS (13.23 mL, 30.91 mmol, 2.4 equiv., 1 M THF) drop wise over 10 min. After 1 hr, reaction was complete and was quenched with acid (10 mL, 6 M HCl) and rotavaped to a small volume. The paste was washed with a mixture of diethyl ether and hexanes along with water before being allowed to dry under vacuum at 100° C. A red solid was obtained of 423 (2.85 g, 91% yield).

300 MHz $^1$H NMR (DMSO-d$_6$) δ (ppm) 8.95 (s, 1H), 8.67 (d, 1H), 7.73 (t, J=7.8 Hz, 1H), 7.54 (t, J=8.8 Hz, 1H), 2H), 6.88 (d, J=8.1 Hz, 1H), 6.56 (d, J=2.1 Hz, 1H), 6.41 (d, J=8.1

Hz, 1H), 4.60 (s, 2H), 4.23 (s, 2H), 3.80 (s, 3H), 3.71 (s, 3H). 300 MHz $^{19}$F NMR (DMSO-d$_6$) δ(ppm) −114.47, −114.20. MS: 539.87 (M+1).

Example 140

Synthesis of Compound 429

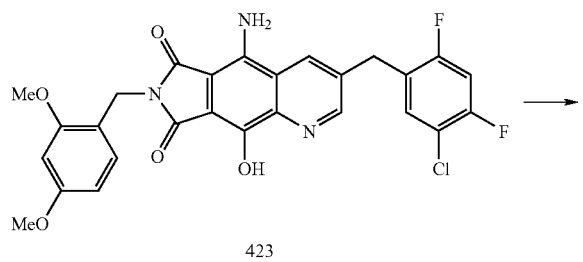

423

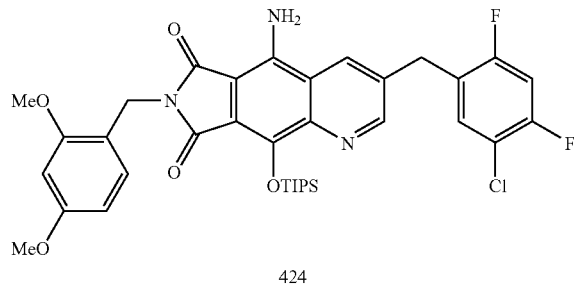

424

Phenol 423 (3.1 g, 5.8 mmol, 1 equiv.) in DMF (20 mL, 0.2 M) was treated with TEA (2.4 mL, 17.3 mmol, 1.5 equiv.) and DMAP (350 mg, 2.9 mmol, 0.5 equiv.). TIPSCl (1.8 mL, 8.63 mmol, 1.5 equiv.) was slowly added and the reaction mixture was stirred at room temperature for 2 h under a nitrogen atmosphere. The reaction mixture was diluted with ethyl acetate (200 mL) and quenched with water (100 mL). The layers were separated and the aqueous layer was extracted with ethyl acetate (200 mL). The combined organic layers were washed with aqueous LiCl (twice), citric acid (5% solution) and brine then dried (over Na$_2$SO$_4$), filtered and concentrated in vacuo. The crude product was triturated in hexane and filtered to afford the desired product 424 (2.9 g, 73%) as a yellow solid. 300 MHz $^1$H NMR (CDCl$_3$) δ (ppm) 8.79 (s, 1H), 7.93 (s, 1H), 7.25-7.15 (m, 2H), 7.10-7.03 (m, 2H), 6.43-6.38 (m, 3H), 5.63 (s, 2H), 4.83 (s, 2H), 4.16 (s, 2H), 3.82 (s, 3H), 3.78 (s, 3H), 1.55-1.50 (m, 3H), 1.11 (d, J=7.5 Hz, 18H). 300 MHz $^{19}$F NMR (CDCl$_3$) δ(ppm) −112.43, −114.71. MS: 696.1 (M+1).

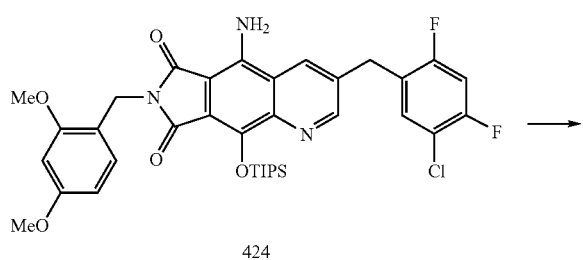

424

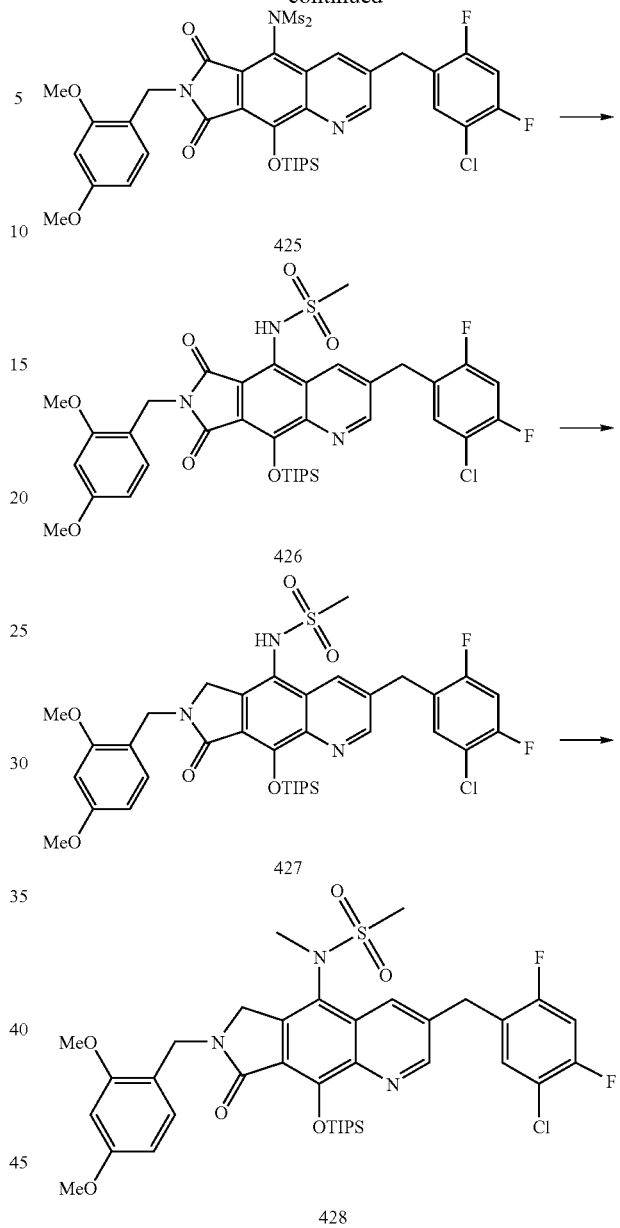

Aniline 424 (2.9 g, 4.1 mmol, 1 equiv.) in CH$_2$Cl$_2$ (40 mL) was treated with TEA (4.6 mL, 32.8 mmol, 8 equiv.) and stirred at −10° C. as a solution of methanesulfonyl chloride (1.3 mL, 16.4 mmol, 4 equiv.) in pre-dissolved in CH$_2$Cl$_2$ (15 mL) was added drop wise over 45 min. After addition, the mixture was stirred for 3 h while warming to 0° C. The volatiles were removed in vacuo then the residue was dissolved in CH$_2$Cl$_2$ (300 mL) then quenched with H$_2$O (200 mL). The layers were separated and the aqueous layer was extracted with CH$_2$Cl$_2$ (100 mL). The combined organic layer was washed with H$_2$O (3×), citric acid (5% solution) and brine then dried (over Na$_2$SO$_4$), filtered and concentrated in vacuo with no further purification to yield the crude intermediate bis-mesylate 425 (3.3 g, 95% mass recovery). 300 MHz $^1$H NMR (CDCl$_3$) δ (ppm) 8.84 (s, 1H), 8.14 (s, 1H), 7.40-7.25 (m, 1H), 7.10-7.03 (m, 1H), 7.00-6.97 (m, 1H), 6.45-6.40 (s, 3H), 4.85 (s, 2H), 4.22 (s, 2H), 3.79 (s, 3H), 3.78 (s, 3H), 3.43 (s, 6H), 1.59-1.52 (m, 3H), 1.12 (d, J=7.8 Hz, 18H). 300 MHz $^{19}$F NMR (CDCl$_3$) δ(ppm) −112.46, −114.70

MS: 851.97 (M+1).

A solution of bis-mesylate 425 (3.3 g, 3.9 mmol, 1 equiv.) in THF (20 mL, 0.2 M) was stirred at −10° C. as potassium t-butoxide (5.9 mL, 5.9 mmol, 1.5 equiv., 1.0 M solution in THF) was added drop wise over 10 min. After 1 hr, the solution was diluted with ethyl acetate (200 mL) and quenched with H$_2$O (200 mL). The layers were separated and the aqueous layer was extracted with ethyl acetate (200 mL, 2×). The combined organic layers were washed with H$_2$O (3×), saturated NH$_4$Cl and brine then dried (over Na$_2$SO$_4$), filtered and concentrated in vacuo. The crude residue (3.0 g) was dissolved in CH$_2$Cl$_2$ (30 mL) and passed through a SiO$_2$ plug, which was pre-washed with 9/1—ethyl acetate/hexane+0.05% TEA. The short column was eluted with 0.05% TEA+9/1—ethyl acetate/hexane then 0.05% TEA+2/1—ethyl acetate/hexane to afford the mono-mesylate 426 (1.9 g, 2.4 mmol) as a light brown solid. 300 MHz $^1$H NMR (CDCl$_3$) δ (ppm) 8.76 (s, 1H), 8.72 (s, 1H), 7.63 (s, 1H), 7.27-7.17 (m, 2H), 7.10-7.03 (m, 1H), 6.44-6.42 (m, 2H), 4.85 (s, 2H), 4.19 (s, 2H), 3.80 (s, 3H), 3.79 (s, 3H), 2.91 (s, 3H), 1.59-1.52 (m, 3H), 1.12 (d, J=7.8 Hz, 18H).

300 MHz $^{19}$F NMR (CDCl$_3$) δ(ppm) −112.76, −114.85.

MS: 770.05 (M+1).

To imide 426 (1.9 g, 2.5 mmol, 1 equiv.) was added THF (13 mL, 0.2 M) and cooled to 0° C. before adding LiBH$_4$ (1.9 mL, 3.8 mmol, 1.5 equiv.) slowly over 5 min. MeOH (203 μL, 19.23 mmol, 7 equiv.) was added slowly. The reaction was refluxed for about two hours until the reaction was complete. After cooling down, the reaction was diluted with water and THF was removed in vacuo. The resulting solution was diluted with EtOAc (200 mL) followed by water and brine. The solution was dried (over Na$_2$SO$_4$), filtered and concentrated to afford crude lactam 427 (1.8 g, 94% mass recovery) as a light yellow solid. 300 MHz $^1$H NMR (CDCl$_3$) δ (ppm) 8.74 (s, 1H), 8.11 (s, 1H), 7.27-7.19 (m, 3H), 7.10-7.03 (m, 2H), 6.44-6.42 (m, 3H), 6.09 (s, 1H), 4.77 (s, 1H), 4.46 (s, 2H), 4.18 (s, 2H), 3.83 (s, 3H), 3.80 (s, 3H), 2.92 (s, 3H), 1.59-1.52 (m, 3H), 1.12 (d, J=7.8 Hz, 18H).

300 MHz $^{19}$F NMR (CDCl$_3$) δ(ppm) −112.48, −114.99. MS: 760.34 (M+1).

Compound 427 (1.8 g, 2.4 mmol, 1 equiv.) was stirred in DMF (15 mL, 0.2 M) and cooled to 0° C. before being treated with Cs$_2$CO$_3$ (1.2 g, 3.5 mmol, 1.5 equiv.). It was stirred for 5 min. before iodomethane (220 μL, 3.5 mmol, 1.5 equiv.) was added. The reaction mixture was diluted with ethyl acetate then quenched with water. The organic layer was washed with water, saturated NaHCO$_3$, and brine. The solution was dried over sodium sulfate, filtered and concentrated in vacuo. The crude residue was purified by chromatography on silica gel (1/3—Ethyl acetate/Hexane) to afford the desired product 428 (760 mg, 41%). 300 MHz $^1$H NMR (CDCl$_3$) δ (ppm) 8.72 (s, 1H), 7.91 (s, 1H), 7.27-7.19 (m, 3H), 7.02-6.85 (m, 1H), 6.44-6.42 (m, 2H), 4.86 (d, J=14.5 Hz, 1H), 4.68 (d, J=14.5 Hz, 1H), 4.55 (d, J=17.6 Hz, 1H), 4.26 (d, J=17.6 Hz, 1H), 4.18 (s, 2H), 3.84 (s, 3H), 3.80 (s, 3H), 3.24 (s, 3H), 2.94 (s, 3H), 1.59-1.52 (m, 3H), 1.12 (d, J=7.8 Hz, 18H). 300 MHz $^{19}$F NMR (CDCl$_3$) δ(ppm) −112.48, −114.99. MS: 774.13 (M+1).

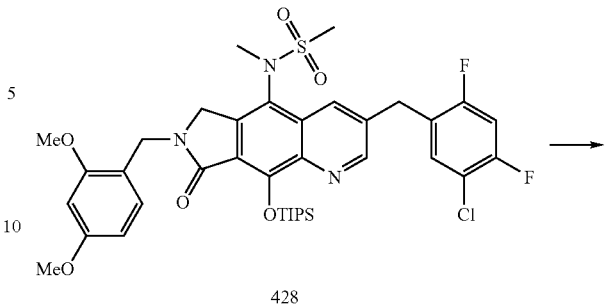

428

Lactam 428 (760 mg, 0.98 mmol, 1 equiv.) was dissolved in trifluoroacetic acid (15 mL) and refluxed to 80° C. overnight. The reaction was concentrated in vacuo and azeotroped with toluene (2×10 mL). The crude residue was suspended in dichloromethane and washed thoroughly via trituration. Sonication was used to aid this washing. The solid was filtered on a sintered funnel and air dried thoroughly. An off-white brownish solid 429 (560 mg) was obtained as the TFA salt. 300 MHz $^1$H NMR (DMSO-d$_6$) δ (ppm) 10.65 (bs, 1H), 8.87 (s, 1H), 8.50 (s, 1H), 8.18 (s, 1H), 7.76 (t, J=8.1 Hz, 1H), 7.53 (t, J=8.7 Hz, 1H), 4.50 (s, 2H), 4.27 (s, 2H), 3.22 (s, 3H), 3.18 (s, 3H). 300 MHz $^{19}$F NMR (DMSO-d$_6$) δ(ppm) −114.45, 114.49

MS: 468.13 (M+1).

Example 141

Synthesis of Compound 432

429

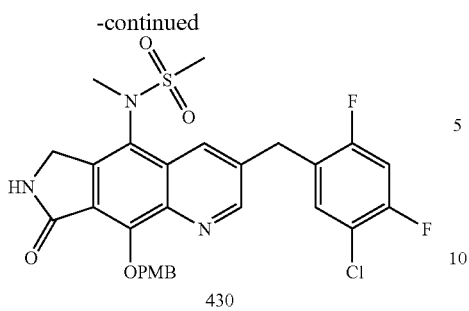

430

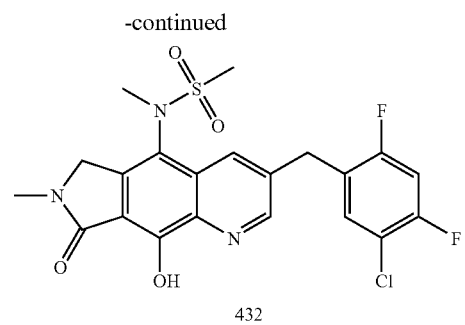

432

To phenol 429 (660 mg, 1.13 mmol, 1 equiv.) was added DMF (12 mL, 0.1 M) followed by $Cs_2CO_3$ (630 mg, 1.9 mmol, 1.7 equiv.) and tetra-butylammonium iodide (83 mg, 0.28 mmol, 0.2 equiv.) before adding p-methoxybenzyl chloride (200 μL, 1.47 mmol, 1.5 equiv.). The reaction was then heated to 65° C. It was cooled to room temperature before diluting with EtOAc (150 mL) and quenching with water. It was extracted with EtOAc and washed with water (2×100 mL), saturated $NH_4Cl$ and brine. The organic layer was dried over sodium sulfate, filtered and concentrated in vacuo. ISCO flash column chromatography was carried out with 4/1 EtOAc/Hexanes to yield 430. 300 MHz $^1H$ NMR ($CDCl_3$) δ (ppm) 8.93 (s, 1H), 7.97 (s, 1H), 7.61 (d, J=8.7 Hz, 2H), 7.28-7.20 (m, 2H), 7.09-7.04 (m, 2H), 6.88 (d, J=8.7 Hz, 2H), 6.26 (bs, 1H), 5.75 (d, J=6.3 Hz, 2H), 4.80 (d, J=17.0 Hz, 1H), 4.50 (d, J=17.0 Hz, 1H), 4.23 (s, 2H), 3.78 (s, 3H), 3.26 (s, 3H), 2.87 (s, 2H).

300 MHz $^{19}F$ NMR ($CDCl_3$) δ(ppm) −112.22, −115.07
MS: 587.86 (M+1).

Lactam 430 (115 mg, 0.2 mmol, 1 equiv.) is dissolved in DMF (3 mL, 0.1 M) and cooled in an ice bath to 0° C. before sodium hydride (9.4 mg, 0.23 mmol, 1.3 equiv., 60% mineral oil) and stirred for 5 minutes under nitrogen atmosphere. Iodomethane (17 μL, 0.27 mmol, 1.4 equiv.) was added and the reaction was allowed to stir for 30 minutes at 0° C. The reaction was quenched with water and diluted with ethyl acetate. The organic layer was washed with water and brine before being dried over $Na_2SO_4$, filtered and concentrated in vacuo. The crude residue was purified by chromatography on silica gel (7/3—Ethyl acetate/Hexane) to afford the desired product 431 (55 mg, 45%). 300 MHz $^1H$ NMR ($CDCl_3$) δ (ppm) 8.94 (d, J=2.1 Hz, 1H), 8.00 (d, J=24.7 Hz, 1H), 7.65 (d, J=8.7 Hz, 1H), 7.28-7.20 (m, 1H), 7.09-7.04 (m, 1H), 6.86 (d, J=8.7 Hz, 2H), 5.74 (d, J=10.8 Hz, 1H), 5.68 (d, J=10.8 Hz, 1H), 4.75 (d, J=17.1 Hz, 1H), 4.46 (d, J=17.1 Hz, 1H), 4.19 (s, 2H), 3.80 (s, 3H), 3.32 (s, 3H), 3.22 (s, 3H), 2.90 (s, 3H). 300 MHz $^{19}F$ NMR ($CDCl_3$) δ(ppm) −112.23, −115.11.
MS: 601.87 (M+1).

Compound 432 was made in a similar fashion as has been previously described for similar reactions. 300 MHz $^1H$ NMR ($CDCl_3$) δ (ppm) 8.97 (s, 1H), 7.97 (s, 1H), 7.28-7.20 (m, 2H), 7.09-7.04 (m, 2H), 4.75 (d, J=18.6 Hz, 1H), 4.46 (d, J=18.6 Hz, 1H), 4.21 (s, 2H), 3.80 (s, 3H), 3.32 (s, 3H), 3.22 (s, 3H), 3.00 (s, 3H). 300 MHz $^{19}F$ NMR ($CDCl_3$) δ(ppm) −112.11, 115.06

MS: 504.07 (M+23).

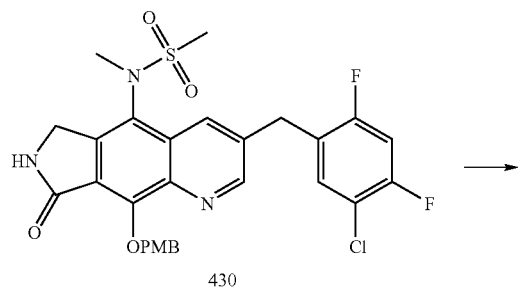

430

Example 142

Synthesis of Compound 433

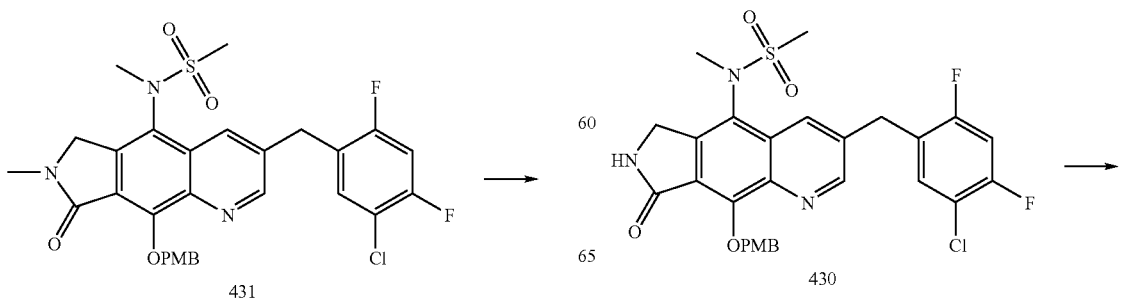

431          430

-continued

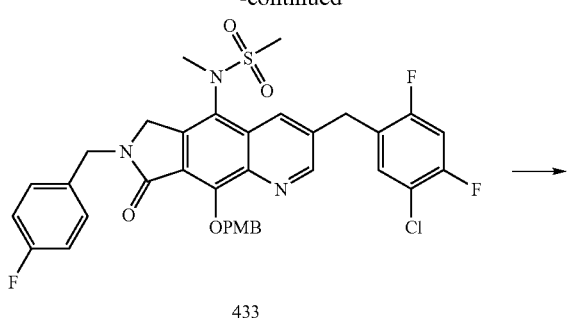

433

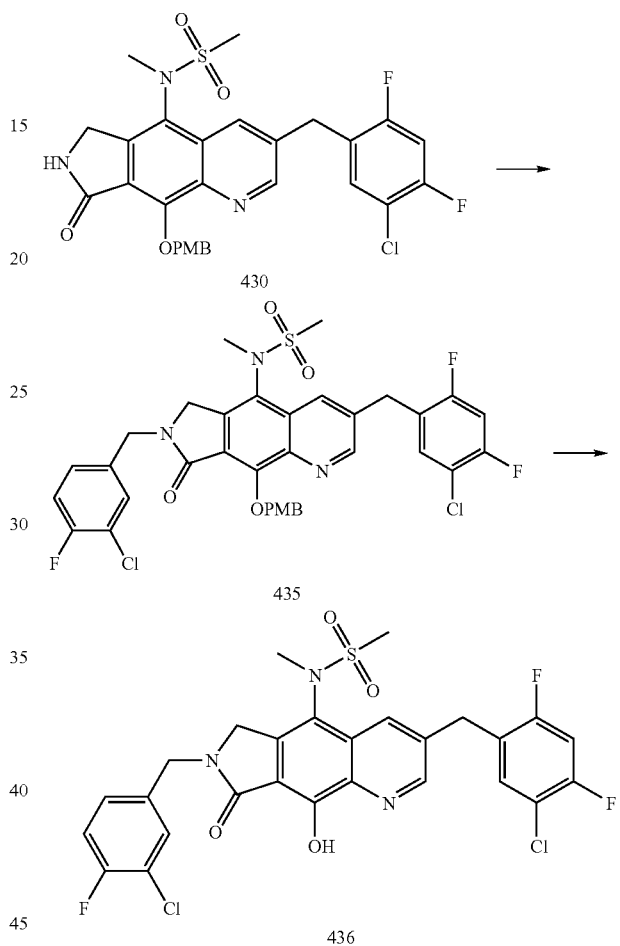

Lactam 430 (35 mg, 0.06 mmol, 1 equiv.) is dissolved in DMF (2 mL, 0.1 M) and cooled in an ice bath to 0° C. before NaHMDS (65 μL, 0.065 mmol, 1.1 equiv., 1 M in THF) and stirred for 5 minutes under nitrogen atmosphere. p-Fluorobenzyl bromide (10 μL, 0.077 mmol, 1.4 equiv.) was added and the reaction was allowed to stir for 30 minutes at 0° C. The reaction was quenched with water and diluted with ethyl acetate. The organic layer was washed with water and brine before being dried over $Na_2SO_4$, filtered and concentrated in vacuo. The crude residue was purified by chromatography on silica gel (7/3—Ethyl acetate/Hexane) to afford the desired product 433. 300 MHz $^1$H NMR ($CDCl_3$) δ (ppm) 8.92 (s, 1H), 7.92 (s, 1H), 7.65 (d, J=8.7 Hz, 2H), 7.36-7.20 (m, 4H), 7.09-7.04 (m, 5H), 5.80 (d, J=10.2 Hz, 1H), 5.70 (d, J=10.2 Hz, 1H), 5.03 (d, J=15.0 Hz, 1H), 4.66 (d, J=16.8 Hz, 1H), 4.59 (d, J=15.0 Hz, 1H), 4.33 (d, J=16.8 Hz, 1H), 4.20 (s, 2H), 3.81 (s, 3H), 3.26 (s, 3H), 2.99 (s, 3H). 300 MHz $^{19}$F NMR ($CDCl_3$) δ(ppm) −112.21, −114.86, −115.11. MS: 695.23 (M+1).

Compound 434 was made in a similar fashion as has been previously described for similar reactions. 300 MHz $^1$H NMR ($CDCl_3$) δ (ppm) 8.87 (s, 1H), 7.94 (s, 1H), 7.36-7.20 (m, 3H), 7.09-7.04 (m, 3H), 4.94 (d, J=15.0 Hz, 1H), 4.67 (d, J=16.8 Hz, 1H), 4.60 (d, J=15.0 Hz, 1H), 4.33 (d, J=16.8 Hz, 1H), 4.21 (s, 2H), 3.26 (s, 3H), 2.99 (s, 3H). 300 MHz $^{19}$F NMR ($CDCl_3$) δ(ppm) −112.10, −115.08, −117.00. MS: 729.93 (M+1).

Example 143

Synthesis of Compound 436

Lactam 430 (35 mg, 0.06 mmol, 1 equiv.) is dissolved in DMF (2 mL, 0.1 M) and cooled in an ice bath to 0° C. before NaHMDS (83 μL, 0.083 mmol, 1.4 equiv., 1 M in THF) and stirred for 5 minutes under nitrogen atmosphere. 3-Chloro, -4-Fluorobenzyl bromide (20 μg, 0.089 mmol, 1.5 equiv.) was added and the reaction was allowed to stir for 30 minutes at 0° C. The reaction was quenched with water and diluted with ethyl acetate. The organic layer was washed with water and brine before being dried over $Na_2SO_4$, filtered and concentrated in vacuo. The crude residue was purified by chromatography on silica gel (7/3—Ethyl acetate/Hexane) to afford the desired product 435. 300 MHz $^1$H NMR ($CDCl_3$) δ (ppm) 8.94 (d, J=1.8 Hz, 1H), 7.91 (s, 1H), 7.65 (d, J=9.0 Hz, 2H), 7.36-7.20 (m, 4H), 7.09-7.04 (m, 3H), 5.80 (d, J=10.8 Hz, 1H), 5.70 (d, J=10.8 Hz, 1H), 5.03 (d, J=15.1 Hz, 1H), 4.66 (d, J=17.1 Hz, 1H), 4.59 (d, J=15.1 Hz, 1H), 4.33 (d, J=17.1 Hz, 1H), 4.20 (s, 2H), 3.81 (s, 3H), 3.27 (s, 3H), 2.99 (s, 3H). 300 MHz $^{19}$F NMR ($CDCl_3$) δ(ppm) −112.21, −114.86, −115.11. MS: 695.23 (M+1).

Compound 436 was made in a similar fashion as has been previously described for similar reactions. 300 MHz $^1$H NMR (CDCl$_3$) δ (ppm) 8.87 (s, 1H), 7.94 (s, 1H), 7.36-7.20 (m, 3H), 7.09-7.04 (m, 2H), 6.98-6.92 (m, 1H), 4.94 (d, J=15.0 Hz, 1H), 4.67 (d, J=16.8 Hz, 1H), 4.60 (d, J=15.0 Hz, 1H), 4.33 (d, J=16.8 Hz, 1H), 4.21 (s, 2H), 3.26 (s, 3H), 2.99 (s, 3H). 300 MHz $^{19}$F NMR (CDCl$_3$) δ(ppm) −111.98, −115.04, −116.67. MS: 610.07 (M+1).

Example 144

Synthesis of Compound 440

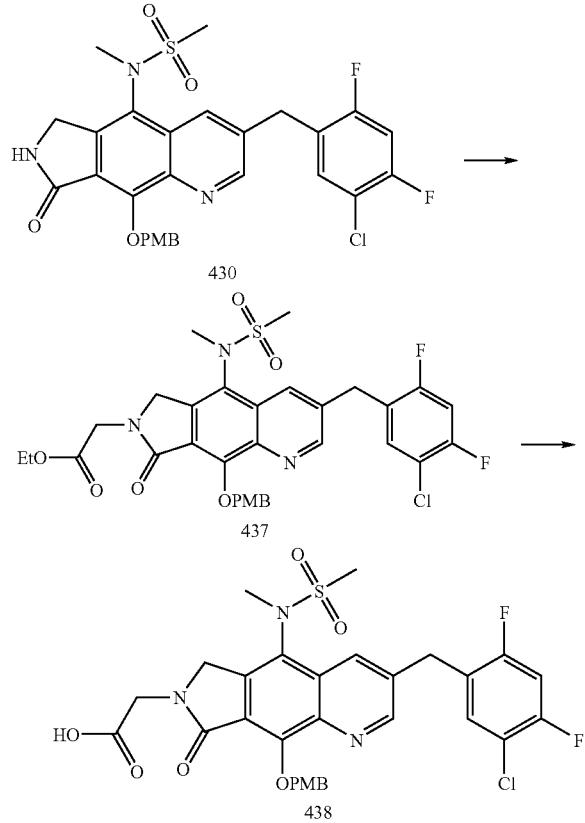

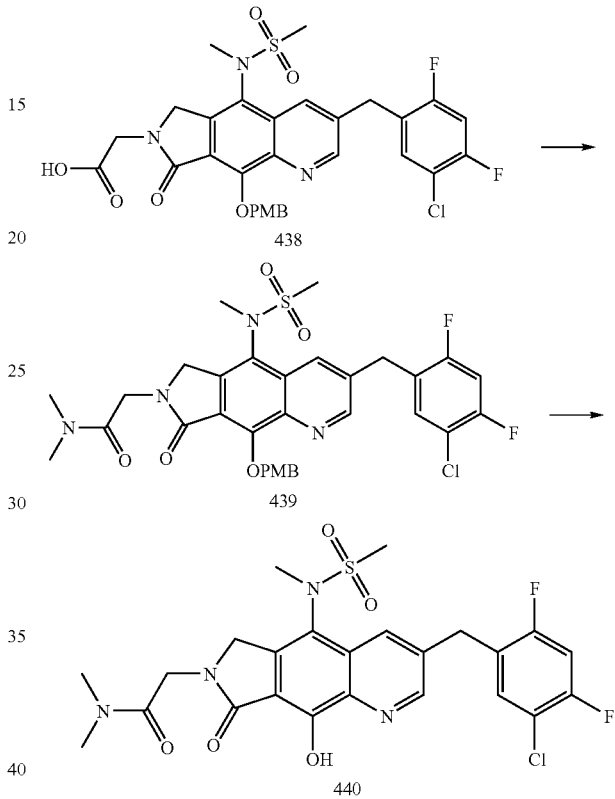

To flask containing lactam 430 (50 mg, 0.085 mmol 0.1 equiv.) was added DMF (0.85 mL, 0.1 M) and LiHMDS (120 μL, 0.12 mmol, 1.4 equiv.). After several minutes, ethyl bromoacetate (15 μL, 0.13 mmol, 1.5 equiv.) was added. When the reaction was complete it was quenched with water and diluted with Ethyl Acetate. The organic layer was washed with water and brine before being dried over Na$_2$SO$_4$, filtered and concentrated in vacuo. The crude residue was purified by chromatography on silica gel (7/3—Ethyl acetate/Hexane) to afford the desired product 437 (55 mg, 45%). 300 MHz $^1$H NMR (CDCl$_3$) δ (ppm) 8.92 (s, 1H), 7.96 (s, 1H), 7.64 (d, J=8.7 Hz, 1H), 7.28-7.20 (m, 1H), 7.00-6.95 (m, 1H), 6.86 (d, J=8.7 Hz, 2H), 5.74 (d, J=10.8 Hz, 1H), 5.68 (d, J=10.8 Hz, 1H), 4.79 (d, J=18.3 Hz, 1H), 4.69 (d, J=14.2 Hz, 1H), 4.46 (d, J=18.3 Hz, 1H), 4.22 (d, J=14.2 Hz, 1H), 4.10-4.32 (m, 5H), 3.80 (s, 3H), 3.33 (s, 3H), 3.02 (s, 3H), 1.3 (t, J=6.3 Hz, 3H). 300 MHz $^{19}$F NMR (CDCl$_3$) δ(ppm) −112.28, −115.06. MS: 673.93 (M+1).

To a flask containing ester 437 (55 mg, 0.082 mmol, 1 equiv.) was added THF (2 mL). A solution of NaOH (13 mg, 0.33 mmol, 4 equiv.) dissolved in H$_2$O (2 mL) was added and allowed to stir until reaction was complete. The reaction was diluted with EtOAc and the organic layer was washed with water and brine before being dried over Na$_2$SO$_4$, filtered and concentrated in vacuo and used as is. A light yellow solid was obtained of acid 438. 300 MHz $^{19}$F NMR (CDCl$_3$) δ(ppm) −112.79, −114.96

MS: 673.07 (M+1).

To acid 438 (59 mg, 0.09 mmol, 1 equiv.) was added DMF (2 mL) followed by DIPEA (90 μl, 0.55 mmol, 6 equiv.) and N,N dimethlyamine (230 μL, 0.45 mmol, 5 equiv., 2 M in THF) and HATU (51 mg, 1.4 mmol, 1.5 equiv.). When the reaction was complete it was quenched with water and diluted with Ethyl Acetate. The organic layer was washed with water and brine before being dried over Na$_2$SO$_4$, filtered and concentrated in vacuo. The crude residue was purified by chromatography on silica gel (4/1—Ethyl acetate/MeOH) to afford the desired product 439. 300 MHz $^1$H NMR (CDCl$_3$) δ (ppm) 8.89 (s, 1H), 7.99 (s, 1H), 7.79 (d, J=8.7 Hz, 2H), 7.28-7.20 (m, 1H), 7.09-7.04 (m, 1H), 6.86 (d, J=8.7 Hz, 2H), 5.74 (d, J=11.1 Hz, 1H), 5.68 (d, J=10.8 Hz, 1H), 4.88-4.70 (m, 3H), 4.19 (s, 2H), 4.10 (d, J=16.5 Hz, 1H), 3.80 (s, 3H), 3.32 (s, 3H), 3.12 (s, 3H), 3.03 (s, 3H), 2.86 (s, 3H). 300 MHz $^{19}$F NMR (CDCl$_3$) δ(ppm) −112.50, −113.64. MS: 672.80 (M+1).

Compound 440 was made in a similar fashion as has been previously described for similar reactions. 300 MHz $^1$H NMR (CDCl$_3$) δ (ppm) 8.88 (s, 1H), 8.07 (s, 1H), 7.32 (t, J=5.2 Hz, 2H), 6.99 (t, J=5.2 Hz, 2H), 4.93 (d, J=10.2 Hz, 1H), 4.8 (d, J=10.2 Hz, 1H), 4.81 (d, J=9.9 Hz, 1H), 4.22 (s, 2H), 4.16 (d, J=9.9 Hz, 1H), 3.32 (s, 3H), 3.12 (s, 3H), 3.03 (s, 3H), 2.86 (s, 3H). 300 MHz $^{19}$F NMR (CDCl$_3$) δ(ppm) −76.74, −112.11, −114.85 (TFA salt). MS: 553.07 (M+1).

Example 145

Synthesis of Compound 442

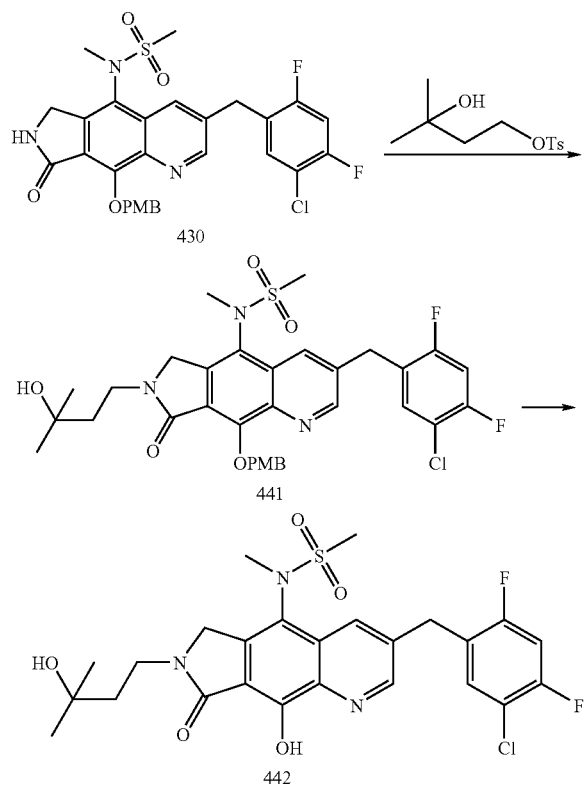

Lactam 430 (35 mg, 0.06 mmol, 1 equiv.) is dissolved in DMF (0.6 mL, 0.1 M) and cooled in an ice bath to 0° C. before LiHMDS (90 µL, 0.09 mmol, 1.3 equiv., 1 M in THF) and stirred for 5 minutes under nitrogen atmosphere. Tosylate (30 mg, 0.12 mmol, 1.4 equiv.), previously reported elsewhere, was added and the reaction was allowed to stir for 45 minutes at 0° C. The reaction was quenched with water and diluted with ethyl acetate. The organic layer was washed with water and brine before being dried over Na$_2$SO$_4$, filtered and concentrated in vacuo. The crude residue was purified by chromatography on silica gel (7/3—Ethyl acetate/Hexane) to afford the desired product 441. 300 MHz $^1$H NMR (CDCl$_3$) δ (ppm) 8.93 (s, 1H), 7.95 (s, 1H), 7.79 (d, J=5.4 Hz, 2H), 7.28-7.20 (m, 1H), 7.09-7.04 (m, 1H), 6.86 (d, J=8.7 Hz, 2H), 5.77 (d, J=11.1 Hz, 1H), 5.68 (d, J=11.1 Hz, 1H), 5.03 (s, 1H), 4.88 (d, J=10.2 Hz, 1H), 4.50 (d, J=10.2 Hz, 1H), 4.19 (s, 2H), 3.95-3.70 (m, 2H), 3.86 (s, 3H), 3.40 (s, 3H), 3.03 (s, 3H), 1.89 (t, J=4.5 Hz, 2H), 1.33 (d, J=4.8 Hz, 1H). 300 MHz $^{19}$F NMR (CDCl$_3$) δ(ppm) −112.50, −113.64. MS: 674.07 (M+1).

Compound 442 was made in a similar fashion as has been previously described for similar reactions. 300 MHz $^1$H NMR (CDCl$_3$) δ (ppm) 8.85 (s, 1H), 7.96 (s, 1H), 7.23 (s, 1H), 6.97 (s, 1H), 4.83 (d, J=12.0 Hz, 1H), 4.50 (d, J=12.0 Hz, 1H), 4.19 (s, 2H), 3.85-3.75 (m, 2H), 3.31 (s, 3H), 2.89 (s, 3H), 1.89 (t, J=4.5 Hz, 2H), 1.33 (d, J=4.8 Hz, 1H). 300 MHz $^{19}$F NMR (CDCl$_3$) δ(ppm) −112.02, −114.96. MS: 554.07 (M+1).

Example 146

Synthesis of Compound 446

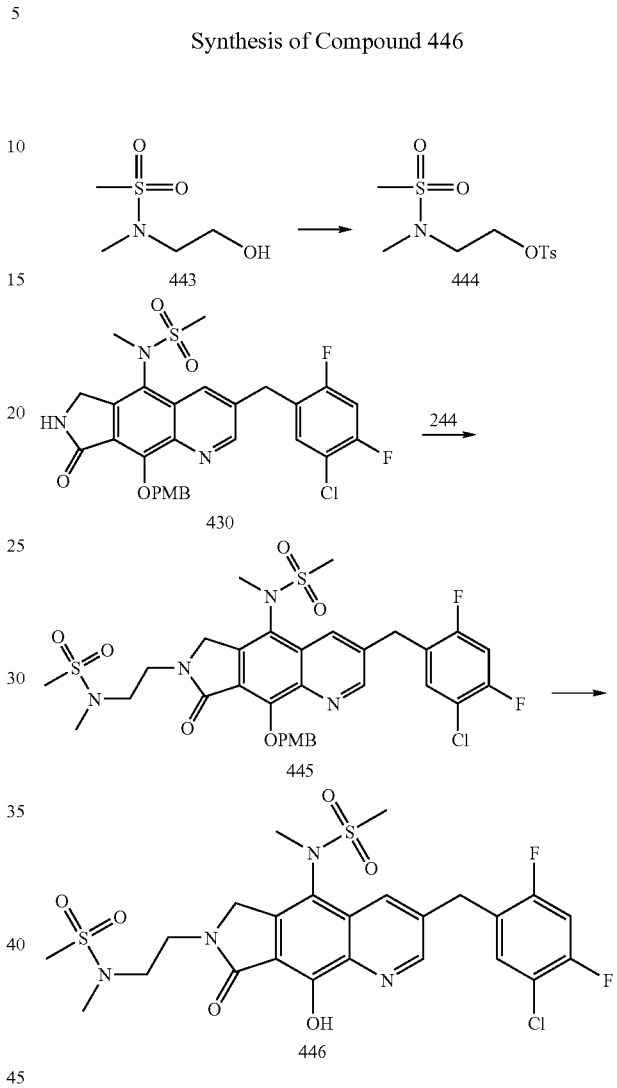

The synthesis of alcohol 443 has been described previously in the literature. 443 (1 gm, 6.53 mol, 1 equiv.) was stirred in CH$_2$Cl$_2$ (20 mL, 0.3 M) followed by addition of TEA (2.3 mL, 16.3 mol, 2.5 equiv.) and DMAP (400 mg, 3.3 mol, 0.5 equiv.) before p-toluenesulfonyl chloride (1.49 g, 7.8 mol, 1.2 equiv.) was added. After 2 hr, the reaction was complete and was diluted with CH$_2$Cl$_2$ and washed with water, saturated NH$_4$Cl and brine before being dried over Na$_2$SO$_4$, filtered and concentrated in vacuo. The crude residue was purified by chromatography on silica gel (1/1—Ethyl acetate/Hexane) to afford the desired product 444 (1.3 g mg, 65%) as a brown oil. 300 MHz $^1$H NMR (CDCl$_3$) δ (ppm) 7.86 (d, J=4.8 Hz, 2H), 7.38 (d, J=4.8 Hz, 1H), 4.17 (t, J=3.0 Hz, 2H), 3.50 (t, J=3.0 Hz, 2H) 2.93 (s, 3H), 2.86 (s, 3H), 2.48 (s, 3H). MS: 307.93 (M+1).

Lactam 430 (30 mg, 0.05 mmol, 1 equiv.) is dissolved in DMF (0.5 mL, 0.1 M) and cooled in an ice bath to 0° C. before NaHMDS (66 µL, 0.066 mmol, 1.3 equiv., 1 M in THF) and stirred for 5 minutes under nitrogen atmosphere. Tosylate 444 (31 mg, 0.11 mmol, 2 equiv.) was added and the reaction was allowed to stir for 45 minutes at 0° C. The reaction was quenched with water and diluted with ethyl acetate. The organic layer was washed with water and brine before being dried over Na₂SO₄, filtered and concentrated in vacuo. The crude residue was purified by chromatography on silica gel (4/1—Ethyl acetate/Hexane) to afford the desired product 445. 300 MHz ¹H NMR (CDCl₃) δ (ppm) 8.90 (s, 1H), 8.03 (s, 1H), 7.62 (s, J=8.4 Hz, 2H H), 7.25-7.15 (m, 1H) 7.05-7.00 (m, 1H), 6.89 (d, J=8.4 Hz, 2H), 5.73 (d, J=7.8 Hz, 1H), 5.71 (d, J=7.8 Hz, 1H), 4.86 (d, J=2.1 Hz, 1H), 4.70 (d, J=2.1 Hz, 1H), 4.20 (s, 2H), 4.10-3.95 (m, 2H), 3.80 (s, 3H), 3.55-3.45 (m, 2H), 3.33 (s, 3H), 3.05 (s, 3H), 2.97 (s, 3H), 2.77 (s, 3H). 300 MHz ¹⁹F NMR (CDCl₃) δ(ppm) −112.48, −115.03. MS: 723.07 (M+1).

Compound 446 was made in a similar fashion as has been previously described for similar reactions. 300 MHz ¹H NMR (CDCl₃) δ (ppm) 8.90 (s, 1H), 8.13 (s, 1H), 7.25-7.15 (m, 2H) 6.89 (d, J=8.4 Hz, 2H), 4.77 (d, J=2.1 Hz, 1H), 4.20 (s, 2H), 4.10-3.95 (m, 2H), 3.55-3.45 (m, 2H), 3.32 (s, 3H), 3.03 (s, 3H), 2.97 (s, 3H), 2.78 (s, 3H). 300 MHz ¹⁹F NMR (CDCl₃) δ(ppm) −76.36, −112.18, −114.93 (TFA salt). MS: 723.07 (M+1).

Example 147

Synthesis of Compound 451

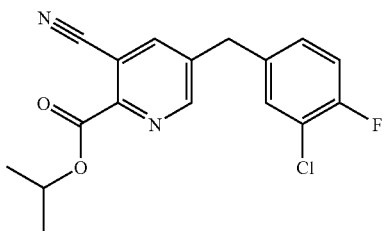

Following the synthetic methods reported for preparing compound 422, 100 g of 2-chloro-1-fluoro-4-iodobenzene was advanced through a seven-step sequence to provide 4.7 g of the Dieckmann condensation precursor 447. 300 MHz ¹H NMR (CDCl₃) shows diagnostic peaks at δ (ppm): 8.78 (s, 1H), 7.85 (s, 1H), 6.94-7.22 (m, 3H), 5.40 (m, 1H), 4.03 (s, 2H), 1.48 (d, 6H). MS=333.2 (M+H).

448

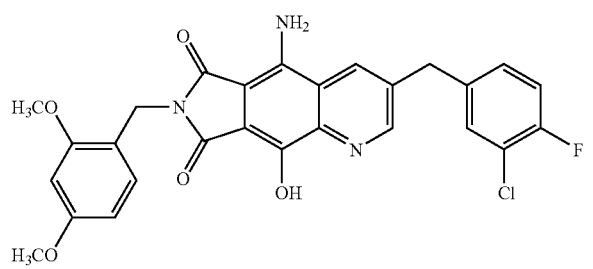

To 4.7 g 447 (14 mmol) in 50 mL THF was added, at 0° C., 3.5 g DMB-imide (14 mmol, 1 equiv) followed by 30 mL LiHMDS (1M solution in THF). The reaction was allowed to stir at rt for 12 h, at which time the solution was quenched with 30 mL 6N aq. HCl. Precipitation of the product resulted. Rinsing with diethyl ether and oven drying on vacuum gave 3.3 g of the pure Dieckmann product 448. ¹H NMR (300 MHz, d6-DMSO) shows diagnostic peaks at δ (ppm): 8.95 (s, 1H), 8.74 (s, 1H), 4.61 (s, 2H) 4.20 (s, 2H), 3.76 (s, 3H), 3.65 (s, 3H). MS=522.2 (M+H).

449

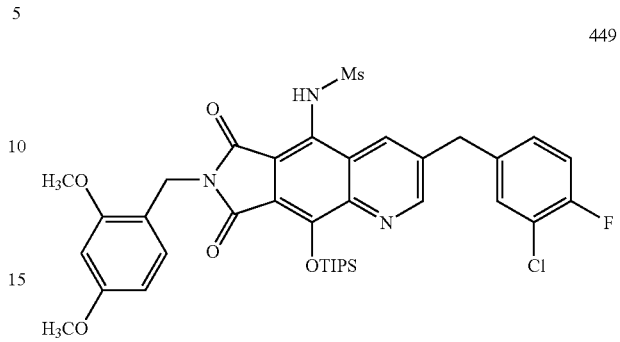

Following TIPS protection of 448 by the standard method, 3.2 g (4.7 mmol) of the resulting TIPS ether was dissolved in 100 mL dichloromethane and cooled to −10° C. 7 ml triethylamine (10 equiv, 47 mmol) was added, followed by 1.5 mL (20 mmol, 4 equiv) mesyl chloride. After 2 h, the reaction is quenched by addition of 100 mL saturated aq. ammonium chloride. Dilution with 200 mL DCM, followed by washing with 100 mL H₂O, 100 mL brine, and drying and concentration of organics gives 3.95 g of the bis-mesyl intermediate. This residue was directly subjected to treatment with 4.8 mL 1M KOtBu solution in 50 mL THF at 0° C. After 20 minutes, the reaction was diluted with 500 mL ethyl acetate, washed 2×150 mL 5% aq. citric acid solution, then with 150 ml H₂O and brine. Drying over sodium sulfate & concentration gave 3.8 g crude product 449. ¹H NMR (300 MHz, CDCl₃) shows diagnostic peaks at δ (ppm): 8.75 (s, 1H), 8.74 (s, 1H), 7.65 (s, 1H), 6.44 (s, 2H), 4.81 (s, 2H) 4.20 (s, 2H), 3.86 (s, 3H), 3.78 (s, 3H), 1.10 (d, 18H). MS=756.2 (M+H).

450

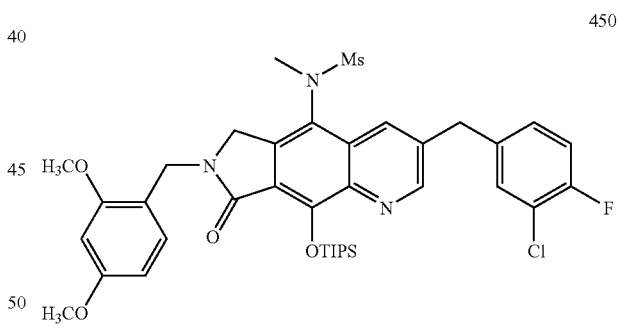

Following conversion of 3.5 g of the imide 449 to lactam by the previously reported method, the resulting TIPS protected lactam was purified by chromatography on Davisil and the resulting 2.2 g of product subjected to sulfonamide methylation by dissolving the material in 50 mL DMF, cooling to 0° C., and addition of 1.44 g (4.5 mmol, 1.5 equiv) Cs₂CO₃. 220 uL MeI was added dropwise and the reaction allowed to stir at low T. After 4 h, 300 mg Cs₂CO₃ and 125 uL additional MeI were added. LC/MS showed the reaction was complete. The reaction was quenched by addition of 800 mL ethyl acetate and washing 2×250 mL 5% aq. citric acid solution, 2×250 mL water, and 1×250 mL sat. aq. NaCl solution. Drying over sodium sulfate and removal of volatiles gave 2.4 product 450. ¹H NMR (300 MHz, CDCl₃) shows diagnostic peaks at δ (ppm): 8.75 (s, 1H), 7.84 (s, 1H), 7.65 (s, 1H), 6.44 (s, 2H), 4.75 (dd, 2H) 4.40 (dd, 2H), 3.86 (s, 3H), 3.78 (s, 3H), 3.25 (s, 3H), 2.96 (s, 3H), 1.10 (d, 18H). MS=756.2 (M+H).

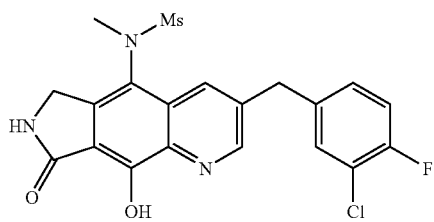

451

To 2 g sulfonamide 450 in 20 mL dichloromethane at rt was added 5 mL triethylsilane, 10 mL TFA. The reaction was stirred for 16 h, at which time 20 mL toluene was added and the reaction was azeotroped to removed residual TFA and other volatiles. Trituration with diethyl ether/hexanes gave 1.9 g yellow solid product 251. $^1$H NMR (300 MHz, d6-DMSO) shows diagnostic peaks at δ (ppm): 8.85 (s, 1H), 8.48 (s, 1H), 8.22 (s, 1H), 4.54 (s, 2H), 4.24 (s, 2H), 3.28 (s, 3H) and 3.21 (s, 3H). MS=450.1 (M+H).

Example 148

Synthesis of Compound 452

Following re-trituration of sulfonamide 451 with diethyl ether/MeOH to provide 1 g of the free base, PMB ether formation was carried out following the previously reported method for preparing compound 432 to provide 740 mg of lactam alkylation precursor as a red powder after trituration with diethyl ether. $^1$H NMR (300 MHz, CD$_3$OD) shows diagnostic peaks at δ (ppm): 8.85 (s, 1H), 8.28 (s, 1H), 5.64 (dd, 2H), 4.25 (s, 2H) 4.18 (s, 2H), and 3.15 (s, 3H). MS=570.2 (M+H).

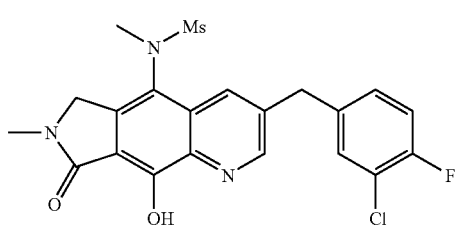

452

To 550 mg of the PMB-protected free lactam in 10 mL DMF at 0° C. was added 40 mg NaH (60% oil dispersion) followed by 70 uL MeI. The alkylation reaction was judged complete after 15 minutes, at which time the solution was diluted with 200 mL ethyl acetate, washed 2×200 mL H$_2$O, 1×200 mL brine, dried over sodium sulfate and concentrated to give 560 mg crude product. Trituration gave 430 mg pure product which was subjected to PMB removal by the previously reported method. Trituration of this final product with diethyl ether/hexanes gave 165 mg of the methyl lactam analog 452 as a light yellow solid. $^1$H NMR (300 MHz, d$_6$-DMSO) shows diagnostic peaks at δ (ppm): 8.85 (s, 1H), 8.23 (s, 1H), 4.61 (s, 2H) 4.23 (s, 2H), 3.35 (s, 3H), 3.18 (s, 3H) and 3.08 (s, 3H). MS=464.2 (M+H).

Example 149

Synthesis of Compound 453

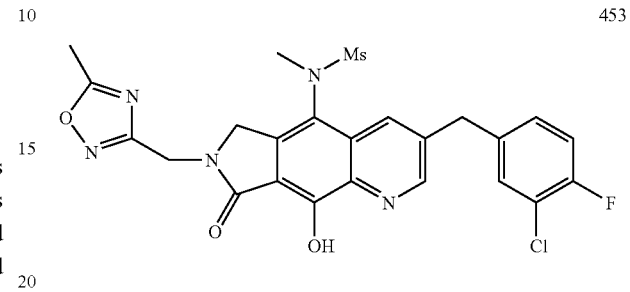

453

To 30 mg of the PMB-protected free lactam (Example 148) in 1 mL DMF at 0° C. was added 60 uL NaHMDS followed by 10 uL of the benzylic bromide. The alkylation reaction was judged 75% complete after 10 minutes. 30 uL NaHMDS and 5 uL of the bromide were then added. After 2 h the reaction was complete, at which time the solution was diluted with 100 mL ethyl acetate, washed 2×50 mL H$_2$O, 1×100 mL brine, dried over sodium sulfate and concentrated to give 38 mg crude product. Combiflash chromatography on silica gel gave 10 mg pure material which was subjected to PMB removal by the previously reported method. Trituration of this final product with diethyl ether/hexanes gave 7 mg of the methyl lactam analog 453 as a light yellow solid. $^1$H NMR (300 MHz, d$_6$-DMSO) shows diagnostic peaks at δ (ppm): 8.85 (s, 1H), 8.20 (s, 1H), 7.62 (m, 1H), 7.32 (m, 2H), 4.82 (s, 2H) 4.63 (d, 2H), 4.16 (s, 2H), 3.25 (s, 3H), 3.17 (s, 3H) and 2.57 (s, 3H). MS=546.2 (M+H).

Example 150

Synthesis of Compounds 455 and 456

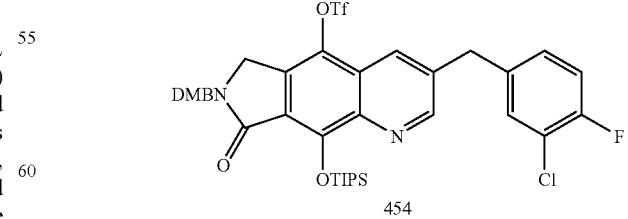

454

The intermediate lactam, synthesized via the method reported previously, 50 mg (0.08 mmol, 1 equiv), was dissolved in 3 mL DMF, and Cs$_2$CO$_3$ (130 mg, 0.40 mmol, 5 equiv) followed by MeI (0.08 mmol, 5 μl, 1 equiv) was added.

The reaction was stirred for 1 h at rt, by which time the reaction had gone to completion as judged by LC/MS analysis. The reaction was then filtered to remove solids and diluted with EtOAc, then washed 3× with water and dried over $Na_2SO_4$ to furnish 30 mg of triflate product 454 that required no additional purification. 300 MHz $^1$H NMR ($CDCl_3$) shows diagnostic peaks at δ (ppm): 8.68 (d, J=3.8 Hz, 1H), 8.15 (d, J=3.8 Hz, 1H), 7.45-7.05 (m, 4H), 6.52-6.45 (m, 3H), 4.78 (s, 2H), 4.38 (s, 2H), 4.08 (s, 2H), 3.91 (s, 3H), 3.85 (s, 3H), 3.82 (s, 3H), 1.55 (m, 3H), 1.15 (d, 18 h).

Following the standard protocol for microwave assisted Suzuki coupling, 100 mg triflate 454 was reacted at 170 C for 5 minutes with para-fluorophenyl boronic acid in the presence of $Cs_2CO_3$ and $Pd(PPh_3)_4$ in toluene/ethanol/water solution. The resulting biaryl product was subjected to DMB and TIPS removal via TFA/TES treatment. HPLC purification gave pure biaryl compound 455 (4 mg): $^1$H NMR (300 MHz, $CD_3CN$) shows diagnostic peaks at δ 8.80 (s, 1H), 7.85 (s, 1H), 4.35 (s, 2H), 4.15 (s, 2H). MS 437.3 (M+H).

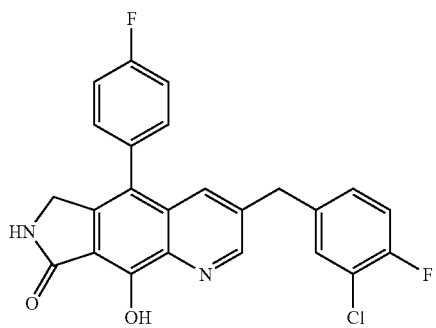

455

A Similar sequence allowed for isolation and characterization of the protonolysis product 456 (2 mg): $^1$H NMR (300 MHz, $CD_3CN$) shows diagnostic peaks at δ (ppm): 8.80 (s, 1H), 8.14 (s, 1H), 4.54 (s, 2H). MS=343.2 (M+H).

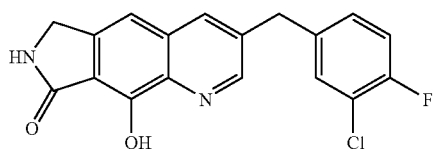

456

Example 151

The following illustrate representative pharmaceutical dosage forms, containing a compound of formula I, II, or III ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The above description is not intended to detail all modifications and variations of the invention. It will be appreciated by those skilled in the art that changes can be made to the embodiments described above without departing from the inventive concept. It is understood, therefore, that the invention is not limited to the particular embodiments described above, but is intended to cover modifications that are within the spirit and scope of the invention, as defined by the language of the following claims.

---

We claim:
1. A compound of formula (II):

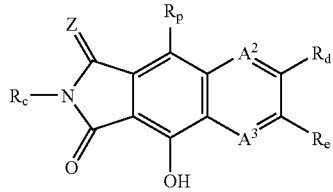

wherein:
$A^2$ and $A^3$ are each independently N or $CR_a$;
each $R_a$ is independently H or $C_1$-$C_4$ alkyl;
$R_c$ is H, $R_k$, or -Q-$R_n$;
$R_d$ is H, halo, or $C_1$-$C_4$ alkyl that is optionally substituted with Rj;
$R_e$ is H, halo, or $C_1$-$C_4$ alkyl that is optionally substituted with Rj provided that at least one of $R_d$ and $R_e$ is $C_1$-$C_4$ alkyl that is substituted with Rj,
Q is $C_1$-$C_4$ alkylene;
Z is O or two hydrogens;
each $R_j$ is phenyl, optionally substituted with one or more F, Cl, Br, I, hydroxy, cyano, trifluoromethyl, trifluoromethoxy, or $C_1$-$C_4$ alkyl;
$R_k$ is $C_1$-$C_6$ alkyl, $C_2$-$C_6$ alkenyl, or $C_2$-$C_6$ alkynyl, each of which is optionally substituted with one or more halo, hydroxy, $C_1$-$C_6$ alkoxy, dimethylamino, diethylamino, N-ethyl-N-methylamino, morpholino, thiomorpholino, piperidino, or piperazino;
$R_n$ is a $C_3$-$C_6$ carbocycle, a phenyl ring, or a 5- or 6-membered heteroaryl ring, which phenyl ring or 5- or 6-membered heteroaryl ring is optionally substituted with one or more F, Cl, Br, I, hydroxy, cyano, trifluoromethyl, trifluoromethoxy, or $C_1$-$C_4$ alkyl;
$R_p$ is OH, $C_1$-$C_4$ alkyl, $C_1$-$C_4$ alkanoyl, $C_1$-$C_4$ alkoxy, $C_2$-$C_6$ alkenyl, $C_2$-$C_6$ alkynyl, —C(=O)$NR_xR_x$, —C(=$NR_{ak}$)$R_{am}$, $NH_2$, —N($R_a$)—C(=O)$NR_xR_x$, 4,5-dihydro-4,4-dimethyloxazole, or —N($R_s$)—S(O)$_2$—$R_t$, wherein each $C_1$-$C_4$ alkyl of $R_p$ is substituted with —C(=O)$NR_xR_x$, —N($R_{ag}$)—C(=O)—$R_{ah}$, or —N($R_{ag}$)—S(O)$_2$—$R_{ah}$; and wherein each $C_1$-$C_4$ alkoxy, $C_2$-$C_6$ alkenyl and $C_2$-$C_6$ alkynyl of $R_p$ is optionally substituted with phenyl, hydroxy, $C_3$-$C_6$ carbocycle or —C(=O)$NR_xR_x$;
$R_s$ is —S(O)$_2$—$R_w$, and $R_t$ is $C_1$-$C_4$ alkyl optionally substituted with $R_v$; or $R_s$ is $C_1$-$C_4$ alkyl substituted with $R_u$, and $R_t$ is $C_1$-$C_4$ alkyl optionally substituted with $R_v$; or $R_s$ is $C_1$-$C_4$ alkyl optionally substituted with $R_u$, and $R_t$ is $R_z$, $NR_xR_x$, or $C_1$-$C_4$ alkyl substituted with $R_v$;
each $R_v$ is fluoro, chloro, phenyl, pyridyl, 1,4 diazepanyl, or piperazino, wherein each phenyl, pyridyl, 1,4-diazepanyl, and piperazino is optionally substituted with one or more fluoro, chloro, bromo, iodo, $C_1$-$C_4$ alkyl, $C_1$-$C_4$ alkyl-C(=O)—, $C_1$-$C_4$ alkyl-S(O)$_2$—, —C(=O)$NR_aR_a$, or —C(=O)$OR_a$;
each $R_u$ is independently dimethylamino, diethylamino, N-ethyl-N-methylamino, or a ring selected from $C_3$-$C_6$ carbocycle, pyrrolidino, morpholino, thiomorpholino, piperidino, and piperazino, which ring is optionally substituted with one or more $C_1$-$C_4$ alkyl; and
$R_w$ is $C_1$-$C_4$ alkyl;
each $R_x$ is independently H, $C_1$-$C_4$ alkyl, $C_3$-$C_6$ carbocycle, or $C_1$-$C_4$ alkyl-$R_y$; or $NR_xR_x$ taken together form a piperidino, morpholino, azetidino, pyrrolidino, or piperazino ring, which ring is optionally substituted with one or more $C_1$-$C_4$ alkyl or halo;
each $R_y$ is independently cyano, phenyl or pyridyl, wherein each phenyl or pyridyl is optionally substituted with one or more fluoro, chloro, bromo, iodo, $C_1$-$C_4$ alkyl, $C_1$-$C_4$ alkyl-C(=O)—, $C_1$-$C_4$ alkyl-S(O)$_2$—, —C(=O)$NR_aR_a$, or —C(=O)$OR_a$;
$R_z$ is phenyl which is optionally substituted with one or more fluoro, chloro, bromo, iodo, $C_1$-$C_4$ alkyl, $C_1$-$C_4$ alkyl-C(=O)—, $C_1$-$C_4$ alkyl-S(O)$_2$—, —C(=O)$NR_aR_a$, or —C(=O)$OR_a$;
each $R_{ag}$ and $R_{ah}$ is independently H or $C_1$-$C_4$ alkyl;
each $R_{ak}$ is hydroxy, $C_1$-$C_4$ alkoxy, or $NR_{am}R_{an}$;
each $R_{ah}$ is independently H or $C_1$-$C_4$ alkyl;
each $R_{am}$ and $R_{an}$ is independently H or $C_1$-$C_4$ alkyl;
or a pharmaceutically acceptable salt thereof.

2. The compound of claim 1 wherein:
$R_p$ is OH, $C_1$-$C_4$ alkoxy, $NH_2$, $N(R_a)$—C(=O)$NR_xR_x$, or —N($R_s$—S(O)$_2$—$R_t$;
each $R_x$ is independently H, $C_1$-$C_4$ alkyl, or $C_1$-$C_4$ alkyl-$R_y$; or $NR_xR_x$ taken together form a piperidino or piperazino ring, which ring is optionally substituted with one or more $C_1$-$C_4$ alkyl; and
each $R_y$ is independently phenyl or pyridyl, wherein each phenyl or pyridyl is optionally substituted with one or more fluoro, chloro, bromo, iodo, $C_1$-$C_4$ alkyl, $C_1$-$C_4$ alkyl-C(=O)—, alkyl-S(O)$_2$—, —C(=O)$NR_aR_a$, or —C(=O)$OR_a$.

3. The compound of claim 1 wherein $A^2$ is CH and $A^3$ is N.
4. The compound of claim 1 wherein $A^2$ is N and $A^3$ is CH.
5. The compound of claim 1 wherein $R_c$ is H.
6. The compound of claim 1 wherein $R_c$ is $R_k$.
7. The compound of claim 1 wherein $R_c$ is -Q-$R_n$.
8. The compound of claim 1 wherein $R_d$ is H.
9. The compound of claim 1 wherein $R_d$ is $C_1$-$C_4$ alkyl that is substituted with Rj.
10. The compound of claim 1 wherein $R_e$ is H.
11. The compound of claim 1 wherein $R_e$ is $C_1$-$C_4$ alkyl that is substituted with Rj.
12. The compound of claim 1 wherein Q is —$CH_2$—.
13. The compound of claim 1 wherein each $R_j$ is 4-fluorophenyl.
14. The compound of claim 1 wherein $R_k$ is ethyl, 2-morpholinoethyl, 2-methoxyethyl, methyl, 2-hydroxyethyl, or 3-hydroxy-3-methylbutyl.
15. The compound of claim 1 wherein Q is —$CH_2$—, and $R_n$ is 4-fluorophenyl.
16. The compound of claim 1 wherein $R_p$ is OH.
17. The compound of claim 1 wherein $R_p$ is $C_1$-$C_4$alkoxy.
18. The compound of claim 1 wherein $R_p$ is $N(R_a)$—C(=O)$NR_xR_x$.
19. The compound of claim 1 wherein $R_p$ is —N($R_s$)—S(O)$_2$—$R_t$.
20. The compound of claim 19 wherein $R_s$ is —S(O)$_2$—$R_w$, and $R_t$ is $C_1$-$C_4$ alkyl optionally substituted with R.
21. The compound of claim 19 wherein $R_s$ is $C_1$-$C_4$ alkyl substituted with $R_u$, and $R_t$ is $C_1$-$C_4$ alkyl optionally substituted with $R_v$.
22. The compound of claim 19 wherein $R_s$ is $C_1$-$C_4$ alkyl optionally substituted with $R_u$, and $R_t$ is $NR_xR_x$ or $C_1$-$C_4$ alkyl substituted with $R_v$.
23. The compound of claim 19 wherein $R_s$ is —S(O)$_2$—$CH_3$ or —S(O)$_2$—$CH_2CH_3$, and $R_t$ is methyl or ethyl.
24. The compound of claim 19 wherein $R_s$ is cyclopropylmethyl, 2-(2,5-dimethylpyrrolidino)ethyl, or 2-morpholinoethyl.

25. The compound of claim 21 wherein $R_t$ is 2-chloroethyl, benzyl, pyrid-4-ylmethyl, 4-methylphenyl, 4-chlorophenyl, 2-(4-ethylpiperazin-1-yl)ethyl, 2-(4-ethylsulfonylpiperazin-1-yl)ethyl, 2-(4-acylpiperazin-1-yl)ethyl, 2-(4-isopropylpiperazin-1-yl)ethyl, N-(4-fluoro-2-methylaminocarbonylbenzyl)-N-methylamino, N-(4-fluoro-2-methoxycarbonylbenzyl)amino, N-(4-fluoro-2-carboxybenzyl)-N-methylamino, or N,N-diethylamino.

26. The compound of claim 1 wherein $R_p$ is N-methyl-N-(4-methylpiperazin-1-ylcarbonyl)amino.

27. The compound of claim 1 wherein $R_p$ is methoxy.

28. The compound of claim 1 wherein $R_p$ is $C_1$-$C_4$ alkyl, $C_1$-$C_4$ alkanoyl, $C_1$-$C_4$ alkoxy, $C_2$-$C_6$ alkenyl, $C_2$-$C_6$ alkynyl, —C(=O)NR$_x$R$_x$, —C(=NR$_{ak}$)R$_{am}$, or 4,5-dihydro-4,4-dimethyloxazole, wherein each $C_1$-$C_4$ alkyl of $R_p$ is substituted with —C(=O)NR$_x$R$_x$, —N(R$_{ag}$)—C(=O)—R$_{ah}$, or —N(R$_{ag}$)—S(O)$_2$—R$_{ah}$; and wherein each $C_1$-$C_4$ alkoxy, $C_2$-$C_6$ alkenyl and $C_2$-$C_6$ alkynyl of $R_p$ is optionally substituted with phenyl, hydroxy, $C_3$-$C_6$ carbocycle or —C(=O)NR$_x$R$_x$.

29. The compound of claim 1 wherein $R_p$ is 2-(N,N-dimethylaminocarbonyl)-2-methylethoxy, allyl, piperidinocarbonyl, 4,4-difluoropiperidinocarbonyl, N-cyclopropyl-N-(2-cyanoethyl)aminocarbonyl, 2-[N-methyl-N-(methylsulfonyl)amino]ethyl, N,N-dimethylaminocarbonylmethyl, N-methylaminocarbonyl, N-(2,2,2-trifluoroethyl)aminocarbonyl, acetyl, piperidinocarbonylmethyl, morpholinocarbonylmethyl, 2-cyclopropylethynyl, azetidinocarbonyl, 4-fluoropiperidinocarbonyl, pyrrolidinocarbonyl, 3,3-difluoropyrrolidinocarbonyl, ethynyl, 1-hydroximinoethyl, 2-phenylethynyl, 4,5-dihydro-4,4-dimethyloxazole, 4-methylpiperazin-1-ylcarbonyl, N-acetyl-N-methylamino, 3,3-dimethylbutyn-1-yl, 1-[N—(N',N'-dimethylamino)imino]ethyl, 2-[N—(N'-methylamino)imino]ethyl, 3-hydroxy-3-methylbutyn-1-yl, 1-methylvinyl, or 1-(N-methoxyimino)ethyl.

30. The compound of claim 1 which has the following formula, or a pharmaceutically acceptable salt thereof.

31. The compound of claim 1 which has the following formula,

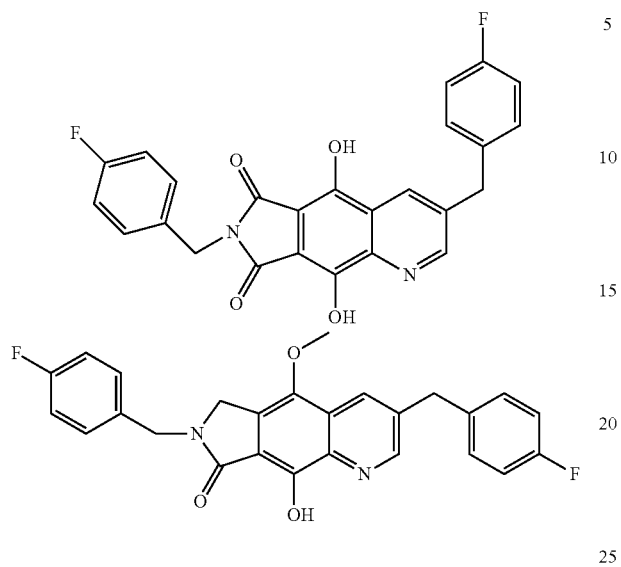

or a pharmaceutically acceptable salt thereof.

32. The compound of claim 1 which has the following formula,

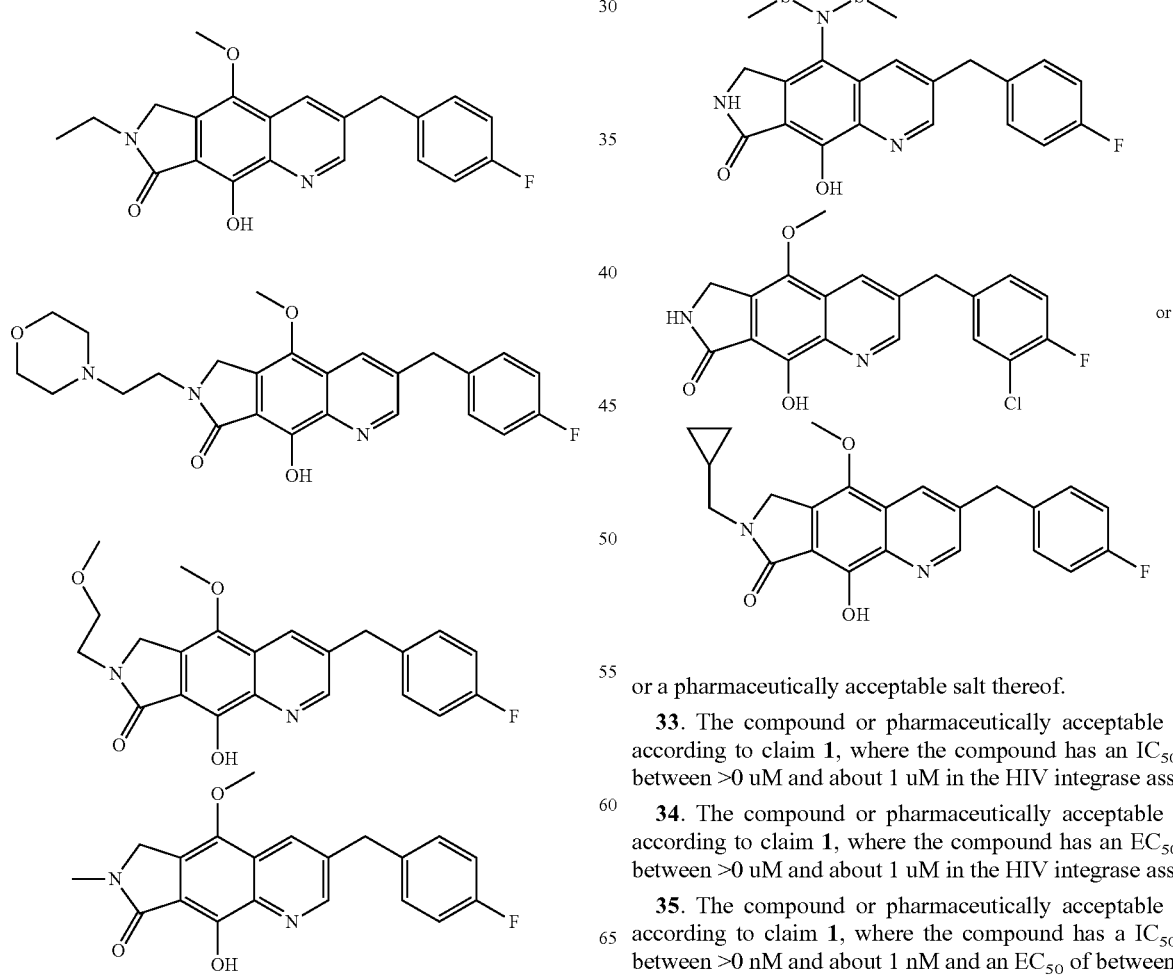

or a pharmaceutically acceptable salt thereof.

33. The compound or pharmaceutically acceptable salt according to claim 1, where the compound has an $IC_{50}$ of between >0 uM and about 1 uM in the HIV integrase assay.

34. The compound or pharmaceutically acceptable salt according to claim 1, where the compound has an $EC_{50}$ of between >0 uM and about 1 uM in the HIV integrase assay.

35. The compound or pharmaceutically acceptable salt according to claim 1, where the compound has a $IC_{50}$ of between >0 nM and about 1 nM and an $EC_{50}$ of between >0 uM and about 1 uM in the HIV integrase assay.

36. A compound of formula (II):

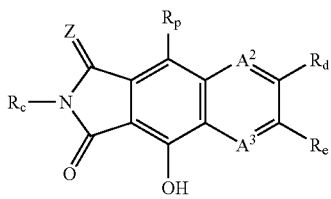

wherein:
A² and A³ are each independently N or CR$_a$;
each R$_a$ is independently H or C$_1$-C$_4$ alkyl;
R$_c$ is H, R$_k$, or -Q-R$_n$;
R$_d$ is C$_1$-C$_4$ alkyl that is substituted with Rj;
R$_e$ is H, halo, or C$_1$-C$_4$ alkyl that is optionally substituted with Rj;
Q is C alkylene;
Z is O or two hydrogens;
each R$_j$ is phenyl, optionally substituted with one or more F, Cl, Br, I, hydroxy, cyano, trifluoromethyl, trifluoromethoxy, or C$_1$-C$_4$ alkyl;
R$_k$ is C$_1$-C$_6$ alkyl, C$_2$-C$_6$ alkenyl, or C$_2$-C$_6$ alkynyl, each of which is optionally substituted with one or more halo, hydroxy, C$_1$-C$_6$ alkoxy, dimethylamino, diethylamino, N-ethyl-N-methylamino, morpholino, thiomorpholino, piperidino, or piperazino;
R$_n$ is a C$_3$-C$_6$ carbocycle, a phenyl ring, or a 5- or 6-membered heteroaryl ring, which phenyl ring or 5- or 6-membered heteroaryl ring is optionally substituted with one or more F, Cl, Br, I, hydroxy, cyano, trifluoromethyl, trifluoromethoxy, —C(=O)NR$_{ac}$R$_{ad}$, or C$_1$-C$_4$ alkyl;
R$_p$ is —N(R$_{ae}$)—S(O)$_2$—R$_{af}$;
R$_z$ is phenyl which is optionally substituted with one or more fluoro, chloro, bromo, iodo, C$_1$-C$_4$ alkyl, C$_1$-C$_4$ alkyl-C(=O)—, C$_1$-C$_4$ alkyl-S(O)$_2$—, —C(=O)NR$_a$R$_a$, or —C(=O)OR$_a$;
each R$_{ac}$ and R$_{ad}$ is independently H or C$_1$-C$_6$ alkyl;
each R$_{ae}$ and R$_{af}$ is independently H or C$_1$-C$_6$ alkyl;
or a pharmaceutically acceptable salt thereof.

37. The compound of claim 36 wherein R$_c$ is 3-chloro-4,6-difluorobenzyl, 4-fluorobenzyl, 3-chloro-4-fluoeobenzyl, 4-fluoro-2-(N,N-dimethylaminocarbonyl)benzyl, or 4-fluoro-2-(N-methylaminocarbonyl)benzyl.

38. The compound of claim 37 wherein R$_d$ is 4-fluorobenzyl.

39. A compound of formula (II):

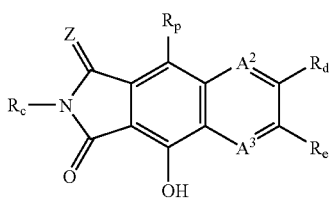

wherein:
A² and A³ are each independently N or CR$_a$;
each R$_a$ is independently H or C$_1$-C$_4$ alkyl;
R$_c$ is H, R$_k$, or -Q-R$_n$;
R$_d$ is C$_1$-C$_4$ alkyl that is substituted with Rj;
R$_e$ is H, halo, or C$_1$-C$_4$ alkyl that is optionally substituted with Rj;
Q is C$_1$-C$_4$ alkylene;
Z is O or two hydrogens;
each R$_j$ is phenyl, optionally substituted with one or more F, Cl, Br, I, hydroxy, cyano, trifluoromethyl, trifluoromethoxy, or C$_1$-C$_4$ alkyl;
R$_k$ is C$_1$-C$_6$ alkyl, C$_2$-C$_6$ alkenyl, or C$_2$-C$_6$ alkynyl, each of which is optionally substituted with one or more halo, hydroxy, C$_1$-C$_6$ alkoxy, dimethylamino, diethylamino, N-ethyl-N-methylamino, morpholino, thiomorpholino, piperidino, or piperazino;
R$_n$ is a C$_3$-C$_6$ carbocycle, a phenyl ring, or a 5- or 6-membered heteroaryl ring, which phenyl ring or 5- or 6-membered heteroaryl ring is optionally substituted with one or more F, Cl, Br, I, hydroxy, cyano, trifluoromethyl, trifluoromethoxy, C$_1$-C$_4$ alkoxy, —C(=O)NR$_{ac}$R$_{ad}$, or C$_1$-C$_4$ alkyl;
R$_p$ is H, NH$_2$, —C(=O)NR$_x$R$_x$, C$_1$-C$_4$ alkyl, pyridyl, 1,3,4-oxadiazole, 5-methyl-1,3,4-oxadiazole, or phenyl that is optionally substituted with one or more F, Cl, CN, hydroxy, or trifluoromethyl, wherein any C$_1$-C$_4$ alkyl of R$_p$ is optionally substituted with one or more hydroxy, cyano, —C(=O)NR$_x$R$_x$, or —NR$_{ar}$R$_{as}$;
each R$_x$ is independently H, C$_1$-C$_4$ alkyl, C$_3$-C$_6$ carbocycle, or C$_1$-C$_4$ alkyl-R$_y$; or NR$_x$R$_x$ taken together form a piperidino, morpholino, azetidino, pyrrolidino, or piperazino ring, which ring is optionally substituted with one or more C$_1$-C$_4$ alkyl or halo;
each R$_y$ is independently cyano, trifluoromethyl, hydroxy, C$_1$-C$_4$ alkoxy, phenyl or pyridyl, wherein each phenyl or pyridyl is optionally substituted with one or more fluoro, chloro, bromo, iodo, C$_1$-C$_4$ alkyl, C$_1$-C$_4$ alkyl-C(=O)—, C$_1$-C$_4$ alkyl-S(O)$_2$—, —C(=O)NR$_a$R$_a$, or —C(=O)OR$_a$;
each R$_{ac}$ and R$_{ad}$ is independently H or C$_1$-C$_6$ alkyl;
each R$_{ae}$ and R$_{af}$ is independently H or C$_1$-C$_6$ alkyl;
each R$_{ar}$ and R$_{as}$ is independently H, C$_1$-C$_6$ alkyl, or C$_1$-C$_6$ alkanoyl;
or a pharmaceutically acceptable salt thereof.

40. The compound of claim 39 wherein R$_d$ is 4-fluorobenzyl.

41. The compound of claim 40 wherein R$_p$ is 4-fluorophenyl, 3,5-difluorophenyl, 4-chlorophenyl, H, 2-(N,N-dimethylaminocarbonyl)ethyl, 4-cyanophenyl, N-pyrid-2-ylmethylaminocarbonyl, N,N-dimethylaminocarbonylmethyl, N-methylaminocarbonyl, N-(2,2,2-trifluoroethyl)aminocarbonyl, N-methyl-N-(methoxymethyl)aminocarbonyl, 2,6-difluorophenyl, N-methyl-N-(2-hydroxyethyl)aminocarbonyl, 2-hydroxy-2-methylethyl, N-(2-hydroxyethyl)aminocarbonyl, N-(2-hydroxy-1-methylethyl)aminocarbonyl, 2-hydroxyethyl, N-methylaminocarbonylmethyl, 4-pyridyl, 3-pyridyl, or 4-hydroxyphenyl.

42. The compound of claim 41 wherein R$_p$ is 2-(N,N-dimethylaminocarbonyl)ethyl, 4-cyanophenyl, N-pyrid-2-ylmethylaminocarbonyl, N,N-dimethylaminocarbonylmethyl, N-methylaminocarbonyl, N-(2,2,2-trifluoroethyl)aminocarbonyl, N-methyl-N-(methoxymethyl)aminocarbonyl, N-methyl-N-(2-hydroxyethyl)aminocarbonyl, 2-hydroxy-2-methylethyl, N-(2-hydroxyethyl)aminocarbonyl, N-(2-hydroxy-1-methylethyl)aminocarbonyl, 2-hydroxyethyl, or N-methylaminocarbonylmethyl.

43. The compound of claim 42 wherein R$_p$ is 4-fluorophenyl, 3,5-difluorophenyl, 4-chlorophenyl, H, 4-cyanophenyl, 2,6-difluorophenyl, 4-pyridyl, 3-pyridyl, or 4-hydroxyphenyl.

44. The compound of claim 43 wherein $R_c$ is 3-chloro-4,6-difluorobenzyl, 4-fluorobenzyl, 3-chloro-4-fluoeobenzyl, 4-fluoro-2-(N,N-dimethylaminocarbonyl)benzyl, or 4-fluoro-2-(N-methylaminocarbonyl)benzyl.
45. Compound
209
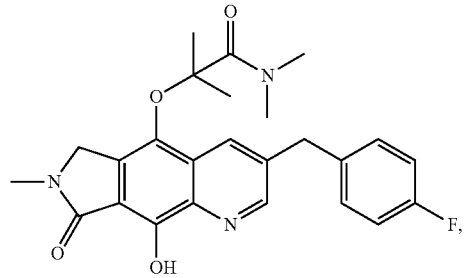
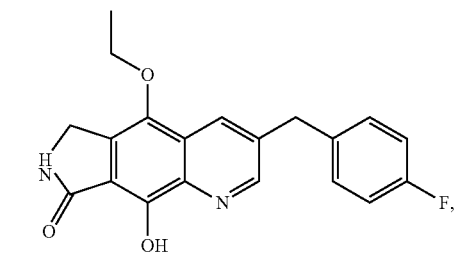
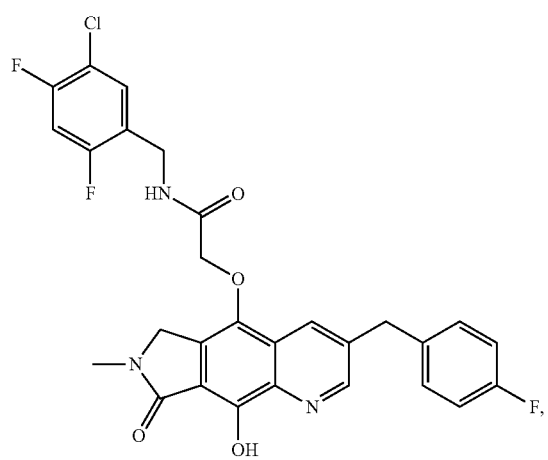
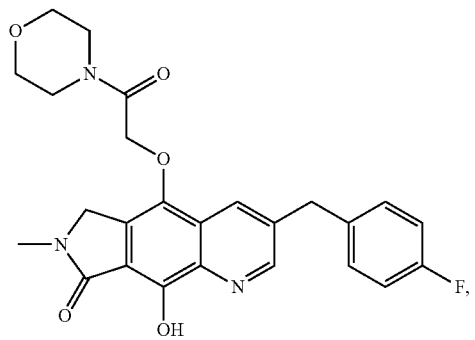
-continued
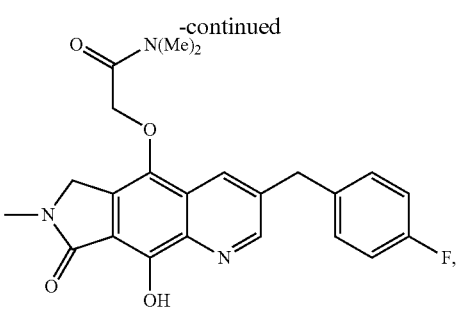
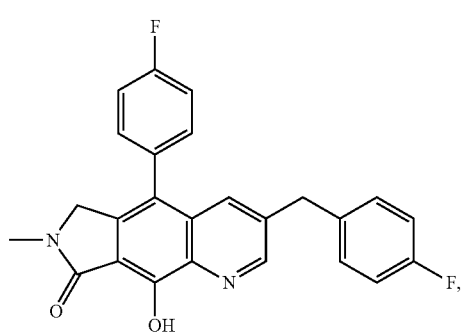
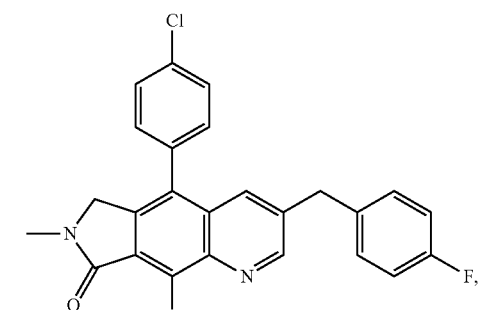
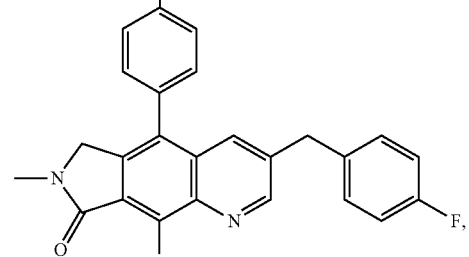
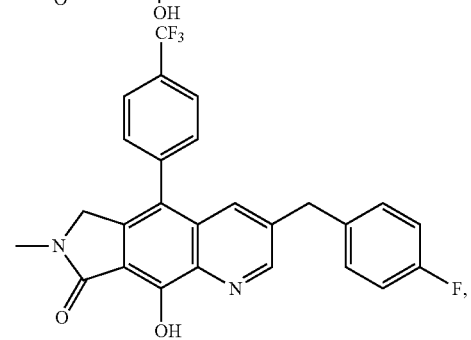

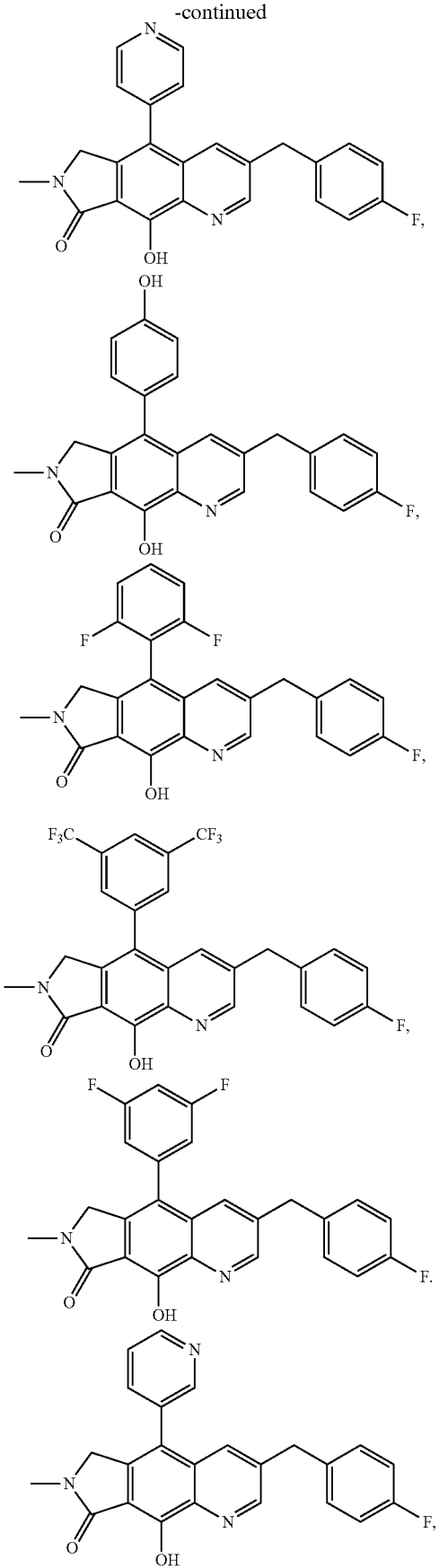

240
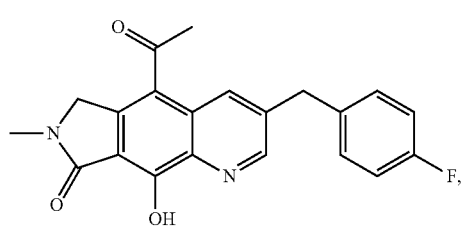
242
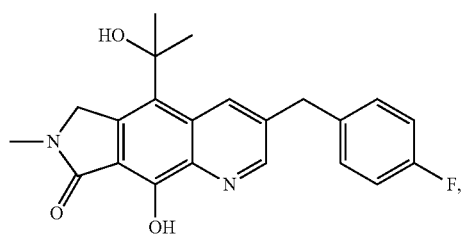
243
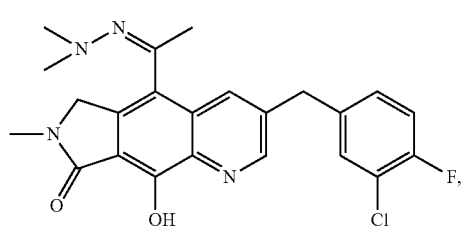
244
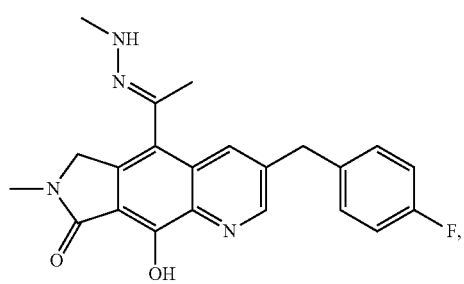
245
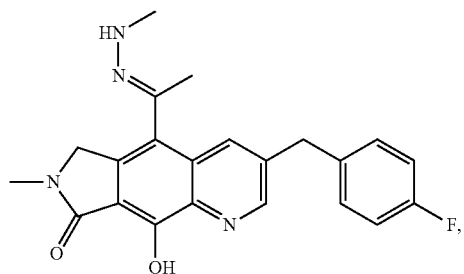
246
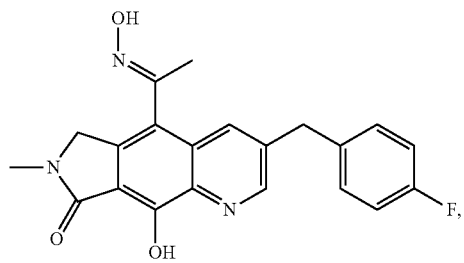
247
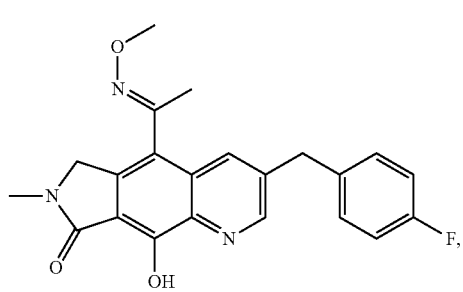
250
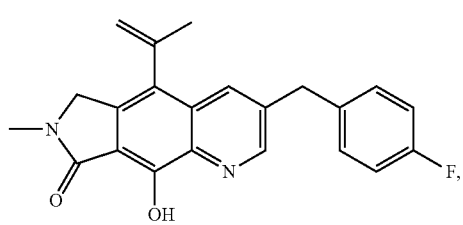
251
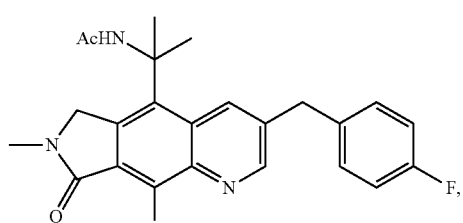
277
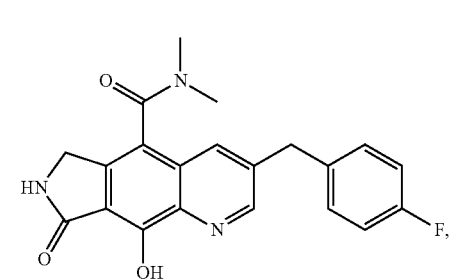
280
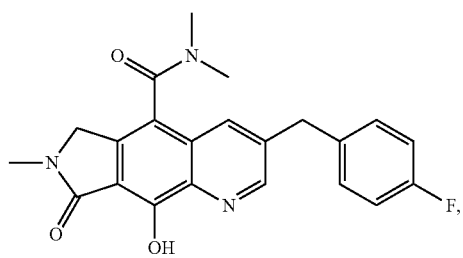
282
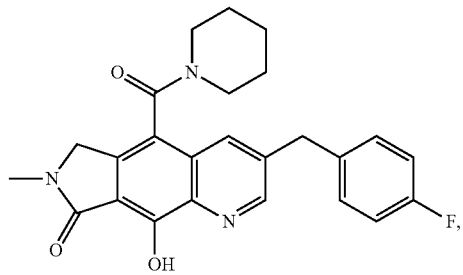

243
-continued
284
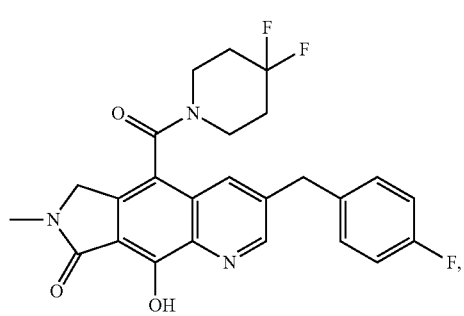
286
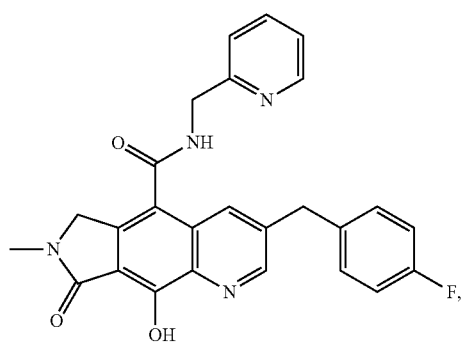
287
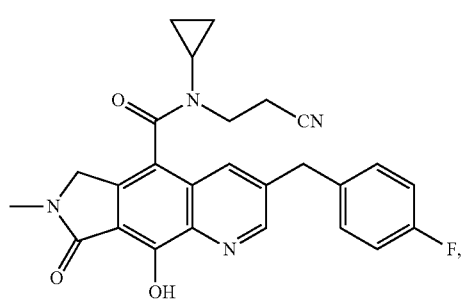
289
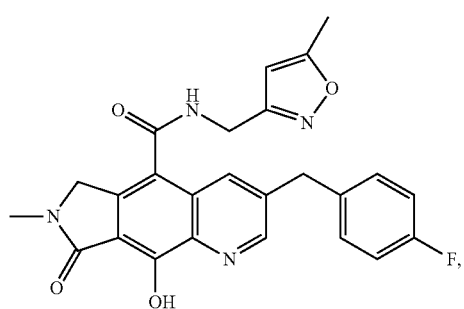
291
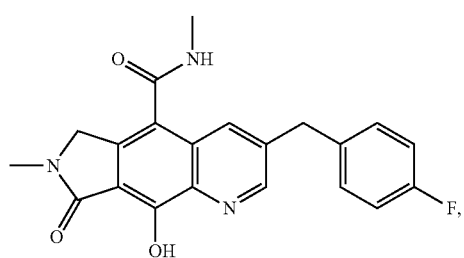
244
-continued
292
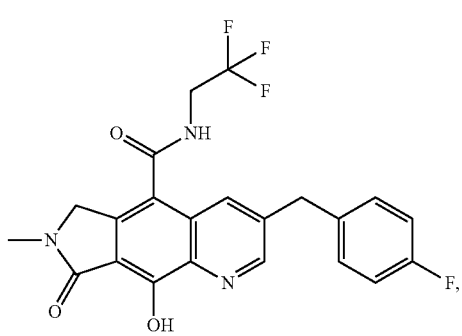
294
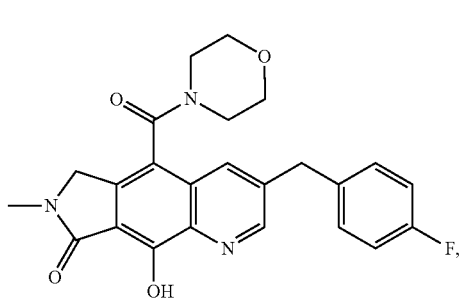
296
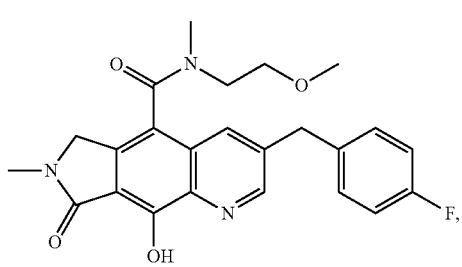
298
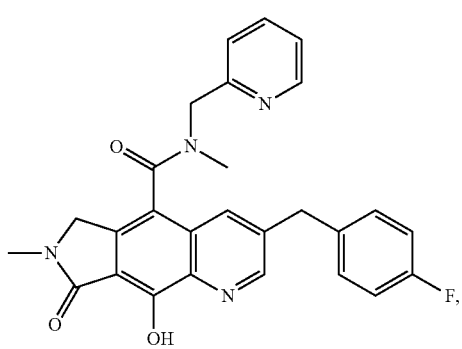
301
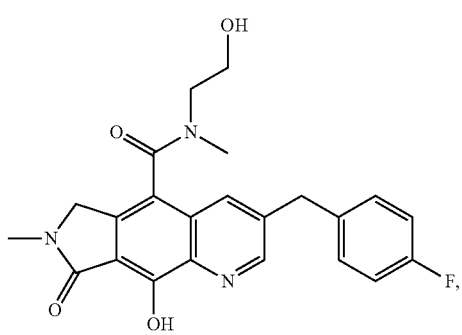

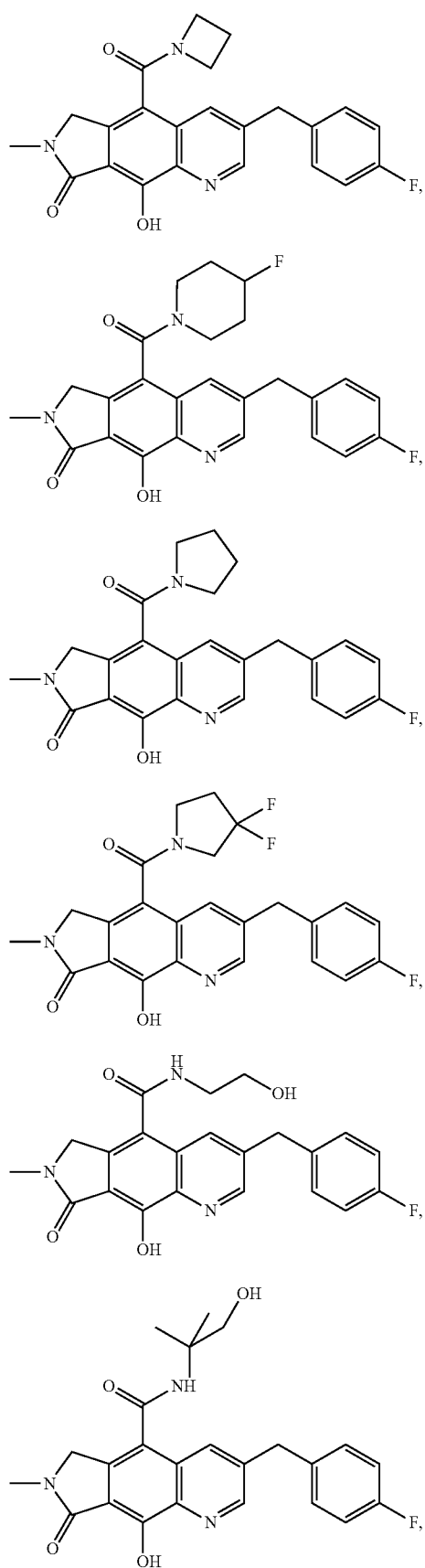
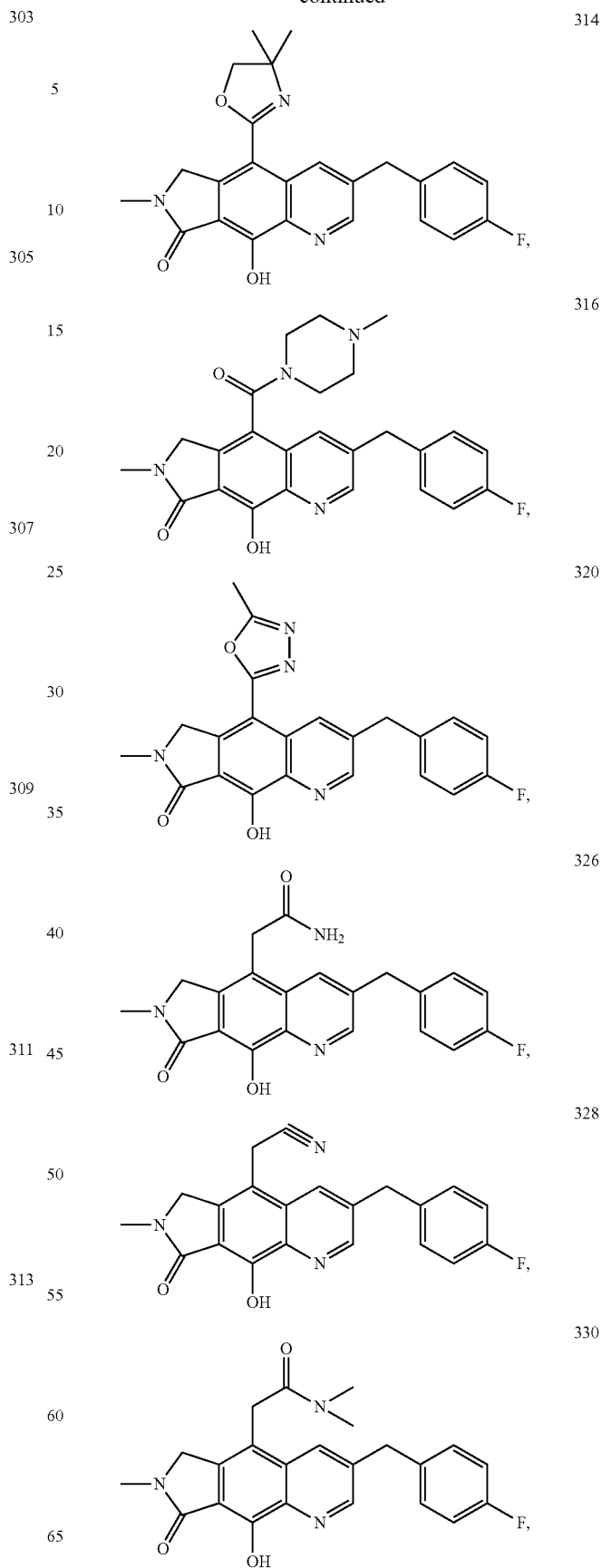

-continued
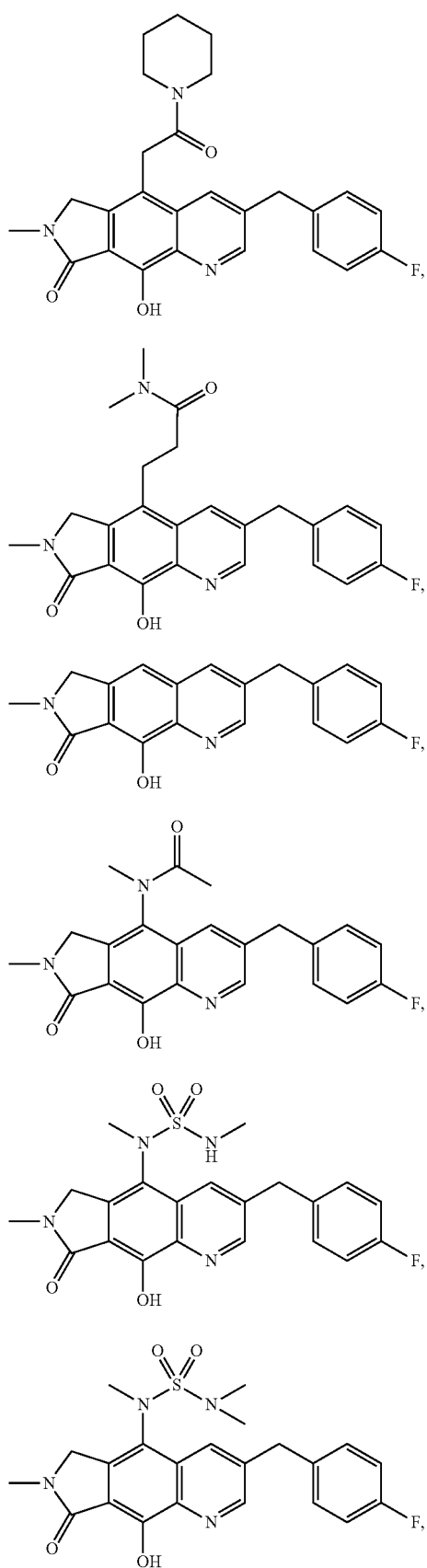
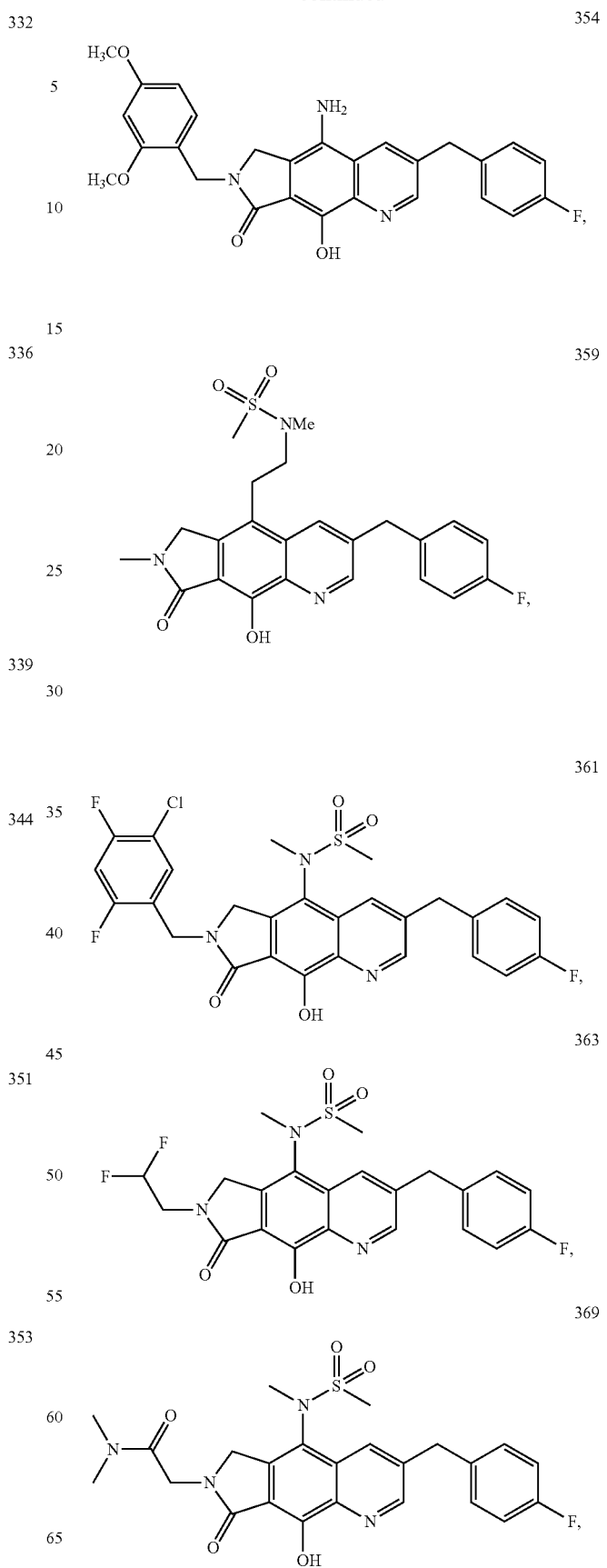

249
-continued
370
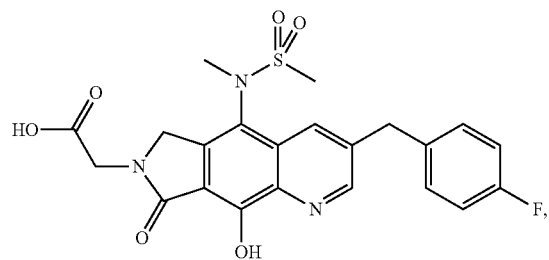
372
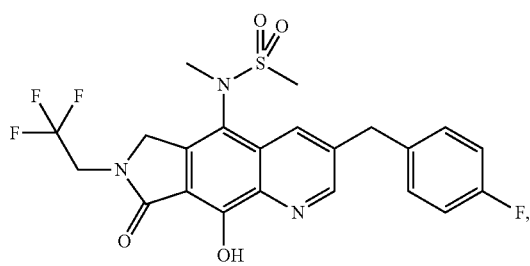
374
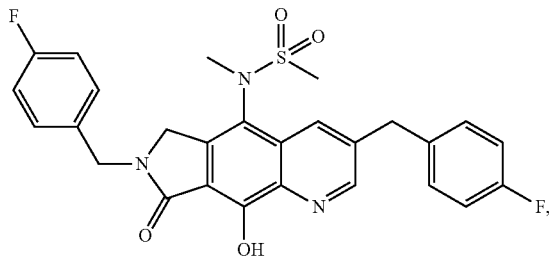
376
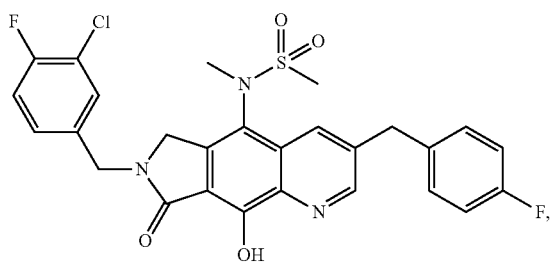
378
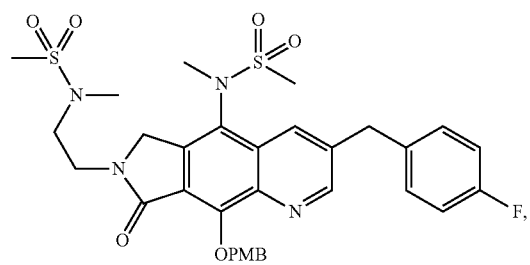
250
-continued
380
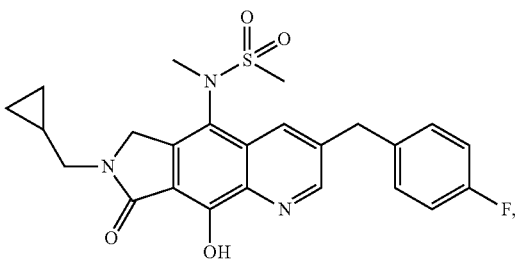
382
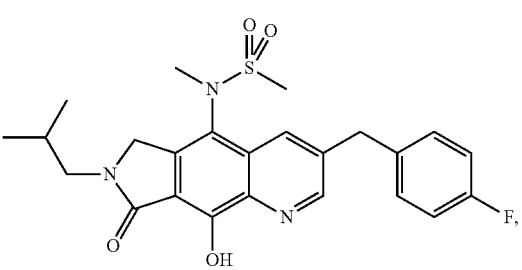
386
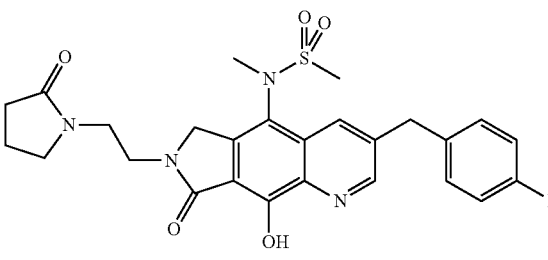
390
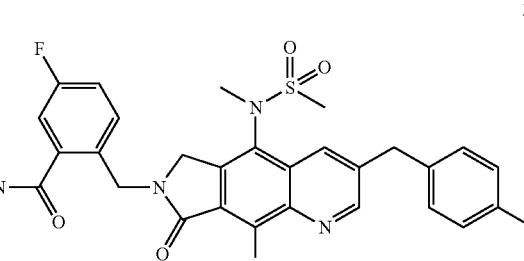
392
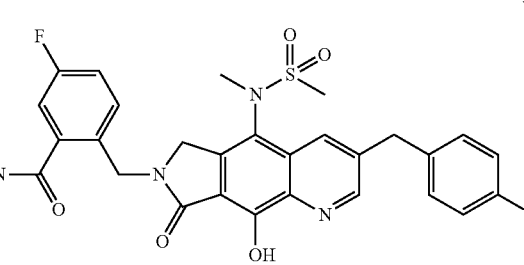

-continued
394
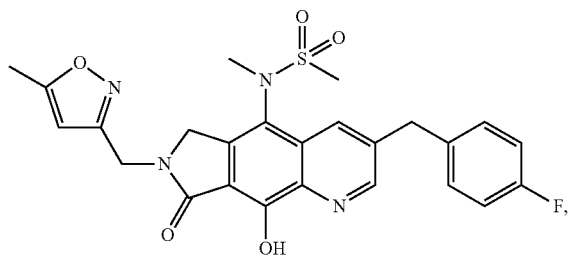
398
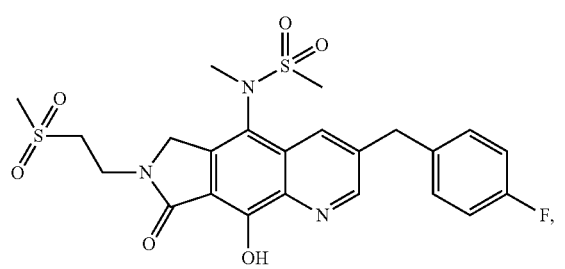
400
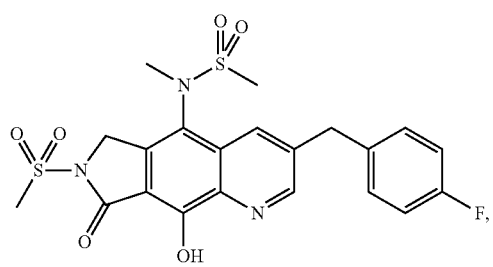
403
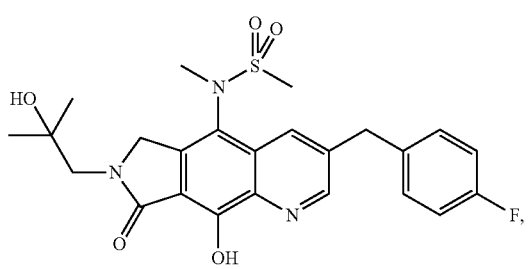
404
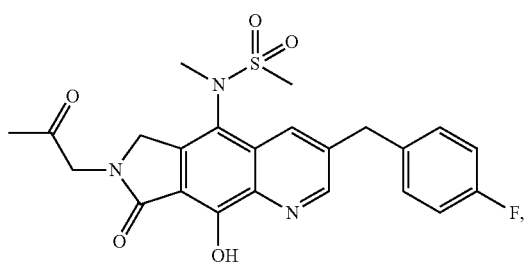
-continued
408
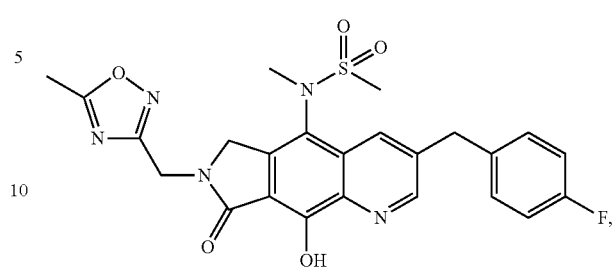
423
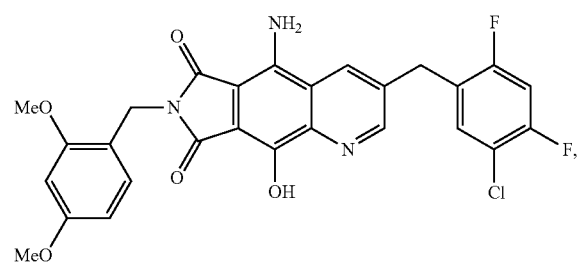
429
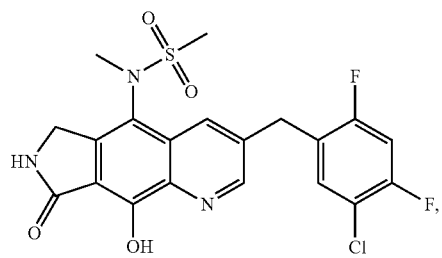
432
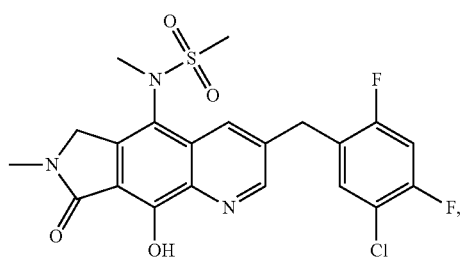
433
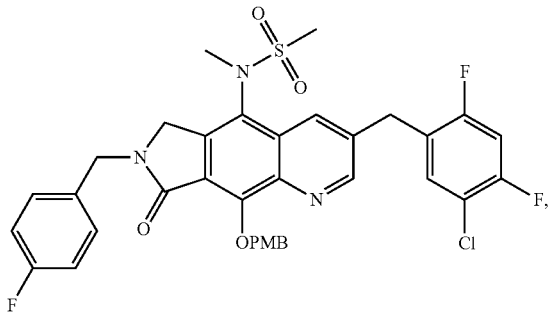

-continued

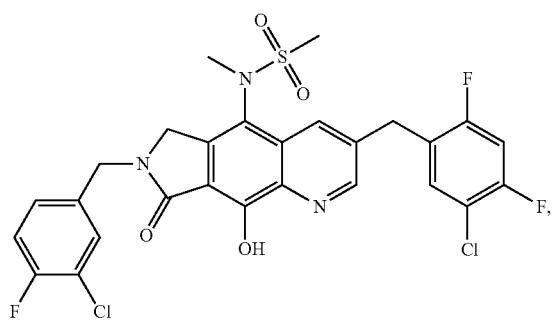
436

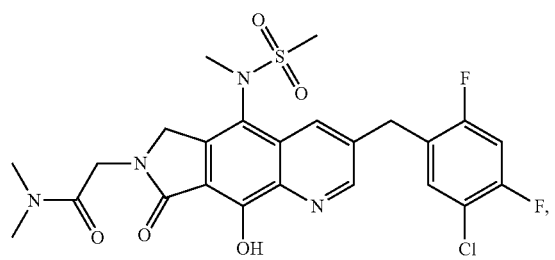
440

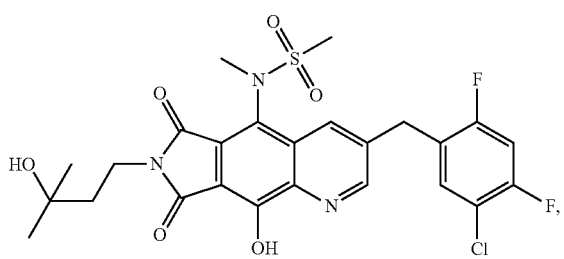
442

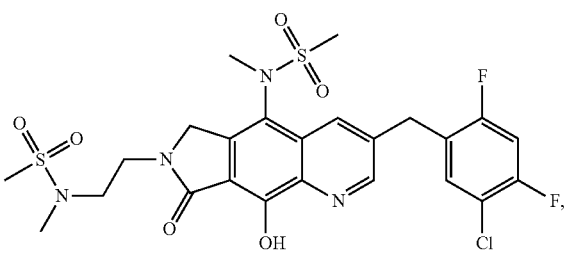
446

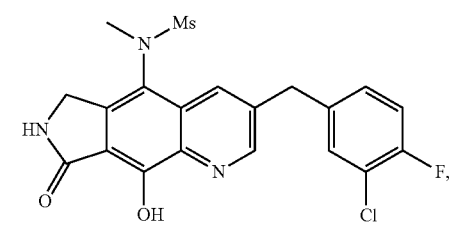
451

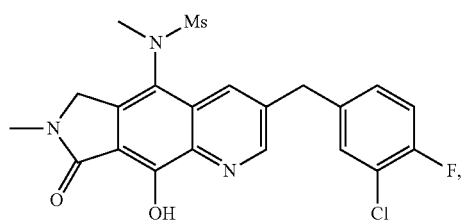
452

-continued

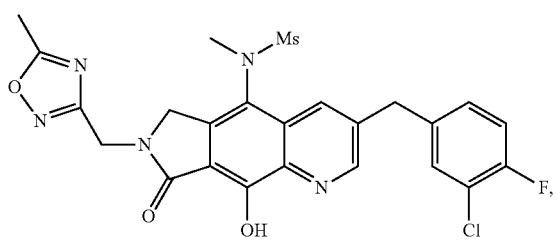
453

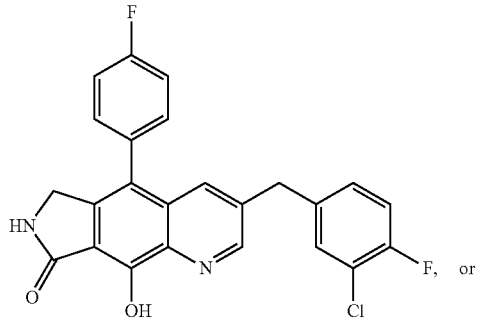
455

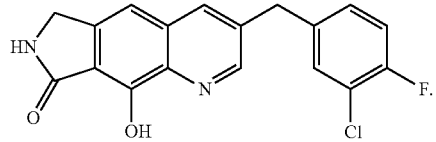
456 as described herein; or a pharmaceutically acceptable salt thereof.

46. A pharmaceutical composition comprising the compound or pharmaceutically acceptable salt according to claim 1, and a pharmaceutically acceptable excipient, diluent or carrier.

47. The pharmaceutical composition of claim 46, further comprising an AIDS treatment agent, an anti-infective agent, an immunomodulator agent, a booster agent or a mixture thereof.

48. The pharmaceutical composition of claim 47, where the AIDS treatment agent is an HIV-protease inhibitor, a nucleoside reverse transcriptase inhibitor, a non-nucleoside reverse transcriptase inhibitor or a mixture thereof.

49. The pharmaceutical composition of claim 46 which is in an oral dosage form.

50. A method of treating the proliferation of HIV virus, treating AIDS, or delaying the onset of AIDS or ARC symptoms, comprising administering to a mammal in need thereof, a therapeutically effective amount of the compound of claim 1.

51. A method of inhibiting HIV integrase, comprising administering to a mammal in need thereof, a therapeutically effective amount of the compound of claim 1.

52. The method of claim 50, further comprising administering to a mammal in need thereof, a booster agent, a therapeutically effective amount of an AIDS treatment agent, a therapeutically effective amount of an anti-infective agent, a therapeutically effective amount of an immunomodulator agent, or a mixture thereof.

* * * * *

SEQUENCE LISTING

<160> NUMBER OF SEQ ID NOS: 4

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 1 accctttttag tcagtgtgga aaatctctag cagt                                  34

<210> SEQ ID NO 2
<211> LENGTH: 31
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 2
actgctagag attttccaca ctgactaaaa g                                      31

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 3
tgaccaaggg ctaattcact                                                   20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 4
agtgaattag cccttggtca                                                   20